United States Patent
Shan et al.

(10) Patent No.: US 11,571,459 B2
(45) Date of Patent: Feb. 7, 2023

(54) METHODS FOR TREATING CANCER USING PS-TARGETING ANTIBODIES WITH IMMUNO-ONCOLOGY AGENTS

(71) Applicant: ONCXERNA THERAPEUTICS, INC., Waltham, MA (US)

(72) Inventors: Joseph S. Shan, Tustin, CA (US); Nikoletta L. Kallinteris, Tustin, CA (US); Min Tang, Tustin, CA (US); F. Andrew Dorr, Tustin, CA (US)

(73) Assignee: ONCXERNA THERAPEUTICS, INC., Waltham, MA (US)

( * ) Notice: Subject to any disclaimer, the term of this patent is extended or adjusted under 35 U.S.C. 154(b) by 58 days.

(21) Appl. No.: 15/943,304

(22) Filed: Apr. 2, 2018

(65) Prior Publication Data

US 2018/0289771 A1    Oct. 11, 2018

Related U.S. Application Data

(60) Provisional application No. 62/507,545, filed on May 17, 2017, provisional application No. 62/481,064, filed on Apr. 3, 2017.

(51) Int. Cl.
| | |
|---|---|
| *A61K 45/06* | (2006.01) |
| *A61P 35/04* | (2006.01) |
| *C07K 14/705* | (2006.01) |
| *A61K 47/68* | (2017.01) |
| *A61K 39/395* | (2006.01) |
| *C07K 16/28* | (2006.01) |
| *A61P 35/00* | (2006.01) |
| *A61K 9/00* | (2006.01) |
| *A61K 39/00* | (2006.01) |
| *A61K 38/17* | (2006.01) |
| *G01N 33/574* | (2006.01) |
| *A61P 31/12* | (2006.01) |
| *A61K 31/555* | (2006.01) |
| *A61K 31/337* | (2006.01) |

(52) U.S. Cl.
CPC ........ *A61K 38/1761* (2013.01); *A61K 9/0019* (2013.01); *A61K 31/337* (2013.01); *A61K 31/555* (2013.01); *A61K 39/39533* (2013.01); *A61K 45/06* (2013.01); *A61K 47/6811* (2017.08); *A61P 31/12* (2018.01); *A61P 35/00* (2018.01); *A61P 35/04* (2018.01); *C07K 14/70596* (2013.01); *C07K 16/28* (2013.01); *C07K 16/2818* (2013.01); *C07K 16/2827* (2013.01); *G01N 33/57488* (2013.01); *G01N 33/57492* (2013.01); *A61K 2039/507* (2013.01); *G01N 2333/57* (2013.01)

(58) Field of Classification Search
None
See application file for complete search history.

(56) References Cited

U.S. PATENT DOCUMENTS

| | | |
|---|---|---|
| 4,816,567 A | 3/1989 | Cabilly et al. |
| 4,861,581 A | 8/1989 | Epstein et al. |
| 4,935,496 A | 6/1990 | Kudo et al. |
| 5,019,368 A | 5/1991 | Epstein et al. |
| 5,223,409 A | 6/1993 | Ladner et al. |
| 5,225,539 A | 7/1993 | Winter |
| 5,427,908 A | 6/1995 | Dower et al. |
| 5,434,131 A | 7/1995 | Linsley et al. |
| 5,569,825 A | 10/1996 | Lonberg et al. |
| 5,585,089 A | 12/1996 | Queen et al. |
| 5,612,205 A | 3/1997 | Kay et al. |
| 5,624,821 A | 4/1997 | Winter et al. |
| 5,648,260 A | 7/1997 | Winter et al. |
| 5,693,761 A | 12/1997 | Queen et al. |
| 5,693,762 A | 12/1997 | Queen et al. |
| 5,731,168 A | 3/1998 | Carter et al. |
| 5,759,817 A | 6/1998 | Barbas |
| 5,811,097 A | 9/1998 | Allison et al. |
| 5,834,598 A | 11/1998 | Lowman et al. |
| 5,849,500 A | 12/1998 | Breitling et al. |
| 5,882,626 A | 3/1999 | Epstein et al. |
| 5,939,598 A | 8/1999 | Kucherlapati et al. |
| 5,969,108 A | 10/1999 | McCafferty et al. |
| 6,111,090 A | 8/2000 | Gorman et al. |
| 6,207,156 B1 | 3/2001 | Kuchroo et al. |
| 6,406,693 B1 | 6/2002 | Thorpe et al. |
| 6,509,173 B1 | 1/2003 | Ni et al. |

(Continued)

FOREIGN PATENT DOCUMENTS

| | | |
|---|---|---|
| AU | 2012201537 A1 | 4/2012 |
| EP | 0090505 A2 | 10/1983 |
| EP | 0171496 A2 | 2/1986 |
| EP | 0173494 A2 | 3/1986 |
| EP | 0239400 A2 | 9/1987 |
| EP | 0388151 A1 | 9/1990 |
| EP | 0519596 A1 | 12/1992 |
| EP | 1947183 A1 | 7/2008 |

(Continued)

OTHER PUBLICATIONS

Altiok, S et al. (J. Thoracic Oncology Sep. 6, 2015, 10(9)(Suppl. 2: S312-S313, Abs. No. MINI14.07) (Year: 2015).*

Agata, Y., et al. "Expression of the PD-1 antigen on the surface of stimulated mouse T and B lymphocytes." International immunology 8(5): 765-772, (1996).

(Continued)

*Primary Examiner* — Peter J Reddig
(74) *Attorney, Agent, or Firm* — Sterne, Kessler, Goldstein & Fox P.L.L.C.

(57) ABSTRACT

Disclosed are surprising new methods and kits for treating patients, particularly cancer patients, using bavituximab in combination therapies with immuno-oncology (IO) agents such as checkpoint inhibitor antibodies. The methods and kits are based on the surprising finding that human patients treated with bavituximab and checkpoint inhibitor antibodies have a statistically significant prolonged survival in controlled studies.

22 Claims, 15 Drawing Sheets

Specification includes a Sequence Listing.

(56) References Cited

U.S. PATENT DOCUMENTS

| | | |
|---|---|---|
| 6,682,736 B1 | 1/2004 | Hanson et al. |
| 6,984,720 B1 | 1/2006 | Korman et al. |
| 7,025,962 B1 | 4/2006 | Gorman et al. |
| 7,109,003 B2 | 9/2006 | Hanson et al. |
| 7,132,281 B2 | 11/2006 | Hanson et al. |
| 7,247,303 B2 | 7/2007 | Thorpe et al. |
| 7,411,057 B2 | 8/2008 | Hanson et al. |
| 7,422,738 B2 | 9/2008 | Thorpe et al. |
| 7,455,833 B2 | 11/2008 | Thorpe et al. |
| 7,572,442 B2 | 8/2009 | Thorpe et al. |
| 7,572,448 B2 | 8/2009 | Thorpe et al. |
| 7,595,048 B2 | 9/2009 | Honjo et al. |
| 7,605,238 B2 | 10/2009 | Korman et al. |
| 7,611,704 B2 | 11/2009 | Thorpe et al. |
| 7,615,223 B2 | 11/2009 | Thorpe et al. |
| 7,618,632 B2 | 11/2009 | Collins et al. |
| 7,622,118 B2 | 11/2009 | Thorpe et al. |
| 7,625,563 B2 | 12/2009 | Thorpe et al. |
| 7,678,386 B2 | 3/2010 | Thorpe et al. |
| 7,714,109 B2 | 5/2010 | Thorpe et al. |
| 7,790,159 B2 | 9/2010 | Thorpe et al. |
| 7,790,860 B2 | 9/2010 | Thorpe et al. |
| 7,807,797 B2 | 10/2010 | Hanson et al. |
| 7,812,135 B2 | 10/2010 | Smith et al. |
| 7,824,679 B2 | 11/2010 | Hanson et al. |
| 7,893,007 B2 | 2/2011 | Ladner et al. |
| 7,906,115 B2 | 3/2011 | Thorpe et al. |
| 7,923,221 B1 | 4/2011 | Cabilly et al. |
| 7,943,743 B2 | 5/2011 | Korman et al. |
| 8,008,449 B2 | 8/2011 | Korman et al. |
| 8,017,114 B2 | 9/2011 | Korman et al. |
| 8,143,379 B2 | 3/2012 | Hanson et al. |
| 8,168,179 B2 | 5/2012 | Honjo et al. |
| 8,217,149 B2 | 7/2012 | Irving et al. |
| 8,318,916 B2 | 11/2012 | Korman et al. |
| 8,354,509 B2 | 1/2013 | Carven et al. |
| 8,383,796 B2 | 2/2013 | Korman et al. |
| 8,388,967 B2 | 3/2013 | Smith et al. |
| 8,486,391 B2 | 7/2013 | Thorpe et al. |
| 8,491,895 B2 | 7/2013 | Hanson et al. |
| 8,586,023 B2 | 11/2013 | Shiku et al. |
| 8,591,886 B2 | 11/2013 | Ponath et al. |
| 8,592,562 B2 | 11/2013 | Kannan et al. |
| 8,709,424 B2 | 4/2014 | Schebye et al. |
| 8,728,474 B2 | 5/2014 | Honjo et al. |
| 8,779,108 B2 | 7/2014 | Queva et al. |
| 8,779,195 B2 | 7/2014 | Miyake et al. |
| 8,784,815 B2 | 7/2014 | Korman et al. |
| 8,883,984 B2 | 11/2014 | Hanson et al. |
| 8,900,587 B2 | 12/2014 | Carven et al. |
| 8,952,136 B2 | 2/2015 | Carven et al. |
| 8,956,616 B2 | 2/2015 | Thorpe et al. |
| 9,067,986 B2 | 6/2015 | Gurney et al. |
| 9,067,999 B1 | 6/2015 | Honjo et al. |
| 9,073,994 B2 | 7/2015 | Honjo et al. |
| 9,084,776 B2 | 7/2015 | Korman et al. |
| 9,102,725 B2 | 8/2015 | Korman et al. |
| 9,150,663 B2 | 10/2015 | Labrijn et al. |
| 9,212,230 B2 | 12/2015 | Schuurman et al. |
| 9,358,289 B2 | 6/2016 | Korman et al. |
| 9,387,247 B2 | 7/2016 | Korman et al. |
| 9,393,301 B2 | 7/2016 | Honjo et al. |
| 9,402,899 B2 | 8/2016 | Honjo et al. |
| 9,421,256 B2 | 8/2016 | Kavlie et al. |
| 9,439,962 B2 | 9/2016 | Honjo et al. |
| 9,492,539 B2 | 11/2016 | Korman et al. |
| 9,492,540 B2 | 11/2016 | Korman et al. |
| 9,493,565 B2 | 11/2016 | Queva et al. |
| 9,505,848 B2 | 11/2016 | Davis et al. |
| 9,580,505 B2 | 2/2017 | Korman et al. |
| 9,580,507 B2 | 2/2017 | Korman et al. |
| 9,835,626 B2 | 12/2017 | Schroit et al. |
| 10,344,050 B2 | 7/2019 | Gramer et al. |
| 10,345,310 B2 | 7/2019 | Schroit et al. |
| 2002/0150993 A1 | 10/2002 | Ashkenazi et al. |
| 2003/0082187 A1* | 5/2003 | Thorpe .............. A61K 47/6849 424/155.1 |
| 2004/0175378 A1 | 9/2004 | Thorpe et al. |
| 2005/0048054 A1 | 3/2005 | Hanabuchi et al. |
| 2005/0136059 A1 | 6/2005 | Thorpe et al. |
| 2005/0202008 A1 | 9/2005 | Williams et al. |
| 2006/0002932 A1 | 1/2006 | Vieweg |
| 2008/0220000 A1 | 9/2008 | Moore et al. |
| 2011/0177070 A1 | 7/2011 | Lofquist et al. |
| 2011/0212086 A1 | 9/2011 | Shankara et al. |
| 2012/0282184 A1 | 11/2012 | Waldmann et al. |
| 2013/0095097 A1 | 4/2013 | Blankenship et al. |
| 2013/0108641 A1 | 5/2013 | Baurin et al. |
| 2015/0203579 A1 | 7/2015 | Papadopoulos et al. |
| 2015/0210769 A1* | 7/2015 | Freeman .............. G01N 33/566 424/136.1 |
| 2016/0009805 A1 | 1/2016 | Kowanetz et al. |
| 2016/0311903 A1 | 10/2016 | West et al. |
| 2017/0058033 A1 | 3/2017 | Ludwig et al. |
| 2018/0051307 A1 | 2/2018 | Igawa et al. |

FOREIGN PATENT DOCUMENTS

| | | |
|---|---|---|
| WO | WO-1986001533 A1 | 3/1986 |
| WO | WO-1987002671 A1 | 5/1987 |
| WO | WO-1990002809 A1 | 3/1990 |
| WO | WO-1991000906 A1 | 1/1991 |
| WO | WO-1992/020791 A1 | 11/1992 |
| WO | WO-2005055808 A2 | 6/2005 |
| WO | WO-2018064013 A1 | 4/2018 |

OTHER PUBLICATIONS

Agostinis et al., "In vivo distribution of β2 glycoprotein I under pathophysiologic conditions", Blood, 118(15):4231-4238 (2011).

Al-Lazikani, B. et al. "Standard conformations for the canonical structures of immunoglobulins," Journal of molecular biology, 273(4), 927-948, (1997).

An, T. et al. "Exosomes serve as tumour markers for personalized diagnostics owing to their important role in cancer metastasis." Journal of extracellular vesicles 4(1):27522, (2015).

Balasubramanian, K. et al. "Estimation of plasma beta-2-glycoprotein levels by competitive ELISA." Thrombosis research 92(2): 91-97, (1998).

Barbas, C. et al. "Assembly of combinatorial antibody libraries on phage surfaces: the gene III site." Proceedings of the National Academy of Sciences 88(18): 7978-7982, (1991).

Beck et al., "Combination of a monoclonal anti-phosphatidylserine antibody with gemcitabine strongly inhibits the growth and metastasis of orthotopic pancreatic tumors in mice", Int. J. Cancer, 118:2639-2643, (2006).

Beidler, C. et al. "Cloning and high level expression of a chimeric antibody with specificity for human carcinoembryonic antigen." The Journal of Immunology 141(11): 4053-4060, (1988).

Best, S. "Viruses play dead to TAMe interferon responses." Cell host & microbe 14(2): 117-118. (2013).

Better, M. et al. "*Escherichia coli* secretion of an active chimeric antibody fragment." Science 240(4855): 1041-1043, (1988).

Bevers, E. et al. "Quantitative determination of the binding of β2-glycoprotein I and prothrombin to phosphatidylserine-exposing blood platelets." Biochemical Journal 386(2): 271-279, (2005).

Bevers, E. et al. "The effect of phospholipids on the formation of immune complexes between autoantibodies and β2-glycoprotein I or prothrombin." Clinical Immunology 112(2): 150-160, (2004).

Bhattacharyya et al., "Enveloped viruses disable innate immune responses in dendritic cells by direct activation of TAM receptors", Cell Host & Microbe, 14(2): 136-147, (2013).

Bird, R. et al. "Single-chain antigen-binding proteins." Science 242(4877): 423-426, (1988).

Birge et al., "Phosphatidylserine is a global immunosuppressive signal in efferocytosis, infectious disease, and cancer", Cell Death Differ 23(6): 1-17, (2016).

Brahmer et al., "Nivolumab versus docetaxel in advanced squamous-cell non-small-cell lung cancer", N. Engl. J. Med. 373(2): 123-135 (2015).

(56) References Cited

OTHER PUBLICATIONS

Bruggeman et al., "Human antibody production in transgenic mice: expression from 100 kb of the human IgH locus," Eur J Immunol 21:1323-1326, (1991).
Bruggeman et al., "Designer mice: the production of human antibody repertoires in transgenic animals" Immunol 7:33-40, (1993).
Brunet, J. et al. "A new member of the immunoglobulin superfamily—CTLA-4." Nature 328(6127): 267-270, (1987).
Butte, M. et al. "Programmed death-1 ligand 1 interacts specifically with the B7-1 costimulatory molecule to inhibit T cell responses." Immunity 27(1): 111-122, (2007).
Chalasani et al., "A Phase I Clinical Trial of Bavituximab and Paclitaxel in Patients with HER2 Negative Metastatic Breast Cancer," Cancer Medicine 4(7): 1051-1059, (2015).
Chen et al., "Phosphatidylserine Vesicles Enable Efficient En Bloc Transmission of Enteroviruses", Cell 160:619-630, (2015).
Cheng et al., "Antibody-Mediated Blockade of Phosphatidylserine Enhances the Antitumor Effect of Sorafenib in Hepatocellular Carcinomas Xenografts", Ann. Surg. Oncol. 5107-5, (2016).
Chothia, C. et al., "Canonical structures for the hypervariable regions of immunoglobulins." Journal of Molecular Biology 196(4): 901-917, (1987).
Clackson, T. et al., "Making antibody fragments using phage display libraries." Nature 352(6336): 624-628, (1991).
Clayson et al., "Release of Simian Virus 40 Virions from Epithelial Cells is Polarized and Occurs without Cell Lysis," J. Virology, 63(5):2278-2288, (1989).
Colcher, D. et al., "Single-chain antibodies in pancreatic cancer." Annals of the New York Academy of Sciences 880(1): 263-280, (1999).
Czuczman et al., "Listeria monocytogenes exploits efferocytosis to promote cell-to-cell spread," Nature 509:230-234, (2014).
Damatta et al., "Trypanosoma cruzi exposes phosphatidylserine as an evasion mechanism," FEMS Microbiol. Lett. 266:29-33, (2007).
Davra et al., "Ligand Activation of TAM Family Receptors—Implications for Tumor Biology and Therapeutic Response," Cancers, 8: 107-120, (2016).
De Groot et al, "[beta]2-Glycoprotein I: evolution, structure and function", Journal of Thrombosis and Haemostasis 9(7):1275-1284, (2011).
De Laat et al., "IgG antibodies that recognize epitope Gly40-Arg43 in domain I of 2-glycoprotein I cause LAC, and their presence correlates strongly with thrombosis", Blood 105(4): 1540-5, (2005).
De Laat, D. et al., "Pathogenic anti-betaz-glycoprotein I antibodies recognize domain I of beta$_2$-glycoprotein I only after a conformational change", Blood 107(5): 1916-24, (2006).
Derose et al., "Development of bavituximab, a vascular targeting agent with immune-modulating properties, for lung cancer treatment", Immunotherapy 3(8):933-944, (2011).
Digumarti et al., "Bavituximab Plus Paclitaxel and Carboplatin for the Treatment of Advanced Non-Small-Cell Lung Cancer", Lung Cancer 86:231-236, (2014).
Eda et al., "Cytoadherence of Malaria-Infected Red Blood Cells Involves Exposure of Phosphatidylserine", Cell Physiol. Biochem. 12:373-384, (2002).
Fehrenbacher et al., "Atezolizumab versus docetaxel for patients with previously treated non-small-cell lung cancer (POPLAR): a multicentre, open-label, phase 2 randomised controlled trial", The Lancet, 387(10030): 1837-1846, (2016).
Feng et al., "Multispectral imaging of formalin-fixed tissue predicts ability to generate tumor-infiltrating lymphocytes from melanoma", J. ImmunoTher Cancer 3:47, (2015).
Finger et al. "The human PD-1 gene: complete cDNA, genomic organization, and developmentally regulated expression in B cell progenitors." Gene 197(1-2):177-187, (1997).
Francis et al., "*Mycobacterium tuberculosis* ESAT-6 is a leukocidin causing Ca2+ influx, necrosis and neutrophil extracellular trap formation", Cell death & disease 5(10): e1474-e1474, (2014).

Freeman, G. et al. "Uncovering of functional alternative CTLA-4 counter-receptor in B7-deficient mice." Science 262(5135): 907-909, (1993).
Freeman, G. et al. "Engagement of the PD-1 immunoinhibitory receptor by a novel B7 family member leads to negative regulation of lymphocyte activation." The Journal of experimental medicine 192(7): 1027-1034, (2000).
Freimark et al., "Antibody-Mediated Phosphatidylserine Blockade Enhances the Antitumor Responses to CTLA-4 and PD-1 Antibodies in Melanoma", Cancer Immunol. Res., 4(6):531-40, (2016).
Fuchs et al. "Targeting recombinant antibodies to the surface of *Escherichia coli*: fusion to a peptidoglycan associated lipoprotein", Biotechnology 9:1370-1372, (1991).
Galli et al., "Anticardiolipin antibodies (ACA) directed not to cardiolipin but to a plasma protein cofactor", Lancet, 335(8705): 1544-1547, (1990).
Garon et al., "Pembrolizumab for the treatment of non-small-cell lung cancer", N. Engl. J. Med., 372(21):2018-2028, (2015).
Garrad et al. "Fab assembly and enrichment in a monovalent phage display system," Biotechnology 9:1373-1377, (1991).
Gaule et al., "A quantitative comparison of antibodies to programmed cell death 1 ligand 1", JAMA Oncol. 3(2):256-259, (2017).
Gerber et al. "Randomized phase III study of docetaxel plus bavituximab in previously treated advanced non-squamous non-small-cell lung cancer", Annals of Oncology 29: 1548-1553, (2018).
Gerber et al., "Docetaxel Combined with Bavituximab in Previously Treated, Advanced Nonsquamous Non-Small-Cell Lung Cancer", Clinical Lung Cancer, 17(3): 169-176, (2016).
Gerber et al., "Phase I Safety and Pharmacokinetic Study of Bavituximab, a Chimeric Phosphatidylserine-Targeting Monoclonal Antibody, in Patients with Advanced Solid Tumors", Clin. Cancer Res., 17(21): 1-9, (2011).
Gong et al., "Measuring Response to Therapy by Near-Infrared Imaging of Tumors Using a Phosphatidylserine-Targeting Antibody Fragment", Molecular Imaging 12(4):244-256, (2013).
Goth et al., "Rapid, Transient Phosphatidylserine Externalization Induced in Host Cells by Infection with *Chlamydia* spp", Infect. Immun., 69(2): 1109-1119, (2001).
Gram, H. et al., "In vitro selection and affinity maturation of antibodies from a naive combinatorial immunoglobulin library." Proceedings of the National Academy of Sciences 89(8):3576-3580, (1992).
Gray et al., "LAG3 is an immunotherapeutic target in murine triple negative breast cancers whose activity is significantly enhanced in combination with phosphatidylserine targeting antibodies", Poster B019, CRI-CIMT-EATI-AACR International Cancer Immunotherapy Conference, New York, NY, Sep. 25-28, 2016b.
Gray et al., "Phosphatidylserine-targeting antibodies augment the anti-tumorigenic activity of anti-PD-1 therapy by enhancing immune activation and downregulating pro-oncogenic factors induced by T-cell checkpoint inhibition in murine triple-negative breast cancers", Breast Cancer Research 18(1):50, (2016a).
Green et al., "Antigen-specific human monoclonal antibodies from mice engineered with human Ig heavy and light chain YACs," Nature genetics 7(1): 13-21, (1994).
Gregorc et al., "Predictive value of a proteomic signature in patients with non-small-cell lung cancer treated with second-line erlotinib or chemotherapy (PROSE): a biomarker-stratified, randomised phase 3 trial", Lancet Oncology 15(7):713-721, (2014).
Griffiths, A. et al. "Human anti-self antibodies with high specificity from phage display libraries." The EMBO journal 12(2):725-734, (1993).
Hagele et al., "Legionella pneumophila kills human phagocytes but not protozoan host cells by inducing apoptotic cell death", FEMS Microbiol. Lett. 169(1):51-58, (1998).
Hawkins, R. et al., "Selection of phage antibodies by binding affinity: mimicking affinity maturation." Journal of molecular biology 226(3): 889-896, (1992).
Hay et al., "Bacteriophage cloning and *Escherichia coli* expression of a human IgM Fab" Hum Antibod Hybridomas 3:81-85, (1992).

(56) References Cited

OTHER PUBLICATIONS

He et al., "Antiphosphatidylserine antibody combined with irradiation damages tumor blood vessels and induces tumor immunity in a rat model of glioblastoma", Clin. Cancer Res. 15(22):6871-80, (2009).
He et al., "Radiation-enhanced vascular targeting of human lung cancers in mice with a monoclonal antibody that binds anionic phospholipids", Clin. Cancer Res. 13(17):5211-5218, (2007).
Hogg et al., "Retargeting Adenoviral Vectors to Improve Gene Transfer into Tumors", Cancer Gene Therapy, 18:275-287, (2011).
Hoogenboom, H. et al., "Multi-subunit proteins on the surface of filamentous phage: methodologies for displaying antibody (Fab) heavy and light chains" Nucleic acids research 19(15): 4133-4137, (1991).
Hotchkiss et al., "Inhibition of endothelial cell function in vitro and angiogenesis in vivo by docetaxel (Taxotere): association with impaired repositioning of the microtubule organizing center", Mol. Cancer Ther. 1(13): 1191-200, (2002).
Huang, B. et al., "A monoclonal antibody that binds anionic phospholipids on tumor blood vessels enhances the antitumor effect of docetaxel on human breast tumors in mice", Cancer Res. 65(10):4408-4416, (2005).
Hunt and Krilis, "The fifth domain of betaz-glycoprotein I contains a phospholipid-binding site (Cys281-Cys288) and a region recognized by anticardiolipin antibodies", J. Immunol 152:653-659, (1994).
Hunt, S., "Identification of a region of $beta_2$-glycoprotein I critical for lipid-binding and anticardiolipin antibody cofactor activity", Proc. Natl. Acad. Sci. 90:2141-2145, (1993).
Huse, W., et al., "Generation of a large combinatorial library of the immunoglobulin repertoire in phage lambda." Science 246(4935): 1275-1281, (1989).
Huston, J. et al., "Protein engineering of antibody binding sites: recovery of specific activity in an anti-digoxin single-chain Fv analogue produced in *Escherichia coli*." Proceedings of the National Academy of Sciences 85(16): 5879-5883, (1988).
Hutchins, F. et al., "Targeting phosphatidylserine-mediated immune suppression enhances the efficacy of immune checkpoint blockade in preclinical tumor models of melanoma and breast", Abstract #105, European Journal of Cancer 51: S2-S3, (2015).
Ioannou, P. et al., "Binding of antiphospholipid antibodies to discontinuous epitopes on domain I of human $beta_2$-glycoprotein I: mutation studies including residues R39 to R43", Arthritis Rheum. 56(1):280-90, (2007).
Izquierdo-Useros et al., "HIV and mature dendritic cells: Trojan exosomes riding the Trojan horse?" PLoS Pathog, 6(3):e1000740, (2010).
Jemielity et al., "TIM-Family Proteins Promote Infection of Multiple Enveloped Viruses through Virion-Associated Phosphatidylserine", PLoS Pathogens 9(3):e1003232, (2013).
Jennewein et al., "Vascular Imaging of Solid Tumors in Rats with a Radioactive Arsenic-Labeled Antibody that Binds Exposed Phosphatidylserine", Clin. Cancer Res. 14(5): 1377-1385, (2008).
Jones et al. "Replacing the complementarity-determining regions in a human antibody with those from a mouse," Nature 321:552-525, (1986).
Judy et al., "Vascular Endothelial-Targeted Therapy Combined with Cytotoxic Chemotherapy Induces Inflammatory Intratumoral Infiltrates and Inhibits Tumor Relapses after Surgery", Neoplasia, 14:352-359, (2012).
Kallinteris et al., "IFN-γ analysis in blood and tissue as a potential prognostic and/or predictive biomarker," Abstract CT159, Proceedings: AACR Annual Meeting 2017 77(13): CT159.
Kallinteris et al., "Ifn-γ analysis in blood and tissue as a potential prognostic and/or predictive biomarker," Poster, Proceedings: AACR Annual Meeting 2017 77(13): CT159.
Kamboh et al., "Genetic Studies of Human Apolipoproteins. IV. Structural Heterogeneity of Apolipoprotein H (Beta$_2$-Glycoprotein I)", Am. J. Hum. Genet. 42:452-457, (1988).
Kennedy, James Randall. "Attenuating a sickle cell crisis with annexin V." Medical hypotheses 84(5): 434-436, (2015).
Kogure et al., "Temporary membrane distortion of vascular smooth muscle cells is responsible for their apoptosis induced by platelet-activating factor-like oxidized phospholipids and their degradation product, lysophosphatidylcholine", Chemistry and Physics of Lipids, 126:29-38, (2003).
Larson et al., "Customization, Scale-Up and Qualification of an Antibody-dependent Cell-mediated Cytotoxicity (ADCC) Bioassay", IBC's 23rd International Intensive Symposium Development, Validation and Maintenance of Biological Assays Conference, Seattle, Washington, May 14-16, 2013; Poster Board #7.
Latchman, Y. et al., "PD-L2 is a second ligand for PD-1 and inhibits T cell activation." Nature immunology 2(3):261-268, (2001).
Lenschow, D., et al. "Long-term survival of xenogeneic pancreatic islet grafts induced by CTLA41g." Science 257(5071): 789-792, (1992).
Lenschow, D. et al. "Expression and functional significance of an additional ligand for CTLA-4." Proceedings of the National Academy of Sciences 90(23): 11054-11058, (1993).
Li et al., "Phosphatidylserine (PS) is Exposed in Choroidal Neovascular Endothelium: PS-Targeting Antibodies Inhibit Choroidal Angiogenesis In vivo and Ex Vivo", Invest. Ophthalmol Vis. Sci. 56:7137-7145, (2015).
Liang et al., "Targeting Mutant P53 Protein and the Tumor Vasculature: An Effective Combination Therapy for Advanced Breast Tumors", Breast Cancer Res. Treat. 125:407-420, (2011).
Linsley, P. et al. "CTLA-4 is a second receptor for the B cell activation antigen B7." The Journal of experimental medicine 174(3): 561-569, (1991).
Linsley, P. et al., "Immunosuppression in vivo by a soluble form of the CTLA-4 T cell activation molecule." Science 257(5071): 792-795, (1992).
Liu, A. et al., "Chimeric mouse-human IgG1 antibody that can mediate lysis of cancer cells." Proceedings of the National Academy of Sciences 84(10): 3439-3443, (1987).
Liu, A. et al., "Production of a mouse-human chimeric monoclonal antibody to CD20 with potent Fc-dependent biologic activity." The Journal of Immunology 139(10): 3521-3526, (1987).
Lobuglio, A. F., et al., "Phase I clinical trial of CO17-1A monoclonal antibody." Hybridoma 5: S117-23, (1986).
Lonberg, N. et al., "Antigen-specific human antibodies from mice comprising four distinct genetic modifications." Nature 368(6474): 856-859, (1994).
Lonsdale et al., "Phosphatidylserine as a Therapeutic Target for the treatment of Francisella tularensis and Yersinia pestis infections", Chemical & Biological Defense Science & Technology Conference, 2011 Las Vegas, NV Poster.
Luster et al., "Plasma Protein beta$_2$-glycoprotein 1 Mediates Interaction between the Anti-tumor Monoclonal Antibody 3G4 and Anionic Phospholipids on Endothelial Cells", J. Biol. Chem. 281(40):29863-29871, (2006).
Mahoney et al., "PD-L1 Antibodies to Its Cytoplasmic Domain Most Clearly Delineate Cell Membranes in Immunohistochemical Staining of Tumor Cells", Cancer Immunol Res. 3(12): 1308-1315, (2015).
Mallat et al., "Shed Membrane Microparticles With Procoagulant Potential in Human Atherosclerotic Plaques", Circulation 99:348-353, (1999).
Marconescu and Thorpe, "Coincident Exposure of PhoSphatidylethanolamine and Anionic Phospholipids on the Surface of Irradiated Cells", Biochemica et Biophysica Acta 1778(10):2217-2224, (2008).
Mcneil, S. et al., "Anti-phospholipid antibodies are directed against a complex antigen that includes a lipid-binding inhibitor of coagulation: Beta$_2$-glycoprotein I (apolipoprotein H)", Proc. Natl. Acad. Sci. 87(11):4120-4124, (1990).
Meckes and Raab-Traub, "Microvesicles and Viral Infection", J. Virology, 85(24): 12844-12854, (2011).
Meckes et al., "Human tumor virus utilizes exosomes for intercellular communication", Proc. Natl. Acad. Sci. 107(47):20370-20375, (2010).

(56) References Cited

OTHER PUBLICATIONS

Meertens et al., "The TIM and TAM families of phosphatidylserine receptors mediate dengue virus entry", Cell Host & Microbe 12(4):544-557, (2012).
Mehdi et al., "Genetic variation in the apolipoprotein H (beta$_2$-glycoprotein I) gene affects plasma apolipoprotein H concentrations", Hum. Genet. 105:63-71, (1999).
Mercer and Helenius, "Vaccinia virus uses macropinocytosis and apoptotic mimicry to enter host cells", Science 320:531-535, (2008).
Miyakis et al., "β2-glycoprotein I—function in health and disease", Thromb. Res. 114:335-346, (2004).
Moller-Tank and Maury, "Phosphatidylserine receptors: Enhancers of enveloped virus entry and infection", Virology 468: 565-580, (2014).
Moody et al, "Anti-phospholipid human monoclonal antibodies inhibit CCR5-tropic HIV-1 and induce β-chemokines", J. Exp. Med. 207(4):763-776, (2010).
Morizono et al, "The soluble serum protein Gas6 bridges virion envelope phosphatidylserine C254 to the TAM receptor tyrosine kinase Ax1 to mediate viral entry", Cell Host Microbe 9:286-298, (2011).
Morrison, S. "Transfectomas provide novel chimeric antibodies." Science 229(4719): 1202-1207, (1985).
Morrison, S. et al. "Chimeric human antibody molecules: mouse antigen-binding domains with human constant region domains." Proceedings of the National Academy of Sciences. 81(21): 6851-6855, (1984).
Murata-Kamiya et al., "Helicobacter pylori Exploits Host Membrane Phosphatidylserine for Delivery, Localization, and Pathophysiological Action of the CagA Oncoprotein", Cell Host Microbe 7:399-411, (2010).
Nishimura, Y. et al., "Recombinant human-mouse chimeric monoclonal antibody specific for common acute lymphocytic leukemia antigen." Cancer research 47(4): 999-1005, (1987).
Nishimura, H. et al., "Developmentally regulated expression of the PD-1 protein on the surface of double-negative (CD4—CD8—) thymocytes." International immunology 8(5): 773-780, (1996).
Oi, V. et al., "Chimeric antibodies." BioTechniques 4(3): 214-221, (1986).
Palmero et al., "Final Clinical Results from SUNRISE: A Phase III, Randomized, Double-Blind, Placebo-Controlled Multicenter Trial of Bavituximab Plus Docetaxel in Patients with Previously Treated Stage IIIb/IV Nonsquamous Non-Small Cell Lung Cancer", Annals Oncol., 28(Suppl. 5):487, Abstract 1364P, (2017).
Pattanapanyasat, K. et al. "Febrile temperature but not proinflammatory cytokines promotes phosphatidylserine expression on Plasmodium falciparum malaria-infected red blood cells during parasite maturation." Cytometry Part A 77(6): 515-523, (2010).
Peregrine Pharmaceuticals, "Phase 3 Study of Bavituximab Plus Docetaxel Versus Docetaxel Alone in Patients With Late-stage Non-squamous Non-small-cell Lung Cancer—NCT01999673", Dec. 3, 2013 (Dec. 3, 2013), Retrieved from the Internet: URL:https://clinicaltrials.gov/ct2/show/study/NCT01999673?term=nct01999673&rank=1.
Petersen, A. et al., "Helicobacter pylori: an invading microorganism? A review." FEMS Immunology & Medical Microbiology 36(3): 117-126, (2003).
Polz, E. et al., "Investigations on beta$_2$-glycoprotein-I in the rat—isolation from serum and demonstration in lipoprotein density fractions", Int. J. Biochem., 11:265-270, (1980).
Prakasam and Thiagarajan, "β2-Glycoprotein I—A Protein in Search of Function", In Antiphospholipid Syndrome, Ed. Alen. Bulikova, ISBN: 978-953-51-0526-8, InTech, Available from: http://www.intechopen.com/books/antiphospholipid-syndrome/beta2- glycoprotein-i-in-search-of-function, (2012).
Ran et al, "Antitumor effects of a monoclonal antibody that binds anionic phospholipids on the surface of tumor blood vessels in mice", Clin. Cancer Res. 11: 1551-1562, (2005).
Rebelatto et al, "Development of a programmed cell death ligand-1 immunohistochemical assay validated for analysis of non-small cell lung cancer and head and neck squamous cell carcinoma", Diagnos. Pathol 11(1):95, (2016).
Reiter, Y. et al. "Antibody engineering of recombinant Fv immunotoxins for improved targeting of cancer: disulfide-stabilized Fv immunotoxins." Clinical cancer research 2(2): 245-252, (1996).
Sabatier et al, "Type 1 and Type 2 Diabetic Patients Display Different Patterns of Cellular Microparticles", Diabetes 51:2840-2845, (2002).
Saha et al, "An Orthotopic Lung Tumor Model for Image-Guided Microirradiation in Rats", Radiat Res., 174:62-71, (2010).
Saleh et al., "A phase II trial of murine monoclonal antibody 17-1A and interferon-γ: Clinical and immunological data." Cancer Immunol. Immunother. 32:185-190, (1990).
Schubert-Unkmeir et al, "Gene Expression Pattern in Human Brain Endothelial Cells in Response to Neisseria meningitidis", Infect. Immun 75(2):899-914, (2007).
Seabra et al., "Toxoplasma gondii exposes phosphatidylserine inducing a TGF-beta1 autocrine effect orchestrating macrophage evasion", Biochem. Biophys. Res. Comm. 324(2):744-752, (2004).
Shaw, D. et al., "Mouse/human chimeric antibodies to a tumor-associated antigen: biologic activity of the four human IgG subclasses." JNCI: Journal of the National Cancer Institute. 80(19): 1553-1559, (1988).
Sheng et al., "Impaired Thrombin Generation in Beta2-Glycoprotein I Null Mice", J. Biol. Chem. 276(17): 13817-13821, (2001).
Shinohara, T. et al., "Structure and chromosomal localization of the human PD-1 gene (PDCD1)." Genomics 23(3): 704-706, (1994).
Sims et al., "Neural stem cell-derived exosomes mediate viral entry", Int. J. Nanomedicine, 9:4893-4897, (2014).
Soares et al., "Targeting inside-out phosphatidylserine as a therapeutic strategy for viral diseases", Nature Medicine 14(12): 1357-1362, (2008).
Souza et al., "Microparticles: markers and mediators of sepsis-induced microvascular dysfunction, immunosuppression, and AKI", Kidney international 87(6): 1100-1108, (2015).
Stafford & Thorpe, "Increased Exposure of Phosphatidylethanolamine on the Surface of Tumor Vascular Endothelium", Neoplasia 13:299-308, (2011).
Stafford et al., "Highly Specific PET Imaging of Prostate Tumors in Mice with an Iodine-124-Labeled Antibody Fragment that Targets Phosphatidylserine", PLoS ONE 8(12):e84864, (2013).
Stasi and Cappuzzo, "Profile of bavituximab and its potential in the treatment of non-small-cell lung cancer", Lung Cancer: Targets and Therapy 5:43-50, (2014).
Steinkasserer et al, "Complete nucleotide and deduced amino acid sequence of human beta$_2$-glycoprotein I", Biochem. J. 277:387-391, (1991).
Sun, L. et al., "Chimeric antibody with human constant regions and mouse variable regions directed against carcinoma-associated antigen 17-1A." Proceedings of the National Academy of Sciences 84(1): 214-218, (1987).
Swallow, M. et al., "B7h, a novel costimulatory homolog of B7.1 and B7.2, is induced by TNFα." Immunity 11(4): 423-432, (1999).
Takeuchi et al, "Coagulation and fibrinolytic activities in 2 siblings with beta$_2$-glycoprotein I deficiency", Blood, 96:1594-1595, (2000).
Tuaillon, N. et al., "Human immunoglobulin heavy-chain minilocus recombination in transgenic mice: gene-segment use in mu and gamma transcripts." Proceedings of the National Academy of Sciences 90(8): 3720-3724, (1993).
Van Der Kleij et al, "A Novel Host-Parasite Lipid Cross-talk: schistosomal lysophosphatidylserine activates toll-like receptor 2 and affects immune polarization", J. Biol. Chem. 277(50):48122-48129, (2002).
Verhoeyen, M. et al., "Reshaping human antibodies: grafting an antilysozyme activity." Science 239(4847): 1534-1536, (1988).
Walker et al., "Cytomegalovirus-infected human endothelial cells can stimulate allogeneic CD4+ memory T cells by releasing antigenic exosomes" J. Immunol 182(3): 1548-1559, (2009).
Walunas, T. et al. "CTLA-4 can function as a negative regulator of T cell activation." Immunity 1(5): 405-413, (1994).

(56) References Cited

OTHER PUBLICATIONS

Wanderley et al., "Cooperation between apoptotic and viable metacyclics enhances the pathogenesis of leishmaniasis", PLoS One 4(5):e5733, (2009).

Wanderley et al., "Phosphatidylserine exposure on the surface of Leishmania amazonensis amastigotes modulates in vivo infection and dendritic cell function", Parasite Immunology 35: 109-119, (2013).

Wandler et al., "A Greasy Foothold for Helicobacter pylori", Cell Host Microbe 7:338-339, (2010).

Weihua et al., "Apoptotic Cells Initiate Endothelial Cell Sprouting via Electrostatic Signaling", Cancer Res. 65(24): 11529-11535, (2005).

Willems et al., "Role of divalency in the high-affinity binding of anticardiolipin antibody-beta$_2$-glycoprotein I complexes to lipid membranes", Biochemistry 35: 13833-13842, (1996).

Wood, C. et al., "The synthesis and in vivo assembly of functional antibodies in yeast." Nature 314(6010): 446-449, (1985).

Wurm, H. "beta$_2$-Glycoprotein-I (apolipoprotein H) interactions with phospholipid vesicles." The International journal of biochemistry 16(5): 511-515, (1984).

Yin et al., "Phosphatidylserine-targeting antibody induces M1 macrophage polarization and promotes myeloid-derived suppressor cell differentiation", Cancer Immunol. Res., 1(4):256-268, (2013).

Yuyama et al., "Sphingolipid-modulated Exosome Secretion Promotes Clearance of Amyloid-β by Microglia", J. Biol. Chem., 287(14): 10977-10989, (2012).

Zandbergen et al., "Leishmania disease development depends on the presence of apoptotic promastigotes in the virulent inoculum", Proc. Natl. Acad. Sci. 103(37): 13837-13842, (2006).

Zhang et al., "Phosphatidylserine-Targeted Bimodal Liposomal Nanoparticles for in vivo Imaging of Breast Cancer in Mice", J. Control. Release, 183: 114-123, (2014).

Zhao et al., "Near-Infrared Optical Imaging of Exposed Phosphatidylserine in a Mouse Glioma Model", Translational Oncology, 4:355-364, (2011).

Zhou et al., "Phosphatidylserine-Targeted Molecular Imaging of Tumor Vasculature by Magnetic Resonance Imaging", J. Biomed. Nanotechnol. 10: 1-10, (2014).

Peregrine Press Release date Aug. 24, 2015, AstraZeneca and Peregrine Pharmaceuticals to Collaborate on Immuno-Oncology Combination Clinical Trial—Collaboration to Focus on Cancer Immunotherapy Combination of Peregrine's PS-Targeting Bavituximab and AstraZeneca's PD-L1 Inhibitor MEDI4736, Tustin, California.

Peregrine Press Release date Oct. 15, 2015, AstraZeneca and Peregrine Pharmaceuticals Expand Ongoing Immuno-Oncology Collaboration to Include Phase II Lung Cancer Combination Clinical Trial—Global, Randomized Phase II Trial to Evaluate Immunotherapy Combination of Peregrine's PS-Targeting Bavituximab and AstraZeneca's PD-L1 Inhibitor Durvalumab (MEDI4736) in Previously Treated NSCLC, Tustin, California.

Peregrine Press Release date Jan. 6, 2016, Peregrine Pharmaceuticals and National Comprehensive Cancer Network (NCCN) From Clinical Collaboration to Evaluate Novel Cancer Treatment Combinations With Bavituximab—NCCN Alliance Includes 26 Leading Cancer Centers and World-Class Thought Leaders on Innovative Cancer Combination Therapies, Tustin, California.

NCCN News, NCCN Awarded $2 Million in Research Funding from Peregrine Pharmaceuticals to Study Bavituximab in Various Cancers, Fort Washington, PA, undated, nccn.org, accessed at https://www.nccn.org/about/news/newsinfo.aspx?NewsID=565, Accessed on Nov. 5, 2018.

American Association for Cancer Research, "108th AACR Annual Meeting 2017 Proceedings," *Proceedings of the American Association for Cancer Research* 58, 1690 pages, United States (Apr. 2017).

Blank, C.U., et al., "Cancer Immunology. The 'cancer immunogram'" *Science* 352(6286):658-660, American Association for the Advancement of Science, United States (May 2016).

Chau, I., et al., "Initial safety and efficacy findings with bavituximab plus pembrolizumab in patients with advanced gastric or gastroesophageal cancer," *Annals of Oncology* 31(S4): S909-S910, Abstract 1446P, accessed at https://www.annalsofoncology.org/article/S0923-7534(20)4 1948-9/fulltext on Jan. 14, 2021, 2 pages (Sep. 2020).

Chau, I., et al., "Initial safety and efficacy findings withbavituximab plus pembrolizumab in patients with advanced gastric or gastroesophageal cancer," presented at: European Society for Medical Oncology, Poster 1446P, accessed at https://onexema.com/wp-content/uploads/2020/09/2020-ESMO-Oncologie-ONCG100-poster-FINAL.pdf on Jan. 14,. 2021, 1 page (Sep. 2020).

Chukwuocha, R.U., et al., "Isolation, Characterization and Sequence Analysis of Five IgG Monoclonal Anti-β$_2$-Glycoprotein-1 and Anti-Prothrombin Antigen-Binding Fragments Generated by Phage Display," *The Journal of Immunology* 163(8):4604-4611, The American Association of Immunologists, United States (Oct. 1999).

Fehrenbacher, L., et al., "Supplement to: Fehrenbacher L, Spira A, Balliner M, et al., for the POPLAR Study Group, 'Atezolizumab versus docetaxel for patients with previously treated nonsmall-cell lung cancer (POPLAR): a multicentre, open-label, phase 2 randomised controlled trial,'" *Lancet* 387(10030):1837-1846, Elsevier, Netherlands (Apr. 2016).

Garon, E.B., et al., "Supplement to: Garon EB, Rizvi NA, Hui R, et al., 'Pembrolizumab for the treatment of non-small-cell lung cancer,'" *New England Journal of Medicine* 372(21):2018-2028. Massachusetts Medical Society, United States (published online Apr. 2015, published in print May 2015).

GlobeNewswire, "New Translational Data Highlights Bavituximab's Ability to Induce Signs of Immune Activation in Lung Cancer Tumor Samples with Negative PD-L1 Expression," FirstWordPharma.com, accessed at https://www.firstwordpharma.com/node/13134577?tsid=17, accessed on Jan. 11, 2021, 3 pages (Sep. 2015).

GlobeNewswire, "Peregrine Pharmaceuticals and National Comprehensive Cancer Network (NCCN) Form Clinical Collaboration to Evaluate Novel Cancer Treatment Combinations With Bavituximab," GlobeNewswire.com, accessed at https://rss.globenewswire.com/en/news-release/2016/01/06/799805/35065/en/Peregrine-Pharmaceuticals-and-National-Comprehensive-Cancer-Network-NCCN-Form-Clinical-Collaboration-to-Evaluate-Novel-Cancer-Treatment-Combinations-With-Bavituximab.html, 3 pages (Jan. 2016).

GlobeNewswire, "Peregrine Pharmaceuticals Provides Update on Planned Expansion of Bavituximab Clinical Program in Lung, Breast and Other Cancers," GlobeNewswire.com, accessed at https://www.globenewswire.com/news-release/2016/01/11/800863/0/en/Peregrine-Pharmaceuticals-Provides-Update-on-Planned-Expansion-of-Bavituximab-Clinical-Program-in-Lung-Breast-and-Other-Cancers.html, 4 pages (Jan. 2016).

GlobeNewswire, "Peregrine Pharmaceuticals Reports Financial Results for Third Quarter of Fiscal Year 2016 and Recent Developments," GlobeNewswire.com, accessed at https://rss.globenewswire.com/en/news-release/2016/03/09/818232/35065/en/Peregrine-Pharmaceuticals-Reports-Financial-Results-for-Third-Quarter-of-Fiscal-Year-2016-and-Recent-Developments.html, 5 pages (Mar. 2016).

GlobeNewswire, "National Comprehensive Cancer Network (NCCN) Awards Three Grants for Combination Studies of Peregrine Pharmaceuticals' Bavituximab in Multiple Cancers," GlobeNewswire.com, accessed at https://ir.avidbio.com/static-files/3ce3c8cl-2725-4ab8-b8c9-c7672137ca21, 3 pages (Sep. 2016).

GlobeNewswire, "Peregrine Pharmaceuticals Reports Financial Results for First Quarter of Fiscal Year 2017 and Recent Developments," GlobeNewswire.com, accessed at https://rss.globenewswire.com/en/news-release/2016/09/08/870643/35065/en/Peregrine-Pharmaceuticals-Reports-Financial-Results-for-First-Quarter-of-Fiscal-Year-2017-and-Recent-Developments.html, 6 pages (Sep. 2016).

GlobeNewswire, "Peregrine Pharmaceuticals Reports Financial Results for Second Quarter of Fiscal Year 2017 and Recent Developments," GlobeNewswire.com, accessed at https://ir.avidbio.com/news-releases/news-release-details/peregrine-pharmaceuticals-reports-financial-results-second-3, 6 pages (Dec. 2016).

(56) References Cited

OTHER PUBLICATIONS

GlobeNewswire, "Peregrine Pharmaceuticals Reports Financial Results for the Third Quarter of Fiscal Year 2017 and Recent Developments," GlobeNewswire.com, accessed at http://www.globenewswire.com/news-release/2017/03/13/936017/0/en/Peregrine-Pharmaceuticals-Reports-Financial-Results-for-the-Third-Quarter-of-Fiscal-Year-2017-and-Recent-Developments.html, 6 pages (Mar. 2017).

GlobeNewswire, "Peregrine Pharmaceuticals Announces Five Abstracts Accepted for Presentation at AACR 2017 Annual Meeting," GlobeNewswire.com, accessed at https://rss.globenewswire.com/en/news-release/2017/03/23/943439/35065/en/Peregrine-Pharmaceuticals-Announces-Five-Abstracts-Accepted-for-Presentation-at-AACR-2017-Annual-Meeting.html, 2 pages (Mar. 2017).

GlobeNewswire, "Peregrine Pharmaceuticals Presents Preliminary Correlative Analysis of PD-L1 Expression from SUNRISE Trial at ASCO 2017," GlobeNewswire.com, accessed at https://www.globenewswire.com/news-release/2017/06/05/1008110/0/en/Peregrine-Pharmaceuticals-Presents-Preliminary-Correlative-Analysis-of-PD-L1-Expression-from-SUNRISE-Trial-at-ASCO-2017.html 2 pages (Jun. 2017).

Gray, M.J., et al., "Monoclonal Antibodies Targeting Phosphatidylserine Augment Combinational Activity of LAG3 and PD-1 Targeting Antibodies In Murine TNBC Through Enhanced Reprogramming of the Immunosuppressive Tumor Microenvironment," presented at 108th AACR Annual Meeting 2017 (Apr. 1-5, 2017), Poster 3652, 1 page (Apr. 2017).

Hedge, P.S., et al., "The Where, the When, and the How of Immune Monitoring for Cancer Immunotherapies in the Era of Checkpoint Inhibition,"*Clin Cancer Res* 22(8): 1865-1874, American Association for Cancer Research, United States (Apr. 2016).

Herbst, R.S., et al., "Predictive correlates of response to the anti-PD-L1 antibody MPDL3280A in cancer patients," *Nature* 515(7528):563-567, Nature Publishing Group, United Kingdom (2014).

Kallinteris, N.L., et al., "Preliminary correlative analysis of PD-L1 expression from the SUNRISE study," *Journal of Clinical Oncology* 35(Suppl 15): 11603-11603, Abstract 11603, accessed at https://ascopubs.org/doi/abs/10.1200/JCO.2017.35.15_suppl.11603. 1 page (May. 2017).

Kallinteris, N.L., et al., "Preliminary Correlative Analysis of PD-L1 expression from the SUNRISE Study," presented at ASCO 2017 (Jun. 2-6, 2017), Poster 11603, 1 page (May 2017).

Mahoney, K.M., et al., "Combination cancer immunotherapy and new immunomodulatory targets," *Nat Rev Drug Discov* 14(8):561-584. Nature Publishing Group, United Kingdom (Aug. 2015).

Rittmeyer, A., et al., "Atezolizumab versus docetaxel in patients with previously treated non-small-cell lung cancer (OAK): a phase 3, open-label, multicentre randomised controlled trial," *Lancet* 389(10066):255-265, Elsevier, Netherlands (Jan. 2017).

Strand-Tibbitts, K., "Development of a diagnostic platform which matches therapies to the tumor microenvironment dominant biology," *Journal of ImmunoTherapy of Cancer* 8( Suppl 3):A155-A156, Abstract 257, accessed https://jtc/bmj.com/content/jitc/8/Suppl_3/A155.2.fullpdf on Jan. 7, 2021, 2 pages (Dec. 2020).

Strand-Tibbitts, K., et al., "Development of an RNA-based Diagnostic Platform Based on the Tumor Microenvironment Dominant Biology," presented at: The Society for Immunotherapy of Cancer (SITC 2020), accessed at https://www.genialis.com/wp-conent/uploads/2020/11/OneXerna-SITC2020cPoster.pdf on Jan. 14, 2021, 1 page (Nov. 2020).

* cited by examiner

3G4-2BVH original sequence:

```
                    M   G   W   T   W   I   F   I   L   I   L   S   V
121                 ATG GGA TGG ACC TGG ATC TTT ATT TTA ATC CTG TCA GTA
                    TAC CCT ACC TGG ACC TAG AAA TAA AAT TAG GAC AGT CAT
                                    PvuII
                                    -----

T   T   G   V   H   S   E   V   Q   L   Q   Q   S   P   E   E   L   E   K   P
181    ACT ACA GGT GTC CAC TCT GAG GTC CAG CTG CAG CAG TCT GGA CCT GAG CTG GAG AAG CCT
       TGA TGT CCA CAG GTG AGA CTC CAG GTC GAC GTC GTC AGA CCT GGA CTC GAC CTC TTC GGA
       G   A   S   V   K   L   S   C   K   A   S   G   Y   S   F   T   G   Y   N   M

G   G   A   V   K   L   S   C   K   A   S   G   Y   S   F   T   G   Y   N   M
241    GGC GCT GTG AAG CTA TCC TGC AAG GCT TCT GGT TAC TCA TTC ACT GGC TAC AAC ATG
       CCG CGA CAT TTC GAT AGG ACG TTC CGA AGA CCA AGT AGT GAA TGA CCG ATG TTG TAC
       P   R   H   L   D   R   T   L   A   R   P   M   S   M   I   P   V   M   Y

N   W   V   K   Q   S   H   G   K   S   L   E   W   I   G   H   I   D   P   Y
301    AAC TGG GTG AAA CAG AGC CAT GGA AAG AGC CTT GAA TGG ATT GGA CAT ATT GAT CCT TAC
       TTG ACC CAC TTT GTC TCG GTA CCT TTC TCG GAA CTT ACC TAA CCT GTA TAA CTA GGA ATG
       Y   G   D   T   S   Y   N   Q   K   F   R   G   K   A   T   L   T   V   D   K

Y   G   D   T   S   Y   N   Q   K   F   R   G   K   A   T   L   T   V   D   K
361    TAT GGT GAT ACT TCC TAC AAT CAG AAG TTC AGG GGC AAG GCC ACA TTG ACT GTA GAC AAA
       ATA CCA CTA TGA AGG ATG TTA GTC TTC AAG TCC CCG TTC CGG TGT AAC TGA CAT CTG TTT
       I   P   I   S   E   V   L   K   P   A   S   N   S   C   L   V   N   S   L   F

S   S   S   T   A   Y   M   Q   L   S   S   L   T   S   E   D   S   A   V   Y
421    TCC TCC AGC ACA GCC TAC ATG CAG CTC AGC AGC CTG ACA TCT GAG GAC TCT GCA GTC TAT
       AGG AGG TCG TGT CGG ATG TAC GTC GAG TCG TCG GAC TGT AGA CTC CTG AGA CGT CAG ATA
       R   R   S   C   R   M   H   V   S   L   L   D   V   R   L   V   R   A   V   Y

Y   C   V   K   G   G   Y   Y   G   H   W   Y   F   D   V   W   G   A   G   T
481    TAC TGT GTA AAG GGG GGT TAC TAC GGG CAC TGG TAC TTC GAT GTC TGG GGC GCA GGG ACC
       ATG ACA CAT TTC CCC CCA ATG ATG CCC GTG ACC ATG AAG CTA CAG ACC CCG CGT CCC TGG
                                                                                    XhoI
                                                                                    -----

T   V   T   V   S   S   A   T   T   T   A   P   S   V   Y   P   L   V   P
541    ACG GTC ACC GTC TCC TCA GCT ACA ACA ACA GCC CCA TCT GTC TAT CCC TTG GTC CCG GGC
       TGC CAG TGG CAG AGG AGT CGA TGT TGT CGT CGG GGT AGA CAG ATA GGG AAC CAG GGC CCG
       BamHI                    EcoRI
       -----                    -----

601    GGA TCC CCC GGG CTG CAG GAA TTC GAT ATC AAG CTT ATC GAT ACC GTC GAC CTC GAG GGG
       CCT AGG GGG CCC GAC GTC CTT AAG CTA TAG TTC GAA TAG CTA TGG CAG CTG GAG CTC CCC
```

FIG. 1A

The RACE product 3G4-2BVH is cloned and grafted onto the human γ1 constant region at the BstEII site. Thus, it contains the mouse leader sequence and its VH is joined with the human CH1 sequence in the following way: leader/3G4VH/VSS-AST...

Mouse Leader     ↓mature protein
  1 MGWTWIFILI LSVTTGVHSE VQLQQSGPEL EKPGASVKLS CKASGYSFTG
 51 YNMNWVKQSH GKSLEWIGHI DPYYGDTSYN QKFFGKATLT VDKSSSTAYM
                                              ↓BstEII graft site
101 QLKSLTSEDS AVYYCVKGGY YGHWYFDVWG AGTTVTVSS ASTKGPSVFPL
151 APSSKSTSG
                                                ↑human γ1CH1

FIG. 1A (cont.)

3G4-2BVL original sequence:

```
                    M   D   M   R   A
                    ATG GAC ATG AGG GCT
                    TAC CTG TAC TCC CGA
         P   A   Q   I   L   G   F   L   L   L   F   P   G   T   R   C   D   I   Q
 61      CCT GCA CAG ATT TTG GGC TTC TTG CTC TTG TTT CCA GGT ACC AGA TGT GAC ATC CAG
         GGA CGT GTC TAA AAC CCG AAG GAG AAC AAA GGT CCA TGG TCT ACA CTG TAG GTC
         M   T   Q   S   P   S   S   L   S   A   S   V   G   E   R   V   S   L   T   C
121      ATG ACC CAG TCT CCA TCC TTA TCT GCC TCT GTC GGA GAA AGA GTC AGT CTC ACT TGT
         TAC TGG GTC AGA GGT AGG AAT AGA CGG AGA CAG CCT CTT TCT CAG TCA GAG TGA ACA
         R   A   S   Q   D   I   G   S   S   L   N   W   L   Q   Q   G   P   D   G   T
181      CGG GCA AGT CAG GAC ATT GGT AGT AGC TTA AAC TGG CTT CAG CAG GGA CCA GAT GGA ACT
         GCC CGT TCA GTC CTG TAA CCA TCA TCG AAT TTG ACC GAA GTC GTC CCT GGT CTA CCT TGA
         I   K   R   L   I   Y   A   T   S   L   D   S   G   V   P   K   R   F   S
241      ATT AAA CGC CTG ATC TAC GCC ACA TCC TTA GAT TCT GGT GTC CCA CCC AAA AGG TTC AGT
         TAA TTT GCG GAC TAG ATG CGG TGT AGG AAT CTA AGA CCA CAG GGT GGG TTT TCC AAG TCA
         G   S   R   S   R   S   D   Y   S   L   T   I   S   S   L   E   S   E   D   F
301      GGC AGT CGG AGT TCT GGG TCA TAT TAT ATA CAA GTT GTT TCT ACC ATC AGC CTT GAG GAT TTT
         CCG TCA GCC TCA AGA CCC AGT ATA TAT TAT GTT CAA CAA AGA TGG TAG TCG GAA CTC CTA AAA
                                                                        EbsI
         V   D   Y   Y   C   Y   Y   C   L   Q   A   G   A   T   P   F   I   F   G   T   K
361      GTA GAT TAC TAC TGT CAA GTT CAA CGA GAT GCT GCA CCA ACT TTC ATC TTC GGG ACC AAG
         CAT CTG ATG ATG ACA GTT CAA GTT GCT CTA CGA CGT GGT TGA AAG TAG AAG CCC TGG TTC
                                                                        BamHI
         L   E   L   K   R   A   D   A   A   P   T   V   F   I   F   P   P   S   K
481      CTG GAG CTG AAA CGG GCT GAT GCT GCA CCA ACT GTC TTC ATC TTC CCG CCC TCC AAG
         GAC CTC GAC TTT GCC CGA CTA CGA CGT GGT TGA CAG AAG TAG AAG GGC GGG AGG TTC
```

FIG. 1B

The RACE product 3G4-2BVL is grafted to human κ constant region at the BbsI site. Thus, it contains the mouse leader sequence and its VL is joined withIN the human CL1 sequence in the following way: leader/3G4-VL/TVF-IFP...

Mouse Leader ↓mature protein
1 MDMRAPAQIL GFLLLLFPGT RCDIQMTQSP SSLSASLGER VSLTCRASQD
51 IGSSLNWLQQ GPDGTIKRLI YATSSIDSGV PKRFSGSRSG SDYSLTISSL
                                              FR4↓  ↓BbsI graft site
101 ESEDFVDYYC LQYVSSPPTF GAGTKLELKR ADAAPTVF IFPPSDEQLKSGTAS
                                                    ↑human kappa constant

FIG. 1B (cont.)

Nucleotide sequence

1N11
<u>CCATGGCC</u>CAGGTGCAGCTGCAGGAGTCGGGCCCAGGACTGGTGAAGCCTTCACAGACCCTG
NcoI       |————VH Start (1N11, SEQ ID NO:20 Start)

TCCCTCACCTGCACTGTCTCTGGTGGCTCCATCAGCAGTGGTGATTACTACTGGAGTTGGAT

CCGCCAGCCCCCAGGGAAGGGTCTGGAGTGGATTGGGTACATCTATTACAGTGGGAGCACCT

ACTACAACCCGTCCCTCAAGAGTCGAGTTACCATATCAGTAGACACGTCCAAGAACCAGTTC

TCCCTGAAGCTGAGCTCTGTGACTGCCGCAGACACGGCCGTGTATTACTGTGCCAGATCTGA

GTGGTCCCTAGCTTTTGATATCTGGGGCCAAGGGACAATGGTCACCGTCTCTTCA<u>AAGCTT</u>
                                                                                   VH End———— ————||—HindIII-Linker start

*TCAGGGAGTGCATCCGCCCCAAAACTTGAAGAAGGTGAATTTTCAGAAGCACGCGTA*CAGCC
                                                                                     Linker end———— MluI—||—VL Start

TGTGCTGACTCAGCCACCCTCAGCGTCTGGGACCCCCGGGCAGAGGGTCACCATCCCTTGTT

CTGGAAGCAGCTCCAACATCGGAGGTAATGATGTATACTGGTACCAGCAAGTCCCAGGAATG

GCCCCCAAACTCCTCATCTATCGGAATCATCAGCGGCCCTCAGGGGTCCCTGACCGATTCTC

TGGCTCCAAGTCTGGCACCTCCGCCTCCCTGGCCATCAGTGGGCTCCGGTCCGAGGATGAGG

CTGATTATTATTGTGCAGCGTGGGATGACAGCCTGGGTGGGGTGGTGTTCGGCGGAGGGACC

AAGGTCACCGTCCTA<u>GCGGCCGC</u>
(1N11, SEQ ID NO:20 End) VL End —|  NotI

Amino acid sequence

1N11
QVQLQESGPGLVKPSQTLSLTCTVSGGSISSGDYYWSWIRQPPGKGLEWIGYIYYSGSTYYN
|———— V$_H$ Start (1N11, SEQ ID NO:21 Start)

PSLKSRVTISVDTSKNQFSLKLSSVTAADTAVYYCARSEWSLAFDIWGQGTMVTVSS*KLSGSAS*
                                                                                          V$_H$ End———— |————Linker

*APKLEEGEFSEARV*QPVLTSASGTPGQRVTIPCSGSSSNIGGNDVYWYQQVPGMAPKLLIYR
———————— —Linker—||—V$_L$ Start NHQRPSGVPDRFSGSKSGTSASLAISGLRSEDEADYYCAAWDDSLGGVVFGGGTKVTVL
                               (1N11, SEQ ID NO:21 End) V$_L$ End————|

FIG. 2A

METHODS FOR TREATING CANCER USING PS-TARGETING ANTIBODIES WITH IMMUNO-ONCOLOGY AGENTS

CROSS-REFERENCE TO RELATED APPLICATIONS

The present application claims priority to provisional application Ser. No. 62/507,545, filed May 17, 2017; and provisional application Ser. No. 62/481,064, filed Apr. 3, 2017, the entire specification, claims, drawings and sequences of which applications are incorporated herein by reference without disclaimer.

BACKGROUND OF THE INVENTION

Sequence Listing

The instant application contains a Sequence Listing which has been submitted electronically in ASCII format and is hereby incorporated by reference in its entirety. Said ASCII copy, created on Mar. 30, 2018, is named O2056-700110_SL.txt and is 39,555 bytes in size.

Field of the Invention

The present invention relates to the field of human treatment, and particularly concerns the use of PS-targeting antibodies such as bavituximab to treat patients, particularly cancer patients, in effective combination with immuno-oncology (IO) agents such as checkpoint inhibitor antibodies, preferably in combination with a blocking antibody that binds to CTLA-4, PD-1 or PD-L1, or a bispecific blocking antibody that binds to any checkpoint inhibitor.

BACKGROUND

In combating all diseases, including cancer and viral infections, a functioning immune system is an important part of a therapeutic response. Significant research has therefore been devoted to immune therapies, including the field of immuno-oncology (IO), which is now recognized as a strategy for treating cancer. In recent years, new targets and compounds that manipulate the immune response have been studied by researchers and clinicians. For example, IO agents that target programmed cell death protein 1 (PD-1) and programmed death-ligand 1 (PD-L1) have already received approval for the treatment of some advanced malignancies, while compounds that interact with other IO targets are in development.

Nonetheless, even these new immunotherapies are only effective in certain patients. Indeed, despite the attention on IO agents, responses and prolonged survival in many patients is still quite poor. Therefore, in light of the variability in response to both long-established therapies and new immunotherapies, and the desire to maximize clinical benefit, there remains a need for improved treatment options, including more effective combinations with IO therapies.

Recently, the membrane phospholipid, phosphatidylserine (PS), has been identified as a unique and highly immunosuppressive molecule, which acts as an upstream immune checkpoint that modulates the host immune response. This means that PS plays an important role in various diseases, including cancer and viral infections, opening up a new field of immunotherapeutics in the form of PS-targeting antibodies that block PS.

The lead PS-targeting antibody is bavituximab, a mouse-human chimeric monoclonal antibody (mAb) derived from the murine mAb termed 3G4 (Ran et al., 2005; Huang et al., 2005; U.S. Pat. No. 7,247,303). 3G4 and bavituximab are part of a family of murine, chimeric and fully human antibodies that target PS in a β2-glycoprotein 1 (β2GPI)-dependent manner. That is, bavituximab and related PS-targeting antibodies bind to PS in the presence of β2GPI, such that they form a high affinity antibody-β2GPI-PS complex (Luster et al., 2006). Operationally, these PS-targeting antibodies are specific for PS in vivo, as most particularly shown by numerous imaging studies (Jennewein et al., 2008; Marconescu & Thorpe, 2008, Saha et al., 2010, Stafford & Thorpe, 2011; Zhao et al., 2011; Zhang et al., 2014; and Zhou, et al., 2014; U.S. Pat. No. 7,790,860), including measuring and predicting response to therapy (Gong et al., 2013; Stafford et al., 2013).

Bavituximab has demonstrated activity in pre-clinical models against a wide range of diseases in which PS is a marker, most particularly cancer and viral infections, but also infections of intracellular parasites, such as the parasitic protozoan, *Leishmania amazonensis* (Wanderley et al., 2013) and intracellular bacterial pathogens, such as *Yersinia pestis* and *Francisella tularensis*, which cause plague and tularemia, respectively (Lonsdale et al., 2011). As to viral infections, PS-targeting antibodies such as bavituximab have been shown to inhibit viral replication, decrease viral load in organs and increase survival (Soares et al., 2008; Moody et al., 2010; U.S. Pat. No. 7,906,115). The anti-cancer activity of bavituximab and related PS-targeting antibodies has been demonstrated in an extensive number of pre-clinical studies and certain clinical trials, in which effects are mediated against tumor blood vessels as well as by blocking the immunosuppressive signaling of PS (Ran et al., 2005; U.S. Pat. No. 7,572,448; DeRose et al., 2011).

The anti-tumor effects of PS-targeting antibodies such as bavituximab are enhanced when the antibodies are used in conjunction with agents or conditions that increase the exposure of PS in the tumor microenvironment, such as by the use of radiation and/or the co-administration of chemotherapy (U.S. Pat. Nos. 7,422,738; 8,486,391; 7,572,448). For example, improved anti-tumor effects have been demonstrated pre-clinically when using the bavituximab family of PS-targeting antibodies in combination with docetaxel to treat breast tumors (Huang et al., 2005); gemcitabine to treat pancreatic tumors (Beck et al., 2006); irradiation to treat lung cancer (He et al., 2007) and the brain cancer, glioblastoma (He et al., 2009), docetaxel to treat prostate cancer and reactivate antitumor immunity (Yin et al., 2013); and sorafenib to treat hepatocellular carcinoma (Cheng et al., 2016). Enhanced anti-tumor effects have been observed pre-clinically when PS-targeting antibodies such as bavituximab are used in combination therapies with other IO agents, as shown pre-clinically for the treatment of melanoma (Freimark et al., 2016) and triple-negative breast cancer (Gray et al., 2016a) in combination with checkpoint inhibitors in the form of antibodies to CTLA-4 or PD-1.

Bavituximab has also been evaluated in completed clinical studies in over 800 patients, most of whom were treated with combination therapies, but not in combination therapies with IO agents or checkpoint inhibitors. These clinical trials have included patients with viral infections such as chronic hepatitis C virus (HCV) and human immunodeficiency virus (HIV), and patients with a number of tumor types, including lung, breast, liver (hepatocellular carcinoma, HCC), pancreatic, colorectal and kidney (renal cell carcinoma, RCC). Promising anti-tumor effects have been reported from clinical trials using bavituximab in combination with paclitaxel in patients with HER2 negative metastatic breast cancer (Chalasani et al., 2015); paclitaxel-carboplatin in advanced non-small cell lung cancer, NSCLC (Digumarti et al., 2014); sorafenib in hepatocellular carcinoma (Cheng et al., 2016); and with docetaxel in previously treated, advanced nonsquamous NSCLC (Gerber et al., 2016), all of which agents are chemotherapeutics.

Overall, results from Phase I and Phase II clinical studies have demonstrated a clinically meaningful treatment effect of bavituximab. Nonetheless, bavituximab therapy has yet to be approved, and so there remains a need for effective methods to optimize treatment with PS-targeting antibodies such as bavituximab. Meanwhile, attempts to maximize the therapeutic benefit of IO agents and checkpoint inhibitors have been hampered by the need for a pre-existing anti-tumor immune response, which is sadly lacking in many cancer patients. Accordingly, there is a need for improved patient treatment methods, including broader and/or optimized treatment with checkpoint inhibitors. Identifying one or more checkpoint inhibitors for effective combination with bavituximab in the treatment of patients would be an important advance, overcoming the difficulties associated with the immune 'cold' status of many patients.

SUMMARY OF THE INVENTION

The present invention addresses the foregoing and other needs of the prior art by providing new methods, compositions and kits for improved treatment with phosphatidylserine (PS)-targeting antibodies such as bavituximab in combination with immuno-oncology (IO) agents such as checkpoint inhibitor antibodies. The invention particularly concerns the use of an antibody that binds to PS (e.g., bavituximab) to treat human patients with cancer in combination with one or more inhibitors of an immune checkpoint modulator (e.g., checkpoint inhibitor antibodies), preferably in combination with a blocking antibody that binds to CTLA-4, PD-1 or PD-L1, or a multispecific (e.g., bispecific) blocking antibody that binds to any immune checkpoint inhibitor.

Suitable IO agents are immune checkpoint antibodies, include agonistic (activating) antibodies that bind to an activating immune checkpoint, receptor or molecule, such as CD28, OX40 and/or GITR, and preferably antagonistic (blocking) antibodies that bind to an immune checkpoint modulator (e.g., an inhibitory or stimulatory receptor or molecule), such as, e.g., PD-1, PD-L1, CTLA-4, TIM-3, LAG-3, OX40, CD2, CD27, CDS, ICAM-1, LFA-1 (CD11a/CD18), ICOS (CD278), 4-1BB (CD137), GITR, CD30, CD40, BAFFR, HVEM, CD7, LIGHT, NKG2C, SLAMF7, NKp80, CD160, VISTA, BTLA, TIGIT, LAIR1, CD160, 2B4 and/or TGF-β. Antagonistic (blocking) antibodies that bind to an inhibitory immune checkpoint, receptor or molecule are also herein termed "immune checkpoint inhibitors" or "ICIs". Examples of immune checkpoint antibodies (or immune checkpoint inhibitors) are blocking antibodies to CTLA-4, PD-1 or PD-L1, such as avelumab, ipilimumab, tremelimumab, nivolumab, pembrolizumab, durvalumab, atezolizumab, pidilizumab, XmAb20717, cemiplimab (REGN2810), CBT-501, CX-072, CX-188, and LY3300054, preferably avelumab, tremelimumab, nivolumab, durvalumab or atezolizumab, cemiplimab (REGN2810), CBT-501, CX-072, or LY3300054, and most preferably cemiplimab (REGN2810), CBT-501, CX-072, or LY3300054.

Enumerated Embodiments

1. A PS-targeting antibody molecule (e.g., bavituximab) for use in a method of treating cancer in a subject (e.g., a human patient), wherein the method comprises administering the PS-targeting antibody molecule to the subject in combination with an immune checkpoint antibody molecule, e.g., a blocking antibody that binds to CTLA-4, PD-1, or PD-L1.

2. A composition comprising a PS-targeting antibody (e.g., bavituximab) and an agent capable of altering the activity of an immune checkpoint modulator (e.g., an immune checkpoint antibody molecule) for use in a method of treating a cancer in a subject, e.g., a human patient.

3. A composition comprising a PS-targeting antibody (e.g., bavituximab) and an agent capable of altering the activity of an immune checkpoint modulator (e.g., an immune checkpoint antibody molecule) for use in a method as described herein.

4. A method for treating cancer in a subject (e.g., a human patient), the method comprising administering to said subject a phosphatidylserine (PS)-targeting antibody molecule (e.g., as described herein) and an agent capable of altering the activity of an immune checkpoint modulator (e.g., an immune checkpoint antibody molecule) in a combined amount effective to treat cancer in said subject, wherein said immune checkpoint antibody molecule binds to an immune checkpoint modulator, e.g., an immune checkpoint inhibitor or an immune checkpoint stimulator.

5. The composition or method of any of the preceding embodiments, wherein said subject has or is identified as having a pre-treatment blood concentration of functional β2-glycoprotein 1 (β2GPI) of equal to or greater than about 200 µg/ml (e.g., about 50, 100, 150, 160, 170, 180, 190, 200, 210, 220, 230, 240, 250, 300, or 400 µg/ml); and wherein said functional β2GPI binds to both phosphatidyl serine (PS) and to bavituximab.

6. The composition or method of any of the preceding embodiments, wherein said subject has or is identified as having a low pre-treatment serum interferon-γ concentration, e.g., wherein said low pre-treatment serum interferon-γ concentration is a serum concentration of interferon-γ of less than about 0.093 pg/mL (e.g., less than about 0.005, 0.006, 0.007, 0.008, 0.009, 0.0091, 0.0092, 0.0093, 0.0094, 0.0095, 0.0096, 0.0097, 0.0098, 0.0099, or 0.01 pg/mL).

7. The composition or method of embodiment 6, wherein said serum concentration if interferon-γ is measured by the Simoa immunoassay.

8. The composition or method of any of the preceding embodiments, wherein said subject has or is identified as having a negative pre-treatment PD-L1 status, e.g., wherein said negative pre-treatment PD-L1 status is defined as TC0, wherein less than about 1% (e.g., less than about 0.01%, 0.1%, 0.5%, 0.6%, 0.7%, 0.8%, 0.9%, 1%, 1.1%, 1.2%, 1.3%, 1.4%, 1.5%, 2%, 3%, 4%, or 5%) of the pre-treatment tumor cells express PD-L1 as measured by the OPAL immunohistochemistry assay.

9. A method for treating cancer in a subject, the method comprising:
(i) optionally determining a blood concentration of functional β2-glycoprotein 1 (β2GPI) in a subject having cancer, and
(ii) responsive to a blood concentration of functional β2GPI of equal to or greater than about 200 µg/ml (e.g., about 50, 100, 150, 160, 170, 180, 190, 200, 210, 220, 230, 240, 250, 300, or 400 µg/ml), administering an immune checkpoint antibody molecule and a PS-targeting antibody molecule (e.g., bavituximab) to the subject.

10. A method for treating cancer in a subject, the method comprising:
  (i) optionally determining a serum interferon-γ concentration in a subject having cancer, e.g., by the Simoa immunoassay, and
  (ii) responsive to a serum interferon-γ concentration of less than about 0.093 pg/mL (e.g., less than about 0.005, 0.006, 0.007, 0.008, 0.009, 0.0091, 0.0092, 0.0093, 0.0094, 0.0095, 0.0096, 0.0097, 0.0098, 0.0099, or 0.01 pg/mL), administering an immune checkpoint antibody molecule and a PS-targeting antibody molecule (e.g., bavituximab) to the subject.

11. A method for treating cancer in a subject, the method comprising:
  (i) optionally determining a serum interferon-γ concentration in a subject having cancer, e.g., by the Simoa immunoassay, and
  (ii) responsive to a serum interferon-γ concentration of less than about 0.093 pg/mL (e.g., less than about 0.005, 0.006, 0.007, 0.008, 0.009, 0.0091, 0.0092, 0.0093, 0.0094, 0.0095, 0.0096, 0.0097, 0.0098, 0.0099, or 0.01 pg/mL), administering an immune checkpoint antibody molecule to the subject;
  wherein the subject has been previously administered a PS-targeting antibody molecule (e.g., bavituximab).

12. A method for treating cancer in a subject, the method comprising:
  (i) optionally determining a PD-L1 status in a subject having cancer, and
  (ii) responsive to a negative PD-L1 status (e.g., wherein said negative pre-treatment PD-L1 status is defined as TC0, wherein less than about 1% (e.g., less than about 0.01%, 0.1%, 0.5%, 0.6%, 0.7%, 0.8%, 0.9%, 1%, 1.1%, 1.2%, 1.3%, 1.4%, 1.5%, 2%, 3%, 4%, or 5%) of the pre-treatment tumor cells express PD-L1, e.g., as measured by the OPAL immunohistochemistry assay), administering an immune checkpoint antibody molecule and a PS-targeting antibody molecule (e.g., bavituximab) to the subject.

13. A method for treating cancer in a subject, the method comprising:
  (i) optionally determining a PD-L1 status in a subject having cancer, and
  (ii) responsive to a negative PD-L1 status (e.g., wherein said negative pre-treatment PD-L1 status is defined as TC0, wherein less than about 1% (e.g., less than about 0.01%, 0.1%, 0.5%, 0.6%, 0.7%, 0.8%, 0.9%, 1%, 1.1%, 1.2%, 1.3%, 1.4%, 1.5%, 2%, 3%, 4%, or 5%) of the pre-treatment tumor cells express PD-L1, e.g., as measured by the OPAL immunohistochemistry assay), administering an immune checkpoint antibody molecule to the subject;
  wherein the subject has been previously administered a PS-targeting antibody molecule (e.g., bavituximab).

14. A method for treating cancer in a subject, the method comprising administering a PS-targeting antibody molecule and an immune checkpoint antibody molecule to a subject having cancer,
  wherein the subject is identified, or was determined to have a blood concentration of functional β2-glycoprotein 1 (β2GPI) of equal to or greater than about 200 μg/ml (e.g., about 50, 100, 150, 160, 170, 180, 190, 200, 210, 220, 230, 240, 250, 300, or 400 μg/ml).

15. A method for treating cancer in a subject, the method comprising administering an immune checkpoint antibody molecule to a subject having cancer,
  wherein the subject has been previously administered a PS-targeting antibody molecule (e.g., bavituximab), and
  wherein the subject is identified, or was determined to have a blood concentration of functional β2-glycoprotein 1 (β2GPI) of equal to or greater than about 200 μg/ml (e.g., about 50, 100, 150, 160, 170, 180, 190, 200, 210, 220, 230, 240, 250, 300, or 400 μg/ml).

16. The composition or method of any of the preceding embodiments, wherein the subject is identified, or was determined to have a blood concentration of functional β2-glycoprotein 1 (β2GPI) of equal to or greater than about 200 μg/ml (e.g., about 50, 100, 150, 160, 170, 180, 190, 200, 210, 220, 230, 240, 250, 300, or 400 μg/ml) prior to administration of the PS-targeting antibody molecule.

17. The composition or method of any of the preceding embodiments, wherein the subject is identified, or was determined to have a blood concentration of functional β2-glycoprotein 1 (β2GPI) of equal to or greater than about 200 μg/ml (e.g., about 50, 100, 150, 160, 170, 180, 190, 200, 210, 220, 230, 240, 250, 300, or 400 μg/ml) after administration of the PS-targeting antibody molecule.

18. A method for treating cancer in a subject, the method comprising administering a PS-targeting antibody molecule and an immune checkpoint antibody molecule to a subject having cancer,
  wherein the subject is identified, or was determined to have a low serum interferon-γ concentration, e.g., a serum concentration of interferon-γ of less than about 0.093 pg/mL (e.g., less than about 0.005, 0.006, 0.007, 0.008, 0.009, 0.0091, 0.0092, 0.0093, 0.0094, 0.0095, 0.0096, 0.0097, 0.0098, 0.0099, or 0.01 pg/mL), e.g., as measured by the Simoa immunoassay.

19. A method for treating cancer in a subject, the method comprising administering an immune checkpoint antibody molecule to a subject having cancer,
  wherein the subject has been previously administered a PS-targeting antibody molecule (e.g., bavituximab), and
  wherein the subject is identified, or was determined to have a low serum interferon-γ concentration, e.g., a serum concentration of interferon-γ of less than about 0.093 pg/mL (e.g., less than about 0.005, 0.006, 0.007, 0.008, 0.009, 0.0091, 0.0092, 0.0093, 0.0094, 0.0095, 0.0096, 0.0097, 0.0098, 0.0099, or 0.01 pg/mL), e.g., as measured by the Simoa immunoassay.

20. The composition or method of any of the preceding embodiments, wherein the subject is identified, or was determined to have a low serum interferon-γ concentration prior to the administration of the PS-targeting antibody molecule.

21. The composition or method of any of the preceding embodiments, wherein the subject is identified, or was determined to have a low serum interferon-γ concentration after the administration of the PS-targeting antibody molecule.

22. A method for treating cancer in a subject, the method comprising administering a PS-targeting antibody molecule and an immune checkpoint antibody molecule to a subject having cancer,
  wherein the subject is identified, or was determined to have a negative pre-treatment PD-L1 status (e.g., wherein said negative pre-treatment PD-L1 status is defined as TC0, wherein less than about 1% (e.g., less than about 0.01%, 0.1%, 0.5%, 0.6%, 0.7%, 0.8%, 0.9%, 1%, 1.1%, 1.2%, 1.3%, 1.4%, 1.5%, 2%, 3%, 4%, or 5%) of the pre-treatment tumor cells express PD-L1, e.g., as measured by the OPAL immunohistochemistry assay).

23. A method for treating cancer in a subject, the method comprising administering an immune checkpoint antibody molecule to a subject having cancer, wherein the subject has been previously administered a PS-targeting antibody molecule (e.g., bavituximab), and wherein the subject is identified, or was determined to have a negative pre-treatment PD-L1 status (e.g., wherein said negative pre-treatment PD-L1 status is defined as TC0, wherein less than about 1% (e.g., less than about 0.01%, 0.1%, 0.5%, 0.6%, 0.7%, 0.8%, 0.9%, 1%, 1.1%, 1.2%, 1.3%, 1.4%, 1.5%, 2%, 3%, 4%, or 5%) of the pre-treatment tumor cells express PD-L1, e.g., as measured by the OPAL immunohistochemistry assay).

24. The composition or method of any of the preceding embodiments, wherein the PS-targeting antibody molecule is bavituximab, or an antigen-binding fragment thereof.

25. The composition or method of any of the preceding embodiments, wherein the PS-targeting antibody molecule is an antibody as described in Table A, or an antigen-binding fragment thereof.

26. The composition or method of embodiment 25, wherein the PS-targeting antibody molecule comprises a heavy chain variable region sequence comprising the amino acid sequence of SEQ ID NO: 3.

27. The composition or method of embodiment 25 or 26, wherein the PS-targeting antibody molecule comprises a heavy chain variable region sequence comprising an amino acid sequence encoded by the nucleic acid sequence of SEQ ID NO: 1.

28. The composition or method of any of embodiments 25-27, wherein the PS-targeting antibody molecule comprises a light chain variable region sequence comprising the amino acid sequence of SEQ ID NO: 4 or 32.

29. The composition or method of any of embodiments 25-28, wherein the PS-targeting antibody molecule comprises a light chain variable region sequence comprising an amino acid sequence encoded by the nucleic acid sequence of SEQ ID NO: 2 or 31.

30. The composition or method of any of embodiments 25-29, wherein the PS-targeting antibody molecule comprises one, two, three, four, five, or six CDR sequences selected from SEQ ID NOs: 5-10 and 24-26.

31. The composition or method of embodiment 30, wherein the PS-targeting antibody molecule comprises one or more framework regions comprising an amino acid sequence selected from SEQ ID NOs: 11-18 and 27-30.

32. The composition or method of embodiment 25, wherein the PS-targeting antibody molecule comprises the amino acid sequence of SEQ ID NO: 21 or 34.

33. The composition or method of embodiment 25, wherein the PS-targeting antibody molecule comprises an amino acid sequence encoded by the nucleic acid sequence of SEQ ID NO: 20 or 33.

34. The composition or method of embodiment 25, wherein the PS-targeting antibody molecule comprises a heavy chain comprising the amino acid sequence of SEQ ID NO: 22.

35. The composition or method of embodiment 25 or 34, wherein the PS-targeting antibody molecule comprises a light chain comprising the amino acid sequence of SEQ ID NO: 23.

36. The composition or method of any of the preceding embodiments, wherein the PS-targeting antibody molecule is 1N11 or 1G15, or an antigen-binding fragment thereof.

37. The composition or method of any of the preceding embodiments, wherein the immune checkpoint modulator comprises an inhibitor of an inhibitory immune checkpoint molecule, e.g., PD-1, PD-L1, PD-L2, CTLA-4, TIM-3, LAG-3, BTLA, TIGIT, VISTA, LAIR1, CD160, 2B4 and/or TGF-β.

38. The composition or method of embodiment 37, wherein the immune checkpoint antibody molecule is a blocking antibody and/or an antagonist of the inhibitory immune checkpoint molecule.

39. The composition or method of any of the preceding embodiments, wherein the immune checkpoint antibody molecule comprises a blocking antibody, or an antigen-binding fragment thereof, that binds to PD-1.

40. The composition or method of embodiment 39, wherein said blocking antibody that binds to PD-1 is CBT-501 or cemiplimab.

41. The composition or method of any of the preceding embodiments, wherein the immune checkpoint antibody molecule comprises a blocking antibody, or an antigen-binding fragment thereof, that binds to PD-L1.

42. The composition or method of embodiment 41, wherein said blocking antibody that binds to PD-L1 is durvalumab, avelumab, CX-072, LY3300054, or atezolizumab.

43. The composition or method of embodiment 42, wherein said blocking antibody that binds to PD-L1 is CX-072.

44. The composition or method of any of the preceding embodiments, wherein the immune checkpoint antibody molecule comprises a blocking antibody, or antigen-binding fragment thereof, that binds to CTLA-4.

45. The composition or method of embodiment 44, wherein said blocking antibody that binds to CTLA-4 is ipilimumab or tremelimumab.

46. The composition or method of any of the preceding embodiments, wherein the immune checkpoint modulator comprises an agonist of a stimulatory immune checkpoint molecule, e.g., GITR, OX40, 4-1BB (CD137), CD2, CD27, CDS, ICAM-1, LFA-1 (CD11a/CD18), ICOS (CD278), CD30, CD40, BAFFR, HVEM, CD7, LIGHT, NKG2C, SLAMF7, NKp80, and/or CD160.

47. The composition or method of any of the preceding embodiments, wherein the immune checkpoint antibody molecule comprises an immunotherapeutic agent, e.g., as listed in Table D or E.

48. The composition or method of any of the preceding embodiments, wherein the immune checkpoint antibody molecule comprises an antibody listed in Table F.

49. The composition or method of any of the preceding embodiments, wherein the immune checkpoint antibody molecule is selected from the group consisting of avelumab, ipilimumab, tremelimumab, nivolumab, pembrolizumab, durvalumab, atezolizumab, pidilizumab, XmAb20717, cemiplimab (REGN2810), CBT-501, CX-072, CX-188, and LY3300054.

50. The composition or method of any of the preceding embodiments, wherein at least a first and second immune checkpoint antibody molecule is administered to said subject.

51. The composition or method of any of the preceding claims, wherein the PS-targeting antibody molecule is a monospecific antibody molecule.

52. The composition or method of any of the preceding claims, wherein the PS-targeting antibody molecule is a multispecific antibody molecule, e.g., a bispecific antibody molecule.

53. The composition or method of embodiment 52, wherein the PS-targeting antibody molecule comprises a variable region capable of binding to PS and a variable region capable of binding to an immune checkpoint modulator, e.g., an immune checkpoint inhibitor or an immune checkpoint stimulator.

54. The composition or method of any of the preceding embodiments, wherein the immune checkpoint antibody molecule is a monospecific antibody molecule.
55. The composition or method of any of the preceding embodiments, wherein the immune checkpoint antibody molecule is a multispecific antibody molecule (e.g., a bispecific antibody molecule or trispecific antibody molecule), e.g., wherein the antibody specifically binds two more immune checkpoint modulators (e.g., two or more immune checkpoint inhibitors or two or more immune checkpoint stimulators).
56. The composition or method of any of the preceding embodiments, wherein the PS-targeting antibody molecule (e.g., bavituximab) and the immune checkpoint antibody molecule are administered to said subject intravenously, subcutaneously, intraperitoneally, intramuscularly, intraparenterally, topically, orally, enterally, intradermally, or intrathecally.
57. The composition or method of embodiment 56, wherein the PS-targeting antibody molecule (e.g., bavituximab) and the immune checkpoint antibody molecule are administered to said subject intravenously.
58. The composition or method of any of the preceding embodiments, wherein the PS-targeting antibody molecule (e.g., bavituximab) and the immune checkpoint antibody molecule are administered to said subject sequentially or concurrently.
59. The composition or method of embodiment 58, wherein the PS-targeting antibody molecule (e.g., bavituximab) is administered before the immune checkpoint antibody molecule, e.g., wherein the PS-targeting antibody molecule (e.g., bavituximab) is administered about 1, 2, 4, 5, or 6 weeks, or more, before the immune checkpoint antibody molecule.
60. The composition or method of embodiment 59, wherein the administration of the PS-targeting antibody molecule increases the sensitivity of the subject to the immune checkpoint antibody molecule, e.g., wherein the subject is immunosuppressed.
61. The composition or method of embodiment 58, wherein the PS-targeting antibody molecule (e.g., bavituximab) is administered after the immune checkpoint antibody molecule, e.g., wherein the PS-targeting antibody molecule (e.g., bavituximab) is administered about 1, 2, 4, 5, or 6 weeks, or more, before the immune checkpoint antibody molecule.
62. The composition or method of embodiment 58, wherein the PS-targeting antibody molecule (e.g., bavituximab) is administered concurrently (e.g., at the same visit as) the immune checkpoint antibody molecule.
63. The composition or method of any of the preceding embodiments, wherein the PS-targeting antibody molecule (e.g., bavituximab) is administered weekly or less frequently that weekly, e.g., about every 1, 2, 3, 4, 5, 6, or more weeks.
64. The composition or method of any of the preceding embodiments, wherein the immune checkpoint antibody molecule is administered weekly or less frequently than weekly, e.g., about every 1, 2, 3, 4, 5, 6, or more weeks.
65. The composition or method of any of the preceding embodiments, wherein said subject has ovarian cancer, gastric cancer, hepatocellular carcinoma, colorectal cancer, breast cancer, esophageal cancer (e.g., metastatic gastroesphogeal cancer), malignant glioma, pancreatic cancer, prostate cancer, merkel cell carcinoma, melanoma, head and neck cancer (e.g., recurrent/metastatic squamous cell head and neck cancer (HNSCC)), renal cell carcinoma, bladder cancer, liver cancer, or lung cancer.
66. The composition or method of embodiment 65, wherein said subject has non-small cell lung cancer (NSCLC).
67. The composition or method of embodiment 66, wherein said subject has non-squamous, non-small cell lung cancer.
68. The composition or method of embodiment 66 or 67, wherein the PS-targeting antibody molecule is bavituximab and/or the immune checkpoint antibody molecule is an anti-PD-1 antibody molecule or an anti-PD-L1 antibody molecule.
69. The composition or method of embodiment 68, wherein the immune checkpoint antibody molecule is CBT-501.
70. The composition or method of embodiment 65, wherein said subject has breast cancer.
71. The composition or method of embodiment 65, wherein said subject has liver cancer.
72. The composition or method of embodiment 65, wherein said subject has pancreatic cancer.
73. The composition or method of embodiment 65, wherein said subject has metastatic gastroesphogeal cancer.
74. The composition or method of embodiment 73, wherein the PS-targeting antibody molecule is bavituximab and/or the immune checkpoint antibody molecule is an anti-PD-1 antibody molecule or an anti-PD-L1 antibody molecule.
75. The composition or method of embodiment 74, wherein the immune checkpoint antibody molecule is CBT-501.
76. The composition or method of embodiment 65, wherein said subject has HNSCC.
77. The composition or method of embodiment 76, wherein the PS-targeting antibody molecule is bavituximab and/or the immune checkpoint antibody molecule is an anti-PD-1 antibody molecule or an anti-PD-L1 antibody molecule.
78. The composition or method of embodiment 77, wherein the immune checkpoint antibody molecule is CBT-501.
79. The composition or method of embodiment 65, wherein said subject has hepatocellular carcinoma.
80. The composition or method of embodiment 79, wherein the PS-targeting antibody molecule is bavituximab and/or the immune checkpoint antibody molecule is an anti-PD-1 antibody molecule.
81. The composition or method of embodiment 80, wherein the immune checkpoint antibody molecule is pembrolizumab.
82. The composition or method of any of the preceding embodiments, wherein the subject does not have breast cancer.
83. The composition or method of any of the preceding embodiments, wherein the subject does not have melanoma.
84. The composition or method of any of the preceding embodiments, wherein the subject is immunosuppressed.
85. The composition or method of any of the preceding embodiments, wherein the PS-targeting antibody molecule (e.g., bavituximab) is administered to said subject in an amount of about 3 mg/kg (e.g., about 0.1, 0.5, 0.6, 0.7, 0.8, 0.9, 1, 2, 3, 4, 5, 6, 7, 8, 9, or 10 mg/kg).
86. The composition or method of any of the preceding embodiments, wherein the immune checkpoint antibody molecule is administered to said subject in an amount of about 3 mg/kg (e.g., about 0.1, 0.5, 0.6, 0.7, 0.8, 0.9, 1, 2, 3, 4, 5, 6, 7, 8, 9, or 10 mg/kg).
87. The composition or method of any of the preceding embodiments, wherein the PS-targeting antibody molecule (e.g., bavituximab) is administered at a dose between about 100-500 mg (e.g., about 150-400 mg, 180-360 mg, or 200-300 mg).
88. The composition or method of any of the preceding embodiments, wherein the immune checkpoint antibody molecule is administered at a dose between about 100-500 mg (e.g., about 150-400 mg, 180-360 mg, or 200-300 mg).

89. The composition or method of any of the preceding embodiments, wherein the PS-targeting antibody molecule (e.g., bavituximab) is administered at a flat dose of 100 mg, 110 mg, 120 mg, 130 mg, 140 mg, 150 mg, 160 mg, 170 mg, 180 mg, 190 mg, 200 mg, 210 mg, 220 mg, 230 mg, 240 mg, 250 mg, 260 mg, 270 mg, 280 mg, 290 mg, 300 mg, 310 mg, 320 mg, 330 mg, 340 mg, 350 mg, 360 mg, or more.

90. The composition or method of embodiment 89, wherein the PS-targeting antibody molecule (e.g., bavituximab) is administered at a flat dose of about 180 mg.

91. The composition or method of embodiment 89, wherein the PS-targeting antibody molecule (e.g., bavituximab) is administered at a flat dose of about 190 mg.

92. The composition or method of embodiment 89, wherein the PS-targeting antibody molecule (e.g., bavituximab) is administered at a flat dose of about 200 mg.

93. The composition or method of embodiment 89, wherein the PS-targeting antibody molecule (e.g., bavituximab) is administered at a flat dose of about 210 mg.

94. The composition or method of embodiment 89, wherein the PS-targeting antibody molecule (e.g., bavituximab) is administered at a flat dose of about 220 mg.

95. The composition or method of any of the preceding embodiments, wherein the immune checkpoint antibody molecule is administered at a flat dose of about 100 mg, 110 mg, 120 mg, 130 mg, 140 mg, 150 mg, 160 mg, 170 mg, 180 mg, 190 mg, 200 mg, 210 mg, 220 mg, 230 mg, 240 mg, 250 mg, 260 mg, 270 mg, 280 mg, 290 mg, 300 mg, 310 mg, 320 mg, 330 mg, 340 mg, 350 mg, 360 mg, or more.

96. The composition or method of embodiment 95, wherein the immune checkpoint antibody molecule (e.g., bavituximab) is administered at a flat dose of about 180 mg.

97. The composition or method of embodiment 95, wherein the immune checkpoint antibody molecule (e.g., bavituximab) is administered at a flat dose of about 190 mg.

98. The composition or method of embodiment 95, wherein the immune checkpoint antibody molecule (e.g., bavituximab) is administered at a flat dose of about 200 mg.

99. The composition or method of embodiment 95, wherein the immune checkpoint antibody molecule (e.g., bavituximab) is administered at a flat dose of about 210 mg.

100. The composition or method of embodiment 95, wherein the immune checkpoint antibody molecule (e.g., bavituximab) is administered at a flat dose of about 220 mg.

101. The composition or method of any of the preceding embodiments, wherein the subject is human.

102. The composition or method of any of the preceding embodiments, further comprising administering to the subject an additional therapeutic agent.

103. The composition or method of embodiment 102, wherein the additional therapeutic agent is an anti-cancer agent, e.g., TGFβR1 Kinase Inhibitor IIILY3200882.

104. The composition or method of embodiment 102, wherein the additional therapeutic agent is a chemotherapeutic agent, e.g., a chemotherapeutic agent listed in Table C.

105. The composition or method of embodiment 104, wherein the chemotherapeutic agent is docetaxel, paclitaxel, carboplatin, sorafenib, gemcitabine, lenvantinib, merestinib, or any combination thereof.

106. The composition or method of any of the preceding embodiments, wherein the PS-targeting antibody molecule and/or the immune checkpoint antibody molecule are comprised in the same or different compositions (e.g., pharmaceutical compositions).

107. A PS-targeting antibody molecule (e.g., bavituximab) for use according to the method of any of the preceding embodiments.

108. A pharmaceutical composition comprising a composition of any of the preceding embodiments.

109. A kit comprising a composition of any of the preceding embodiments.

Definitions

As used herein, the term "antibody molecule" refers to a protein, e.g., an immunoglobulin chain or fragment thereof, comprising at least one immunoglobulin variable domain sequence. The term "antibody molecule" includes, for example, a monoclonal antibody (e.g., including a full length antibody which has an immunoglobulin Fc region). In embodiments, an antibody molecule comprises a full length antibody, or a full length immunoglobulin chain. In embodiments, an antibody molecule comprises an antigen binding or functional fragment of a full length antibody, or a full length immunoglobulin chain, e.g., an scFv, Fab, Fab', $F(ab')_2$, Fc, Fd, Fd', Fv, single chain antibody (e.g., scFv), or diabody. In embodiments, an antibody molecule is monospecific, e.g., binds to a single epitope. In embodiments, an antibody molecule is multispecific, e.g., bispecific. In embodiments, an antibody molecule is multivalent (e.g., bivalent). Antibodies and antibody fragments can be from any class of antibodies including, but not limited to, IgG, IgA, IgM, IgD, and IgE, and from any subclass (e.g., IgG1, IgG2, IgG3, and IgG4) of antibodies. An antibody can have a heavy chain constant region chosen from, e.g., IgG1, IgG2, IgG3, or IgG4. The antibody can also have a light chain chosen from, e.g., kappa or lambda.

As used herein, the term "immune checkpoint modulator" refers to a molecule (e.g., a protein) capable of modulating, e.g., inhibiting or stimulating, an immune response. An immune checkpoint modulator may be a protein expressed by a cell, e.g., a cell surface receptor, which has an activity of inhibiting or stimulating an immune response. Examples of inhibitory immune checkpoint molecules (also referred to herein as "immune checkpoint inhibitors") include, without limitation, PD-1, PD-L1, PD-L2, CTLA-4, TIM-3, LAG-3, BTLA, TIGIT, VISTA, LAIR1, CD160, 2B4 and TGF-β. Examples of stimulatory immune checkpoint molecules (also referred to herein as "immune checkpoint stimulators" or "immune checkpoint activators") include, without limitation, GITR, OX40, 4-1BB (CD137), CD2, CD27, CDS, ICAM-1, LFA-1 (CD11a/CD18), ICOS (CD278), CD30, CD40, BAFFR, HVEM, CD7, LIGHT, NKG2C, SLAMF7, NKp80, and/or CD160.

"Immune checkpoint antibody molecule," as used herein, refers to an antibody molecule capable of altering the activity of an immune checkpoint modulator (e.g., an immune checkpoint inhibitor or an immune checkpoint stimulator). An "immune checkpoint antibody" refers to an antibody capable of altering the activity of an immune checkpoint modulator (e.g., an immune checkpoint inhibitor or an immune checkpoint stimulator). Generally, an immune checkpoint antibody molecule is capable of binding to an immune checkpoint modulator, and this binding activity results in alteration of the activity of the immune checkpoint modulator. An immune checkpoint antibody molecule may comprise one or more variable regions that contribute to binding to the immune checkpoint modulator. An immune checkpoint antibody molecule may be capable of stimulating an immune response, e.g., by inhibiting (e.g., antagonizing) the activity of an immune checkpoint inhibitor (e.g., as described herein), and/or by promoting the activity (e.g., agonizing) an immune checkpoint activator. In some embodiments, an immune checkpoint antibody molecule is monospecific for a particular immune checkpoint modulator. In some embodiments, an immune checkpoint antibody molecule is multispecific, e.g., capable of binding to a plurality of immune checkpoint modulators. For example, an immune checkpoint antibody molecule can be bispecific, e.g., capable of simultaneously binding to two different immune checkpoint modulators.

The term "Programmed Death 1" or "PD-1" refers to a member of the immunoglobulin gene superfamily that functions as a coinhibitory receptor having PD-L1 and PD-L2 as known ligands. PD-1 was previously identified using a subtraction cloning based approach to select for proteins involved in apoptotic cell death. PD-1 is a member of the CD28/CTLA-4 family of molecules based on its ability to bind to PD-L1. Like CTLA-4, PD-1 is rapidly induced on the surface of T-cells in response to anti-CD3 (Agata et al. 25 (1996) Int. Immunol. 8:765). In contrast to CTLA-4, however, PD-1 is also induced on the surface of B-cells (in response to anti-IgM). PD-1 is also expressed on a subset of thymocytes and myeloid cells (Agata et al. (1996) supra; Nishimura et al. (1996) Int. Immunol. 8:773). It is contemplated that the term "PD-1" can include isoforms of mammalian, e.g., human PD-1, species homologs of human PD-1, and analogs comprising at least one common epitope with PD-1. The amino acid sequence of PD-1, e.g., human PD-1, is known, e.g., Shinohara T et al. (1994) Genomics 23(3):704-6, Finger L R, et al. Gene (1997) 197(1-2): 177-87.

PD-1 polypeptides are inhibitory receptors capable of transmitting an inhibitory signal to an immune cell to thereby inhibit immune cell effector function, or are capable of promoting costimulation (e.g., by competitive inhibition) of immune cells, e.g., when present in soluble, monomeric form. Preferred PD-1 family members share sequence identity with PD-1 and bind to one or more B7 family members, e.g., B7-1, B7-2, PD-1 ligand, and/or other polypeptides on antigen presenting cells.

The term "PD-1 activity," includes the ability of a PD-1 polypeptide to modulate an inhibitory signal in an activated immune cell, e.g., by engaging a natural PD-1 ligand on an antigen presenting cell. PD-1 transmits an inhibitory signal to an immune cell in a manner similar to CTLA4. Modulation of an inhibitory signal in an immune cell results in modulation of proliferation of, and/or cytokine secretion by, an immune cell. Thus, the term "PD-1 activity" includes the ability of a PD-1 polypeptide to bind its natural ligand(s), the ability to modulate immune cell costimulatory or inhibitory signals, and the ability to modulate the immune response.

The term "PD-1 ligand" refers to binding partners of the PD-1 receptor and includes both PD-L1 (Freeman et al. (2000) J. Exp. Med. 192:1027) and PD-L2 (Latchman et al. (2001) Nat. Immunol. 2:261). At least two types of human PD-1 ligand polypeptides exist. PD-1 ligand proteins comprise a signal sequence, and an IgV domain, an IgC domain, a transmembrane domain, and a short cytoplasmic tail. Both PD-L1 (See Freeman et al. (2000) J. Exp. Med. 192:1027 for sequence data) and PD-L2 (See Latchman et al. (2001) Nat. Immunol. 2:261 for sequence data) are members of the B7 family of polypeptides. Both PD-L1 and PD-L2 are expressed in placenta, spleen, lymph nodes, thymus, and heart. Only PD-L2 is expressed in pancreas, lung and liver, while only PD-L1 is expressed in fetal liver. Both PD-1 ligands are upregulated on activated monocytes and dendritic cells, although PD-L1 expression is broader. For example, PD-L1 is known to be constitutively expressed and upregulated to higher levels on murine hematopoietic cells (e.g., T cells, B cells, macrophages, dendritic cells (DCs), and bone marrow-derived mast cells) and non-hematopoietic cells (e.g., endothelial, epithelial, and muscle cells), whereas PD-L2 is inducibly expressed on DCs, macrophages, and bone marrow-derived mast cells (see, Butte et al. (2007) Immunity 27:111).

PD-1 ligands comprise a family of polypeptides having certain conserved structural and functional features. The term "family" when used to refer to proteins or nucleic acid molecules, is intended to mean two or more proteins or nucleic acid molecules having a common structural domain or motif and having sufficient amino acid or nucleotide sequence homology, as defined herein. Such family members can be naturally or non-naturally occurring and can be from either the same or different species. For example, a family can contain a first protein of human origin, as well as other, distinct proteins of human origin or alternatively, can contain homologues of non-human origin. Members of a family may also have common functional characteristics. PD-1 ligands are members of the B7 family of polypeptides. The term "B7 family" or "B7 polypeptides" as used herein includes costimulatory polypeptides that share sequence homology with B7 polypeptides, e.g., with B7-1 (CD80), B7-2 (CD86), inducible costimulatory ligand (ICOS-L), B7-H3, B7-H4, VISTA, B7-H6, B7h (Swallow et al. (1999) Immunity 11:423), and/or PD-1 ligands (e.g., PD-L1 or PD-L2). For example, human B7-1 and B7-2 share approximately 26% amino acid sequence identity when compared using the BLAST program at NCBI with the default parameters (Blosum62 matrix with gap penalties set at existence 11 and extension 1 (see the NCBI website). The term B7 family also includes variants of these polypeptides which are capable of modulating immune cell function. The B7 family of molecules share a number of conserved regions, including signal domains, IgV domains and the IgC domains. IgV domains and the IgC domains are art-recognized Ig superfamily member domains. These domains correspond to structural units that have distinct folding patterns called Ig folds. Ig folds are comprised of a sandwich of two β sheets, each consisting of anti-parallel β strands of 5-10 amino acids with a conserved disulfide bond between the two sheets in most, but not all, IgC domains of Ig, TCR, and MHC molecules share the same types of sequence patterns and are called the C1-set within the Ig superfamily. Other IgC domains fall within other sets. IgV domains also share sequence patterns and are called V set domains. IgV domains are longer than IgC domains and contain an additional pair of β strands.

"CTLA-4," as used herein, refers to a T cell surface molecule identified by differential screening of a murine cytolytic T cell cDNA library, Brunet et al. (1987) Nature 328:267-270. The role of CTLA-4 as a second receptor for B7 is discussed, for example, in Linsley et al. (1991) J. Exp. Med. 174:561-569. Freeman et al. (1993) Science 262:907-909 discusses CTLA-4 in B7 deficient mice. Ligands for CTLA-4 are described in Lenschow et al. (1993) P.N.A.S. 90:11054-11058. Linsley et al. (1992) Science 257:792-795 describes immunosuppression in vivo by a soluble form of CTLA-4. Lenschow et al. (1992) Science 257:789-792 discusses long term survival of pancreatic islet grafts induced by CTLA-4Ig. Walunas et al. (1994) Immunity 1:405-413 suggest that CTLA-4 can function as a negative regulator of T cell activation. The amino acid and nucleotide sequence of CTLA-4 (e.g., human CTLA-4) are known (e.g., as described in U.S. Pat. Nos. 5,811,097 and 5,434,131, incorporated herein by reference).

Additional terms are defined below and throughout the application.

As used herein, the articles "a" and "an" refer to one or to more than one (e.g., to at least one) of the grammatical object of the article.

The term "or" is used herein to mean, and is used interchangeably with, the term "and/or", unless context clearly indicates otherwise.

"About" and "approximately" shall generally mean an acceptable degree of error for the quantity measured given the nature or precision of the measurements. Exemplary degrees of error are within 20 percent (%), typically, within 10%, and more typically, within 5% of a given value or range of values.

The phrase "in combination with" or "in a combined amount" is not intended to imply that the therapy or the therapeutic agents must be administered at the same time and/or formulated for delivery together, although these methods of delivery are within the scope described herein. The anti-PS antibody molecules can be administered concurrently with, prior to, or subsequent to, one or more other additional therapies or therapeutic agents. The anti-PS antibody molecule and the other agent or therapeutic protocol can be administered in any order. In general, each agent will be administered at a dose and/or on a time schedule determined for that agent. In will further be appreciated that the additional therapeutic agent utilized in this combination may be administered together in a single composition or administered separately in different compositions. In general, it is expected that additional therapeutic agents utilized in combination be utilized at levels that do not exceed the levels at which they are utilized individually. In some embodiments, the levels utilized in combination will be lower than those utilized individually.

The term "functional variant" refers to polypeptides that have a substantially identical amino acid sequence to the naturally-occurring sequence, or are encoded by a substantially identical nucleotide sequence, and are capable of having one or more activities of the naturally-occurring sequence.

The term "isolated," as used herein, refers to material that is removed from its original or native environment (e.g., the natural environment if it is naturally occurring). For example, a naturally-occurring polynucleotide or polypeptide present in a living animal is not isolated, but the same polynucleotide or polypeptide, separated by human intervention from some or all of the co-existing materials in the natural system, is isolated. Such polynucleotides could be part of a vector and/or such polynucleotides or polypeptides could be part of a composition, and still be isolated in that such vector or composition is not part of the environment in which it is found in nature.

A further summary of the present invention can be found by reference to the claims in view of the detailed description provided herein.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1A and FIG. 1B. DNA and amino acid sequences of the variable regions of the 3G4 antibody. DNA and amino acid sequences for the heavy (FIG. 1A; SEQ ID NO:35 and SEQ ID NO:36) and light (FIG. 1B; SEQ ID NO:37 and SEQ ID NO:38) chains of the 3G4 antibody are presented, and the restriction sites in the DNA sequences are shown. The leader sequence is distinguished from the mature protein, which begins as shown by the first arrow in each of FIG. 1A and FIG. 1B. Exemplary means of grafting each variable sequence with a human constant region are set forth, wherein the first part of the respective human constant region sequences (SEQ ID NO:39 and SEQ ID NO:40) is shown by the second arrow in each of FIG. 1A and FIG. 1B.

FIG. 2A and FIG. 2B. Sequences and PS binding of the 1N11 (PGN635) antibody. FIG. 2A, nucleotide and amino acid sequences of the heavy (VH) and light (VL) chain variable region of an scFv form of the 1N11 antibody. ScFv were cloned via Nco/NotI site into pHOG21 (3.7 Kb). The restriction sites used for initial cloning (NcoI, HindIII, MluI and NotI) are italicized and underlined. The linker sequence between VH and VL is in italic. FIG. 2B, the 1N11 antibody binds to PS in a serum-dependent manner. Binding of the scFv form of 1N11 was tested by ELISA against plated PS, and a mix of phosphatidylcholine (PC) and sphingomyelin (SM), (PC/SM). Polystyrene plates were coated with 10 µg/ml PS or the same amount of a mix of PC/SM (each dissolved in hexane). After the hexane had evaporated, 10% human serum (+10% serum) or 1% ovalbumin (+1% OV) in PBS was added and incubated for one hour. 20 µg/ml purified 1N11 scFv was added in either 10% human serum (+10% serum) or 1% ovalbumin (+1% OV) to the first of six wells for each antigen and titrated with 3-fold dilutions. Remaining bound scFv was detected with an HRP-conjugated anti-c-myc tag mouse monoclonal antibody (Invitrogen).

FIG. 7A, in patients having functional β2GPI≥200 μg/mL, those treated with docetaxel and bavituximab (black lines) have prolonged survival as opposed to control patients treated with docetaxel and placebo (grey lines), including those receiving SACT-IO ("with SACT IO", solid lines) and those without SACT-IO ("without SACT IO", broken lines). FIG. 7B shows the same treatment groups, but in which all patients had functional β2GPI<200 μg/mL.

FIG. 8A, in patients treated with docetaxel and bavituximab, those having negative pre-treatment PD-L1 expression of TC0, <1% ("CK+<1%", grey line) have prolonged survival as opposed to patients with positive PD-L1 expression of TC1/2/3, ≥1% ("CK+>=1%"; black line). FIG. 8B, shows the same PD-L1 negative ("CK+<1%", grey line) and positive groups ("CK+>=1%"; black line), but in which the patients were treated with docetaxel and placebo.

DETAILED DESCRIPTION OF EMBODIMENTS OF THE INVENTION

Figure 2B:
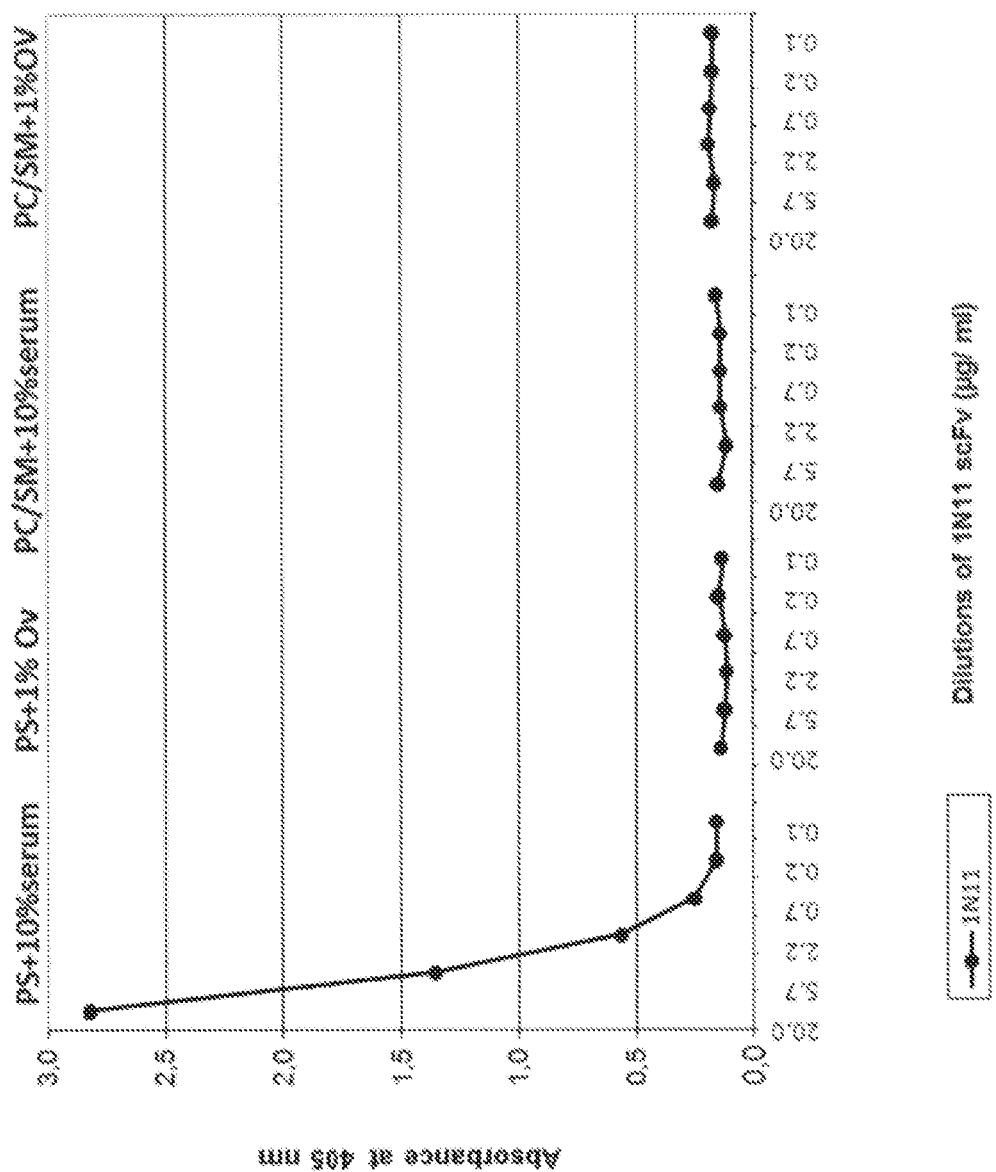

In the present era, there is an increasing emphasis on tailoring treatments to the individual patient, based on factors such as their risk of disease and/or predicted response. This concept can generally be described as "personalized medicine". A greater understanding of different components contributing to the effectiveness of a particular therapy can provide a basis on which to stratify patients, thereby improving treatment outcomes for successive patient populations. The present invention represents an advance along such lines, by providing new biomarkers by which to optimize immunotherapy using PS-targeting antibodies, such as bavituximab, or antigen-binding fragments thereof.

Antibody Molecules

The present invention features antibody molecules capable of binding, for example, to PS or an immune checkpoint modulator. As used herein, the term "antibody molecule" generally refers to a protein, e.g., an immunoglobulin chain or fragment thereof, comprising at least one immunoglobulin variable domain sequence, e.g., an antibody or an antigen-binding fragment thereof. In an embodiment, an antibody molecule comprises a full length antibody, or a full length immunoglobulin chain. In an embodiment, an antibody molecule comprises an antigen binding or functional fragment of a full length antibody, or a full length immunoglobulin chain.

In an embodiment, an antibody molecule is a monospecific antibody molecule and binds a single epitope. E.g., a monospecific antibody molecule having a plurality of immunoglobulin variable domain sequences, each of which binds the same epitope.

In an embodiment an antibody molecule is a multispecific antibody molecule, e.g., it comprises a plurality of immunoglobulin variable domains sequences, wherein a first immunoglobulin variable domain sequence of the plurality has binding specificity for a first epitope and a second immunoglobulin variable domain sequence of the plurality has binding specificity for a second epitope. In an embodiment the first and second epitopes are on the same antigen, e.g., the same protein (or subunit of a multimeric protein). In an embodiment the first and second epitopes overlap. In an embodiment the first and second epitopes do not overlap. In an embodiment the first and second epitopes are on different antigens, e.g., the different proteins (or different subunits of a multimeric protein). In an embodiment a multispecific antibody molecule comprises a third, fourth or fifth immunoglobulin variable domain. In an embodiment, a multispecific antibody molecule is a bispecific antibody molecule, a trispecific antibody molecule, or tetraspecific antibody molecule, In an embodiment a multispecific antibody molecule is a bispecific antibody molecule. A bispecific antibody has specificity for no more than two antigens. A bispecific antibody molecule is characterized by a first immunoglobulin variable domain sequence which has binding specificity for a first epitope and a second immunoglobulin variable domain sequence that has binding specificity for a second epitope. In an embodiment the first and second epitopes are on the same antigen, e.g., the same protein (or subunit of a multimeric protein). In an embodiment the first and second epitopes overlap. In an embodiment the first and second epitopes do not overlap. In an embodiment the first and second epitopes are on different antigens, e.g., the different proteins (or different subunits of a multimeric protein). In an embodiment a bispecific antibody molecule comprises a heavy chain variable domain sequence and a light chain variable domain sequence which have binding specificity for a first epitope and a heavy chain variable domain sequence and a light chain variable domain sequence which have binding specificity for a second epitope. In an embodiment a bispecific antibody molecule comprises a half antibody having binding specificity for a first epitope and a half antibody having binding specificity for a second epitope. In an embodiment a bispecific antibody molecule comprises a half antibody, or fragment thereof, having binding specificity for a first epitope and a half antibody, or fragment thereof, having binding specificity for a second epitope. In an embodiment a bispecific antibody molecule comprises a scFv, or fragment thereof, have binding specificity for a first epitope and a scFv, or fragment thereof, have binding specificity for a second epitope. In an embodiment the first epitope is located on PD-1 and the second epitope is located on a TIM-3, LAG-3, PD-L1, or PD-L2.

In an embodiment, an antibody molecule comprises a diabody, and a single-chain molecule, as well as an antigen-binding fragment of an antibody (e.g., Fab, F(ab')₂, and Fv). For example, an antibody molecule can include a heavy (H) chain variable domain sequence (abbreviated herein as VH), and a light (L) chain variable domain sequence (abbreviated herein as VL). In an embodiment an antibody molecule comprises or consists of a heavy chain and a light chain (referred to herein as a half antibody. In another example, an antibody molecule includes two heavy (H) chain variable domain sequences and two light (L) chain variable domain sequence, thereby forming two antigen binding sites, such as Fab, Fab', F(ab')$_2$, Fc, Fd, Fd', Fv, single chain antibodies (scFv for example), single variable domain antibodies, diabodies (Dab) (bivalent and bispecific), and chimeric (e.g., humanized) antibodies, which may be produced by the modification of whole antibodies or those synthesized de novo using recombinant DNA technologies. These functional antibody fragments retain the ability to selectively bind with their respective antigen or receptor. Antibodies and antibody fragments can be from any class of antibodies including, but not limited to, IgG, IgA, IgM, IgD, and IgE, and from any subclass (e.g., IgG1, IgG2, IgG3, and IgG4) of antibodies. The a preparation of antibody molecules can be monoclonal or polyclonal. An antibody molecule can also be a human, humanized, CDR-grafted, or in vitro generated antibody. The antibody can have a heavy chain constant region chosen from, e.g., IgG1, IgG2, IgG3, or IgG4. The antibody can also have a light chain chosen from, e.g., kappa or lambda. The term "immunoglobulin" (Ig) is used interchangeably with the term "antibody" herein.

Examples of antigen-binding fragments of an antibody molecule include: (i) a Fab fragment, a monovalent fragment consisting of the VL, VH, CL and CHI domains; (ii) a F(ab')$_2$ fragment, a bivalent fragment comprising two Fab fragments linked by a disulfide bridge at the hinge region; (iii) a Fd fragment consisting of the VH and CHI domains; (iv) a Fv fragment consisting of the VL and VH domains of a single arm of an antibody, (v) a diabody (dAb) fragment, which consists of a VH domain; (vi) a camelid or camelized variable domain; (vii) a single chain Fv (scFv), see e.g., Bird et al. (1988) Science 242:423-426; and Huston et al (1988) Proc. Natl Acad Sci. USA 85:5879-5883); (viii) a single domain antibody. These antibody fragments are obtained using conventional techniques known to those with skill in the art, and the fragments are screened for utility in the same manner as are intact antibodies.

The term "antibody" includes intact molecules as well as functional fragments thereof. Constant regions of the antibodies can be altered, e.g., mutated, to modify the properties of the antibody (e.g., to increase or decrease one or more of: Fc receptor binding, antibody glycosylation, the number of cysteine residues, effector cell function, or complement function).

Antibody molecules can also be single domain antibodies. Single domain antibodies can include antibodies whose complementary determining regions are part of a single domain polypeptide. Examples include, but are not limited to, heavy chain antibodies, antibodies naturally devoid of light chains, single domain antibodies derived from conventional 4-chain antibodies, engineered antibodies and single domain scaffolds other than those derived from antibodies. Single domain antibodies may be any of the art, or any future single domain antibodies. Single domain antibodies may be derived from any species including, but not limited to mouse, human, camel, llama, fish, shark, goat, rabbit, and bovine. According to another aspect of the invention, a single domain antibody is a naturally occurring single domain antibody known as heavy chain antibody devoid of light chains. Such single domain antibodies are disclosed in WO 9404678, for example. For clarity reasons, this variable domain derived from a heavy chain antibody naturally devoid of light chain is known herein as a VHH or nanobody to distinguish it from the conventional VH of four chain immunoglobulins. Such a VHH molecule can be derived from antibodies raised in Camelidae species, for example in camel, llama, dromedary, alpaca and guanaco. Other species besides Camelidae may produce heavy chain antibodies naturally devoid of light chain; such VHHs are within the scope of the invention.

The VH and VL regions can be subdivided into regions of hypervariability, termed "complementarity determining regions" (CDR), interspersed with regions that are more conserved, termed "framework regions" (FR or FW).

The extent of the framework region and CDRs has been precisely defined by a number of methods (see, Kabat, E. A., et al. (1991) Sequences of Proteins of Immunological Interest, Fifth Edition, U.S. Department of Health and Human Services, NIH Publication No. 91-3242; Chothia, C. et al. (1987) J. Mol. Biol. 196:901-917; and the AbM definition used by Oxford Molecular's AbM antibody modeling software. See, generally, e.g., Protein Sequence and Structure Analysis of Antibody Variable Domains. In: Antibody Engineering Lab Manual (Ed.: Duebel, S. and Kontermann, R., Springer-Verlag, Heidelberg).

The terms "complementarity determining region," and "CDR," as used herein refer to the sequences of amino acids within antibody variable regions which confer antigen specificity and binding affinity. In general, there are three CDRs in each heavy chain variable region (HCDR1, HCDR2, HCDR3) and three CDRs in each light chain variable region (LCDR1, LCDR2, LCDR3).

The precise amino acid sequence boundaries of a given CDR can be determined using any of a number of well-known schemes, including those described by Kabat et al. (1991), "Sequences of Proteins of Immunological Interest," 5th Ed. Public Health Service, National Institutes of Health, Bethesda, Md. ("Kabat" numbering scheme), Al-Lazikani et al., (1997) JMB 273,927-948 ("Chothia" numbering scheme). As used herein, the CDRs defined according the "Chothia" number scheme are also sometimes referred to as "hypervariable loops."

For example, under Kabat, the CDR amino acid residues in the heavy chain variable domain (VH) are numbered 31-35 (HCDR1), 50-65 (HCDR2), and 95-102 (HCDR3); and the CDR amino acid residues in the light chain variable domain (VL) are numbered 24-34 (LCDR1), 50-56 (LCDR2), and 89-97 (LCDR3). Under Chothia the CDR amino acids in the VH are numbered 26-32 (HCDR1), 52-56 (HCDR2), and 95-102 (HCDR3); and the amino acid residues in VL are numbered 26-32 (LCDR1), 50-52 (LCDR2), and 91-96 (LCDR3). By combining the CDR definitions of both Kabat and Chothia, the CDRs consist of amino acid residues 26-35 (HCDR1), 50-65 (HCDR2), and 95-102 (HCDR3) in human VH and amino acid residues 24-34 (LCDR1), 50-56 (LCDR2), and 89-97 (LCDR3) in human VL.

Generally, unless specifically indicated, the anti-PD-1 antibody molecules can include any combination of one or more Kabat CDRs and/or Chothia hypervariable loops, e.g., described in Table 1. In one embodiment, the following definitions are used for the anti-PD-1 antibody molecules described in Table 1: HCDR1 according to the combined CDR definitions of both Kabat and Chothia, and HCCDRs 2-3 and LCCDRs 1-3 according the CDR definition of Rabat. Under all definitions, each VH and VL typically includes three CDRs and four FRs, arranged from amino-terminus to carboxy-terminus in the following order: FR1, CDR1, FR2, CDR2, FR3, CDR3, FR4.

As used herein, an "immunoglobulin variable domain sequence" refers to an amino acid sequence which can form the structure of an immunoglobulin variable domain. For example, the sequence may include all or part of the amino acid sequence of a naturally-occurring variable domain. For example, the sequence may or may not include one, two, or more N- or C-terminal amino acids, or may include other alterations that are compatible with formation of the protein structure.

The term "antigen-binding site" refers to the part of an antibody molecule that comprises determinants that form an interface that binds to the PD-1 polypeptide, or an epitope thereof. With respect to proteins (or protein mimetics), the antigen-binding site typically includes one or more loops (of at least four amino acids or amino acid mimics) that form an interface that binds to the PD-1 polypeptide. Typically, the antigen-binding site of an antibody molecule includes at least one or two CDRs and/or hypervariable loops, or more typically at least three, four, five or six CDRs and/or hypervariable loops.

The terms "compete" or "cross-compete" are used interchangeably herein to refer to the ability of an antibody molecule to interfere with binding of an anti-PD-1 antibody molecule, e.g., an anti-PD-1 antibody molecule provided herein, to a target, e.g., human PD-1. The interference with binding can be direct or indirect (e.g., through an allosteric modulation of the antibody molecule or the target). The extent to which an antibody molecule is able to interfere with the binding of another antibody molecule to the target, and therefore whether it can be said to compete, can be determined using a competition binding assay, for example, a FACS assay, an ELISA or BIACORE assay. In some embodiments, a competition binding assay is a quantitative competition assay. In some embodiments, a first anti-PD-1 antibody molecule is said to compete for binding to the target with a second anti-PD-1 antibody molecule when the binding of the first antibody molecule to the target is reduced by 10% or more, e.g., 20% or more, 30% or more, 40% or more, 50% or more, 55% or more, 60% or more, 65% or more, 70% or more, 75% or more, 80% or more, 85% or more, 90% or more, 95% or more, 98% or more, 99% or more in a competition binding assay (e.g., a competition assay described herein).

The terms "monoclonal antibody" or "monoclonal antibody composition" as used herein refer to a preparation of antibody molecules of single molecular composition. A monoclonal antibody composition displays a single binding specificity and affinity for a particular epitope. A monoclonal antibody can be made by hybridoma technology or by methods that do not use hybridoma technology (e.g., recombinant methods).

An "effectively human" protein is a protein that does not evoke a neutralizing antibody response, e.g., the human anti-murine antibody (HAMA) response. HAMA can be problematic in a number of circumstances, e.g., if the antibody molecule is administered repeatedly, e.g., in treatment of a chronic or recurrent disease condition. A HAMA response can make repeated antibody administration potentially ineffective because of an increased antibody clearance from the serum (see, e.g., Saleh et al., Cancer Immunol. Immunother., 32:180-190 (1990)) and also because of potential allergic reactions (see, e.g., LoBuglio et al., Hybridoma, 5:5117-5123 (1986)).

The antibody molecule can be a polyclonal or a monoclonal antibody. In other embodiments, the antibody can be recombinantly produced, e.g., produced by phage display or by combinatorial methods.

Phage display and combinatorial methods for generating antibodies are known in the art (as described in, e.g., Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) Bio/Technology 9:1370-1372; Hay et al. (1992) Hum Antibod Hybridomas 3:81-85; Huse et al. (1989) Science 246:1275-1281; Griffths et al. (1993) EMBO J 12:725-734; Hawkins et al. (1992) J Mol Biol 226:889-896; Clackson et al. (1991) Nature 352:624-628; Gram et al. (1992) PNAS 89:3576-3580; Garrad et al. (1991) Bio/Technology 9:1373-1377; Hoogenboom et al. (1991) Nuc Acid Res 19:4133-4137; and Barbas et al. (1991) PNAS 88:7978-7982, the contents of all of which are incorporated by reference herein).

In one embodiment, the antibody is a fully human antibody (e.g., an antibody made in a mouse which has been genetically engineered to produce an antibody from a human immunoglobulin sequence), or a non-human antibody, e.g., a rodent (mouse or rat), goat, primate (e.g., monkey), camel antibody. Preferably, the non-human antibody is a rodent (mouse or rat antibody). Methods of producing rodent antibodies are known in the art.

Human monoclonal antibodies can be generated using transgenic mice carrying the human immunoglobulin genes rather than the mouse system. Splenocytes from these transgenic mice immunized with the antigen of interest are used to produce hybridomas that secrete human mAbs with specific affinities for epitopes from a human protein (see, e.g., Wood et al. International Application WO 91/00906, Kucherlapati et al. PCT publication WO 91/10741; Lonberg et al. International Application WO 92/03918; Kay et al. International Application 92/03917; Lonberg, N. et al. 1994 Nature 368:856-859; Green, L. L. et al. 1994 Nature Genet. 7:13-21; Morrison, S. L. et al. 1994 Proc. Natl. Acad Sci. USA 81:6851-6855; Bruggeman et al. 1993 Year Immunol 7:33-40; Tuaillon et al. 1993 PNAS 90:3720-3724; Bruggeman et al. 1991 Eur J Immunol 21:1323-1326).

An antibody can be one in which the variable region, or a portion thereof, e.g., the CDRs, are generated in a non-human organism, e.g., a rat or mouse. Chimeric, CDR-grafted, and humanized antibodies are within the invention. Antibodies generated in a non-human organism, e.g., a rat or mouse, and then modified, e.g., in the variable framework or constant region, to decrease antigenicity in a human are within the invention.

Chimeric antibodies can be produced by recombinant DNA techniques known in the art (see Robinson et al., International Patent Publication PCT/US86/02269; Akira, et al., European Patent Application 184,187; Taniguchi, M., European Patent Application 171,496; Morrison et al., European Patent Application 173,494; Neuberger et al., International Application WO 86/01533; Cabilly et al. U.S. Pat. No. 4,816,567; Cabilly et al., European Patent Application 125, 023; Better et al. (1988 Science 240:1041-1043); Liu et al. (1987) PNAS 84:3439-3443; Liu et al., 1987, J. Immunol. 139:3521-3526; Sun et al. (1987) PNAS 84:214-218; Nishimura et al., 1987, Canc. Res. 47:999-1005; Wood et al. (1985) Nature 314:446-449; and Shaw et al., 1988, J. Natl Cancer Inst. 80:1553-1559).

A humanized or CDR-grafted antibody will have at least one or two but generally all three recipient CDRs (of heavy and or light immuoglobulin chains) replaced with a donor CDR. The antibody may be replaced with at least a portion of a non-human CDR or only some of the CDRs may be replaced with non-human CDRs. It is only necessary to replace the number of CDRs required for binding of the humanized antibody to PD-1. Preferably, the donor will be a rodent antibody, e.g., a rat or mouse antibody, and the recipient will be a human framework or a human consensus framework. Typically, the immunoglobulin providing the CDRs is called the "donor" and the immunoglobulin providing the framework is called the "acceptor." In one embodiment, the donor immunoglobulin is a non-human (e.g., rodent). The acceptor framework is a naturally-occurring (e.g., a human) framework or a consensus framework, or a sequence about 85% or higher, preferably 90%, 95%, 99% or higher identical thereto.

As used herein, the term "consensus sequence" refers to the sequence formed from the most frequently occurring amino acids (or nucleotides) in a family of related sequences (See e.g., Winnaker, From Genes to Clones (Verlagsgesellschaft, Weinheim, Germany 1987). In a family of proteins, each position in the consensus sequence is occupied by the amino acid occurring most frequently at that position in the family. If two amino acids occur equally frequently, either can be included in the consensus sequence. A "consensus framework" refers to the framework region in the consensus immunoglobulin sequence.

An antibody can be humanized by methods known in the art (see e.g., Morrison, S. L., 1985, *Science* 229:1202-1207, by Oi et al., 1986, *BioTechniques* 4:214, and by Queen et al. U.S. Pat. Nos. 5,585,089, 5,693,761 and 5,693,762, the contents of all of which are hereby incorporated by reference).

Humanized or CDR-grafted antibodies can be produced by CDR-grafting or CDR substitution, wherein one, two, or all CDRs of an immunoglobulin chain can be replaced. See e.g., U.S. Pat. No. 5,225,539; Jones et al. 1986 *Nature* 321:552-525; Verhoeyan et al. 1988 *Science* 239:1534; Beidler el al. 1988 *J. Immunol.* 141:4053-4060; Winter U.S. Pat. No. 5,225,539, the contents of all of which are hereby expressly incorporated by reference. Winter describes a CDR-grafting method which may be used to prepare the humanized antibodies of the present invention (UK Patent Application GB 2188638A, filed on Mar. 26, 1987; Winter U.S. Pat. No. 5,225,539), the contents of which is expressly incorporated by reference.

Also within the scope of the invention are humanized antibodies in which specific amino acids have been substituted, deleted or added. Criteria for selecting amino acids from the donor are described in U.S. Pat. No. 5,585,089, e.g., columns 12-16 of U.S. Pat. No. 5,585,089, e.g., columns 12-16 of U.S. Pat. No. 5,585,089, the contents of which are hereby incorporated by reference. Other techniques for humanizing antibodies are described in Padlan et al. EP 519596 A1, published on Dec. 23, 1992.

The antibody molecule can be a single chain antibody. A single-chain antibody (scFV) may be engineered (see, for example, Colcher, D. et al. (1999) *Ann N Y Acad Sci* 880:263-80; and Reiter, Y. (1996) *Clin Cancer Res* 2:245-52). The single chain antibody can be dimerized or multimerized to generate multivalent antibodies having specificities for different epitopes of the same target protein.

In yet other embodiments, the antibody molecule has a heavy chain constant region chosen from, e.g., the heavy chain constant regions of IgG1, IgG2, IgG3, IgG4, IgM, IgA1, IgA2, IgD, and IgE; particularly, chosen from, e.g., the (e.g., human) heavy chain constant regions of IgG1, IgG2, IgG3, and IgG4. In another embodiment, the antibody molecule has a light chain constant region chosen from, e.g., the (e.g., human) light chain constant regions of kappa or lambda. The constant region can be altered, e.g., mutated, to modify the properties of the antibody (e.g., to increase or decrease one or more of: Fc receptor binding, antibody glycosylation, the number of cysteine residues, effector cell function, and/or complement function). In one embodiment the antibody has: effector function; and can fix complement. In other embodiments the antibody does not; recruit effector cells; or fix complement. In another embodiment, the antibody has reduced or no ability to bind an Fc receptor. For example, it is a isotype or subtype, fragment or other mutant, which does not support binding to an Fc receptor, e.g., it has a mutagenized or deleted Fc receptor binding region.

Methods for altering an antibody constant region are known in the art. Antibodies with altered function, e.g. altered affinity for an effector ligand, such as FcR on a cell, or the C1 component of complement can be produced by replacing at least one amino acid residue in the constant portion of the antibody with a different residue (see e.g., EP 388,151 A1, U.S. Pat. Nos. 5,624,821 and 5,648,260, the contents of all of which are hereby incorporated by reference). Similar type of alterations could be described which if applied to the murine, or other species immunoglobulin would reduce or eliminate these functions.

In certain embodiments, the antibody molecule is a multispecific (e.g., a bispecific or a trispecific) antibody molecule. Protocols for generating bispecific or heterodimeric antibody molecules are known in the art; including but not limited to, for example, the "knob in a hole" approach described in, e.g., U.S. Pat. No. 5,731,168; the electrostatic steering Fc pairing as described in, e.g., WO 09/089004, WO 06/106905 and WO 2010/129304; Strand Exchange Engineered Domains (SEED) heterodimer formation as described in, e.g., WO 07/110205; Fab arm exchange as described in, e.g., WO 08/119353, WO 2011/131746, and WO 2013/060867.

Phosphatidylserine-Targeting Antibodies

A. Phosphatidylserine as a Therapeutic Target

Phosphatidylserine (PS) is a highly immunosuppressive molecule that functions as an upstream immune checkpoint and modulates the host immune response. Accordingly, PS is involved in various diseases, including cancer and viral infections. Immunotherapeutic agents in the form of PS-targeting antibodies therefore provide new treatment options for those diseases, including cancer.

In more detail, in normal cells, PS is segregated to the inner leaflet of the plasma membrane, but becomes externalized to the outer leaflet of the plasma membrane in diseased and aberrant cells in various disease states, particularly in cancer and viral infections. In the context of cancer, some of the environmental stressors that cause PS externalization are hypoxia/reoxygenation, oxidative stress and exposure to certain cytokines. PS externalization also occurs under conditions of cell death and immune phagocytic cell clearance (Birge et al., 2016). Subsequently, PS is recognized and bound by PS receptors (e.g., TIM 3 and TIM 4, and other TIM family members, TAM family (Davra et al., 2016), BAI1, stabilin 2 and RAGE) on immune cells, optionally via one or more of a number of bridging proteins, such that PS induces and maintains immune suppression. In the tumor microenvironment, PS is exposed on the surface of tumor vascular endothelial cells, tumor cells and tumor-derived exosomes, and the process of immune suppression is duplicated, thus preventing antitumor and inflammatory reactions from occurring.

Exposed PS is a phagocytic signal that facilitates the recognition and clearance of dying cells, triggers the release of immunosuppressive cytokines (e.g., TGF-β and IL-10)

and inhibits the production of proinflammatory cytokines (e.g., TNF-α and IL-12). PS also polarizes macrophages towards the immunosuppressive M2 phenotype, inhibits dendritic cell (DC) maturation and the ability of DCs to present antigen, while stimulating DCs to secrete immunosuppressive mediators that promote T cell tolerance. In summary, PS is a central factor in the induction and maintenance of an immunosuppressed tumor microenvironment.

B. PS-Targeting Antibodies

Due to the propensity of PS exposure in the tumor microenvironment to promote tumor progression, PS-targeting antibodies can be used to block the binding of PS to specific receptors on immune cells, and thus provide an effective cancer therapy (Yin et al., 2013). A number of such PS-targeting antibodies have been developed as therapeutics, as exemplified below.

B1. Bavituximab

An early monoclonal antibody generated to evaluate the preclinical potential of PS-targeting antibodies is the antibody termed 3G4, a mouse IgG$_3$ mAb (Example I; Ran et al., 2005; Huang et al., 2005). Samples of the hybridoma cell line secreting the 3G4 antibody were deposited with the American Type Culture Collection (ATCC) and given ATCC Accession number PTA 4545. Availability of the deposited hybridoma is not to be construed as a license to practice the invention in contravention of the rights granted under the authority of any government in accordance with its patent laws.

Bavituximab is a human chimeric version of the 3G4 mouse antibody, in which the murine variable (antigen binding) regions are operatively attached to a human antibody constant region (Example I, C). The bavituximab family of antibodies is described in detail in numerous U.S. Patents, e.g., U.S. Pat. Nos. 7,247,303 and 7,572,448. Bavituximab is less immunogenic when given to patients, because significant portions of the antibody are from human origin.

The 3G4 and bavituximab antibodies bind strongly to anionic phospholipids, particularly PS, but also to phosphatidylinositol (PI), phosphatidic acid (PA), phosphatidylglycerol (PG) and cardiolipin (CL), in the presence of serum (Ran et al., 2005). Of these anionic phospholipids, PS is the most relevant, physiologically and pathologically. 3G4 and bavituximab exhibit no detectable binding to the neutral phospholipids, phosphatidylcholine (PC), sphingomyelin (SM) or phosphatidylethanolamine (PE), irrespective of the presence of serum.

Although it was initially thought that the 3G4 and bavituximab antibodies bound to PS directly, it was later determined that the PS-binding is mediated by a serum protein, which was identified as β2-glycoprotein 1 (β2GPI) (Example I; Luster et al., 2006). Indeed, 3G4 and bavituximab bind strongly to PS in enzyme-linked immunosorbent assays (ELISAs) conducted in the presence of β2GPI, which includes purified β2GPI as well as β2GPI provided simply by being present in the 10% serum typically used in ELISAs.

β2GPI, also known as apolipoprotein H, has five domains, I, II, III, IV and V, and the domain structure is conserved across mammals. β2GPI folds as a tertiary structure into those five discernable domains, and may have a closed, circular structure or an open, J-shape or hook structure. β2GPI binds to anionic phospholipids, particularly PS, through positively-charged regions in its C terminal domain, domain V, so long as domain V is not "nicked", such as by cleavage with the enzyme plasmin, at the Lys317/Thr318 cleavage site, which destroys PS binding (Hunt et al., 1993; Hunt & Krilis, 1994). The 3G4 and bavituximab antibodies bind to domain II of β2GPI. This reinforces the safety of 3G4 and bavituximab as therapeutic antibodies, because certain other antibodies that bind to β2GPI have been associated with pathologies, but those antibodies bind to domain I of β2GPI.

High affinity binding of the 3G4 and bavituximab antibodies to PS requires bivalent interaction of the antibodies with β2GPI (Example I; Luster et al., 2006). In the absence of such antibodies, β2GPI binds to anionic phospholipids, particularly PS, with only low affinity. This has been quantified in studies showing that 3G4 and bavituximab bind to PS in the presence of β2GPI as a high affinity complex, modulating β2GPI binding to PS from 1 µM to 1 nM.

The β2GPI-dependent binding of the 3G4 and bavituximab antibodies to PS is dependent on antibody binding to domain II of β2GPI. As mentioned, because bavituximab binds to domain II of β2GPI, it is not linked with side-effects such as those associated with anti-phospholipid syndrome, in which antibodies are present that bind to domain I of β2GPI (de Laat et al., 2005; de Laat et al., 2006; Ioannou et al., 2007). The high affinity bivalent interaction of the antibody with β2GPI coordinates the resultant high-affinity binding to PS, including when PS is externalized on cell surfaces and membranes.

Although the 3G4 and bavituximab antibodies bind to β2GPI, they are referred to as "PS-targeting antibodies" because they specifically localize and bind to PS exposed in disease states in vivo. As PS is maintained on the inside of healthy, normal cells, and only becomes exposed on the cell surface in disease states, antibody localization in vivo is not only specific to PS, but is specific for diseases in which PS is a marker, particularly cancer, but also viral infections and certain other pathologies.

β2GPI-dependent antibody binding to PS is the same in vitro as in vivo, such that an ELISA is an accurate model for therapy. In particular, in an ELISA in which the plate is coated with PS and the ELISA is conducted in the presence of serum, the 3G4, bavituximab and like antibodies are able to form a stable binding complex with PS. The ELISA assay therefore mimics the in vivo situation during therapy, in which PS is uniquely exposed only on cells in the disease environment, such as cells in the tumor microenvironment or virally-infected cells. As with the ELISA, when the 3G4 and bavituximab antibodies encounter exposed PS, they are able to form a stable binding complex with the β2GPI present in the blood. Whether the PS is on an ELISA well, or a diseased cell, the antibody-β2GPI complex has more than 1,000-times higher affinity for PS than does monomeric β2GPI, i.e., β2GPI without a PS-targeting antibody.

B2. Direct PS-Binding Antibodies, Such as 11.31

In addition to indirect PS-binding antibodies such as bavituximab, the entire family of PS-targeting antibodies includes antibodies that do bind directly to PS, i.e., direct PS-binding antibodies. Such a "direct PS-binding antibody" is an antibody that is not only functionally specific for PS, and targets and binds to PS in vivo (as do the indirect binding antibodies), but that does not require a serum protein, such as β2GPI, to form a tight binding complex with PS, even in in vitro binding assays.

One particular example of such an antibody is the mouse monoclonal antibody termed 9D2 (Ran et al., 2002). The 9D2 antibody has been shown to localize to tumor blood vessels and to exert anti-tumor effects in vivo (Ran et al., 2002). Another example of a direct PS-binding antibody is the fully-human antibody termed 11.31 (PGN632). The 11.31 antibody has also been shown to exert anti-tumor effects in vivo (e.g., in mice bearing MDA-MB-435 mammary carcinoma xenografts) and shows impressive anti-viral effects (Moody et al., 2010; U.S. Pat. No. 7,455,833).

The direct PS-binding antibodies are therefore contemplated for use in treating the various diseases in which PS is a marker, most particularly cancer and viral infections. Biomarkers for optimizing treatment with such direct binding, PS-targeting antibodies will typically not rely on serum proteins, such as β2GPI, but on other factors. Useful biomarkers for the direct binding antibodies include the immune biomarkers for PS-targeting antibodies disclosed herein, and particular aspects thereof, such as low interferon gamma (IFNγ) and "negative" PD-L1 expression, i.e., TC0 (TC0<1%).

B3. Other β2GPI-Dependent PS-Binding Antibodies, Such as 1N11

The preferred embodiments of invention relate to the other part of the PS-binding antibody family, the indirect PS-binding antibodies. An "indirect PS-binding antibody", as used herein, is an antibody that is functionally specific for PS, and targets and binds to PS in vivo, but that requires a serum protein to form a tight binding complex with PS. The present invention is particularly concerned with a sub-set of the indirect PS-binding antibodies, namely the β2GPI-dependent PS-binding antibodies. A "β2GPI-dependent PS-binding antibody", as used herein, is an antibody that is functionally specific for PS, and targets and binds to PS in vivo, but that requires the serum protein, β2GPI to form a tight binding complex with PS. As set forth above, examples of such antibodies include the mouse antibody, 3G4 and the chimeric antibody, bavituximab.

Other currently preferred examples of β2GPI-dependent PS-binding antibodies are the fully-human antibodies termed 1N11 (PGN635) and 1G15, preferably the 1N11 antibody. Several studies using the 1N11 antibody, and a murine chimeric version thereof, have been described, including imaging and therapy (Gong et al., 2013; Freimark et al., 2016; Gray et al., 2016a). The sequences and PS binding properties of the 1N11 antibody are shown in FIG. 2A and FIG. 2B. In addition, further sequence information for the 1N11 and 1G15 antibodies is provided in Table A and in (1N11) SEQ ID NO:22 and (1N11) SEQ ID NO:23, in which each "SEQ ID NO" refers uniquely to 1N11 antibody sequences and has no relation to the 3G4 or bavituximab antibody sequences of FIG. 1A and FIG. 1B (Example I).

TABLE A

Exemplary β2GPI-Dependent Antibody Sequences

| SEQ ID NO | Description | Sequence |
|---|---|---|
| | | 1N11 scFv |
| 1 | VH domain (nt) | CAGGTGCAGCTGCAGGAGTCGGGCCCAGGACTGGTG AAGCCTTCACAGACCCTGTCCCTCACCTGCACTGTC TCTGGTGGCTCCATCAGCAGTGGTGATTACTACTGG AGTTGGATCCGCCAGCCCCCAGGGAAGGGTCTGGAG TGGATTGGGTACATCTATTACAGTGGGAGCACCTAC TACAACCCGTCCCTCAAGAGTCGAGTTACCATATCA GTAGACACGTCCAAGAACCAGTTCTCCCTGAAGCTG AGCTCTGTGACTGCCGCAGACACGGCCGTGTATTAC TGTGCCAGATCTGAGTGGTCCCTAGCTTTTGATATC TGGGGCCAAGGGACAATGGTCACCGTCTCTTCA |
| 2 | VL domain (nt) | CAGCCTGTGCTGACTCAGCCACCCTCAGCGTCTGGG ACCCCCGGGCAGAGGGTCACCATCCCTTGTTCTGGA AGCAGCTCCAACATCGGAGGTAATGATGTATACTGG TACCAGCAAGTCCCAGGAATGGCCCCCAAACTCCTC ATCTATCGGAATCATCAGCGGCCCTCAGGGGTCCCT GACCGATTCTCTGGCTCCAAGTCTGGCACCTCCGCC TCCCTGGCCATCAGTGGGCTCCGGTCCGAGGATGAG GCTGATTATTATTGTGCAGCGTGGGATGACAGCCTG GGTGGGGTGGTGTTCGGCGGAGGGACCAAGGTCACC GTCCTA |

TABLE A-continued

Exemplary β2GPI-Dependent Antibody Sequences

| SEQ ID NO | Description | Sequence |
|---|---|---|
| 3 | VH domain (aa) | QVQLQESGPGLVKPSQTLSLTCTVSGGSISSGDYYW SWIRQPPGKGLEWIGYIYYSGSTYYNPSLKSRVTIS VDTSKNQFSLKLSSVTAADTAVYYCARSEWSLAFDI WGQGTMVTVSS |
| 4 | VL domain (aa) | QPVLTQPPSASGTPGQRVTIPCSGSSSNIGGNDVYW YQQVPGMAPKLLIYRNHQRPSGVPDRFSGSKSGTSA SLAISGLRSEDEADYYCAAWDDSLGGVVFGGGTKVT VL |
| 5 | VH CDR1 | SGDYYWS |
| 6 | VH CDR2 | YIYYSGSTYYNPSLKS |
| 7 | VH CDR3 | SEWSLAFDI |
| 8 | VL CDR1 | SGSSSNIGGNDVY |
| 9 | VL CDR2 | RNHQRPS |
| 10 | VL CDR3 | AAWDDSLGGVV |
| 11 | VH FR1 | QVQLQESGPGLVKPSQTLSLTCTVSGGSIS |
| 12 | VH FR2 | WIRQPPGKGLEWIG |
| 13 | VH FR3 | RVTISVDTSKNQFSLKLSSVTAADTAVYYCAR |
| 14 | VH FR4 | WGQGTMVTVSS |
| 15 | VL FR1 | QPVLTQPPSASGTPGQRVTIPC |
| 16 | VL FR2 | WYQQVPGMAPKLLIY |
| 17 | VL FR3 | GVPDRFSGSKSGTSASLAISGLRSEDEADYYC |
| 18 | VL FR4 | FGGGTKVTVL |
| 19 | Linker | KLSGSASAPKLEEGEFSEARV |
| 20 | Whole scFv clone (nt) | CAGGTGCAGCTGCAGGAGTCGGGCCCAGGACTGGTG AAGCCTTCACAGACCCTGTCCCTCACCTGCACTGTC TCTGGTGGCTCCATCAGCAGTGGTGATTACTACTGG AGTTGGATCCGCCAGCCCCCAGGGAAGGGTCTGGAG TGGATTGGGTACATCTATTACAGTGGGAGCACCTAC TACAACCCGTCCCTCAAGAGTCGAGTTACCATATCA GTAGACACGTCCAAGAACCAGTTCTCCCTGAAGCTG AGCTCTGTGACTGCCGCAGACACGGCCGTGTATTAC TGTGCCAGATCTGAGTGGTCCCTAGCTTTTGATATC TGGGGCCAAGGGACAATGGTCACCGTCTCTTCAAAG CTTTCAGGGAGTGCATCCGCCCCAAAACTTGAAGAA GGTGAATTTTCAGAAGCACGCGTACAGCCTGTGCTG ACTCAGCCACCCTCAGCGTCTGGGACCCCCGGGCAG AGGGTCACCATCCCTTGTTCTGGAAGCAGCTCCAAC ATCGGAGGTAATGATGTATACTGGTACCAGCAAGTC CCAGGAATGGCCCCCAAACTCCTCATCTATCGGAAT CATCAGCGGCCCTCAGGGGTCCCTGACCGATTCTCT GGCTCCAAGTCTGGCACCTCCGCCTCCCTGGCCATC AGTGGGCTCCGGTCCGAGGATGAGGCTGATTATTAT |

TABLE A-continued

Exemplary β2GPI-Dependent Antibody Sequences

| SEQ ID NO | Description | Sequence |
|---|---|---|
| | | TGTGCAGCGTGGGATGACAGCCTGGGTGGGGTGGTG TTCGGCGGAGGGACCAAGGTCACCGTCCTA |
| 21 | Whole scFv clone (aa) | QVQLQESGPGLVKPSQTLSLTCTVSGGSISSGDYYW SWIRQPPGKGLEWIGYIYYSGSTYYNPSLKSRVTIS VDTSKNQFSLKLSSVTAADTAVYYCARSEWSLAFDI WGQGTMVTVSSKLSGSASAPKLEEGEFSEARVQPVL TQPPSASGTPGQRVTIPCSGSSSNIGGNDVYWYQQV PGMAPKLLIYRNHQRPSGVPDRFSGSKSGTSASLAI SGLRSEDEADYYCAAWDDSLGGVVFGGGTKVTVL |

1N11 IgG

| SEQ ID NO | Description | Sequence |
|---|---|---|
| 22 | IgG heavy chain (aa) | See immediately below Table A |
| 23 | IgG light chain (aa) | See immediately below Table A |

1G15 Antibody

| SEQ ID NO | Description | Sequence |
|---|---|---|
| 24 | VL CDR1 | SGSSSNIGSNTVN |
| 25 | VL CDR2 | SNNQRPS |
| 26 | VL CDR3 | AAWDDSLNGPYV |
| 27 | VL FR1 | QPGLTQPPSASGTPGQRVTISC |
| 28 | VL FR2 | WYQQLPGTAPKLLIY |
| 29 | VL FR3 | GVPDRFSGSKSGTSASLAISGLQSEDEADYYC |
| 30 | VL FR4 | FGTGTKLTVL |
| 31 | VL domain (nt) | CAGCCAGGGCTGACTCAGCCACCCTCAGCGTCTGGG ACCCCCGGGCAGAGGGTCACCATCTCTTGTTCTGGA AGCAGCTCCAACATCGGAAGTAATACTGTAAACTGG TACCAGCAGCTCCCAGGAACGGCCCCCAAACTCCTC ATCTATAGTAATAATCAGCGGCCCTCAGGGGTCCCT GACCGATTCTCTGGCTCCAAGTCTGGCACCTCAGCC TCCCTGGCCATCAGTGGGCTCCAGTCTGAGGATGAG GCTGATTATTACTGTGCAGCATGGGATGACAGCCTG AATGCCCTTATGTCTTCGGAACTGGGACCAAGCTC ACCGTCCTA |
| 32 | VL domain (aa) | QPGLTQPPSASGTPGQRVTISCSGSSSNIGSNTVNW YQQLPGTAPKLLIYSNNQRPSGVPDRFSGSKSGTSA SLAISGLQSEDEADYYCAAWDDSLNGPYVFGTGTKL TVL |
| 33 | Whole scFv (nt) | CAGGTGCAGCTGCAGGAGTCGGGCCCAGGACTGGTG AAGCCTTCACAGACCCTGTCCCTCACCTGCACTGTC TCTGGTGGCTCCATCAGCAGTGGTGATTACTACTGG AGTTGGATCCGCCAGCCCCCAGGGAAGGGTCTGGAG TGGATTGGGATACATCTATTACAGTGGGAGCACCTAC TACAACCCGTCCCTCAAGAGTCGAGTTACCATATCA GTAGACACGTCCAAGAACCAGTTCTCCCTGAAGCTG AGCTCTGTGACTGCCGCAGACACGGCCGTGTATTAC TGTGCCAGATCTGAGTGGTCCCTAGCTTTTGATATC TGGGGCCAAGGGACAATGGTCACCGTCTCTTCAAAG CTTTCAGGGAGTGCATCCGCCCCAAAACTTGAAGAA GGTGAATTTTCAGAAGCACGCGTACAGCCAGGGCTG ACTCAGCCACCCTCAGCGTCTGGGACCCCCGGGCAG AGGGTCACCATCTCTTGTTCTGGAAGCAGCTCCAAC ATCGGAAGTAATACTGTAAACTGGTACCAGCAGCTC CCAGGAACGGCCCCCAAACTCCTCATCTATAGTAAT AATCAGCGGCCCTCAGGGGTCCCTGACCGATTCTCT GGCTCCAAGTCTGGCACCTCAGCCTCCCTGGCCATC AGTGGGCTCCAGTCTGAGGATGAGGCTGATTATTAC TGTGCAGCATGGGATGACAGCCTGAATGGCCCTTAT GTCTTCGGAACTGGGACCAAGCTCACCGTCCTA |
| 34 | Whole scFv (aa) | MAQVQLQESGPGLVKPSQTLSLTCTVSGGSISSGDY YWSWIRQPPGKGLEWIGYIYYSGSTYYNPSLKSRVT ISVDTSKNQFSLKLSSVTAADTAVYYCARSEWSLAF DIWGQGTMVTVSSKLSGSASAPKLEEGEFSEARVQP GLTQPPSASGTPGQRVTISCSGSSSNIGSNTVNWYQ QLPGTAPKLLIYSNNQRPSGVPDRFSGSKSGTSASL AISGLQSEDEADYYCAAWDDSLNGPYVFGTGTKLTV LAA |

3G4 Antibody

| SEQ ID NO | Description | Sequence |
|---|---|---|
| 35 | | See FIG. 1A |
| 36 | | See FIG. 1A |
| 37 | | See FIG. 1B |
| 38 | | See FIG. 1B |
| 39 | CH1 (aa) | ASTLGPSVFPLAPSSKSTSG |
| 40 | CL1 (aa) | IFPPSDEQLKSGTAS |

The amino acid sequences of the complete heavy and light chains of the IgG antibody are shown below:

1N11 IgG Heavy chain (amino acid sequence)
QVQLQESGPGLVKPSQTLSLTCTVSGGSISS

GDYYWSWIRQPPGKGLEWIGYIYYSGSTYYNPSLKSRVTISVDTSKNQFS

LKLSSVTAADTAVYYCARSEWSLAFDIWGQGTMVTVSS*ASTKGPSVFPLA*

*PSSKSTSGGTAALGCLVKDYFPEPVTVSWNSGALTSGVHTFPAVLQSSGL*

*YSLSSVVTVPSSSLGTQTYICNVNHKPSNTKVDKKVEPKSCDKTHTCPPC*

*PAPELLGGPSVFLFPPKPKDTLMISRTPEVTCVVVDVSHEDPEVKFNWYV*

*DGVEVHNAKTKPREEQYNSTLTVLHQDWLNGKEYKCKVSNKALP*

*APIEKTISKAKGQPREPQVYTLPPSRDELTKNQVSLTCLVKGFYPSDIAV*

*EWESNGQPENNYKTTPPVLDSDGSFFLYSKLTVDKSRWQQGNVFSCSVMH*

*EALHNHYTQKSLSLSPGK*

Constant regions are in bold/italics.

(1N11)                                                    SEQ ID NO: 22

1N11 IgG Light chain (amino acid sequence)
QPVLTQPPSASGTPGQRVTIPCSGSSSNIG

GNDVYWYQQVPGMAPKLLIYRNHQRPSGVPDRFSGSKSGTSASLAISGLR

SEDEADYYCAAWDDSLGGVVFGGGTKVTVL*GQPKAAPSVTLFPPSSEELQ*

-continued
ANKATLVCLISDFYPGAVTVAWKADSSPVKAGVETTTPSKQSNNKYAASS

YLSLTPEQWKSHRSYSCQVTHEGSTVEKTVAPTECS

Constant regions are in bold/italics.

(1N11)                              SEQ ID NO: 23

C. Therapeutic Uses

As predicted from the PS biology discussed above, signals from PS inhibit the ability of immune cells to recognize and fight tumors. Bavituximab and related antibodies override this PS-mediated immunosuppressive signaling by blocking the engagement of PS with its receptors, as well as by sending an alternate immune activating signal. PS-targeting antibodies have thus been shown to shift the functions of immune cells in tumors, resulting in multiple signs of immune activation and anti-tumor immune responses.

PS-targeting antibodies such as bavituximab achieve this blocking of PS-mediated immunosuppression by multifocal reprograming of the immune cells in the tumor microenvironment to support immune activation (Yin et al., 2013). Bavituximab and related antibodies thus break immune tolerance in the tumor microenvironment. Antibody-mediated PS blockade reduces the levels of myeloid-derived suppressor cells (MDSCs), transforming growth factor-beta (TGFβ) and interleukin-10 (IL-10), and increases the levels of pro-inflammatory cytokines such as interferon gamma (IFNγ), tumor necrosis factor-alpha (TNFα) and interleukin-12 (IL-12). This PS blockade also repolarizes MDSCs and tumor-associated macrophages (TAMs) from predominant M2 to predominant M1 phenotype, promotes the maturation of dendritic cells (DCs), activates cytotoxic T-cells and induces potent adaptive antitumor T-cell immunity (Yin et al., 2013).

Bavituximab and related antibodies also activate innate immunity, i.e., NK cells as well as M1 macrophages. Importantly, these antibodies also cause the selective shutdown of pre-existing tumor blood vessels, which uniquely expose PS (Ran et al., 2005; U.S. Pat. No. 7,572,448), and this activity includes antibody-dependent cell-mediated cytotoxicity (ADCC) mediated by tumor infiltrating M1 macrophages and NK cells. Destroying the tumor blood vessels in this way leads to tumor cell destruction. These dual mechanisms of immunotherapy and vascular targeting, particularly the ADCC actions, mean that bavituximab can be effective against tumors that are resistant to immune activation or conventional anti-proliferative chemotherapy.

As with other immunotherapeutics, the anti-tumor effects of PS-targeting antibodies are increased when used in combination therapies. One group of agents for use with PS-targeting antibodies (e.g., bavituximab and related antibodies) are agents and/or conditions that increase the exposure of PS in the tumor microenvironment, such as radiation and/or chemotherapeutics (U.S. Pat. Nos. 7,422,738; 8,486,391; 7,572,448). Enhanced anti-tumor effects have thus been demonstrated pre-clinically in combination with docetaxel to treat breast tumors (Huang et al., 2005) and prostate cancer (Yin et al., 2013), gemcitabine to treat pancreatic tumors (Beck et al., 2006); irradiation to treat lung cancer (He et al., 2007) and glioblastoma (He et al., 2009); PRIMA-1, which reactivates the mutant tumor suppressor, p53, for advanced breast tumors (Liang et al., 2011); an adenoviral vector to re-target the adenovirus to tumor vasculature (Hogg et al., 2011); cisplatin to treat lung cancer relapse after surgery (Judy et al, 2012); and sorafenib to treat hepatocellular carcinoma (Cheng et al., 2016).

Another group of agents for use with PS-targeting antibodies such as bavituximab are other IO agents. From pre-clinical studies, the mechanism of action of bavituximab is believed to be complementary to the available therapeutic agents, as PS is an upstream immune checkpoint. Preclinically, impressive combination therapies have been shown for the bavituximab family of antibodies in combination with other checkpoint inhibitors in the form of antibodies to CTLA-4, PD-1 and PD-L1 (Freimark et al., 2016; Gray et al., 2016a). Such anti-tumor activity, which included increased survival, was associated with increases in intratumoral activated CD8 T cells, a reduction of M2 macrophages and MDSCs coupled with PD-L1 expression, and increased tumor reactive T cells in the spleen when compared to PD-1 blockade alone. Preclinical results such as these therefore suggest that the bavituximab family of PS-targeting antibodies reverses PS-mediated immunosuppression and initiates therapeutically effective adaptive anti-tumor immunity.

In light of the advantageous safety profile of PS-targeting antibodies such as bavituximab, these antibodies may also be effectively combined in triple combination therapies, including triple combinations with radiation, chemotherapeutics and/or immunotherapeutics, and triple combinations with two immunotherapeutic agents. Impressive pre-clinical results were recently shown for a triple combination using antibodies that target PS, PD-1 and LAG-3 (Gray et al., 2016b). Those techniques are also described in U.S. provisional patent applications, Ser. No. 62/398,695, filed 23 Sep. 2016 and Ser. No. 62/414,834 filed 31 Oct. 2016 (each specifically incorporated herein by reference).

Building on such preclinical data, bavituximab has been evaluated in clinical studies in over 800 patients, mostly in combination with other indication-approved therapeutics, but not in combination therapies with IO agents or checkpoint inhibitors. A range of anti-viral and anti-tumor studies have shown therapeutic activity. Based on extensive pre-clinical work and the pharmacokinetic profile in humans (Example II; see also, Gerber et al., 2011; Digumarti et al., 2014), a dose of 3 mg/kg bavituximab given intravenously (IV) was determined and selected for most clinical studies in oncology, including in patients with lung, breast, liver, pancreatic, colorectal and kidney cancers. Promising clinical anti-tumor results have now been published, including for bavituximab in combination with the chemotherapeutics: paclitaxel in patients with HER2 negative metastatic breast cancer (Chalasani et al., 2015); paclitaxel-carboplatin in advanced non-small cell lung cancer, NSCLC (Digumarti et al., 2014); sorafenib in hepatocellular carcinoma (Cheng et al., 2016); and with docetaxel in previously treated, advanced nonsquamous NSCLC (Gerber et al., 2016).

In summary, results from the Phase I and Phase II clinical studies demonstrated a clinically meaningful treatment effect of bavituximab. Although there is now a significant body of work showing successful treatment of a range of diseases using PS-targeting antibodies, to date, bavituximab has not been approved for such therapies. The clinical experience with PS-targeting antibodies is largely based on the combination of bavituximab with chemotherapeutics. In addition to biomarkers to optimize bavituximab treatment, what is most needed are effective new combination therapies for improved treatment outcomes in humans.

D. Biomarkers for PS-Targeting Antibodies

In the field of cancer therapeutics, biomarkers play an increasingly important role in identifying specific patient characteristics that impact responses to treatment. This has been seen historically with targeted cancer treatments, as well as more recently with checkpoint inhibitors, including PD-1 and PD-L1 inhibitors.

The present invention concerns analyses of several biomarkers of importance to treatment with PS-binding antibodies such as bavituximab. As used herein, a "bavituximab biomarker" is a biomarker for use, either alone or as one of two or more, or multiple biomarkers, in selecting patients or patient populations for improved clinical benefit from treatment with therapies that comprise a PS-binding antibody, preferably bavituximab, as at least part of the therapy. Such bavituximab biomarkers, including β2GPI, may thus be used in methods to predict, in advance of treatment, whether a patient, patient population or sub-population is likely to benefit from a treatment comprising a PS-binding antibody, preferably bavituximab, including a combination therapy that comprises a PS-binding antibody, preferably bavituximab.

Also provided herein is a multi-marker signature for identifying the most appropriate patient populations for improved clinical benefit from bavituximab-containing therapeutic regimens. The first biomarker identified in these analysis is β2GPI (Section E; Section F). Overall, the pattern of biomarkers identified is a bavituximab "signature" to guide clinical development and treatment.

As part of the bavituximab immune biomarkers, low levels of IFNγ, pre-treatment, correlate with better outcomes on bavituximab treatment. "Negative" pre-treatment PD-L1 expression, i.e., TC0 (TC0<1%), also correlates with better outcomes on bavituximab treatment.

These results support the use of a PS-targeting antibody (e.g., bavituximab) to "prime" the immune system, i.e., to amplify anti-tumor immune responses. In this regard, it is now known that tumors can be placed on a scale from "hot" to "cold", depending on how deeply they have been invaded by T cells and other immune cells. The level of immune infiltration ("heat") reflects whether the immune system is recognizing and engaging the tumor. Patients with a tumor that is "hot" have a better prognosis; with a "cold" tumor, the probability of relapsing is much higher. Importantly, it has been determined that bavituximab is able to make a positive impact on the cold tumors, making them more amenable to therapy, including with other checkpoint inhibitors. The bavituximab immune biomarkers therefore have additional uses in not only selecting patients for bavituximab therapy, but in identifying patients for treatment with bavituximab and intelligently selected agents for combination therapies.

D1. Samples

For biomarkers other than β2GPI (Section E), the invention may be used to test any biological sample that contains or is suspected to contain one or more of the biomarkers, including any tissue sample or biopsy from an animal, subject or patient, including fecal matter. Clarified lysates from biological tissue samples may be used. However, the invention is preferably used with natural body fluids, thus providing tests that can be performed on biological samples obtained using minimally- or non-invasive techniques, also termed "liquid biopsies". This is an advantage over more rigorous techniques like biopsies, which typically take longer to provide results and may pose health risks in themselves.

Examples of biological fluids (biofluids) that contain or are suspected to contain one or more biomarkers include blood, urine, ascites, cerebral and cerebrospinal fluid (CSF), sputum, saliva, nasal secretions, bone marrow aspirate, joint or synovial fluid, aqueous humor, amniotic fluid, follicular fluid, cerumen, breast milk (including colostrum), bronchioalveolar lavage fluid, semen, seminal fluid (including prostatic fluid), Cowper's fluid or pre-ejaculatory fluid, female ejaculate, sweat, tears, cyst fluid, pleural and peritoneal fluid or lavage, pericardial fluid, lymph, chyme, chyle, bile, liver perfusate, interstitial fluid, menses, pus, sebum, vomit, vaginal secretions, mucosal secretion, stool water, faecal fluid, pancreatic juice, lavage fluids from sinus cavities, bronchopulmonary aspirates or other lavage fluids. A biological sample may also include the blastocyl cavity, umbilical cord blood or maternal circulation, which may be of fetal or maternal origin.

Preferred examples of biological fluids for testing are blood, urine and ascites fluid, particularly ascites fluid from an animal, subject or patient having or suspected of having ovarian cancer. Where a urine sample is used, it will preferably be used in connection with cancers of the urinary, genitourinary and reproductive systems, such as, e.g., ovarian, prostate, renal, bladder, testicular, urethral and penile cancer. As with β2GPI, detecting and quantifying one or more of the other biomarkers is preferably performed from peripheral blood samples, preferably plasma, and most preferably serum.

D2. PS-Positive Exosomes

Exosomes have recently gained attention in connection with cancer. Exosomes are 40-50 to 100 nanometer (nm) size membrane-derived vesicles that are constitutively released by all cells in vivo and in vitro. Exosomes are biologically active molecular shuttles that play important roles in intercellular communication and influence many physiological and pathological processes. In cancer, exosome functions include the transfer of oncogenes between cancer cells and the tumor stroma that primes the so-called "metastatic niche" for metastatic spread (An et al., 2015).

Due to the multiple intracellular fusion events involved in exosome formation, the luminal contents and proteomic profile of the extracellularly released exosomes mirror those of the originating cell. Thus, tumor-derived exosomes ("tumor exosomes") have profiles that reflect the cancer cell from which they arose. Indeed, the presence of cytosolic (particularly nucleic acids) and plasma membrane components from the originating cell means that circulating exosomes are readily accessible surrogates that reflect the properties of the parent cell for biomarker analysis.

Tumor exosomes, as opposed to exosomes from normal cells, are characterized by having PS on their surface. PS-positive tumor exosomes can thus be used in the diagnosis of cancer. New and improved methods, compositions and kits for diagnosing cancer by detecting and quantifying PS-positive tumor exosomes in biological fluid samples using solid phase assays were recently reported. Such techniques are described in U.S. patent application Ser. No. 15/177,747 and PCT patent application No. PCT/US16/036629, each filed Jun. 9, 2016 (each specifically incorporated herein by reference).

As PS is highly immunosuppressive, the release of PS-positive tumor exosomes is another means by which tumors foster an immunosuppressive environment. Accordingly, the levels of pre-treatment PS-positive tumor exosomes have been proposed for use as a predictive marker for response to therapy for any cancer treatment. Evidently, PS-targeting antibodies need to bind to PS in the disease microenvironment. Therefore, measuring the level of pre-treatment PS-positive tumor exosomes is particularly compelling for use as a predictive biomarker for response to therapy using PS-targeting antibodies such as bavituximab.

Methods such as those in U.S. Ser. No. 15/177,747 and PCT Application No. PCT/US16/036629 can thus be used as part of the biomarker tests of the invention. Their combined use with the present quantification of β2GPI, and/or the other biomarkers disclosed herein, may be preferred in certain embodiments, e.g., to enhance the sensitivity of the predictive analyses overall.

D3. Low Pre-Treatment IFNγ

One suitable immune biomarker for a PS-targeting antibody (e.g., bavituximab) is low pre-treatment IFNγ, preferably low pre-treatment serum IFNγ, which correlates with better survival outcomes on bavituximab treatment (Example XVIII). Preferably, pre-treatment serum IFNγ is measured by the Simoa® immunoassay. As used herein, "low pre-treatment serum IFNγ" is defined as a level of pre-treatment serum IFNγ less than the median pre-treatment serum IFNγ level in a controlled study, preferably in a clinical trial, and most preferably less than the median pre-treatment serum IFNγ level in the treatment arm of a clinical trial. One example of a low pre-treatment serum IFNγ level is 0.093 μg/mL, preferably as measured by the Simoa® immunoassay.

The correlation of low pre-treatment IFNγ, preferably low pre-treatment serum IFNγ, with increased overall survival on bavituximab treatment is surprising, and contrasts with the current art for other immunotherapies. For example, increased survival for cancer patients treated with checkpoint inhibitors, such as antibodies to PD-1 and PD-L1, typically correlates with higher levels of pre-treatment IFNγ. For example, in the Fehrenbacher et al., 2016 study for treating NSCLC with the anti-PD-L1 antibody, atezolizumab, on which the present biomarker analyses were partly based, increased overall survival was associated with increasing IFNγ levels, i.e., the opposite trend to the present findings for bavituximab. The identification of low pre-treatment IFNγ as an immune biomarker for bavituximab thus supports the use of bavituximab to treat patients with "immune cold" tumors, who are most in need of new treatments.

D4. Negative Pre-Treatment PD-L1 Expression Another suitable immune biomarker for a PS-targeting antibody (e.g., bavituximab) is very low pre-treatment PD-L1 expression, classified as "negative" PD-L1 expression, which correlates with better survival outcomes on bavituximab treatment (Example XV). In certain preferred embodiments, PD-L1 expression is measured as part of an OPAL® immunohistochemistry (IHC) assay (PerkinElmer, Waltham, Mass., USA) using the rabbit, anti-human PD-L1 antibody termed E1L3N® (Cell Signaling Technology, Catalogue #13684; Mahoney et al., 2015). Other preferred and further suitable assays are known those of skill in the art and are exemplified below.

As used herein, "negative" PD-L1 expression is preferably defined as "TC0", which itself is defined as "TC0<1%", as measured according to the methods and classifications taught by Fehrenbacher et al., 2016. As known in the art, "TC" in the context of PD-L1 expression refers to tumor cells, and negative PD-L1 expression is preferably measured on pre-treatment tumor cells. However, negative PD-L1 expression may also be measured on pre-treatment immune-cells (Fehrenbacher et al., 2016), and this form of negative PD-L1 also correlated with survival on bavituximab treatment.

Certain suitable assays and antibodies for measuring pre-treatment PD-L1 expression are those used in connection with nivolumab, particularly a validated automated IHC assay (Dako, North America), as described in Brahmer et al., 2015, using the rabbit, anti-human PD-L1 antibody termed 28-8 (Abcam, Catalogue #ab205921), which has been approved by the FDA as a complementary diagnostic test. Other suitable assays and antibodies are those used in connection with pembrolizumab, particularly an IHC assay as described in Garon et al., 2015, using the mouse anti-human PD-L1 antibody clone termed 22C3 (Merck), which has been approved by the FDA as a companion diagnostic test. Further suitable assays and antibodies are those used in connection with durvalumab, particularly a validated assay in the form of a Ventana OptiView® DAB IHC detection kit using the automated Ventana BenchMark Ultra platform (Ventana Medical Systems, Tucson, Ariz.), as described in Rebelatto et al., 2016, which uses the Ventana anti-PD-L1 antibody termed SP263. The 73-10 anti-PD-L1 antibody (Dako), as used in connection with avelumab, may also be used; as may anti-PD-L1 antibodies termed 5H1, 7G11, 015, 9A11, CD274, MAB1561 and SAB2900365.

In addition to using the E1L3N® antibody in IHC (Example XV), other preferred assays and antibodies for measuring pre-treatment PD-L1 expression are those used in connection with atezolizumab, particularly a validated assay in the form of a Ventana OptiView® DAB IHC assay using the automated Ventana BenchMark Ultra platform, as described in Fehrenbacher et al., 2016, which uses the Ventana anti-PD-L1 antibody termed SP142 (e.g., patent application US 2016-0009805). In genetically engineered cell lines, PD-L1 expression levels using the E1L3N antibody are highly concordant with those using the SP142 antibody using chromogenic IHC and quantitative immunofluorescence (Gaule et al., 2017). This emphasizes the technical link between the present studies in Example XV and those of Fehrenbacher et al., 2016 (and the surprising differences in the predictive results).

In the "SP142" PD-L1 assay, the sample should preferably have at least about 50 tumor cells with associated stroma; PD-L1 is expressed as membranous and granular cytoplasmic staining in these cells. The SP142 assay is performed using a stepwise approach; tumor cells are scored by determining the percentage of area covered by PD-L1 positive viable tumor cells and associated intratumoral and contiguous peri-tumoral stroma. If desired, immune cells may be scored by determining the proportion of the tumor area that is occupied by PD-L1 positive immune cells of any intensity. This assay has been approved by the FDA as a complementary diagnostic tool to select patients with advanced urothelial carcinoma and advanced NSCLC for atezolizumab therapy.

The correlation of negative PD-L1 expression with improved survival on bavituximab treatment is also surprising, and again contrasts with the state of the art for other immunotherapies. In particular, increased survival for cancer patients treated with checkpoint inhibitors, such as antibodies to PD-1 and PD-L1, typically correlates with higher levels of pre-treatment PD-L1. Notably, in the Fehrenbacher et al., 2016 study for treating NSCLC with the anti-PD-L1 antibody, atezolizumab, on which the present biomarker analyses were based, increased overall survival was associated with increasing PD-L1 expression on tumor cells (and tumor-infiltrating immune cells), which is the opposite of the present findings for bavituximab. The identification of negative PD-L1 as an immune biomarker for bavituximab also supports the use of bavituximab to treat patients with "immune cold" tumors, which patients currently receive the least, if any, benefit from checkpoint inhibitors and are thus in most need of new treatments.

E. β2GPI as a Biomarker

Despite extensive data indicating otherwise (e.g., Example I, E), the present inventors decided to investigate whether pre-treatment levels of β2GPI could be used as a biomarker, or as part of a panel of biomarkers, to predict treatment outcomes for therapies using a PS-targeting antibody (e.g., bavituximab and related antibodies). In addition to the present disclosure, such techniques are described in provisional application Ser. No. 62/400,589, filed Sep. 27, 2016; Ser. No. 62/406,727, filed Oct. 11, 2016, and Ser. No. 62/407,983, filed Oct. 13, 2016 (each specifically incorporated herein by reference).

β2GPI is an abundant plasma (serum) glycoprotein found both free and associated with lipoprotein. The DNA and amino acid sequences of β2GPI from various mammalian species are known, including mouse, rat, dog, cow, chimp and human (Steinkasserer et al., 1991). For exemplary reference, the human β2GPI amino acid sequence is provided as Accession number 1C1ZA. β2GPI is glycosylated and is routinely reported as a 50 kDa protein (Example I; see also, McNeil et al., 1990 at FIG. 4; Balasubramanian et al., 1998 at FIG. 1; Luster et al., 2006 at FIG. 1D). Although β2GPI has been studied for decades, a precise physiological role for β2GPI remains unknown (Prakasam & Thiagarajan, 2012). Indeed, the apparently healthy life of knockout mice deficient in β2GPI indicates that its role is not critical (Sheng et al., 2011).

Surprisingly, it was determined that pre-treatment blood concentrations of β2GPI, particularly functional β2GPI, are effective as a biomarker to predict successful responses to therapies using PS-targeting antibodies such as bavituximab. Indeed, levels of "functional" β2GPI, meaning β2GPI that binds to both PS and to PS-targeting antibodies such as bavituximab, are useful alone as a biomarker for response to bavituximab.

In embodiments of the invention in which pre-treatment β2GPI levels are used alone as a biomarker for response to PS-targeting antibodies such as bavituximab, those β2GPI levels are both numerically defined and measured in assays that are capable of detecting "functional" β2GPI, as defined herein. However, in embodiments of the invention in which pre-treatment β2GPI levels are used as one of two or more, or a plurality, of biomarkers for response to PS-targeting antibodies such as bavituximab, the β2GPI levels need not be so tightly numerically defined, nor solely measured in assays for functional β2GPI.

Accordingly, the β2GPI levels as part of a dual or multi-marker signature for bavituximab-containing therapies can be "β2GPI high" vs. "β2GPI low", akin to descriptions such as VeriStrat® Good (VS Good) and VS Poor, and tumors that are "hot" or "cold". In this context, the levels of β2GPI that are "β2GPI high" are pre-treatment levels of β2GPI, either total β2GPI, or preferably functional β2GPI, of equal to or greater than about 180, 190, 200, 210, 220, 230, 240, 250 or 260 μg/mL, preferably of equal to or greater than about 200 μg/mL. "β2GPI high" thus includes pre-treatment levels of β2GPI, either total β2GPI, or preferably functional β2GPI, of equal to about 180, 190, 200, 210, 220, 230, 240, 250, 260, 270, 280, 290, 300, 310 or 320 μg/mL.

Figure 3:
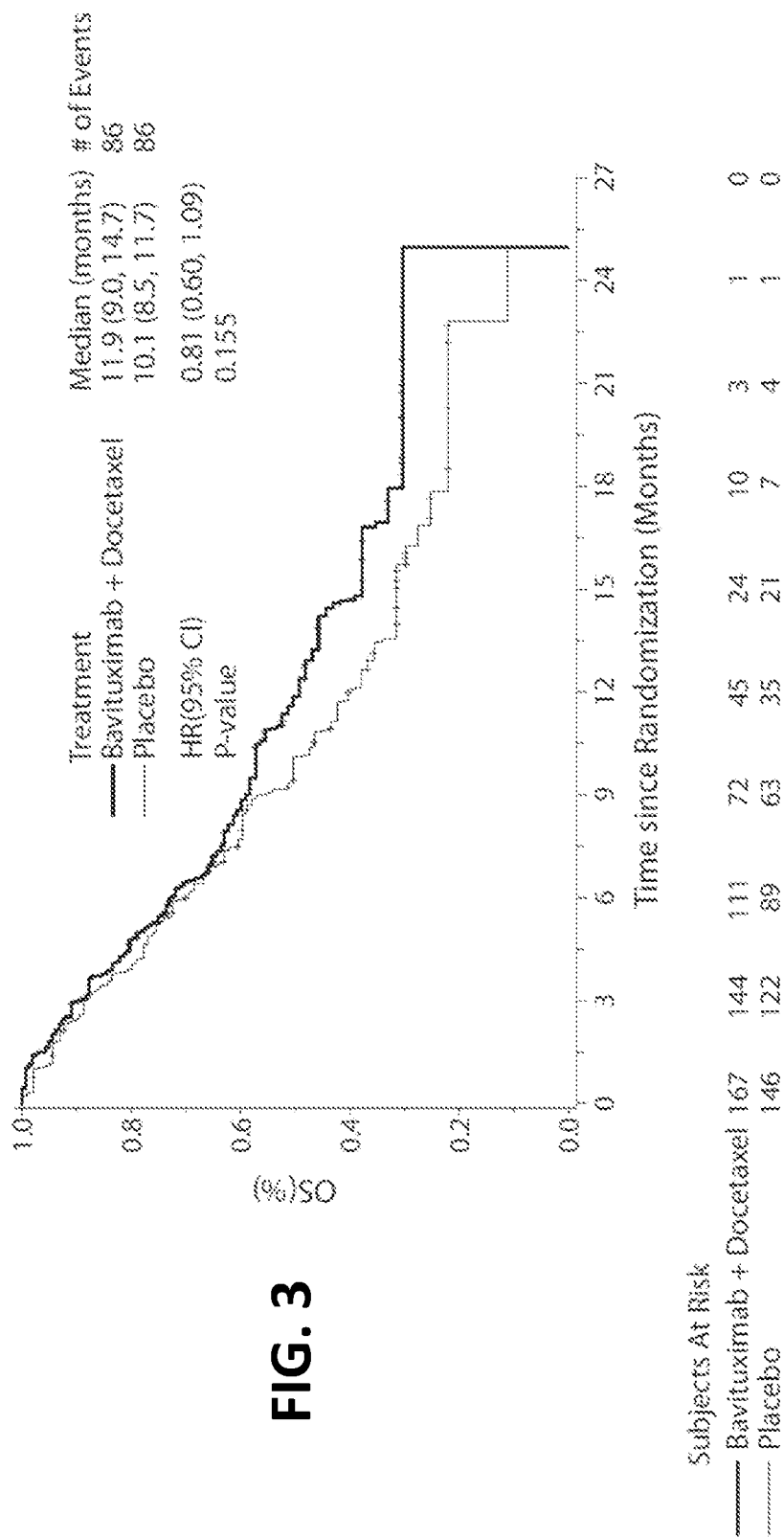
FIG. 3. Kaplan-Meier survival curve from the Phase III trial showing that NSCLC patients having functional β2GPI levels of equal to or greater than 200 µg/mL have a trend for prolonged survival (mOS) when treated with bavituximab and docetaxel (black, top line) as opposed to patients having the same β2GPI levels (200 µg/ml or above) treated with placebo and docetaxel ("Placebo"; grey, bottom line).

The invention also provides biomarkers in terms of certain numerically defined amounts and ranges of functional β2GPI, measured in assays that are capable of detecting functional β2GPI. In certain embodiments, the invention concerns the selection and treatment of patients based on pre-treatment levels of functional β2GPI of equal to or greater than 200 μg/mL (Example XIII; FIG. 3; Example XIV; Example XVII), i.e., about 200 μg/mL. This includes pre-treatment levels of functional β2GPI of equal to about 200, 210, 220, 230, 240, 250, 260, 270, 280, 290, 300, 310 or 320 μg/mL.

Figure 4:
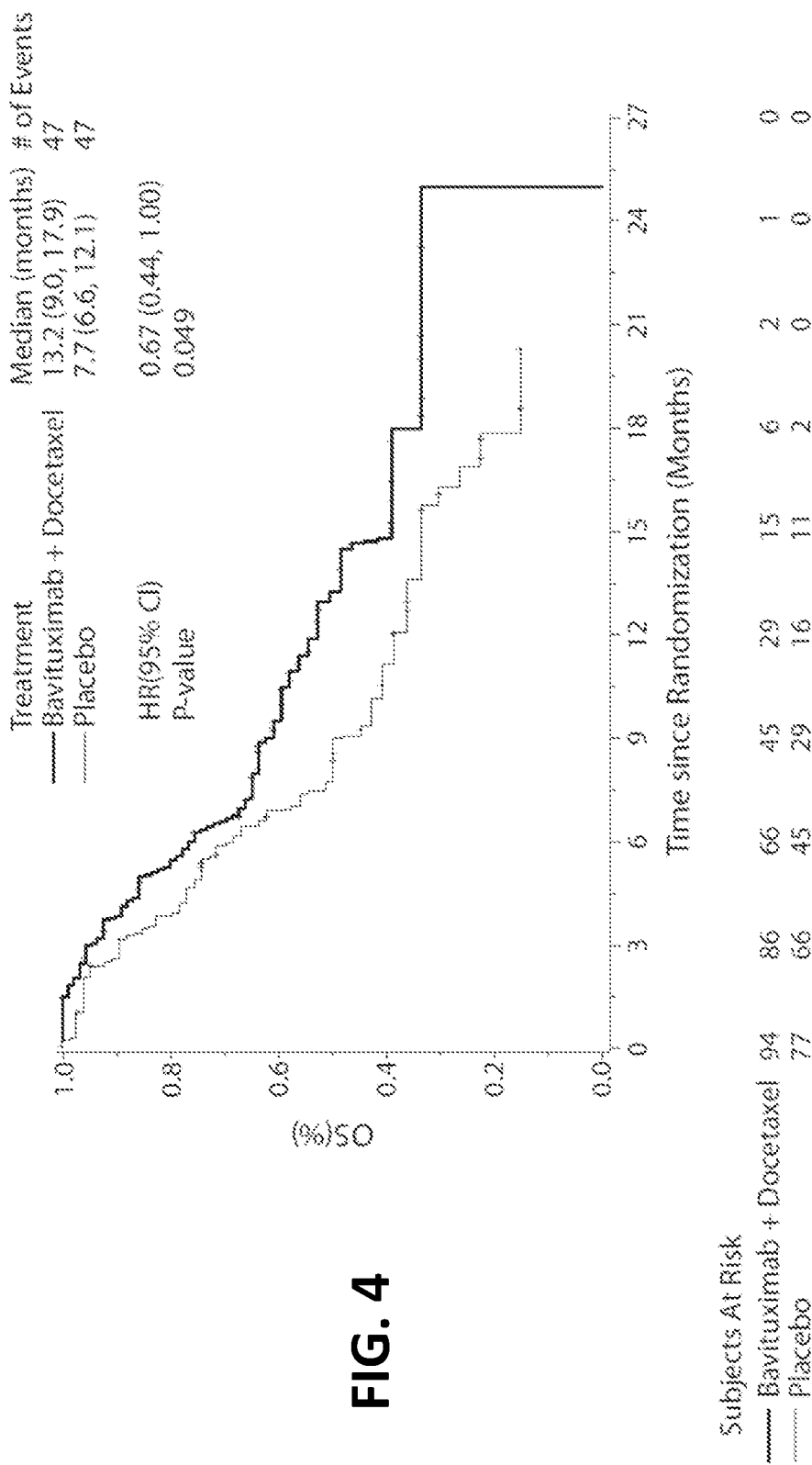
FIG. 4. Kaplan-Meier survival curve from the Phase III trial showing that NSCLC patients having functional β2GPI levels in the range of between 200 µg/ml and 240 µg/ml have a statistically significant better mOS when treated with bavituximab and docetaxel (black, top line) as opposed to patients having the same β2GPI levels (200-240 µg/ml) treated with placebo and docetaxel ("Placebo"; grey, bottom line).

Currently, certain preferred embodiments of the invention concerns the selection and treatment of patients based on pre-treatment levels of functional β2GPI in the range of 200-240 μg/mL (Example XIII; FIG. 4), i.e., about 200-240 μg/mL, particularly for treating NSCLC. This also includes pre-treatment levels of functional β2GPI in the ranges of 200-210, 200-220, 200-230, 210-220, 210-230, 210-240, 220-230, 220-240 and 230-240 μg/mL.

In further embodiments, the invention concerns the selection and treatment of patients based on pre-treatment levels of functional β2GPI in the ranges of from any one of about 180, 190, 200, 210 or 220 μg/mL as the low number, to any one of about 230, 240, 250, 260, 270, 280, 290, 300, 310 or 320 μg/mL as the high number. These ranges include all the following, from within which, the range of about 200-280 μg/mL is preferred:

about 180-230, 180-240, 180-250, 180-260, 180-270, 180-280, 180-290, 180-300, 180-310 and 180-320;
about 190-230, 190-240, 190-250, 190-260, 190-270, 190-280, 190-290, 190-300, 190-310 and 190-320;
about 200-230, 200-240, 200-250, 200-260, 200-270, 200-280, 200-290, 200-300, 200-310 and 200-320;
about 210-230, 210-240, 210-250, 210-260, 210-270, 210-280, 210-290, 210-300, 210-310 and 210-320; and
about 220-230, 220-240, 220-250, 220-260, 220-270, 220-280, 220-290, 220-320, 220-310 and 220-320.

Whichever one or more of the above numbers or ranges are chosen, the use of pre-treatment levels of β2GPI, preferably functional β2GPI, as a biomarker, or as part of a panel of biomarkers, applies to the selection of patients with a wide range of diseases in which PS is a marker, most particularly cancer and viral infections, but also infections of intracellular parasites, and their treatment using any PS-targeting antibody, such as bavituximab, either alone, or preferably in any combination therapy.

F. Assays for β2GPI

As pre-treatment levels of β2GPI are a biomarker for a PS-targeting antibody (e.g., bavituximab and related antibodies), the following guidance is provided concerning assays for β2GPI. The present invention also provides certain preferred assays for quantifying functional β2GPI (Section G).

F1. β2GPI Samples

As a serum protein, β2GPI is ideal for detection in peripheral blood (plasma, serum) samples, as described below. However, studies have suggested that under various pathophysiologic conditions in which PS is involved, β2GPI localizes to endothelial cells in vivo (Agostinis et al., 2011). Therefore, the full range of biological samples (Section D1) can potentially be used for β2GPI detection.

Nonetheless, peripheral blood, plasma and serum samples are particularly preferred for detecting and quantifying β2GPI, whether total β2GPI or functional β2GPI (Section G). Whole blood may be used (red blood cells, white blood cells, platelets, proteins and plasma). Preferably, plasma is used, which is the liquid remaining after the precipitation of red cells and white cells. Plasma contains fibrinogen and other clotting factors, so tends to clot on standing. Less clot-prone plasma is available, which is preferred; platelet-free plasma may also be used. Most preferably, serum is used for detecting and quantifying β2GPI. Serum is plasma without the clotting factors, mainly without fibrinogen, so serum does not clot on standing. Animal and human sera are routinely used for diagnostic purposes, and preparative techniques are widely known. Exemplary methods for preparing serum samples for β2GPI testing are shown herein (Example XI, A).

It is an advantage of the invention that the tests may be carried out directly on the biological sample, preferably blood, plasma or serum. Due to the sensitivity, β2GPI can readily be detected without any prior enrichment or concentration (although this is not excluded). The test samples, preferably serum samples, may be fresh or previously frozen and then thawed. Example XI, Example XII, Example XIII and Example XIV show that β2GPI is stable to long-term storage at −70° C. Industry-standard techniques of freezing, storage and/or thawing should preferably be used, such as using cryogenic tubes or vials and/or protease inhibitors to limit proteolysis overall.

F2. Range of β2GPI Assays

The breadth of assays for measuring β2GPI without reference to whether it is "functional" β2GPI, i.e., assays for "total" β2GPI, are applicable for use with those embodiments of the invention in which the pre-treatment β2GPI levels are used as only one of two or more biomarkers for bavituximab. Where levels of β2GPI are used alone as a biomarker for bavituximab, a "functional" β2GPI assay should be used, such as described in Section G.

Total β2GPI levels may be detected and preferably quantified using any one or more of the many in vitro binding assays and kits known in the art. Suitable binding assays include, for example, immunoblots, Western blots, dot blots, RIAs, immunohistochemistry, fluorescent activated cell sorting (FACS), immunoprecipitation, affinity chromatography, and the like. Although solid phase binding assays are typically preferred, various other methods for detecting β2GPI have been described in the literature, any of which may be used. For example, β2GPI levels may be accurately determined by radial immunodiffusion. Indeed, radial immunodiffusion has been used to quantify β2GPI from the late 1960s to more contemporary times (e.g., Balasubramanian et al., 1998). Isoelectric focusing (IEF) followed by immunoblotting may also be used to quantify β2GPI (Kamboh et al., 1988), as may Western blotting, immunoelectrophoresis and Ouchterlony double immunodiffusion (Takeuchi et al., 2000).

F3. Solid Phase β2GPI Binding Assays

Numerous sensitive, solid phase binding assays for β2GPI are known in the art and total β2GPI will preferably be detected and quantified using one or more of such assays. A preferred example of such an assay is as an enzyme linked immunosorbent assay (ELISA). Various ELISAs specific for total β2GPI have been reported in the literature, including modified capture ELISAs (e.g., Mehdi et al., 1999) and competitive ELISAs (e.g., Balasubramanian et al., 1998). Numerous commercial kits for assaying total β2GPI are available, as are commercially available anti-β2GPI antibodies, including those attached to diagnostic labels. Any such kits or antibodies may be used to detect and quantify total β2GPI. For example, anti-β2GPI antibodies from US Biological are used herein in comparative assays (Example XII, A10, B2).

In general terms, ELISAs for total β2GPI use one or more anti-β2GPI antibodies. Even though antibody technology is very advanced, the commercial kits and commercial anti-β2GPI antibodies often use polyclonal anti-β2GPI antibodies, which are completely suitable for use in such embodiments. In an exemplary assay for total β2GPI, anti*β2GPI antibodies are adsorbed to a solid surface, such as a 96 well plastic plate, and incubated with the biological sample suspected of containing β2GPI (in this case, the "antigen"). Bound β2GPI (antigen) is detected using a secondary binding agent that is directly or indirectly labeled with a detectable agent, i.e., an agent that produces a detectable signal, such as color or fluorescence, which can be detected and quantified. Preferably, the secondary binding agent is an anti-β2GPI antibody that is labeled with a detectable agent.

Such ELISAs for total β2GPI are exemplified in Example XII, A10, B2 and many general components and steps, such as solid supports and detectable agents, are also described more fully below in terms of the functional β2GPI assay of the present invention (Section G). Therefore, unless evident that particular reagents or steps apply only to use in the functional β2GPI assay, their application in assays for detecting total β2GPI is contemplated herein.

G. Preferred ELISA for Functional β2GPI

Figure 5:
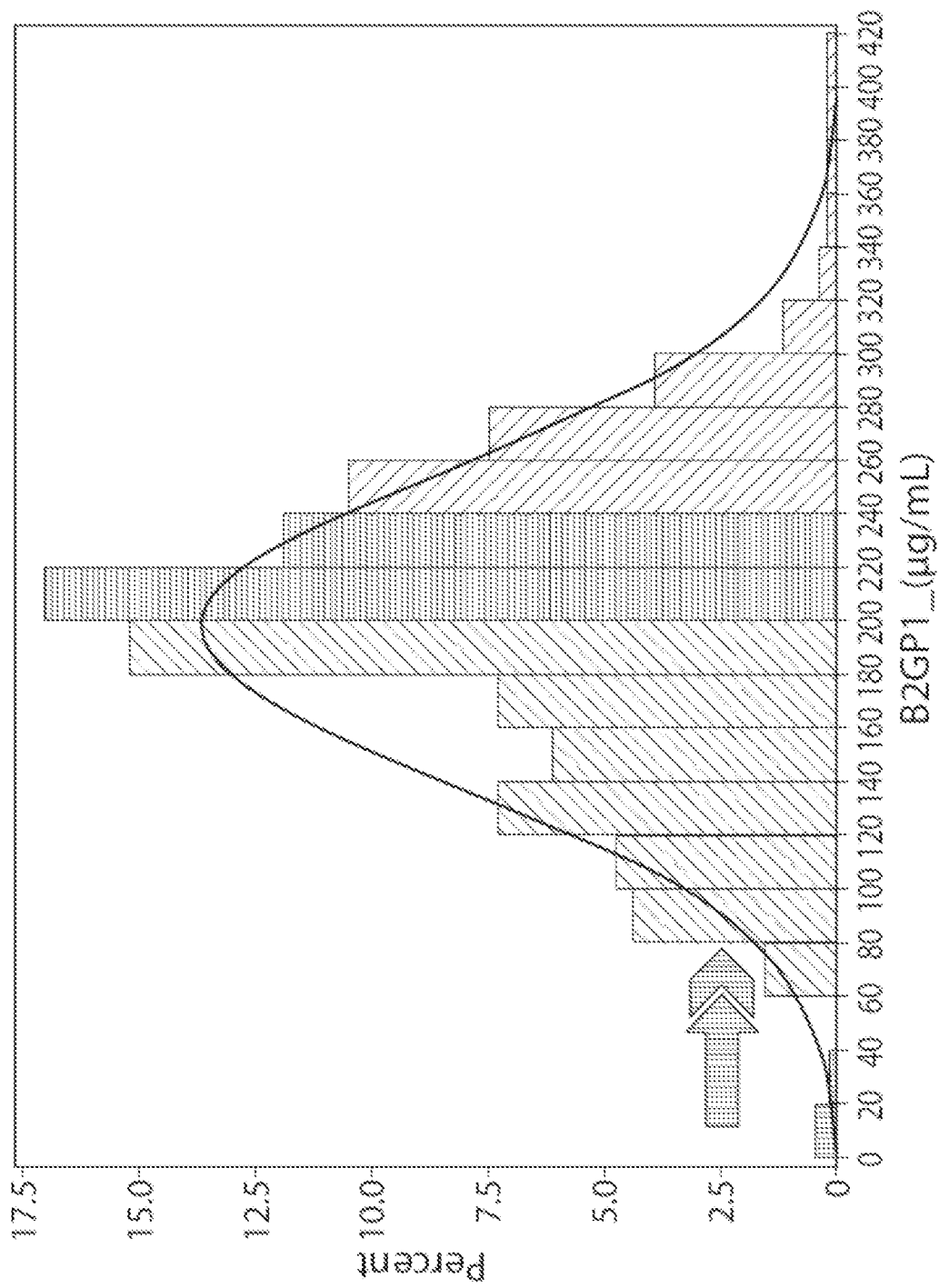
FIG. 5. Comparison of the β2GPI levels that support the PS-binding, functional and anti-tumor activity of the 3G4 antibody in preclinical studies to the β2GPI levels in patients in the Phase III trial. The distribution of pre-treatment functional β2GPI levels in 592 evaluable patients in the Phase III trial is described in Example XIII. Functional β2GPI levels of equal to or greater than 200 µg/mL (horizontally striped bars and diagonally striped bars pointing downward to the right) provide a trend for prolonged survival of patients treated with bavituximab (FIG. 3). Functional β2GPI levels in the range of between 200 µg/ml and 240 µg/ml (horizontally striped bars) provide a statistically significant better mOS for patients treated with bavituximab (FIG. 4). Functional β2GPI levels of about 10 µg/mL or above (→, long arrow) or about 60 µg/mL or above (>, short arrow) are sufficient for PS-binding, functional and anti-tumor activities of bavituximab in preclinical studies (Example I, E).

Although various commercial assays and research tools are available to analyze clinical trial results for biomarkers to predict better outcomes, none were known to be uniquely applicable to PS-targeting antibodies such as bavituximab. Despite the extensive pre-clinical modelling and significant prior clinical experience indicating that low and/or varying levels of serum β2GPI would not significantly impact treatment outcomes for bavituximab (Example I, E; FIG. 5), an analysis of the β2GPI concentrations in the patients from the Phase III trial (Example X) was sought.

However, reliable and quantitative β2GPI assays to specifically detect β2GPI that can bind to PS, as opposed to total β2GPI, were not available. Such an assay is necessary for the most precise measurements as applied to biomarkers, particularly because it is well known that a portion of β2GPI ("total" β2GPI) will exist as nicked β2GPI, which cannot bind to PS and thus cannot mediate antibody binding in the disease site. Moreover, there was a marked lack of any assay to specifically detect β2GPI that can bind not only to PS, but also to PS-targeting antibodies such as bavituximab. This is particularly important for the highest fidelity biomarker measurements, e.g., to rule out the possibility that β2GPI with other meaningful changes was being detected, particularly mutations and/or nicking or cleavage in, or impacting, domain II, as any such β2GPI alterations would diminish or negate antibody binding and the formation of the antibody: β2GPI:PS complex required for therapeutic activity.

Therefore, in order to conduct the optimal analyses of β2GPI concentrations in patients treated (or to be treated) with PS-targeting antibodies such as bavituximab, including patients from the Phase III trial (Example X), it was necessary to first invent a new assay. The present application discloses such an advantageous assay, which is uniquely adapted for the purpose of detecting and quantifying the amount of functional (active) β2GPI in human blood samples, such as plasma and serum, which assay can determine the level of β2GPI that is able to bind to both PS and to PS-targeting antibodies such as bavituximab.

It is by use of such an assay for functional β2GPI that the present invention provides defined levels of pre-treatment β2GPI for use as a single biomarker for response to treatment with bavituximab and related PS-targeting antibodies. Notably, functional β2GPI of equal to or greater than 200 μg/mL (Example XIII; FIG. 3; Example XIV; Example XVII) and functional β2GPI in the range of 200-240 μg/mL (Example XIII; FIG. 4). The preferred ELISAs for functional β2GPI provided by the invention are exemplified by the detailed teaching in Example XII and are also described more fully below.

G1. Assay Methods

In general terms, solid phase assays such as ELISAs for functional β2GPI use both PS and a PS-targeting antibody such as bavituximab, at least one of which is operatively associated with a solid support and/or at least one of which is directly or indirectly labeled with a detectable agent. All binding formats can be used. For example, the PS-targeting antibody could be adsorbed to the solid support and the PS labeled with a detectable agent. Many lipids such as PS labeled with detectable agents are known in the art, any of which could be used. However, for simplicity, the currently preferred embodiments are those in which PS is adsorbed to a solid surface, such as a 96 well plastic plate. This means that the PS-targeting antibody, such as bavituximab or 1N11, can be labeled with a detectable agent, which is preferably a direct label attached to the antibody.

In performing the assay steps, the PS-coated solid support, such as an ELISA well, is incubated with the biological sample suspected of containing β2GPI (the "antigen"). "Incubating" is under conditions and for a time effective to allow specific binding. Only β2GPI that is capable of binding to PS binds specifically to the PS-coated solid support, i.e., is not removed by routine washing.

Bound β2GPI (antigen) is detected using at least a secondary binding agent in the form of at least a PS-targeting antibody, preferably bavituximab or 1N11, which is directly or indirectly labeled with a detectable agent. An unlabeled PS-targeting antibody can be used in connection with a tertiary binding agent, preferably another antibody, which binds to the PS-targeting antibody and that is directly labeled with a detectable agent. However, and again for simplicity, the currently preferred embodiments are those in which the PS-targeting antibody is itself directly attached to the detectable agent. The detectable agent is an agent that produces a detectable signal, such as color or fluorescence, which can be detected and quantified. Typically, the quantity of bound material measured from the signal is compared to the level of a "reference signal", such as a standard curve.

In preferred embodiments, functional β2GPI is thus measured in an assay comprising:
(a) coating an ELISA plate with PS to prepare a PS-coated ELISA plate;
(b) adding a biological fluid sample, preferably a blood, plasma or serum sample, to the PS-coated ELISA plate under conditions effective to allow binding of β2GPI in the biological fluid sample to the PS-coated ELISA plate to prepare a PS and β2GPI-coated ELISA plate;
(c) adding a PS-targeting antibody, preferably bavituximab or 1N11, most preferably bavituximab, to the PS and β2GPI-coated ELISA plate under conditions effective to allow binding of the PS-targeting antibody to the PS and β2GPI-coated ELISA plate; and
(d) detecting the binding of the PS-targeting antibody to the PS and β2GPI-coated ELISA plate, thereby measuring the functional β2GPI in the sample.

Preferably, the PS-targeting antibody such as bavituximab is attached to a detectable agent that produces a detectable signal, and wherein the binding of the PS-targeting antibody to the PS and β2GPI-coated ELISA plate is detected and measured by detecting and measuring said detectable signal. An exemplary detectable agent is the enzyme horseradish peroxidase (HRP), wherein the HRP cleaves the substrate 3,3'5,5' tetramethylbenzidine (TMB) to produce a colored signal that is detected and measured at 450 nm.

In all formats of these assays, the only β2GPI that is ultimately detected is β2GPI capable of binding to both PS and to the PS-targeting antibody, i.e., β2GPI that is not removed overall by routine washing. These assays are therefore uniquely suited for detecting pre-treatment β2GPI in the form most relevant to clinical treatment, i.e., β2GPI that "functions" to form a binding complex with the administered antibody, preferably bavituximab, and the PS exposed in the disease site, preferably in the tumor microenvironment. The use of these assays is therefore advantageous in the selection of patients for improved treatment outcomes on bavituximab therapy.

The functional β2GPI assays provided by the invention are also simple, reproducible, sensitive, cost-effective and ideal for use with biological samples obtained by minimally invasive techniques, particularly blood (serum and plasma) samples. The rapid nature of the assays provides the important advantage that the biomarker test can be performed quickly and treatment decisions made and implemented in a timely manner.

G2. Solid Supports

The solid phase binding assays of the invention typically require operatively associating the binding constructs with a solid support or substrate (which has at least one surface for coating or attachment). "Binding constructs", as used herein, include constructs that bind to components useful in the detection of biomarkers. In connection with the β2GPI biomarker, binding constructs include anti-β2GPI antibodies, PS and PS-targeting antibodies such as bavituximab.

Such solid supports or substrates include, e.g., plates, beads and fibers. In preferred embodiments of the invention, the solid support or substrate is a multi-well plate, such as a standard 96-well plate. The solid support or substrate may be fabricated from any suitable material, such as sepharose, latex, glass, polystyrene, polyvinyl, nitrocellulose, silicon, silica, polydimethylsiloxane (PDMS) and the like. The binding construct is operatively associated with the solid support or substrate by effectively contacting at least one surface of the support or substrate with the binding construct. Preferably, the binding construct is immobilized on at least one surface of the solid support or substrate. The binding constructs can also be printed onto coated glass slides and used in biomarker arrays or microarrays. Both non-contact and contact printing can be used to prepare such microarrays, with contact printing being preferred.

G3. Detectable Agents

Suitable detectable agents include, e.g., enzymes, such as horseradish peroxidase (HRP), alkaline phosphatase (AP), β-galactosidase and urease. A horseradish-peroxidase detection system can be used, for example, with the chromogenic substrate tetramethylbenzidine (TMB), which yields a soluble product in the presence of hydrogen peroxide that is detectable at 450 nm. Other convenient enzyme-linked systems include, for example, the alkaline phosphatase detection system, which can be used with the chromogenic substrate p-nitrophenyl phosphate to yield a soluble product readily detectable at 405 nm. Similarly, a β-galactosidase detection system can be used with the chromogenic substrate O-nitrophenyl-β-D-galactopyranoside (ONPG) to yield a soluble product detectable at 410 nm, or a urease detection system can be used with a substrate such as urea-bromocresol purple.

Further examples of detectable agents include chemiluminescent labels and labels for fluorescent detection. Useful fluorochromes include DAPI, fluorescein, Hoechst 3325S, R-phycocyanin, B-phycoerythrin, R-phycoerythrin, rhodamine, Texas red and lissamine. Fluorescein or rhodamine labeled antibodies or annexins, and/or fluorescein- or rhodamine-labeled secondary antibodies can be used. Isotopes can also be useful in the detection methods, which moieties and assays are well known in the art.

The detectable agent produces a detectable signal, which is then detected and preferably quantified. A detectable signal can be analyzed, e.g., using a spectrophotometer to detect color from a chromogenic substrate; a radiation counter to detect radiation, such as a gamma counter for detection of $^{125}$I; or a fluorometer to detect fluorescence in the presence of light of a certain wavelength. Where an enzyme-linked assay is used, quantitative analysis of the detectable signal can be performed using a spectrophotometer.

G4. Kits

The invention also provides a series of biomarker-based kits, including diagnostic, prognostic and predictive therapy kits. The biomarker kits will typically comprise one or more of the binding constructs useful in the detection of the biomarkers taught herein. Kits in connection with the β2GPI biomarker will generally comprise at least a first β2GPI binding construct, such as anti-β2GPI antibodies, PS and PS-targeting antibodies such as bavituximab.

Other kits will comprise both binding constructs for biomarker detection and at least a first therapeutic agent for use in treating a selected patient, e.g., a PS-targeting antibody such as bavituximab or 1N11, or an immunoconjugate thereof. Such kits may further comprise at least a second or third distinct therapeutic agent for use in combination treatment with the PS-targeting antibody. For example, one or more chemotherapeutic, radiotherapeutic, anti-angiogenic, immunotherapeutic and/or anti-viral agents.

In general, the kits will contain the stated components in at least a first suitable container (or container means). The containers will generally include at least one vial, test tube, flask, bottle, syringe or other container or container means, into which the desired agents are placed and, preferably, suitably aliquoted. The kits will also typically include a means for containing the individual vials, or such like, in close confinement for delivery, such as, e.g., injection or blow-molded plastic containers into which the desired vials and other apparatus are placed and retained.

The components of the kits may be contained either in aqueous media or in lyophilized form. When reagents or components are provided as a dry powder, the powder can be reconstituted by the addition of a suitable solvent. The solvent may also be provided in another container within the kit. Any therapeutic components will preferably be in a pharmaceutically acceptable formulation, or ready for reconstitution as such. The kits may also contain a means by which to administer the therapeutic agents to an animal or patient, e.g., one or more needles or syringes, or an eye dropper, pipette, or other such like apparatus, from which the formulations may be injected into the animal or applied to a diseased area of the body.

The kits will preferably have distinct containers for each desired component or agent, particularly the biomarker detection and diagnostic components. However, for use in combined therapies, the kits may comprise one container that contains two or more therapeutics, pre-mixed; either in a molar equivalent combination, or with one component in excess of the other. The kits may include pre-labeled antibodies in fully conjugated form, or separate label moieties to be conjugated by the user of the kit, preferably with instructions for attachment. For immunodetection, one or more of the components, such as PS, may already be bound to a solid support, such as a well of a microtitre plate.

The kits will preferably also include written or electronic instructions for use, e.g. in quantification, pre-clinical, clinical and/or veterinary embodiments, including for use in combined therapy. Being biomarker-based, the kits will preferably further comprise control agents, such as suitably aliquoted biological compositions, whether labeled or unlabeled, as may be used to prepare a standard curve for a detection assay.

G5. Chip and Nano Assay Formats

The solid phase and ELISA-type biomarker assays, including for total β2GPI and/or functional β2GPI, can be automated or performed robotically, if desired, and the signal from multiple samples can be detected simultaneously. Various such assay formats have been used to detect and quantify biomarkers in general, although not in the context of the present invention. For example, nano-plasmonic sensors and microfluidic devices termed "Chips" have been described and used for on-chip isolation, quantification and characterization of circulating biomarkers from cancer patients. The present assays can thus be accomplished using such microfluidic, chip, nano-tech and other streamlined and automated assays, whilst still retaining the specificities of the invention.

In addition to the predictive methods and biomarker-guided treatment methods, the present invention also provides computer-based hardware and tests. Such computer-based embodiments of the invention include an interface configured for reading one or more laboratory biomarker tests, including for total β2GPI and/or functional β2GPI, and a computer programmed to analyze data from such biomarker tests and, preferably, to compare the analyzed data to established data sets, including test data sets and control data sets. The computer-implemented embodiments of the invention will preferably include memory storage, output functions and instructions configured to guide therapy based upon the output.

H. Immunotherapy (IO) Combinations

A challenge to effective immunotherapy is to overcome multiple pathways that inhibit innate or adaptive immune activation. The PD-1 immune checkpoint has been identified as a major immunosuppressive pathway and has emerged as a promising target for cancer immunotherapy with less toxicity than chemotherapy. It functions to exhaust activated tumor-specific T cells and dampen their tumor-killing activity. PD-1 is absent on naïve T cells, B cells, macrophages, DCs, and monocytes but expressed highly on their activated counterparts. Notably, tumors and associated myeloid cells exploit the PD-1 pathway to generate innate and adaptive immune resistance through up-regulation of PD-L1 expression. Mechanistic studies indicate that blockade of these immune checkpoints is most effective when there is a de novo or pre-existing anti-tumor immune response. Unfortunately, pre-existing tumor specific immune activity is limited in cancer patients because of the exposure of PS and other immunosuppressive factors that often dominate the tumor microenvironment.

Although durable anti-tumor immune responses have been observed in multiple cancer types with agents that block PD-1 signaling, only a subset of patients respond; consequently, a significant unmet medical need remains. In particular, patients that express low levels of PD-1 and PD-L1 (a biomarker of immunosuppression and lack of T cell activation) in the tumor microenvironment appear less responsive to checkpoint blockade therapy. In this context, the present application shows that bavituximab treatment can increase the proportion of patients who may benefit from anti PD-1/PD-L1 and other checkpoint therapies.

Figure 6:
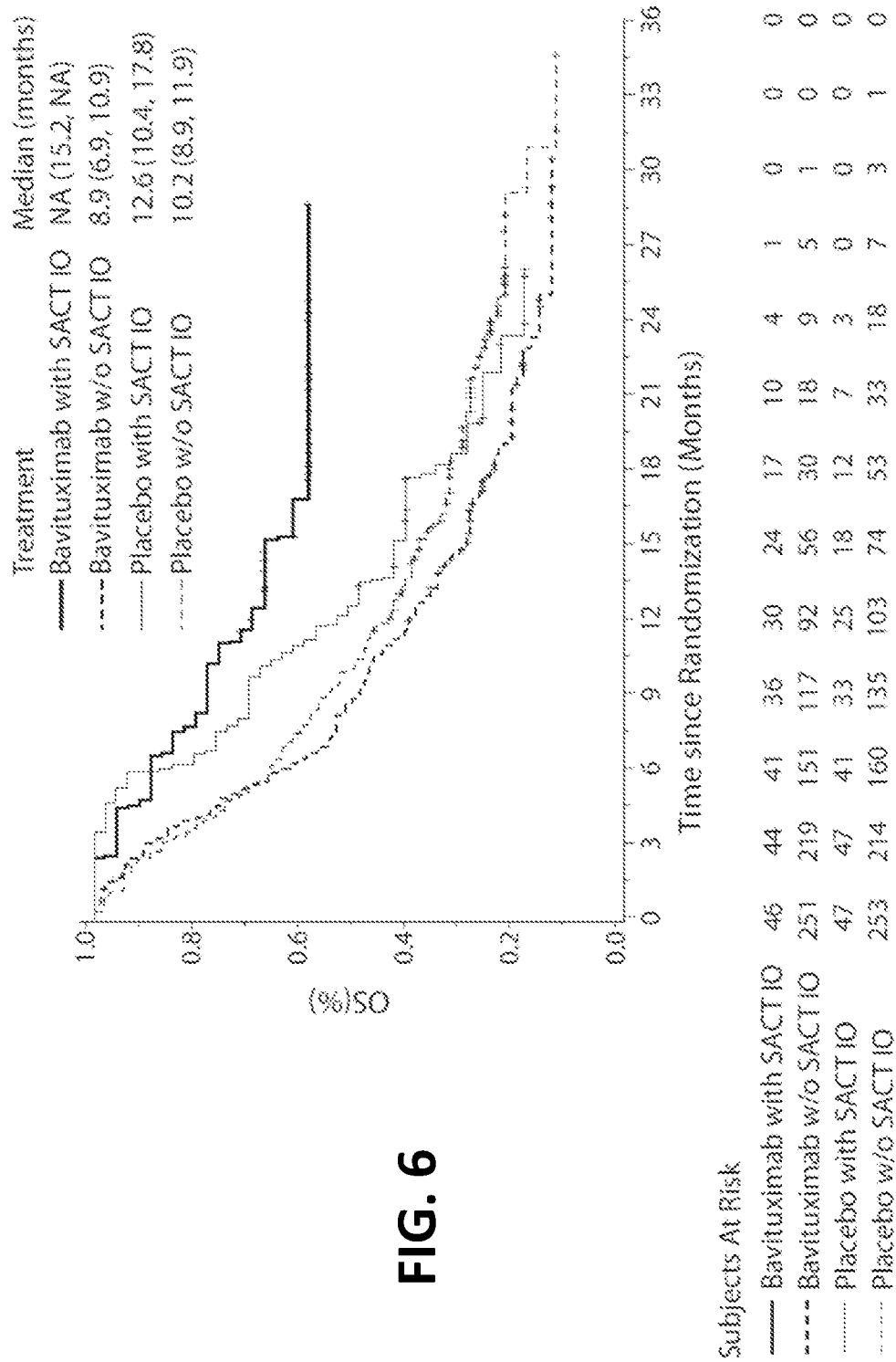
FIG. 6. Kaplan-Meier survival curves showing that patients treated with bavituximab and docetaxel followed by subsequent immunotherapy ("SACT-IO") (black, solid line) have a statistically significant better mOS as opposed to patients treated with docetaxel alone followed by subsequent immunotherapy (gray, solid line). The treatment groups, mOS and statistical analyses are tabulated for these survival curves in Table 11 (Example XVI).

Indeed, presented herein are clinical data showing, for the first time, that human patients treated with bavituximab and immunotherapy have a meaningful survival advantage. In particular, the results in Example XVI demonstrate that patients treated with bavituximab (and docetaxel) followed by subsequent immunotherapy ("SACT-IO") have a statistically significant better overall survival in comparison to patients treated with placebo (docetaxel alone) followed by subsequent immunotherapy. The prolonged survival was statistically significant (p=0.006) and even more impressive because mOS for bavituximab patients receiving subsequent IO has yet to be reached (Example XVI; FIG. 6; Table 11). Thus, bavituximab does, indeed, enhance the activity of immunotherapy agents in human patients.

Because of its PS-targeting activity, bavituximab blocks the activity of TIMs and TAMs, among other PS receptors, and as stated elsewhere, exposed phosphatidyl serine on external cell membranes is a hallmark of cancer and apoptosis. TIMs and TAMs, which are enriched and activated in the tumor microenvironment, contribute to immunosuppression, preventing a proper immune response to the cancerous cells. Patients with exhausted or poorly functioning anti-tumor immune responses, as exemplified by patients with low IFNγ levels, are less likely to respond to antibody therapy directed against immune checkpoint inhibitors (ICI), such as the inhibitors of PD-1 and PD-L1. The correlation between low IFNγ levels and response to bavituximab was a surprise because to date high IFNγ levels are correlated with immune checkpoint inhibitor responses. In the clinical trial described in Example XVI, patients treated with bavituximab for a length of time prior to subsequent checkpoint inhibitor therapy (SACT-IO) had a much better response (FIGS. 6, 7, and 8). These data strongly suggest that bavituximab increased the sensitivity of patients to the anti-PD-1 and anti-PD-L1 therapies, which could be due to bavituximab having restored the potency of an exhausted anti-tumor immune response, not fully, but to a point where the immune cells can be optimally enhanced by checkpoint blockade. Therefore, the combination therapy of bavituximab with the anti-PD-1 and anti-PD-L1 therapeutic agents of Table 12 in Example XVI gave the surprising benefit of restoring sensitivity to and increasing the response to the checkpoint inhibitor when administered to the same patient. Thus the inhibitors listed in Table F, when given with bavituximab to the same patient will provide better patient outcomes than these drugs alone. Bavituximab is a true immunomodulator that is effective at altering the tumor microenvironment and improving anti-tumor immune responses to checkpoint inhibitors.

Accordingly, as exemplified by the data in Example XVI, important embodiments of the present invention are the treatment of cancer patients with PS-targeting antibodies such as bavituximab in combination with immunotherapy or immuno-oncology (IO) agents. Exemplary immunotherapeutic agents for combined therapy are listed in Table D. Certain preferred examples of IO agents are those approved for clinical treatment or in human clinical trials, preferably in late-stage clinical trials, such as those described in Table E. The doses for use and indications for treatment are well-known to those of ordinary skill in the art, as exemplified by the details in Table E.

Particularly preferred IO agents for combination therapy with PS-targeting antibodies such as bavituximab, as directly supported by the data in Example XVI, are "checkpoint inhibitors", also termed herein "immune checkpoint antibodies". Suitable "immune checkpoint antibodies" include agonistic (activating) antibodies that bind to an activating immune checkpoint, receptor or molecule, such as CD28, OX40 and/or GITR, and antagonistic (blocking) antibodies that bind to an inhibitory immune checkpoint, receptor or molecule, such PD-1, PD-L1, CTLA-4, TIM-3 and/or LAG-3. Such blocking antibodies are routinely termed "immune checkpoint inhibitors", which is also used herein. Several such antibodies are also described in Table E, as being approved for clinical treatment or in late-stage clinical trials.

The currently most preferred examples of immune checkpoint antibodies (immune checkpoint inhibitors) are "blocking antibodies that bind to CTLA-4, PD-1 or PD-L1". Several such blocking antibodies that bind to CTLA-4, PD-1 or PD-L1, and methods, including functional assays, for their selection, preparation and use, are well-known to those of ordinary skill in the art, as described in Table F. These include blocking antibodies to CTLA-4, such as ipilimumab and tremelimumab; blocking antibodies to PD-1, such as nivolumab, cemiplimab (REGN2810), CBT-501, CX-072, and pembrolizumab; blocking antibodies to PD-L1, such as durvalumab (MEDI4736), avelumab, LY-3300054, CX-188, and atezolizumab; and combinations of any one or more of such antibodies, known as an "IO doublet".

Of the above blocking antibodies, tremelimumab, nivolumab, durvalumab and atezolizumab are preferred, and atezolizumab is particularly preferred. The main U.S. patents for tremelimumab, nivolumab, durvalumab and atezolizumab are U.S. Pat. Nos. 6,682,736, 8,008,449, 8,779,108 and 8,217,149, respectively. The use of bavituximab in combination with atezolizumab is set forth in detail in Example XIX. Not as part of the same study, but in one or more other treatment options, atezolizumab may be replaced by another immune checkpoint antibody, such as another blocking antibody that binds to CTLA-4, PD-1, PD-L1, or a bispecific blocking antibody that binds to any checkpoint inhibitor. In selecting a different blocking antibody, those of ordinary skill in the art will know the suitable dose and administration schedule from the literature, e.g., as referenced in Table E, optionally with Table F.

In addition to Table F, other suitable examples of anti-CTLA-4 antibodies are those described in U.S. Pat. No. 6,207,156, which particularly concerns anti-CTLA-4 antibodies that comprise a CDR (CDR3, CDR2 or CDR1) selected from a defined antibody from a deposited hybridoma.

In addition to Table F, other suitable examples of anti-PD-L1 antibodies are those described in U.S. Pat. No. 8,168,179, which particularly concerns treating PD-L1 over-expressing cancers with human anti-PD-L1 antibodies, including chemotherapy combinations; U.S. Pat. No. 9,402,899, which particularly concerns treating tumors with antibodies to PD-L1, including chimeric, humanized and human antibodies; and U.S. Pat. No. 9,439,962, which particularly concerns treating cancers with anti-PD-L1 antibodies and chemotherapy. These anti-PD-L1 antibody compositions and methods include those in development by Ono Pharmaceuticals and collaborators.

Further suitable antibodies to PD-L1 are those in U.S. Pat. Nos. 7,943,743, 9,580,505 and 9,580,507, kits thereof (U.S. Pat. No. 9,580,507) and nucleic acids encoding the antibodies (U.S. Pat. No. 8,383,796). Such antibodies bind to PD-L1 and compete for binding with a reference antibody; are defined by VH and VX genes; or are defined by heavy and light chain CDR3 (U.S. Pat. No. 7,943,743), or heavy chain CDR3 (U.S. Pat. No. 8,383,796), of defined sequences or conservative modifications thereof; or have 90% or 95% sequence identity to reference antibodies. These anti-PD-L1 antibodies also include those with defined quantitative (including binding affinity) and qualitative properties, immunoconjugates and bispecific antibodies. Further included are methods of using such antibodies, and those with defined quantitative (including binding affinity) and qualitative properties, including antibodies in single chain format and those that are in the format of an isolated CDR, in enhancing an immune response (U.S. Pat. No. 9,102,725). Enhancing an immune response, as in U.S. Pat. No. 9,102,725, may be used to treat cancer or an infectious disease, such as a pathogenic infection by a virus, bacterium, fungus or parasite. These anti-PD-L1 antibody compositions and methods include the product, BMS936559.

Further suitable antibodies to PD-L1 are those in U.S. Patent Application No. 2016/0009805, which concerns antibodies to particular epitopes on PD-L1, including antibodies of defined CDR sequences and competing antibodies; nucleic acids, vectors, host cells, immunoconjugates; detection, diagnostic, prognostic and biomarker methods; and treatment methods.

Combinations of Checkpoint Modulators

The invention features antibody molecules capable of binding to immune checkpoint modulators (e.g., immune checkpoint inhibitory molecules and immune checkpoint stimulatory molecules), e.g., for use in conjunction with a PS-targeting antibody molecule, e.g., as described herein. Such antibody molecules may be administered in combinations, e.g., alongside a PS-targeting antibody molecule, e.g., as described herein. Exemplary immune checkpoint antibody molecules include agonistic (activating) antibody molecules that bind to an activating immune checkpoint, receptor or molecule and antagonistic (blocking) antibody molecules that bind to an immune checkpoint modulator (e.g., an inhibitory or stimulatory receptor or molecule). Examples of immune checkpoint modulators include, without limitation, PD-1, PD-L1, CTLA-4, TIM-3, LAG-3, OX40, CD2, CD27, CDS, ICAM-1, LFA-1 (CD11a/CD18), ICOS (CD278), 4-1BB (CD137), GITR, CD30, CD40, BAFFR, HVEM, CD7, LIGHT, NKG2C, SLAMF7, NKp80, CD160, VISTA, BTLA, TIGIT, LAIR1, CD160, 2B4 and/or TGF-β. Examples of immune checkpoint antibody molecules include, without limitation, avelumab, ipilimumab, tremelimumab, nivolumab, pembrolizumab, durvalumab, atezolizumab, pidilizumab, XmAb20717, cemiplimab (REGN2810), CBT-501, CX-072, CX-188, and LY3300054.

In embodiments, an immune checkpoint antibody molecule is capable of binding to PD-1 (e.g., an anti-PD-1 antibody molecule). In embodiments, the anti-PD-1 antibody molecule is administered in combination with a modulator, e.g., agonist, of a costimulatory molecule. In one embodiment, the agonist of the costimulatory molecule is chosen from an agonist (e.g., an agonistic antibody or antigen-binding fragment thereof, or soluble fusion) of OX40, CD2, CD27, CDS, ICAM-1, LFA-1 (CD11a/CD18), ICOS (CD278), 4-1BB (CD137), GITR, CD30, CD40, BAFFR, HVEM, CD7, LIGHT, NKG2C, SLAMF7, NKp80, or CD160. In another embodiment, the anti-PD-1 antibody molecule is used in combination with a costimulatory molecule, e.g., an agonist associated with a positive signal that includes a costimulatory domain of CD28, CD27, ICOS and GITR.

Exemplary GITR agonists include, e.g., GITR fusion proteins and anti-GITR antibodies (e.g., bivalent anti-GITR antibodies), such as, a GITR fusion protein described in U.S. Pat. No. 6,111,090, European Patent No.: 090505B1, U.S. Pat. No. 8,586,023, PCT Publication Nos.: WO 2010/003118 and 2011/090754, or an anti-GITR antibody described, e.g., in U.S. Pat. No. 7,025,962, European Patent No.: 1947183B1, U.S. Pat. Nos. 7,812,135, 8,388,967, 8,591,886, European Patent No.: EP 1866339, PCT Publication No.: WO 2011/028683, PCT Publication No.: WO 2013/039954, PCT Publication No.: WO2005/007190, PCT Publication No.: WO 2007/133822, PCT Publication No.: WO2005/055808, PCT Publication No.: WO 99/40196, PCT Publication No.: WO 2001/03720, PCT Publication No.: WO99/20758, PCT Publication No.: WO2006/083289, PCT Publication No.: WO 2005/115451, U.S. Pat. No. 7,618,632, and PCT Publication No.: WO 2011/051726.

In one embodiment, the anti-PD-1 antibody molecule is administered in combination with an inhibitor of an inhibitory molecule of an immune checkpoint molecule. It will be understood by those of ordinary skill in the art, that the term "immune checkpoints" means a group of molecules on the cell surface of CD4 and CD8 T cells. These molecules can effectively serve as "brakes" to down-modulate or inhibit an anti-tumor immune response. Immune checkpoint molecules include, but are not limited to, Programmed Death 1 (PD-1), Cytotoxic T-Lymphocyte Antigen 4 (CTLA-4), B7H1, B7H4, OX-40, CD137, CD40, LAG-3 and TIM-3, which directly inhibit immune cells. Immunotherapeutic agents which can act as immune checkpoint inhibitors useful in the methods of the present invention, include, but are not limited to, inhibitors of PD-L1, PD-L2, CTLA4, TIM-3, LAG-3, VISTA, BTLA, TIGIT, LAIR1, CD160, 2B4, and/or TGF-beta. Inhibition of an inhibitory molecule can be performed by inhibition at the DNA, RNA or protein level. In embodiments, an inhibitory nucleic acid (e.g., a dsRNA, siRNA or shRNA), can be used to inhibit expression of an inhibitory molecule. In other embodiments, the inhibitor of an inhibitory signal is, a polypeptide e.g., a soluble ligand, or an antibody or antigen-binding fragment thereof, that binds to the inhibitory molecule.

In one embodiment, the inhibitor is a soluble ligand (e.g., a CTLA-4-Ig or a TIM-3-Ig), or an antibody or antibody fragment that binds to PD-L1, PD-L2 or CTLA4. For example, the anti-PD-1 antibody molecule can be administered in combination with an anti-CTLA-4 antibody, e.g., ipilimumab, for example, to treat a cancer (e.g., a cancer chosen from: a melanoma, e.g., a metastatic melanoma; a lung cancer, e.g., a non-small cell lung carcinoma; or a prostate cancer). Exemplary anti-CTLA4 antibodies include Tremelimumab (IgG2 monoclonal antibody available from Pfizer, formerly known as ticilimumab, CP-675,206); and Ipilimumab (CTLA-4 antibody, also known as MDX-010, CAS No. 477202-00-9). In one embodiment, the anti-PD-1 antibody molecule is administered after treatment, e.g., after treatment of a melanoma, with an anti-CTLA4 antibody (e.g., ipilimumab) with or without a BRAF inhibitor (e.g., vemurafenib or dabrafenib). Exemplary doses that can be use include a dose of anti-PD-1 antibody molecule of about 1 to 10 mg/kg, e.g., 3 mg/kg, and a dose of an anti-CTLA-4 antibody, e.g., ipilimumab, of about 3 mg/kg.

I. Disease Treatment and Prevention

As the present invention provides biomarker methods, compositions and kits for selecting animals and humans and optimizing treatment with PS-targeting antibodies such as bavituximab, the following guidance concerning animals, subjects and patients, including human patients, applies to both the biomarker detection and the treatment of the selected population.

I1. Animals, Subjects and Patients

The invention is most directly applicable to human subjects and patients, such that the selection and treatment of humans are the most preferred embodiments. Nonetheless, the commonality and conservation of the biomarkers across species means that invention is applicable to animals other than humans. Within animals, mammals are preferred, most preferably, valued and valuable animals such as domestic pets, race horses and animals used to directly produce (e.g., meat) or indirectly produce (e.g., milk) food for human consumption, although experimental animals are also included. The invention therefore includes clinical, veterinary and research uses. In addition to humans, the invention therefore applies to dogs, cats, horses, cows, pigs, boar, sheep, goat, buffalo, bison, llama, deer, elk and other large animals, as well as their young, including calves and lambs, and to mice, rats, rabbits, guinea pigs, primates such as monkeys and other experimental animals.

I2. Antibody Doses

A "therapeutically effective" amount or dose of a PS-targeting antibody such as bavituximab is an amount or dose that exerts a beneficial therapeutic effect when administered to an animal, preferably a human patient, in need of such a therapy, including when administered as part of a combination therapy. For example, a therapeutically effective anti-cancer dose is an amount or dose that exerts a beneficial anti-cancer effect when administered to an animal, preferably a human patient, with cancer, including when administered as part of a combination cancer therapy. A therapeutically effective anti-viral dose is an amount or dose that exerts a beneficial anti-viral effect when administered to an animal, preferably a human patient, with a viral infection or disease, including when administered as part of a combination viral therapy.

"Beneficial anti-cancer effects" include any consistently detectable anti-tumor and anti-cancer effect, including tumor vasculature thrombosis and/or destruction, tumor necrosis, tumor regression and tumor remission, up to and including cures. Clinical measures of beneficial anti-cancer effects include, for example, improvements in overall response rate (ORR), including complete response (CR), partial response (PR), and CR+PR; time to tumor progression (TTP); duration of response (DOR or DR); and improvements or extensions in progression-free survival (PFS), disease-free survival (DFS) and overall survival (OS), including median overall survival (mOS), in individual patients, patient populations and sub-populations, as applicable.

"Beneficial anti-viral effects" include any consistently detectable anti-viral effect, including inhibiting viral infection, replication, maturation, reproduction and egress and/or ongoing infection of, or spread to, additional cells (host cells) or tissues. Clinical measures of beneficial anti-viral effects include, for example, early virological response, reductions in viral load and clearance of virus, as well as improvements in the symptoms caused by the viral infection.

It will be understood that beneficial therapeutic effects, particularly anti-cancer effects, may not be curative, particularly in the intermediate or long term, but that does not negate the usefulness of the therapies. In this regard, but also in general, "beneficial" therapeutic, anti-cancer and anti-viral effects also include comparative and/or modest treatment effects, but with improvements in any one or more measures of safety. Another consideration for "beneficial" therapeutic effects is the fact that the PS-targeting antibodies such as bavituximab may predispose the disease or tumor to further therapeutic treatment, such that a subsequent treatment can result in an overall improved effect.

Therapeutically effective doses of PS-targeting antibodies such as bavituximab or 1N11 are now readily determinable using a wide range of data, including from animal models, but particularly based on clinical studies, such as those detailed herein, and published in the literature. In general, the effective dose ranges of PS-targeting antibodies such as bavituximab, given intravenously (IV) and quoted in mg/kg, will be between about 0.1 and about 13-15, preferably between about 0.1 and about 6-10; preferably, between about 0.3 and about 6; more preferably, between about 0.5 and about 6; more preferably, between about 1 and about 6; more preferably, between about 0.5 and about 3 or between about 3 and about 6; more preferably, between about 1 and about 3. Exemplary effective doses of PS-targeting antibodies such as bavituximab, given IV and quoted in mg/kg, will be about 1, 2, 3, 4, 5, 6, 7, 8, 9, 10, 11, 12, 13, 14 and about 15; preferably about 0.1, 0.3, 0.5, 1, 1.5, 2, 2.5, 3, 3.5, 4, 4.5, 5, 5.5 and about 6; more preferably, about 2 or 3; and most preferably, of about 3 mg/kg. One use of the term dose, which may or may not include a reference to weight, or "flat dose" with regard to the methods and dosages of the disclosure means a dose that is administered to a patient without regard for the weight or body surface area (BSA) of the patient. The flat dose is therefore not provided as a mg/kg dose, but rather as an absolute amount of the agent (e.g., bavituximab antibody and or immuno-oncology (IO) agents such as checkpoint inhibitor antibodies). For example, a 60 kg person and a 100 kg person would receive the same dose of an antibody (e.g., 100 mg, 110 mg, 120 mg, 130 mg, 140 mg, 150 mg, 160 mg, 170 mg, 180 mg, 190 mg, 200 mg, 210 mg, 220 mg, 230 mg, 240 mg, 250 mg, 260 mg, 270 mg, 280 mg, 290 mg, 300 mg, 310 mg, 320 mg, 330 mg, 340 mg, 350 mg, 360 mg, or more).

The currently preferred dose of 3 mg/kg bavituximab given intravenously (IV) for clinical treatment, particularly for all oncology indications, is recommended based on extensive pre-clinical and clinical data, and particularly on the pharmacokinetic profile in humans (Example II), along with the extensive safety data. Nonetheless, a range of doses have been shown to be effective, including clinical anti-viral activity at 0.3 mg/kg (Example II). In addition, bavituximab has been safely administered to rats and monkeys at doses above 10 mg/kg, up to 100 mg/kg. At the 100 mg/kg dose level in monkeys, bavituximab transiently decreased β2GPI in the systemic circulation, so such ultra-high doses are not recommended.

Therefore, from the breadth of data, it is evident that the dose of 3 mg/kg, although preferred, is not limiting on the invention. Accordingly, it will be understood that, given the parameters and detailed guidance presented herein, further variations in the active or optimal dose ranges and doses will be encompassed within the present invention. It will thus be understood that lower doses may be more appropriate in combination with certain agents, and that high doses can still be tolerated, particularly when treating a usually fatal disease.

In administering PS-targeting antibodies such as bavituximab, a pharmaceutically acceptable composition (according to FDA standards of sterility, pyrogenicity, purity and general safety) is administered to the animal or patient systemically. Intravenous injection is generally preferred, and a continuous infusion over a period of several hours is most preferred.

In addition to varying the dose itself, the administration regimen can also be adapted to optimize the treatment strategy, as is well known to those of skill in the art. Some variation in dosage and treatment regimen may be necessary depending on the condition of the subject being treated. The physician(s) responsible will, in light of the present disclosure, be able to determine the appropriate treatment for the individual subject. Such optimization and adjustment is routinely carried out in the art, and by no means reflects an undue amount of experimentation.

I3. Supplementing Treatment with β2GPI

In using pre-treatment β2GPI levels as a biomarker for response to PS-targeting antibodies such as bavituximab, either alone, or as part of a multi-biomarker selection, and irrespective of whether total β2GPI or functional β2GPI is measured, the methods will select only a sub-set of patients for treatment.

Another embodiment of the present application is thus to restore and non-selected patients to treatment eligibility by co-administering β2GPI to those patients along with the PS-targeting antibody such as bavituximab. In this manner, the entire population becomes treatable with PS-targeting antibodies. For example, in selecting patients for treatment based on pre-treatment levels of functional β2GPI of equal to or greater than 200 μg/mL, a patient with a pre-treatment level of functional β2GPI of 150 μg/mL could be returned to the treatable group by co-administering bavituximab in conjunction with sufficient functional β2GPI to restore the β2GPI levels to at least about 200 μg/mL. The sample applies to whichever pre-treatment level of β2GPI is used in the biomarker analyses.

J. Treating Diseases in which PS is a Marker

As PS-targeting antibodies such as bavituximab specifically target PS, the first, and most important, indication for treatment is cancer (Section L), particular solid tumors and their metastases, but also liquid tumors, such as leukemias, and preferably, Hodgkin's Lymphoma.

In normal and healthy cells, PS is maintained on the inside of the cell membrane and not accessible to binding. Only cells in diseases have PS exposed on the outside of the cell membrane, most particularly, cells in the tumor microenvironment, but also dying cells, aberrant cells, inappropriately activated cells, infected cells and pathogenic organisms themselves. In cancer, PS exposure in the tumor microenvironment is "immunosuppressive", meaning that the body cannot adequately fight the cancer. By blocking PS, bavituximab overrides the PS-mediated immunosuppression, helping the body attack the tumor.

In cells in the tumor microenvironment, most particularly cells lining the blood vessels in tumors (and in virally-infected cells and viruses), PS is a relatively stable marker, meaning that it is an ideal target for therapy. In diseases where there is a lot of cell death, PS is also exposed on the outside of cells, which means that bavituximab can be used in diagnosis and particularly for "imaging", i.e., in vivo diagnostics, of a variety of diseases in which increased or inappropriate cell death occurs, including such conditions as, e.g., cancer and heart attacks, (see below for imaging).

Prominent pathogens that cause the host cell to externalize PS are viruses (Section K). Indeed, the role of PS and PS receptors as enhancers of enveloped virus entry and infection is now well-documented and applies to a wide range of viruses. Moreover, the connection between PS and viruses is not limited to enveloped viruses, but extends to non-enveloped viruses. In particular, it is known that "PS lipid vesicles" released from virally-infected cells enable efficient en bloc transmission of enteroviruses.

In addition to cancer and viral infections, a wide range of diseases and pathogenic infections cause PS to flip from its interior location in healthy cells to become exposed on the outside of the cell, meaning that PS-targeting antibodies such as bavituximab can localize to those cells and pathogens and exert beneficial effects. Collectively, these are "diseases and disorders in which PS is a marker".

Other than cancer, viral and pathogenic infections, prominent diseases and disorders in which PS is a marker are diseases in which aberrant vasculature (blood vessels) is involved, including diseases and disorders having prothrombotic blood vessels (prone to clotting) and those involving aberrant angiogenesis. Angiogenesis is the process through which new blood vessels form from pre-existing vessels; the development of new blood vessels begins with the formation of endothelial cell sprouts, which requires PS (Weihua et al., 2005). Aberrant angiogenesis is involved in many diseases, most notably in cancer. In light of their aberrant vasculature, PS-targeting antibodies such as bavituximab can treat benign (as opposed to malignant) tumors, such as benign prostatic hyperplasia (BPH), acoustic neuroma, neurofibroma, trachoma, granulomas including pyogenic granulomas and sarcoidosis (sarcoid), meningioma, angiofibroma, angioma, hemangiomas and systemic forms of hemangiomas, the hemangiomatoses.

Conditions directly associated with aberrant vasculature that can be treated with PS-targeting antibodies such as bavituximab include vascular restenosis (narrowing of blood vessels), including restenosis following angioplasty, vein occlusion, artery occlusion and carotid obstructive or occlusive disease; vasculitis (disorders that destroy blood vessels by inflammation), including Behcet's disease (also an eye disease), polyarteritis nodosa (panarteritis nodosa or PAN) and Wegener's granulomatosis (WG) or sarcoidosis (granulomatosis with polyangiitis, GPA), arteriovenous malformations (AVM) and arteriovenous fistula; epistaxis (nose-bleeds); vascular adhesions; and hyperviscosity syndromes.

Due to their connection with aberrant vasculature, PS-targeting antibodies such as bavituximab can treat clinically important diseases including joint diseases such as arthritis, including rheumatoid arthritis and osteoarthritis, synovitis, hemophilic joints and Paget's disease; skin diseases such as psoriasis, dermatitis, scleroderma (systemic sclerosis or CREST syndrome), pseudoxanthoma elasticum (PXE, known as Gronblad-Strandberg syndrome), rosacea, Stevens-Johnson syndrome or disease (PXE, rosacea and Stevens-Johnson syndrome are also eye diseases), pemphigoid, hypertrophic scars and keloids; Grave's disease; endometriosis; and Osler-Weber (or Osier-Weber-Rendu) syndrome or disease (also known as hereditary hemorrhagic telangiectasia, HHT).

Particularly important examples of diseases involving aberrant vasculature to be treated by PS-targeting antibodies such as bavituximab are ocular neovascular diseases. These diseases are characterized by invasion of new blood vessels into the structures of the eye, such as the retina, choroid and/or cornea. They are the most common cause of blindness and are involved in approximately twenty eye diseases. The most common ocular neovascular diseases are (proliferative) diabetic retinopathy, macular degeneration, including age-related macular degeneration (AMD), retinopathy of prematurity (ROP or Terry syndrome, previously known as retrolental fibroplasia, RLF), neovascular glaucoma, corneal graft neovascularization and corneal graft rejection. Choroidal neovascularization (CNV) accounts for 90% of cases of severe vision loss in patients with advanced AMD, and has been effectively treated with PS-targeting antibodies, including both direct and indirect PS-binding antibodies (Li et al., 2015).

Other diseases associated with retinal/choroidal neovascularization that can be treated with PS-targeting antibodies such as bavituximab include syphilitic, mycobacterial and/or other eye infections causing retinitis or choroiditis; uveitis (iridocyclitis), including vitritis and pars planitis; Eales disease, presumed ocular histoplasmosis syndrome (POHS), Best's disease (vitelliform macular dystrophy), Stargardt disease, eye trauma and post-laser complications.

Further diseases particularly associated with corneal neovascularization that can be treated with PS-targeting antibodies such as bavituximab include all forms of keratoconjunctivitis, including keratitis (only the cornea is inflamed) and conjunctivitis (only the conjunctiva is inflamed), such as atopic keratitis, superior limbic keratitis, pterygium keratitis sicca and marginal keratolysis; phylectenulosis; Mooren ulcer; chemical burns, bacterial ulcers, fungal ulcers, Herpes infections and traumas of the eye and contact lens overwear.

Other ocular diseases that can be treated with PS-targeting antibodies such as bavituximab include scleritis, rubeosis (neovascularization of the iris), neovascularization of the angle (NVA), and diseases caused by the abnormal proliferation of fibrovascular or fibrous tissue, including all forms of proliferative vitreoretinopathy (PVR), whether or not associated with diabetes.

The formation of endothelial cell sprouts requires PS, so the development of new blood vessels also requires PS (Weihua et al., 2005). This process is also involved in certain normal physiological events, particularly wound healing and reproduction, and is important in ovulation and in the implantation of the blastula after fertilization. Prevention of this process using bavituximab can thus be used to induce amenorrhea (absence of a menstrual period in women of reproductive age), to block ovulation and/or to prevent implantation by the blastula, i.e., as a contraceptive. In wound healing, excessive repair or fibroplasia can be a detrimental side effect of surgical procedures and adhesions are a frequent complication of surgery, which can lead to problems such as small bowel obstruction. These can also be treated by PS-targeting antibodies such as bavituximab.

Chronic inflammation also involves aberrant and pathological vasculature. In particular, chronic inflammatory disease states such as ulcerative colitis and Crohn's disease show histological changes with the ingrowth of new blood vessels into the inflamed tissues. Those diseases can thus also be treated by PS-targeting antibodies such as bavituximab.

Several other diseases and disorders are known in which the host cells expose PS and/or in which PS-positive extracellular microvesicles and exosomes have been documented. For example, in sickle cell disease (also called sickle cell anemia) and crisis, 30-40% of erythrocytes are prematurely senescent and PS-positive ("sickle erythrocytes"), as opposed to only about 1% in healthy people. The PS-positive sickle erythrocytes remain in circulation, adhere to the endothelium and their exposed PS acts as a platform for the initiation of the coagulation cascade that is responsible for clot propagation (Kennedy et al., 2015).

PS is also expressed in atherosclerosis and PS-positive extracellular microvesicles are released from atherosclerotic plaques (Mallat et al., 1999). The plaques formed within the lumen of blood vessels, which are positive for PS, have also been shown to have angiogenic stimulatory activity. There is particular evidence of the pathophysiological significance of angiogenic markers, such as VEGF, in the progression of human coronary atherosclerosis, as well as in recanalization processes in obstructive coronary diseases. PS-targeting antibodies such as bavituximab thus provide an effective treatment for atherosclerosis and obstructive coronary diseases.

Both Type 1 and Type 2 diabetic patients have PS-positive extracellular microvesicles, as shown by being annexin V-positive (Sabatier et al., 2002). In Alzheimer's disease, brain exosomes contain PS and amyloid β-peptide (Aβ), the pathogenic agent of the disease (Yuyama et al., 2012). PS and PS-positive extracellular microvesicles are also involved in sepsis (septic shock), where they are markers and mediators of sepsis-induced microvascular dysfunction and immunosuppression (Souza et al., 2015).

Antiphospholipid syndrome (APS) and systemic lupus erythematosis (SLE or lupus), autoimmune disorders in which antibodies are produced against the body's own phospholipids, are associated with coagulation disorders, including miscarriages and thrombocytopenia (low platelet counts). Accordingly, the anti-phospholipid antibodies in these patients are pathogenic antibodies, which cause thrombosis. PS-targeting antibodies such as bavituximab, however, target PS without exhibiting any such side effects. Accordingly, bavituximab can also treat antiphospholipid syndrome, associated diseases and complications thereof. In particular, bavituximab can antagonize or compete with the pathogenic antibodies in APS patients, thus displacing the pathogenic antibodies from their phospholipid-protein targets in the body.

As to pathogenic infections, for example, intracellular parasites, such as the parasitic protozoan, *Leishmania amazonemis*, which causes leishmaniasis (Zandbergen et al., 2006; Wanderley et al., 2009; Wanderley et al., 2013); *Plasmodium falciparum*, which causes malaria (Eda & Sherman, 2002; Pattanapanyasat et al., 2010); and *Trypanosoma cruzi*, a parasitic protozoan that causes trypanosomiasis (DaMatta et al., 2007), all result in PS exposure. Likewise, *Schistosoma*, parasitic flatworms that cause schistosomiasis, also expose PS (van der Kleij et al., 2002), as does *Toxoplasma gondii*, which causes toxoplasmosis (Seabra et al., 2004). PS exposure has also been shown on the exterior cell surface following infection by intracellular bacterial pathogens, such as *Yersinia pestis* and *Francisella tularensis*, which cause plague and tularemia, respectively (Lonsdale et al., 2011). *Listeria monocytogenes*, which causes listeriosis, also promotes the release of membrane-derived vesicles with exofacial PS from infected host cells (Czuczman et al., 2014). Similarly, endothelial cells infected with the meningitis-causing pathogen, *Neisseria meningitidis*, exhibit PS translocation to the cell surface (Schubert-Unkmeir et al., 2007). Infection with *Mycobacterium tuberculosis*, which replicates intracellularly in macrophages and causes tuberculosis (TB), is associated with PS externalization in neutrophils in the tubercle lesion (Francis et al., 2014). Likewise, *Legionella pneumophila*, a facultative intracellular parasite that causes Legionnaires' disease, induces PS externalization in human monocytes (Hagele et al., 1998).

Thus, the PS externalization common to the facultative intracellular parasites detailed above is likely to occur for other such pathogens, such as *Brucella* and *Salmonella*, which cause brucellosis and illnesses such as typhoid fever, paratyphoid fever and food poisoning, respectively. This has also been documented for infection by obligate intracellular parasites, such as *Chlamydia* spp., which cause sexually transmitted *chlamydia* infections, in which PS externalization is important to pathogenesis and has been shown on infected epithelial, endothelial, granulocytic and monocytic cells (Goth & Stephens, 2001). *Chlamydia trachomatis* can also be treated, which causes trachoma (also see above).

Indeed, PS externalization on host cells is now a generally recognized phenomenon in response to infection with a range of bacteria and pathogens (Wandler et al., 2010). This further includes *Helicobacter pylori*, which invades gastric epithelial cells (Petersen & Krogfelt, 2003) and causes stomach ulcers. When *H. pylori* has direct contact with gastric epithelial cells, it induces externalization of PS to the outer leaflet of the host plasma membrane (Murata-Kamiya et al., 2010). PS is also present on *Treponema pallidum*, which causes syphilis. Bartonellosis, a bacterial infection found in South America, can be treated with bavituximab, particularly because bartonellosis results in a chronic stage that is characterized by proliferation of vascular endothelial cells, and one of bavituximab's mechanisms of action, as clearly shown in cancer treatment, is to destroy vascular endothelial cells.

With reference to in vivo diagnostics, PS-targeting antibodies such as bavituximab may be used for imaging any of the foregoing diseases, disorders and infections, most preferably, for imaging vascularized tumors (Jennewein et al., 2008; Marconescu & Thorpe, 2008; Saha et al., 2010; Stafford & Thorpe, 2011; Gong et al., 2013; Stafford et al., 2013; U.S. Pat. No. 7,790,860). Bavituximab may also be used for imaging vascular thromboses, particularly in or near the heart, such as in deep vein thrombosis, pulmonary embolism, myocardial infarction, atrial fibrillation, problems with prosthetic cardiovascular materials, stroke (cerebrovascular accident (CVA) or cerebrovascular insult (CVI)), and the like. PS-targeting antibodies such as bavituximab may also be used in imaging activated platelets, e.g., in conditions such as abscesses, restenosis, inflammation of joints and in hemostatic disorders, such as arterial, coronary, venous and cerebral thrombosis and such like.

PS-targeting antibodies such as bavituximab are thus suitable for treating and/or diagnosing all the above diseases and disorders, in which PS is a documented marker.

K. Treating Viral Infections

Prominent pathogens that cause the host cell to externalize PS are viruses. The presence of PS has been demonstrated on the surface of viruses and virally-infected cells from a wide range of viral families, as set forth in Table B1 and Table B2. In addition, data are presented in Table B3 and Table B4 to demonstrate that such PS exposure on viruses and virally-infected cells is not merely incidental, but has an important role in viral infections (see also, U.S. Pat. No. 7,906,115; WO 2015/131153 A1). This is shown by the use of PS-targeting antibodies to inhibit infections from diverse viral families, both in vitro and in vivo.

TABLE B1

PS Expression and Importance Across Diverse Viral Families - Viruses

| Virus Family | Virus | Model For | Method | PS+ve |
| --- | --- | --- | --- | --- |
| Arenaviridae | Pichinde virus | Lassa Fever | Flow Cytometry ELISA | YES |
| | Junin virus Candid #1 | Hemorrhagic fever | Bead depletion ELISA Immunogold label | YES |
| Bunyaviridae | Punta Toro Virus | River Valley Fever Virus | ELISA | YES |
| Flaviviridae | Bovine viral diarrhea virus | Hepatitis C | RT-PCR | YES |
| Filoviridae | Ebola Zaire Virus (strain ME718) | Ebola | ELISA | YES |
| Herpesviridae | Varicella-zoster virus 1 | Shingles | PCR | YES |
| Orthomyxoviridae | Influenza A | Influenza | QRT-PCR | YES |
| | Influenza B | Influenza | RT-PCR | YES |
| | Avian Influenza (H5N1) | Influenza | RT-PCR | YES |
| Paramyxoviridae | Bovine parainfluenza 3 | Influenza | RT-PCR | YES |
| | Measles | Measles | RT-PCR | YES |
| | Respiratory syncitial virus (RSV) | Pneumonia | RT-PCR | YES |
| Retroviridae | Feline immunodeficiency virus (FIV) | AIDS | RT-PCR | YES |
| | Human immunodeficiency virus 1 (HIV-1) | AIDS | ELISA | YES |
| | Human immunodeficiency virus 2 (HIV-2) | AIDS | ELISA | YES |

TABLE B2

PS Expression and Importance Across Diverse Viral Families - Infected Cells

| Virus Family | Virus and Cells | Model For | Method | PS+ve |
| --- | --- | --- | --- | --- |
| Arenaviridae | P388D1 cells; Pichinde | Lassa Fever | FACS Analyses | YES |
| | Vero cells; Junin Virus Candid #1 | Hemorrhagic fever | Immunofluorescence Microscopy | YES |
| Bunyaviridae | RAW 264.7 cells; Punta Toro Virus | River Valley Fever Virus | FACS Analyses | YES |
| Flaviviridae | Vero cells; Yellow Fever Virus | Yellow Fever | FACS Analyses | YES |
| | Raji cells; Dengue Virus type 1 and 3 | Dengue Fever | FACS Analyses | YES |
| Filoviridae | Vero cells; Ebola Zaire Virus (strain ME718) | Ebola | FACS Analyses | YES |
| Herpesviridae | Human primary foreskin fibroblasts; human CMV | Pneumonia | FACS Analyses | YES |
| | Mouse cells infected with mouse CMV | pneumonia | FACS Analyses | YES |
| Orthomyxoviridae | U937 cells; Influenza | Influenza | FACS Analyses | YES |
| Poxviridae | U937 cells; Vaccinia | Smallpox | FACS Analyses | YES |
| Retroviridae | H9 T cells; HIV-1 | AIDS | FACS Analyses | YES |

TABLE B3

PS Expression and Importance Across Diverse Viral Families - PS-targeting Abs In Vitro

| Virus Family | In Vitro Infection | Model For | Agent | Inhibition |
|---|---|---|---|---|
| Arenaviridae | P388D1 cells; Pichinde | Lassa Fever | PS-targeting Abs | YES |
| | Guinea pig splenocytes; Pichinde | Lassa Fever | PS-targeting Abs | YES |
| | Vero cells; Pichinde | Lassa Fever | PS-targeting Abs | YES |
| Herpesviridae | HHF-R2 cells; human CMV | Pneumonia | PS-targeting Abs | YES |
| Paramyxoviridae | A549 cells; respectively | Pneumonia | PS-targeting Abs | YES |
| Retroviridae | PBMCs; HIV-1 | AIDS | PS-targeting Abs | YES |
| Rhabdoviridae | HHF-R2 cells; vesicular stomatitis virus (VSV) | Respiratory Disease | PS-targeting Abs | YES |

TABLE B4

PS Expression and Importance Across Diverse Viral Families: PS-targeting Abs In Vivo

| Virus Family | In Vivo Infection | Model/Disease | Inhibition and Comments |
|---|---|---|---|
| Arenaviridae | Guinea pigs; lethal dose of Pichinde | Lassa Fever | YES; 50% survival vs. 0% control |
| | Guinea pigs; lethal Pichinde, after symptoms develop | Lassa Fever | YES 50% survival vs. 0% control |
| | Surviving guinea pigs re-challenged with lethal Pichinde | Lassa Fever | YES 100% survival |
| | Guinea pigs; lethal Pichinde, combo with ribavirin | Lassa Fever | YES Additive anti-viral effect |
| | Hamsters - Pichinde | Lassa Fever | YES 30% survival vs. 5% control |
| Flaviviridae | Human Patients; Hepatitis C virus (HCV) | Hepatitis C | YES Dose-dependent reduced viral load |
| Herpesviridae | BALB/c mice; $LD_{80}$ mCMV | Pneumonia | YES 100% survival vs. 21% control |
| | SCID mice; $LD_{80}$ mCMV | Pneumonia | YES 67% survival vs. 17% control |
| | Rabbits; ocular HSV-1 | Herpetic keratitis | YES Equal or better than standard of care (ganciclovir) |
| Orthomyxoviridae | Ferrets; low pathogenic influenza | Influenza | YES Reduced lung pathology |
| Rhabdoviridae | Mice; non-lethal VSV | Respiratory Disease | YES Significantly lower viral titers |

The connection between PS and viral infections is also now well documented in the literature (e.g., U.S. Pat. No. 7,906,115; Soares et al., 2008; Mercer and Helenius, 2008; Moody et al., 2010; Morizono et al., 2011; Meertens et al., 2012; Best, 2013; Bhattacharyya et al., 2013; Jemielity et al., 2013; Moller-Tank & Maury, 2014; Birge et al., 2016). This includes the role of PS and PS receptors as enhancers of enveloped virus entry and infection (see, e.g., Table 1 in Moller-Tank & Maury, 2014). The relationship between PS, viral infections and extracellular microvesicles such as exosomes has also become increasingly apparent in recent years (Meckes & Raab-Traub, 2011; Sims et al., 2014), and again applies to a wide range of viruses (e.g., Walker et al., 2009; Meckes et al., 2010; Izquierdo-Useros et al., 2010; Meckes & Raab-Traub, 2011).

Moreover, the connection between PS and viruses is not limited to enveloped viruses, but extends to non-enveloped viruses (Clayson et al., 1989; Chen et al., 2015). In particular, see the Figure on the cover page of the Cell article by Chen et al., 2015, which shows "PS lipid vesicles" and accompanies data showing that PS vesicles enable efficient en bloc transmission of enteroviruses. While not being bound by the particular mechanisms, the following rationale explains that PS is involved in infections from both enveloped and non-enveloped viruses.

All viruses orchestrate a timed exit of mature virions from the host cell to ensure successful infection of a new host cell. Enveloped viruses utilize the host cell plasma membrane to embed viral proteins that mediate efficient entry of the progeny virions with the next host cell. PS is found on the exterior of virus infected cells prior to virus release and enveloped viruses incorporate PS into the viral envelope upon exiting the host cell.

Viruses that do not incorporate an envelope into their mature virion leave the host cell by other mechanisms. Some strategies non-enveloped viruses use to release new virions from the cell include lysis of the cell, which can be caused directly by the host immune response to the infected cells (T cells or macrophages), or due to the activity of virus directly on host cell protein synthesis or cellular structures. An example of a virus alters the cell structure to induce cell lysis is Adenovirus. Adenovirus expresses several proteins late during infection that alter the structural integrity of the cell by disrupting filament networks and protein synthesis. Some non-enveloped viruses are able to release their progeny viruses via a nondestructive mechanism without any cytopathic effect. While poliovirus induces cell lysis rapidly (about 8 hours), it is also released from cells in PS lipid vesicles that are capable of infecting new host cells. Poliovirus particles in PS-vesicles are more efficient in infecting HeLa cells and primary macrophages than virus particles removed from PS-vesicles and blocking the vesicles with Annexin V inhibited the vesicles from infected cells in a dose dependent manner, suggesting the PS lipids are cofactors for poliovirus infection. In addition to poliovirus, Coxsackievirus B3 and Rhinovirus particles are also released into PS lipid vesicles (Chen et al., 2015), indicating a common mechanism utilized by enteroviruses to selectively release mature particles without lysis of the cell.

In regard to SV40, it is likely that SV40 is also released from cells in the above types of PS-lipid vesicles. For example, it has been reported that SV40 particles can be found released from cells before induction of cytopathic effects (Clayson et al., 1989). Also, SV40 virions have been observed in cytoplasmic smooth vesicles at 48 hour post infection and the release of SV40 particles was inhibited by monensin, a sodium ionophore that blocks intracellular protein transport by blocking cation transport across lipid membranes. Other examples of polyomaviruses, the family of viruses to which SV40 belongs, include JC virus, BK virus, and Merkel cell carcinoma virus (MCV).

Also, many viruses need to induce activation of the host cell in order to create the environment in which to replicate efficiently. Cell activation by either viral or non-viral activating agents leads to rises in intracellular calcium ($Ca^{2+}$) that activates PS translocation. Potential mechanisms of action of PS-targeting antibodies such as bavituximab thus include interference with proteins needed in cell activation or their ability to mediate viral egress, reversing the PS-mediated immunosuppression and clearance of infected cells or the virus by immune clearance mechanisms.

In vivo viral models demonstrate increased survival of virally-infected animals treated with PS-targeting antibodies. The potential mechanisms by which PS-targeting antibodies such as bavituximab have been shown to exert such anti-viral properties include: 1) binding to viral particles; 2) binding to infected cells; 3) inhibition of viral replication; and 4) enhancement of immune responses by blocking the immunosuppressive cell receptors that bind PS. Data in an HIV-1 model demonstrate that virions produced by virally infected macrophages have elevated levels of PS which serve as a cofactor for HIV-1 infection of macrophages. Blocking PS on HIV-1 with PS-targeting antibodies may prevent cell-cell interactions and block virus-target cell fusion. Results also indicate that bavituximab binds to pichinde viral particles and treatment of pichinde virus-infected guinea pigs enhances development of both of anti pichinde antibodies and cellular responses.

Overall, the treatment of all viral infections, including enveloped and non-enveloped viruses, using PS-targeting antibodies such as bavituximab is taught in U.S. Pat. Nos. 7,611,704 and 7,906,115, which are both specifically incorporated herein by reference for supplementing the present disclosure concerning such treatments. In particular, Table H, Table J and Table G of those patents are specifically incorporated to exemplify the treatment of viral infections and associated diseases in animals and humans (Table H, Table J), along with common anti-viral drugs that may be used in combination therapies with PS-targeting antibodies such as bavituximab (Table G).

L. Treating Cancer

Extensive sections of the present application concern treating tumors and cancer using PS-targeting antibody molecules, such as bavituximab, e.g., in combination with immune checkpoint antibody molecules. The treatment of benign tumors is included, such as acoustic neuroma, neurofibroma, trachoma, pyogenic granulomas and BPH. The treatment of malignant tumors is preferred. As used herein, "tumor, tumors, cancer and cancers" are generally intended to indicate malignancy, unless expressly stated otherwise.

The treatment of blood-born tumors, such as leukemias and lymphomas, and various acute or chronic neoplastic diseases of the bone marrow is encompassed. Preferably, the tumors to be treated are solid or vascularized tumors, including tumors in which angiogenesis is active and tumors having prothrombotic blood vessels. "Solid" and "vascularized" tumors are tumors having a vascular component, i.e., which require tumor blood vessels for the provision of oxygen and nutrients to the tumor cells.

All cancers are included, whether primary or metastatic, as exemplified by breast, ovarian, thoracic, lung, liver (hepatocellular carcinoma, HCC), colon, colorectal, rectal, prostate, pancreatic, brain (gliomas and glioblastomas), cervical, uterine, endometrial, head and neck, parotid, esophageal, gastroesophageal, larynx, thyroid, gastrointestinal, stomach, kidney (renal cell carcinoma, RCC), biliary tract, bladder, testicular and other cancers, including carcinomas (squamous and non-squamous, small cell and non-small cell), adenocarcinomas and neuroblastomas, as well as melanoma, merkel cell carcinoma and hematological malignancies. In certain embodiments, the invention particularly applies to non-small cell lung cancer (NSCLC) or to breast, pancreatic, liver, kidney, rectal or ovarian cancer or melanoma. Most particularly, the invention applies to NSCLC such as non-squamous NSCLC.

In addition to published literature, the treatment of all cancers using PS-targeting antibodies such as bavituximab is taught in a number of U.S. patents. For example, U.S. Pat. Nos. 6,406,693; 7,422,738; 8,486,391; 7,247,303; and 7,572,448, all of which are specifically incorporated herein by reference for supplementing the present disclosure concerning such treatments. See also, the above discussion regarding therapeutically effective anti-cancer amounts (Section 12). As the modes of action of PS-targeting antibodies such as bavituximab are substantially or entirely the same in all solid tumors, it will be understood that the present invention is widely applicable to the treatment of all solid tumors, irrespective of the particular phenotype or genotype of the tumor cells themselves.

M. Combination Therapies

Considerable sections of the present application, published literature and a number of U.S. patents also concern treating cancer using PS-targeting antibodies, such as bavituximab, in combination therapies (e.g., U.S. Pat. Nos. 7,422,738; 8,486,391; 7,572,448).

The treatment methods may thus be combined with any other methods generally employed in the treatment of the particular disease or disorder that the animal or patient exhibits, particularly cancer and viral infections and diseases. So long as a given therapeutic approach is not known to be detrimental to the patient's condition in itself, and does not significantly counteract the PS-targeting antibody therapy, its combination with the present invention is contemplated. Combination therapies for non-malignant diseases are also contemplated.

In connection cancer treatment, the present invention may be used in combination with classical approaches, such as surgery, chemotherapy, radiotherapy, cytokine therapy, anti-angiogenesis and the like, and newer approaches such as immuno-oncology (IO) agents. The invention therefore provides combined therapies in which the PS-targeting antibodies such as bavituximab are used simultaneously with, before, or after surgery or radiation treatment; or are administered to patients with, before, or after conventional chemotherapeutic or radiotherapeutic agents, cytokines, anti-angiogenic agents, apoptosis-inducing agents, targeted therapies, IO agents or such like.

In terms of surgery, any surgical intervention may be practiced in combination with the present invention. In connection with radiotherapy, any mechanism for inducing DNA damage locally within tumor cells is contemplated, such as γ-irradiation, X-rays, UV-irradiation, microwaves and even electronic emissions and the like. The directed delivery of radioisotopes to tumor cells is also contemplated, and this may be used in connection with a targeting antibody or other targeting means.

The general use of combinations of substances in cancer treatment is well known. When one or more agents are used in combination with PS-targeting antibodies such as bavituximab, there is no requirement for the combined results to be additive of the effects observed when each treatment is conducted separately. Although at least additive effects are generally desirable, any increased therapeutic effect or benefit (e.g., reduced side-effects) above one of the single therapies would be of value. Also, there is no particular requirement for the combined treatment to exhibit synergistic effects, although this is possible and advantageous.

The "primary therapeutic agents" or "first anti-cancer agents" of the present invention, as used herein, are the PS-targeting antibodies such as bavituximab. The "secondary therapeutic agents" or "at least a second anti-cancer agent", as used herein, are second, distinct therapeutic agents, anti-cancer agents, including immuno-oncology (IO) agents, or anti-viral agents, i.e., therapeutic agents, anti-cancer agents, including immuno-oncology (IO) agents, or anti-viral agents "other than" the primary therapeutic agent. Any secondary therapeutic agent may be used in the combination therapies of the present invention. Also, secondary therapeutic agents, "second anti-cancer agents" or "second anti-viral agents" may be selected with a view to achieving additive, greater than additive and potentially synergistic effects, according to the guidance in the present application and the knowledge of those of skill in the art.

To practice combined therapy, anti-tumor therapy or anti-viral therapy, one would simply administer to an animal or patient a PS-targeting antibody such as bavituximab in combination with another, i.e., a second, distinct therapeutic agent, anti-cancer or anti-viral agent, in a manner effective to result in their combined therapeutic, anti-tumor or anti-viral actions within the animal or patient. The agents would therefore be provided in amounts effective and for periods of time effective to result in their combined presence within the disease site, e.g., the tumor, tumor environment or microenvironment, and/or to exert their combined therapeutic actions in the animal or patient, preferably, to exert their combined therapeutic actions on the immune system of the animal or patient. To achieve this goal, the primary therapeutic agent and the second, distinct therapeutic agent may be administered substantially simultaneously, either in a single composition, or as two distinct compositions using different administration routes.

Alternatively, the PS-targeting antibody such as bavituximab may precede, or follow, the second, distinct therapeutic agent, anti-cancer or anti-viral agent by, e.g., intervals ranging from minutes to weeks. In certain embodiments where the primary therapeutic agent and the second, distinct therapeutic agent are applied separately to the animal or patient, one would ensure that an inoperative period of time did not exist between the time of each delivery, such that each agent would still be able to exert an advantageously combined effect. From standard practice, including the clinical experience to date with bavituximab, one or two weeks is not an inoperative period of time between administering bavituximab and a second, distinct therapeutic agent. Indeed, an interval of about one week may be preferred. Three, four, five, or six-week delivery intervals between delivery of bavituximab and a second distinct therapeutic agent, such as an immuno-oncology (IO) agent, may also exert an advantageous effect and may be used in combination therapy.

The secondary therapeutic agents for separately timed combination therapies may be selected based upon certain criteria, including those discussed herein and known in the art. However, a preference for selecting one or more second, distinct therapeutic agents for prior or subsequent administration does not preclude their use in substantially simultaneous administration if desired.

In terms of cancer, second, distinct anti-cancer agents selected for administration "prior to" the primary therapeutic agents, and designed to achieve increased and potentially synergistic effects, include agents that induce the expression of PS in the tumor microenvironment. For example, agents that stimulate localized calcium production, activate membrane transporters that move PS to the outer surface of the plasma membrane, injure the tumor endothelium, cause preapoptotic changes and/or induce apoptosis in the tumor endothelium or tumor cells will generally result in increased PS expression. Examples of such agents are docetaxel and paclitaxel. The PS can then be targeted using the PS-targeting antibody such as bavituximab, thus amplifying the overall therapeutic effect, and also giving increased attack via host effectors (complement, ADCC, antibody-mediated phagocytosis, CDC).

Drugs that have selectivity for angiogenic, remodeling or activated endothelial cells, such as are present in tumor blood vessels, but not in normal resting blood vessels, can also be used to selectively causes exposure of PS in the tumor microenvironment. Examples of such agents are combretastatins and docetaxel. This again would lead to increased antibody binding and enhanced initiation of host effector mechanisms.

Second, distinct anti-cancer agents selected for administration "subsequent to" the primary therapeutic agents, and designed to achieve increased and potentially synergistic effects, include agents that benefit from the effects of the primary therapeutic agent. PS-targeting antibodies such as bavituximab cause tumor necrosis. Accordingly, effective second, distinct anti-cancer agents for subsequent administration include anti-angiogenic agents, which inhibit metastasis; agents targeting necrotic tumor cells, such as antibodies specific for intracellular antigens that become accessible from malignant cells in vivo (U.S. Pat. Nos. 5,019,368; 4,861,581 and 5,882,626); and chemotherapeutic agents and anti-tumor cell immunoconjugates, which attack any tumor cells that may survive at the periphery.

In some situations, it may be desirable to extend the time period for treatment significantly, where several days (2, 3, 4, 5, 6 or 7), several weeks (1, 2, 3, 4, 5, 6, 7 or 8) or even several months (1, 2, 3, 4, 5, 6, 7 or 8) lapse between the respective administrations. This would be advantageous in circumstances where one treatment was intended to substantially destroy the tumor, and another treatment was intended to prevent micrometastasis or tumor re-growth, such as the administration of an anti-angiogenic agent. Anti-angiogenics should be administered at a careful time after surgery, however, to allow effective wound healing. Anti-angiogenic agents may then be administered for the lifetime of the patient.

It is also envisioned that more than one administration of either the primary therapeutic agent or the second, distinct therapeutic agent will be utilized. The primary therapeutic agent and the second, distinct therapeutic may be administered interchangeably, on alternate days or weeks; or a sequence of one agent treatment may be given, followed by a sequence of the other treatment. In any event, to achieve a therapeutic effect using a combined therapy, all that is required is to deliver both agents in a combined amount effective to exert a therapeutic effect, irrespective of the times for administration.

M1. Chemotherapy

Whether administered substantially simultaneously or sequentially, the PS-targeting antibodies such as bavituximab may be administered in combination with one or more chemotherapeutic agents or drugs. Chemotherapeutic drugs can kill proliferating tumor cells, enhancing the necrotic areas created by the overall treatment. The drugs can thus enhance the action of the primary therapeutic agents of the invention.

Most cancer chemotherapeutic drugs are selective for dividing, oxygenated cells. These have advantages in combined therapy as the chemotherapeutic drug acts on different targets from the primary therapeutic agents, leading to a more complete anti-tumor effect. For example, chemotherapeutic drugs are selectively active against the rapidly dividing, oxygenated tumor cells in the tumor periphery. Anti-angiogenic drugs that are selective for well-oxygenated, angiogenic vessels in the tumor periphery would also be effective in combination.

By inducing the formation of thrombi in tumor vessels, the primary therapeutic agents of the present invention can also enhance the action of the chemotherapeutic drugs by retaining or trapping the drugs within the tumor. The chemotherapeutics are thus retained within the tumor, while the rest of the drug is cleared from the body. Tumor cells are thus exposed to a higher concentration of drug for a longer period of time. This entrapment of drug within the tumor makes it possible to reduce the dose of drug, making the treatment safer as well as more effective.

Further drugs for combined use in the present invention are those that act on cells that are "sensitized" to the drug by the action of the primary therapeutic agent, such that reduced doses of the second drug are needed to achieve its anti-tumor effect. For example, this could occur where a major component of the second drug's action is exerted on tumor blood vessels and the antibodies or agents of the invention sensitize the cells to the drug. The same is true where the primary therapeutic agent of the invention sensitizes tumor cells to a second drug, either directly or through stimulation of cytokine release.

Other suitable second anti-cancer agents for combination therapy are those that enhance the activity of host effector cells, e.g., by selectively inhibiting the activity of immunosuppressive components of the immune system. Such agents enable the primary therapeutic agents of the invention, which stimulate attack by effector cells as part of their mechanism, to work more aggressively. An example of such an agent is docetaxel.

Other preferred anti-cancer agents include the TGFβR1 Kinase Inhibitor IILY3200882, lenvantinib (active against the VEGFR1, VEGFR2, and VEGFR3 kinases), and merestinib (a small molecule inhibitor of MET and several other receptor tyrosine kinases such as MST1R, FLT3, AXL, MERTK, TEK, ROS1, NTRK1/2/3, and DDR1/2).

Although an understanding of the precise mechanism(s) of action of the primary therapeutic agents is not necessary to practice the treatment of the invention, data and reasoned deductions concerning such mechanisms can be used to select particular second anti-cancer agents for combined use in the present invention. The effectiveness of the chosen combination therapy, in turn, supports the original data and proposed mechanisms of action, and also leads to preferred categories of second anti-cancer agents for practicing combination therapy.

Drugs that induce apoptosis are preferred for use in the combination therapies. Docetaxel, for example, induces apoptosis and therefore PS exposure by binding to microtubules and disrupting cell mitosis (Hotchkiss et al., 2002). Treatment of endothelial cells, which line tumor blood vessels, and tumor cells with docetaxel at subclinical concentrations is known to induce PS expression at the cell surface.

The anti-tumor effects of PS-targeting antibodies such as bavituximab include Fc domain-mediated augmentation of immune effector functions, such as ADCC, CDC, stimulation of cytokine production, and such mechanisms in combination. This is also relevant to docetaxel, as other studies have shown that the treatment of breast cancer patients with docetaxel leads to increases in serum IFNγ, IL-2, IL-6 and GM-CSF cytokine levels, augmenting the anti-tumor immune responses in these patients by enhancing the activity of natural killer (NK) and lymphokine activated killer (LAK) cells.

Therefore, docetaxel will both induce PS expression and binding of the administered antibody, and also enhance the activities of immune effectors, which mediate anti-tumor effects. Based upon the foregoing considerations, combination of the antibodies with docetaxel is a preferred embodiment.

Accordingly, docetaxel and other chemotherapeutic agents that induce apoptosis are preferred agents for use in the combination treatments of the present invention. Combinations with chemotherapeutics drugs that induce apoptosis, such as docetaxel, should synergistically attack tumor vasculature endothelial cell and tumor cell compartments, leading to not only significantly enhanced treatment efficacy but also lower toxicity. These combinations are contemplated for use in breast cancer treatment, particularly the combination of metronomic chemotherapy using docetaxel with an antibody of the present invention.

Exemplary chemotherapeutic agents for combined therapy are listed in Table C. Each of the agents listed are exemplary and not limiting. Variation in dosage can occur depending on the condition treated. The treating physician will be able to determine the appropriate dose for the individual subject. In certain preferred embodiments docetaxel is used, such as docetaxel administered at a starting dose of 60 mg/m$^2$ or docetaxel administered to a patient in an amount of 75 mg/m$^2$.

TABLE C

Exemplary Chemotherapeutic Agents for Combination Therapies

| CLASS | TYPE OF AGENT | EXAMPLES | DISEASE |
|---|---|---|---|
| Alkylating Agents | Nitrogen Mustards | Mechlorethamine (chlormethine, mustine, nitrogen mustard, $HN_2$) Mustargen ® | Hodgkin's disease, non-Hodgkin's lymphomas |
| | | Cyclophosphamide (cytophosphane) Cytoxan ®, Neosar ®, Revimmune ® | Acute and chronic lymphocytic leukemias, Hodgkin's disease, non-Hodgkin's lymphomas, multiple myeloma, neuroblastoma, breast, ovary, lung, Wilms' tumor, cervix, testis, soft-tissue sarcomas |
| | | Ifosfamide Mitoxana ®, Ifex ® | Non-Hodgkin's lymphomas, soft tissue sarcoma, osteogenic sarcoma, testicular, breast, lung, cervical, ovarian, bone |
| | | Melphalan (L-sarcolysin) Alkeran ® | Multiple myeloma, breast, ovary, melanoma |
| | | Chlorambucil Leukeran ® | Chronic lymphocytic leukemia, primary macroglobulinemia, Hodgkin's disease, non-Hodgkin's lymphomas, ovarian |
| | Ethylenimenes and Methylmelamines | Hexamethylmelamine (Altretamine, HMM) Hexalen ® | Ovary |
| | | ThioTEPA | Bladder, breast, ovary |
| | Alkyl Sulfonates | Busulfan Myleran ®, Busulfex ® | Chronic granulocytic leukemia |
| | Nitrosoureas | Carmustine BiCNU ® | Hodgkin's disease, non-Hodgkin's lymphomas, primary brain tumors, multiple myeloma, malignant melanoma, glioma, glioblastoma multiforme, medulloblastoma, astrocytoma |
| | | Lomustine (CCNU) CeeNU ® | Hodgkin's disease, non-Hodgkin's lymphomas, primary brain tumors, small-cell lung |
| | | Semustine (methyl-CCNU) | Primary brain tumors, stomach, colon |
| | | Streptozocin (streptozotocin) Zanosar ® | Malignant pancreatic insulinoma, malignant carcinoid |
| | Triazines | Dacarbazine (dimethyltriazeno-imidazole-carboxamide, imidazole carboxamide) DTIC ®, DTIC-Dome ® | Malignant melanoma, Hodgkin's disease, soft-tissue sarcomas, malignant pancreatic insulinoma |
| | | Temozolomide Temodar ®, Temodal ® | Astrocytoma |
| | Methyl Hydrazine Derivative | Procarbazine (N-methylhydrazine, MIH) Matulane ®, Natulan ®, Indicarb ® | Hodgkin's disease, glioblastoma multiforme |
| | Folic Acid Analogs Folate antimetabolites | Methotrexate (amethopterin) | Acute lymphocytic leukemia, choriocarcinoma, mycosis fungoides, breast, head and neck, lung, osteogenic sarcoma, glioblastoma |
| | | Aminopterin | Leukemia |
| | | Pemetrexed Alimta ® | pleural mesothelioma, non-small cell lung cancer, esophageal |

TABLE C-continued

Exemplary Chemotherapeutic Agents for Combination Therapies

| CLASS | TYPE OF AGENT | EXAMPLES | DISEASE |
|---|---|---|---|
| Anti-metabolites | | Raltitrexed Tomudex ® | Colorectal |
| | Pyrimidine Analogs | Fluorouracil (5-fluorouracil, 5-FU, fluouracil, fluorodeoxyuridine) Efudex ®, Carac ®, Fluoroplex ® Floxuridine (prodrug) FUDR ® Doxifluridine | Breast, colon, stomach, pancreas, ovary, head and neck, urinary bladder, premalignant skin lesions (topical) |
| | | Cytarabine (cytosine arabinoside, ara C) Cytosar-U ®, Tarabine PFS ®, Depocyt ® Capecitabine (prodrug) Xeloda ® Azacitidine | Acute granulocytic and acute lymphocytic leukemias, non-Hodgkin's lymphoma |
| | | Gemcitabine Gemzar ® | Pancreatic, bladder, breast, oesophageal and non-small cell lung cancers, lymphomas |
| | Purine Analogs and Related Inhibitors | Thioguanine (tioguanine, 6-thioguanine; TG) | Acute granulocytic, acute lymphocytic, chronic granulocytic and chronic myeloid leukemias |
| | | Pentostatin (2-deoxycoformycin) | Hairy cell leukemia, mycosis fungoides, chronic lymphocytic leukemia |
| | | Mercaptopurine (6-mercaptopurine, 6-MP) Purinethol ® | Acute lymphocytic, acute granulocytic and chronic granulocytic leukemias, non-Hodgkin's lymphoma |
| | | Cladribine (2CDA) Leustatin ® | Hairy cell leukemia, Bcell leukemias, lymphomas |
| | | Clofarabine Clolar ®, Evoltra ® | Acute lymphoblastic leukaemia, acute myeloid leukaemia, juvenile myelomonocytic leukaemia |
| | | Fludarabine (fludarabine phosphate) Fludara ® | Hematological malignancies |
| | Vinca Alkaloids | Vinblastine (VLB) | Hodgkin's disease, non-Hodgkin's lymphomas, breast, testis, non-small cell lung cancer |
| | | Vincristine Oncovin ® | Acute lymphocytic leukemia, neuroblastoma, Wilms' tumor (nephroblastoma), rhabdomyosarcoma, Hodgkin's disease, non-Hodgkin's lymphomas, small-cell lung |
| | | Vindescine Eldisine ® | Leukaemia, lymphoma, melanoma, breast, lung |
| | | Vinorelbine Navelbine ® | Breast, non-small cell lung |
| | Podophyllotoxins Epipodo-phyllotoxins Inhibitors of Topoisomerase II | Etoposide (etoposide phosphate) Eposin ®, Etopophos ®, Vepesid ®, VP-16 ® | Testis, small-cell lung and other lung, breast, Hodgkin's disease, non-Hodgkin's lymphomas, acute granulocytic leukemia, Kaposi's sarcoma, glioblastoma multiforme |
| | | Teniposide Vumon ®, VM-26 ® | Acute lymphocytic leukemia |
| | Anthracycline | Daunorubicin (daunomycin, rubidomycin) Cerubidine ® | Acute granulocytic and acute lymphocytic leukemias, neuroblastoma |
| | | Doxorubicin (hydroxy-daunorubicin, adriamycin) Rubex ®, Doxil ® | Soft-tissue, osteogenic and other sarcomas; Hodgkin's disease, non-Hodgkin's lymphomas, acute leukemias; breast, genitourinary, thyroid, lung, stomach, ovarian, thyroid, bladder, neuroblastoma, multiple myeloma |

TABLE C-continued

Exemplary Chemotherapeutic Agents for Combination Therapies

| CLASS | TYPE OF AGENT | EXAMPLES | DISEASE |
|---|---|---|---|
| Natural Products | Antibiotics (Anthracyclines) | Epirubicin Ellence ®, Pharmorubicin ®, Ebewe ® | Breast, ovarian, gastric, lung; lymphomas |
| | | Idarubicin (4-demethoxy-daunorubicin) Zavedos ® Idamycin ® | Acute myeloid leukemia |
| | | Valrubicin (N-trifluoro-acetyl-adriamycin-14-valerate) Valstar ® | Bladder |
| | Anthracenedione | Mitoxantrone | Acute granulocytic leukemia, breast, non-Hodgkin's lymphoma |
| | | Pixantrone | Breast, non-Hodgkin's lymphoma |
| | Polypeptide and peptide Antibiotics | Bleomycin Blenoxane ® | Testis, head and neck, skin, esophagus, lung and genitourinary tract; Hodgkin's disease, non-Hodgkin's lymphomas, squamous cell carcinomas |
| | | Actinomycin-D Dactinomycin ® | Choriocarcinoma, Wilms' tumor, rhabdomyosarcoma, testis, Kaposi's sarcoma |
| | | Plicamycin (mithramycin) Mithracin ® | Testis, malignant hypercalcemia |
| | | Mitomycin (mitomycin C) | Stomach, cervix, colon, breast, pancreas, bladder, head and neck, esophageal |
| | Enzymes | L-Asparaginase Elspar ® | Acute lymphocytic leukemia, mast cell tumors |
| | Biological Response Modifiers | Interferon alpha (IFNα) Pegylated interferons Multiferon ®, Roferon ®, Pegasys ®, IntronA ®, PegIntron ® | Hairy cell leukemia, Kaposi's sarcoma, melanoma, carcinoid, renal cell, ovary, bladder, non-Hodgkin's lymphomas, mycosis fungoides, multiple myeloma, chronic granulocytic leukemia |
| Other Agents | Retinoids | Tretinoin | Promyelocytic leukemia |
| | | Alitretinoin | Kaposi's sarcoma |
| | | Bexarotene Targretin ® | Cutaneous T cell lymphoma |
| | Adrenocortical | Mitotane (o,p'-DDD) Lysodren ® | Adrenal cortex |
| | Steroid Suppressant | Aminoglutethimide Cytadren ® | Breast |
| | Tyrosine Kinase Inhibitors | Axitinib | Breast, renal cell carcinoma, pancreas |
| | | Dasatinib (BMS-354825) Sprycel ® | Chronic myelogenous leukemia, acute lymphoblastic leukemia, metastatic melanoma |
| | | Erlotinib (OSI-774) Tarceva ® | Non-small cell lung cancer, pancreatic |
| | | Gefitinib (ZD1839) Iressa ® | Non-small cell lung cancer |
| | | Imatinib (CGP57148 B or STI-571) Gleevec ®, Glivec ® | Chronic myelogenous leukemia, gastrointestinal |
| | | Lapatinib (GW572016) Tykerb ®, Tyverb ® | Breast |
| | | Sorafenib Nexavar ® | Renal cell carcinoma, hepatocellular carcinoma |
| | | Lenvatinib LENVIMA ® | Renal cell carcinoma, radioactive iodine-refractory differentiated thyroid cancer (RAI-refractory DTC) |
| | | Merestinib (LY2801653) | AML, NSCLC, solid tumors, |
| | | LY3200882 | Advanced or metastatic cancers |
| | | Sunitinib (SU11248) Sutent ® | Renal cell carcinoma, gastrointestinal, non-small cell lung cancer, breast |

TABLE C-continued

Exemplary Chemotherapeutic Agents for Combination Therapies

| CLASS | TYPE OF AGENT | EXAMPLES | DISEASE |
|---|---|---|---|
| | | Vemurafenib Zelboraf ® | Late-stage melanoma |
| | | Vismodegib Erivedge ® | Basal-cell carcinoma (BCC) |
| Monoclonal Antibodies | Receptor tyrosine kinase antibodies | Cetuximab (anti-EGFR) Erbitux ® | Colorectal, head and neck |
| | | Panitumumab (anti-EGFR) Vectibix ® | Colorectal |
| | | Trastuzumab (anti-HER2/neu, erbB2 receptor) Herceptin ® | Breast, HER2/neu cancers |
| | CD20 | Rituximab Rituxan ®, MabThera ®, Reditux ® | Non-Hodgkin's lymphoma, B-cell leukemias |
| | | Tositumomab (anti-CD20-$^{131}$I) Bexxar ® | Follicular lymphoma, non-Hodgkin's lymphoma |
| | | Alemtuzumab (anti-CD52) Campath ® | Chronic lymphocytic leukemia (CLL), T-cell lymphoma |
| | | Bevacizumab (anti-VEGF) Avastin ® | Colon, non-small cell lung cancer, breast, renal cell carcinoma, glioblastoma multiforme, hormone-refractory prostate cancer, pancreas |
| | | Gemtuzumab (anti-CD33-calicheamicin) Mylotarg ® | Acute myelogenous leukemia |
| Hormones and Antagonists | Adreno-corticosteroids | Prednisone | Acute and chronic lymphocytic leukemias, non-Hodgkin's lymphomas, Hodgkin's disease, breast, multiple myeloma |
| | Progestins | Hydroxyprogesterone caproate Medroxyprogesterone acetate Megestrol acetate Megace ® | Endometrium, breast |
| | Estrogens | Diethylstilbestrol Ethinyl estradiol Estramustine ® (mechlorethamine derivative) | Breast, prostate |
| | Antiestrogen | Tamoxifen Nolvadex ®, Istubal ®, Valodex ® | Breast |
| | Androgens | Testosterone propionate Fluoxymesterone (Halotestin) | Breast |
| | Antiandrogen type II 5-α reductase inhibitors | Flutamide (Flutamin) Eulexin ® | Prostate |
| | | Finasteride Proscar ®, Fincar ® | Prostate |
| | Androgen Receptor Antagonists | Nilutamide Anandron ®, Nilandron ® | Prostate |
| | | Bicalutamide Casodex ® | Prostate |
| | Gonadotropin-releasing hormone (GnRH) antagonist | Abarelix Plenaxis ® | Prostate |
| | Gonadotropin-releasing hormone (GnRH) analog or agonist | Goserelin Zoladex ® | Prostate |
| | | Leuprolide Lupron ®, Lupron Depot ®, Viadur ®, Eligard ®, Prostap ® | Prostate, breast |

N. Immunotherapy (IO) Combinations

Embodiments of the present invention include the treatment of cancer patients with PS-targeting antibodies such as bavituximab in combination with immunotherapy or immuno-oncology (IO) agents. Exemplary immunotherapeutic agents for combined therapy are listed in Table D. Certain preferred examples of IO agents are those approved for clinical treatment or in human clinical trials, preferably in late-stage clinical trials, such as those described in Table E. The doses for use and indications for treatment are well-known to those of ordinary skill in the art, as exemplified by the details in Table E.

Particularly preferred IO agents for combination therapy with PS-targeting antibodies such as bavituximab, as directly supported by the data in Example XVI, are "checkpoint inhibitors", also termed herein "immune checkpoint antibodies". Suitable "immune checkpoint antibodies" include agonistic (activating) antibodies that bind to an activating immune checkpoint, receptor or molecule, such as CD28, OX40 and/or GITR, and antagonistic (blocking) antibodies that bind to an inhibitory immune checkpoint, receptor or molecule, such PD-1, PD-L1, CTLA-4, TIM-3 and/or LAG-3. Such blocking antibodies are routinely termed "immune checkpoint inhibitors", which is also used herein. Several such antibodies are also described in Table E, as being approved for clinical treatment or in late-stage clinical trials.

The currently most preferred examples of immune checkpoint antibodies (immune checkpoint inhibitors) are "blocking antibodies that bind to CTLA-4, PD-1 or PD-L1". Several such blocking antibodies that bind to CTLA-4, PD-1 or PD-L1, and methods, including functional assays, for their selection, preparation and use, are well-known to those of ordinary skill in the art, as described in Table F. These include blocking antibodies to CTLA-4, such as ipilimumab and tremelimumab; blocking antibodies to PD-1, such as nivolumab, cemiplimab (REGN2810), CBT-501, CX-072, and pembrolizumab; blocking antibodies to PD-L1, such as durvalumab (MEDI4736), avelumab, LY-3300054, CX-188, and atezolizumab; and combinations of any one or more of such antibodies, known as an "IO doublet".

Of the above blocking antibodies, tremelimumab, nivolumab, durvalumab and atezolizumab are preferred, and atezolizumab is particularly preferred. The main U.S. patents for tremelimumab, nivolumab, durvalumab and atezolizumab are U.S. Pat. Nos. 6,682,736, 8,008,449, 8,779,108 and 8,217,149, respectively. The use of bavituximab in combination with atezolizumab is set forth in detail in Example XIX. Not as part of the same study, but in one or more other treatment options, atezolizumab may be replaced by another immune checkpoint antibody, such as another blocking antibody that binds to CTLA-4, PD-1, PD-L1, or a bispecific blocking antibody that binds to any checkpoint inhibitor. In selecting a different blocking antibody, those of ordinary skill in the art will know the suitable dose and administration schedule from the literature, e.g., as referenced in Table E, optionally with Table F.

In addition to Table F, other suitable examples of anti-CTLA-4 antibodies are those described in U.S. Pat. No. 6,207,156, which particularly concerns anti-CTLA-4 antibodies that comprise a CDR (CDR3, CDR2 or CDR1) selected from a defined antibody from a deposited hybridoma.

In addition to Table F, other suitable examples of anti-PD-L1 antibodies are those described in U.S. Pat. No. 8,168,179, which particularly concerns treating PD-L1 over-expressing cancers with human anti-PD-L1 antibodies, including chemotherapy combinations; U.S. Pat. No. 9,402,899, which particularly concerns treating tumors with antibodies to PD-L1, including chimeric, humanized and human antibodies; and U.S. Pat. No. 9,439,962, which particularly concerns treating cancers with anti-PD-L1 antibodies and chemotherapy. These anti-PD-L1 antibody compositions and methods include those in development by Ono Pharmaceuticals and collaborators.

Further suitable antibodies to PD-L1 are those in U.S. Pat. Nos. 7,943,743, 9,580,505 and 9,580,507, kits thereof (U.S. Pat. No. 9,580,507) and nucleic acids encoding the antibodies (U.S. Pat. No. 8,383,796). Such antibodies bind to PD-L1 and compete for binding with a reference antibody; are defined by VH and WL genes; or are defined by heavy and light chain CDR3 (U.S. Pat. No. 7,943,743), or heavy chain CDR3 (U.S. Pat. No. 8,383,796), of defined sequences or conservative modifications thereof; or have 90% or 95% sequence identity to reference antibodies. These anti-PD-L1 antibodies also include those with defined quantitative (including binding affinity) and qualitative properties, immunoconjugates and bispecific antibodies. Further included are methods of using such antibodies, and those with defined quantitative (including binding affinity) and qualitative properties, including antibodies in single chain format and those that are in the format of an isolated CDR, in enhancing an immune response (U.S. Pat. No. 9,102,725). Enhancing an immune response, as in U.S. Pat. No. 9,102,725, may be used to treat cancer or an infectious disease, such as a pathogenic infection by a virus, bacterium, fungus or parasite. These anti-PD-L1 antibody compositions and methods include the product, BMS936559.

Further suitable antibodies to PD-L1 are those in U.S. Patent Application No. 2016/0009805, which concerns antibodies to particular epitopes on PD-L1, including antibodies of defined CDR sequences and competing antibodies; nucleic acids, vectors, host cells, immunoconjugates; detection, diagnostic, prognostic and biomarker methods; and treatment methods.

TABLE D

Exemplary Immunotherapeutic Agents for Combination Therapies

| Drug Name | Target | Therapy | Combination Details | Indication | Trial Phase |
|---|---|---|---|---|---|
| ACA-125 | CA-125/MUC-16 | Monotherapy | | Ovarian Cancer | II/III |
| Actimmune | Immune system | Combination | Actimmune in addition to chemotherapy. | Ovarian Cancer | II |
| | Immune system | Combination | Actimmune with carboplatin and paclitaxel | Ovarian Cancer | III |
| | Immune system | Combination | interferon-gamma and nivolumab | Solid Tumors | I |
| AdhTAP | HER2/neu or ErbB-2, MHC | Monotherapy | | Breast Cancer | I |
| Ad-REIC/Dkk-3 | Apoptosis (Cell Death) | Monotherapy | | Prostate Cancer | I |
| | Apoptosis (Cell Death) | Monotherapy | | Prostate Cancer | I/II |
| ADU-214 | Immune system | Monotherapy | | Non-Small Cell Lung Cancer (NSCLC) | I |
| ADU-623 | EGFR, NY-ESO-1 | Monotherapy | | Brain Cancer (malignant glioma; AA and GBM) | I |
| ADU-741 | Immune system | Monotherapy | | Prostate Cancer | Preclinical |
| | Immune system | Monotherapy | | Prostate Cancer | I |
| ADXS-cHER2 | HER2/neu or ErbB-2 | Monotherapy | | Breast Cancer | Preclinical |
| | HER2/neu or ErbB-2 | Monotherapy | | Breast Cancer | I/II |
| | HER2/neu or ErbB-2 | Monotherapy | | Bone Cancer | I/II |
| | HER2/neu or ErbB-2 | Monotherapy | | Bone Cancer | Preclinical |
| ADXS-PSA | PSA | Monotherapy | | Prostate Cancer | Preclinical |
| | PSA | Monotherapy and Combo Therapy | ADXS-PSA + Pembrolizumab | Prostate Cancer | I/II |
| AE37 | HER2/neu or ErbB-2 | Combination | AE37 + GM-CSF | Breast Cancer | II |
| | HER2/neu or ErbB-2 | Monotherapy | | Prostate Cancer | I |
| AEZS-120 | PSA | Monotherapy | | Prostate Cancer | Preclinical |
| AG-858 | Immune system | Combination | AG-858 in combination with Gleevec (imatinib mesylate) | Chronic Myelogenous Leukemia (CML) | I |
| | Immune system | Combination | AG-858 with Gleevec | Chronic Myelogenous Leukemia (CML) | II |
| AGI-101H | Immune system | Monotherapy | | Melanoma | I/II |
| AGS-003 | Stem Cells | Combination | AGS-003 + Sutinib | Renal Cell Cancer (RCC) | II |
| | Stem Cells | Combination | | Renal Cell Cancer (RCC) | I/II |
| | Stem Cells | Combination | AGS-003 + Sunitinib | Renal Cell Cancer (RCC) | III |
| | Stem Cells | Monotherapy | | Renal Cell Cancer (RCC) | II |
| ALECSAT | Immune system | Monotherapy | | Non-Small Cell Lung Cancer (NSCLC) | II |
| | Immune system | Monotherapy | | Brain Cancer (malignant glioma; AA and GBM) | II |
| | Immune system | Monotherapy | | Prostate Cancer | I |
| | Immune system | Monotherapy | | Prostate Cancer | I |
| | Immune system | Monotherapy | | Pancreatic Cancer | I |
| AlloStim | Stem Cells | Monotherapy | | Breast Cancer | I/II |
| | Stem Cells | Monotherapy | | Breast Cancer | I/II |
| | Stem Cells | Monotherapy | | Breast Cancer | I/II |
| | Stem Cells | Combination | Allostim + Radiofrequency Ablation | Hepatocellular (Liver) Cancer (HCC) (including secondary metastases) | I/II |
| | Stem Cells | Combination | AlloStim + Cryoablation | Breast Cancer | II/III |
| | Stem Cells | Monotherapy | | Breast Cancer | I/II |
| | Stem Cells | Combination | | Colorectal Cancer (CRC) | IIb |
| AlloVax | Immune system | Monotherapy | | Head and Neck Cancer | I/II |
| | Immune system | Monotherapy | | Hepatocellular (Liver) Cancer (HCC) (including secondary metastases) | I/II |

TABLE D-continued

| | | | | |
|---|---|---|---|---|
| Allovectin | TCR | Monotherapy | | Melanoma | II |
| | TCR | Monotherapy | | Melanoma | III |
| | TCR | Monotherapy | | Melanoma | II |
| | TCR | Monotherapy | | Melanoma | III |
| | TCR | Monotherapy | | Melanoma | Preclinical |
| ALVAC | Immune system | Combination | ALVAC and GM-CSF injections, followed by interferon | Melanoma | II |
| Amolimogene | HPV | Monotherapy | | Cervical Dysplasia | II/III |
| | HPV | Monotherapy | | Cervical Dysplasia | IIb |
| AMP-224 | PD-1/PD-L1 and PD-L2 | Monotherapy | | Solid Tumors | I |
| | PD-1/PD-L1 and PD-L2 | Combination | | Colorectal Cancer (CRC) | I |
| Ampligen | TLR3 | Combination | Oxidized tumor cell lysate (OC-L) + Ampligen + Prevnar | Ovarian Cancer | I/II |
| | TLR4 | Combination | Ampligen + HER-2 vaccine; <br> Ampligen + GM-CSF + HER-2 vaccine | Breast Cancer | I/II |
| | TLR5 | Combination | Celecoxib + Rintatolimod + IFN | Colorectal Cancer (CRC) | I/II |
| | TLR6 | Monotherapy | | Colorectal Cancer (CRC) | Preclinical |
| | TLR7 | Monotherapy | | Melanoma | Preclinical |
| | TLR8 | Combination | | Ovarian Cancer | I/II |
| Aneustat | Immune system | Monotherapy | | Solid Tumors | I |
| Anti-GD2-CAR engineered T cells | CAR-T, GD2, Stem Cells/, T lymphocytes | Combination | Anti-GD2 CAR-T and lymphodepleting chemotherapy | Solid Tumors | I |
| Anti-mesothelin CAR | CAR-T, Mesothelin, Stem Cells, T lymphocytes | Combination | Anti-mesothelin CAR-T and lymphodepleting chemotherapy | Solid Tumors | I/II |
| Anyara | 5T4 tumor antigen | Combination | ABR-217620; IFN-alpha: 3 MIU, 6 MIU, and 9 MIU, subcutaneous or intramuscular injection 3 times/week | Renal Cell Cancer (RCC) | II/III |
| APC 101 | Immune system | Monotherapy | | Cancer | Preclinical |
| APVAC Glioblastoma Vaccine (immatics) | Immune system | Monotherapy | | Brain Cancer (malignant glioma; AA and GBM) | I/II |
| AST-VAC1 | Telomerase | Monotherapy | | Acute Myelogenous Leukemia (AML) | I/II |
| Atezolizumab | PD-1/PD-L1 and PD-L2 | Combination | MPDL3280A + Avastin +/- Chemotherapy | Non-Small Cell Lung Cancer (NSCLC) | I |
| | PD-1/PD-L1 and PD-L2 | Monotherapy | | Non-Small Cell Lung Cancer (NSCLC) | I |
| | PD-1/PD-L1 and PD-L2 | Combination | MPDL3280A + Vemurafenib (Zelboraf), MPDL3280A + Zelboraf (vemurafenib) + cobimetinib | Melanoma | I |
| | PD-1/PD-L1 and PD-L2 | Combination | MPDL3280A + Avastin +/- Chemotherapy | Melanoma | I |
| | PD-1/PD-L1 and PD-L2 | Monotherapy | | Melanoma | II |
| | PD-1/PD-L1 and PD-L2 | Monotherapy | | Non-Small Cell Lung Cancer (NSCLC) | II |
| | PD-1/PD-L1 and PD-L2 | Monotherapy | | Non-Small Cell Lung Cancer (NSCLC) | II |
| | PD-1/PD-L1 and PD-L2 | Monotherapy | | Non-Small Cell Lung Cancer (NSCLC) | III |
| | PD-1/PD-L1 and PD-L2 | Monotherapy | | Non-Small Cell Lung Cancer (NSCLC) | I |
| | PD-1/PD-L1 and PD-L2 | Monotherapy | | Solid Tumors | I |
| | PD-1/PD-L1 and PD-L2 | Monotherapy | | Non-Small Cell Lung Cancer (NSCLC) | II |
| | PD-1/PD-L1 and PD-L2 | Monotherapy | | Renal Cell Cancer (RCC) | II |
| | PD-1/PD-L1 and PD-L2 | Monotherapy | | Non-Small Cell Lung Cancer (NSCLC) | II |
| | PD-1/PD-L1 and PD-L2 | Monotherapy | | Bladder Cancer | II |
| | PD-1/PD-L1 and PD-L2 | Monotherapy | | Bladder Cancer | II |
| | PD-1/PD-L1 and PD-L2 | Combination | MPDL3280A + ipilimumab <br> MPDL3280A + interferon alfa-2b | Solid Tumors | I |
| | PD-1/PD-L1 and PD-L2 | Combination | RG7446 with Gazyva | Indolent Non-Hodgkin's Lymphoma - NHL | I |
| | PD-1/PD-L1 and PD-L2 | Combination | RG7446 with Gazyva | Diffuse Large B-Cell Lymphoma (DLBCL) - NHL | I |
| | PD-1/PD-L1 and PD-L2 | Monotherapy | | Bladder Cancer | III |
| | PD-1/PD-L1 and PD-L2 | Combination | MPDL3280A + INCB024360 | Non-Small Cell Lung Cancer (NSCLC) | I |
| | PD-1/PD-L1 and PD-L2 | Combination | MPDL3280A + Avastin +/- chemotherapy | Breast Cancer | I |
| | PD-1/PD-L1 and PD-L2 | Combination | RO7009789 with MPDL3280A | Solid Tumors | I |
| | PD-1/PD-L1 and PD-L2 | Monotherapy | | Solid Tumors | I |

TABLE D-continued

| | | | | |
|---|---|---|---|---|
| | PD-1/PD-L1 and PD-L2 | Combination | MPDL3280A + Paclitaxel + Carboplatin +/- Bevacizumab | Non-Small Cell Lung Cancer (NSCLC) | III |
| | PD-1/PD-L1 and PD-L2 | Combination | MPDL3280A + Nab-Paclitaxel + Carboplatin | Non-Small Cell Lung Cancer (NSCLC) | III |
| | PD-1/PD-L1 and PD-L2 | Combination | MPDL3280A + Paclitaxel + Carboplatin or MPDL3280A + Nab-paclitaxel + Carboplatin | Non-Small Cell Lung Cancer (NSCLC) | III |
| | PD-1/PD-L1 and PD-L2 | Combination | Varlilumab + MPDL3280A | Renal Cell Cancer (RCC) | I/II |
| | PD-1/PD-L1 and PD-L2 | Monotherapy | | Breast Cancer | I |
| | PD-1/PD-L1 and PD-L2 | Monotherapy | | Non-Small Cell Lung Cancer (NSCLC) | III |
| | PD-1/PD-L1 and PD-L2 | Monotherapy and Combo Therapy | (Carboplatin or Cisplatin) + Pemetrexed | Non-Small Cell Lung Cancer (NSCLC) | III |
| | PD-1/PD-L1 and PD-L2 | Monotherapy and Combo Therapy | | Renal Cell Cancer (RCC) | III |
| | PD-1/PD-L1 and PD-L2 | Combination | MPDL3280a plus nab-paclitaxel | Breast Cancer | III |
| | PD-1/PD-L1 and PD-L2 | Monotherapy | | Bladder Cancer | III |
| | PD-1/PD-L1 and PD-L2 | Monotherapy | | Ovarian Cancer | I |
| | PD-1/PD-L1 and PD-L2 | Combination | GDC-0919 + MPDL3280A | Solid Tumors | I |
| | PD-1/PD-L1 and PD-L2 | Monotherapy | | Non-Small Cell Lung Cancer (NSCLC) | III |
| | PD-1/PD-L1 and PD-L2 | Monotherapy and Combo Therapy | MPDL3280A + Lenalidomide | Multiple Myeloma (MM) | I |
| | PD-1/PD-L1 and PD-L2 | Combination | Rociletinib + Atezolizumab | Non-Small Cell Lung Cancer (NSCLC) | I/II |
| | PD-1/PD-L1 and PD-L2 | Combination | CMB305 + atezolizumab | Sarcoma | II |
| | PD-1/PD-L1 and PD-L2 | Combination | Entinostat + Atezolizumab | Breast Cancer | I/II |
| | PD-1/PD-L1 and PD-L2 | Combination | Atezolizumab + carboplatin +/- paclitaxel or pemetrexed or nab-paclitaxel | Non-Small Cell Lung Cancer (NSCLC) | I |
| | PD-1/PD-L1 and PD-L2 | Combination | Azacitidine + MPDL3280A | Myelodysplastic Syndrome (MDS) | I |
| | PD-1/PD-L1 and PD-L2 | Monotherapy | | Brain Cancer (malignant glioma; AA and GBM) | I |
| | PD-1/PD-L1 and PD-L2 | Combination | ATEZOLIZUMAB IN COMBINATION WITH OBINUTUZUMAB PLUS LENALIDOMIDE | Diffuse Large B-Cell Lymphoma (DLBCL) - NHL | I/II |
| | PD-1/PD-L1 and PD-L2 | Combination | Atezolizumab + Pertuzumab + Trastuzumab, Atezolizumab + Trastuzumab emtansine, Atezolizumab + Carboplatin + Pertuzumab + Trastuzumab | Breast Cancer | I |
| | PD-1/PD-L1 and PD-L2 | Combination | Atezolizumab + Carboplatin or + Cisplatin + Pemetrexed | Non-Small Cell Lung Cancer (NSCLC) | III |
| | PD-1/PD-L1 and PD-L2 | Combination | Atezolizumab + Bendamustine + Obinutuzumab; Atezolizumab + Obinutuzumab + CHOP | Diffuse Large B-Cell Lymphoma (DLBCL) - NHL | I/II |
| | PD-1/PD-L1 and PD-L2 | Monotherapy and Combo Therapy | daratumumab + atezolizumab | Solid Tumors | I |
| | PD-1/PD-L1 and PD-L2 | Combination | CPI-444 + atezolizumab | Solid Tumors | I |
| ATIR101 | P-gp | Monotherapy | | Solid Tumors | I |
| AU105 | CAR-T | Monotherapy | | Acute Myelogenous Leukemia (AML) | II |
| | CAR-T | Monotherapy | | Brain Cancer (malignant glioma; AA and GBM) | I |
| AUNP-12 | PD-1/PD-L1 and PD-L2 | Monotherapy | | Bone Cancer | I |
| Autologous Idiotype Vaccine (magnICON) | Immune system | Monotherapy | | Solid Tumors | Preclinical |
| AV0113 | | Monotherapy | | Indolent Non-Hodgkin's Lymphoma - NHL | I |
| Avelumab | Stem Cells, Tumor Cells | Monotherapy | | Brain Cancer (malignant glioma; AA and GBM) | II |
| | PD-1/PD-L1 and PD-L2 | Monotherapy | | Non-Small Cell Lung Cancer (NSCLC) | I |
| | PD-1/PD-L1 and PD-L2 | Monotherapy | | Merkel Cell Carcinoma | I |
| | PD-1/PD-L1 and PD-L2 | Monotherapy | | Merkel Cell Carcinoma | I |
| | PD-1/PD-L1 and PD-L2 | Monotherapy | | Non-Small Cell Lung Cancer (NSCLC) | III |
| | PD-1/PD-L1 and PD-L2 | Monotherapy | | Ovarian Cancer | I |
| | PD-1/PD-L1 and PD-L2 | Monotherapy | | Gastric Cancer | I |
| | PD-1/PD-L1 and PD-L2 | Monotherapy | | Gastric Cancer | I |
| | PD-1/PD-L1 and PD-L2 | Monotherapy | | Mesothelioma | I |
| | PD-1/PD-L1 and PD-L2 | Monotherapy | | Bladder Cancer | I |

TABLE D-continued

| | Target | Therapy Type | Combination | Indication | Phase |
|---|---|---|---|---|---|
| | PD-1/PD-L1 and PD-L2 | Monotherapy | | Non-Small Cell Lung Cancer (NSCLC) | III |
| | PD-1/PD-L1 and PD-L2 | Monotherapy and Combo Therapy | avelumab + PLD | Ovarian Cancer | III |
| | PD-1/PD-L1 and PD-L2 | Monotherapy | | Gastric Cancer | III |
| | PD-1/PD-L1 and PD-L2 | Monotherapy | | Gastric Cancer | III |
| | PD-1/PD-L1 and PD-L2 | Monotherapy | | Bladder Cancer | III |
| | PD-1/PD-L1 and PD-L2 | Combination | Avelumab + Crizotinib; <BR> Avelumab + PF-06463922 | Non-Small Cell Lung Cancer (NSCLC) | I/II |
| | PD-1/PD-L1 and PD-L2 | Combination | Avelumab + Entinostat | Ovarian Cancer | III |
| | PD-1/PD-L1 and PD-L2 | Combination | Avelumab (MSB0010718C) + Axitinib (AG-013736) | Renal Cell Cancer (RCC) | III |
| | PD-1/PD-L1 and PD-L2 | Combination | | Ovarian Cancer | I/II |
| Avicine | hCG | Monotherapy | | Colorectal Cancer (CRC) | II |
| AVX901 | HER2/neu or ErbB-2 | Monotherapy | | Breast Cancer | I |
| Axalinogene Filolisbac | HPV | Monotherapy | | Cervical Dysplasia | II |
| | HPV | Monotherapy and Combo Therapy | ASXS11-001 +/− Platinum based chemotherapy | Cervical Cancer | II |
| | HPV | Monotherapy | | Cervical Cancer | II |
| | HPV | Monotherapy | | Head and Neck Cancer | I/II |
| | HPV | Monotherapy | | Anal Cancer | I/II |
| | HPV | Combination | ADXS-HPV + PD1 Antibody | Cervical Cancer | Preclinical |
| | HPV | Monotherapy | | Head and Neck Cancer | I/II |
| | HPV | Monotherapy and Combo Therapy | MEDI-4736 + ADXS-HPV | Cervical Cancer | I/II |
| | HPV | Monotherapy | | Cervical Cancer | I/II |
| | HPV | Monotherapy and Combo Therapy | MEDI-4736 + ADXS-HPV | Head and Neck Cancer | I/II |
| | HPV | Monotherapy | | Cervical Cancer | III |
| | HPV | Monotherapy and Combo Therapy | ADXS-HPV as a monotherapy and in combination with epacadostat (INCB24360) | Cervical Cancer | II |
| | HPV | Monotherapy | | Anal Cancer | I/II |
| | HPV | Combination | Concurrent chemotherapy of mitomycin C/5FU and radiation therapy (CCRT) + ADXS-HPV | Anal Cancer | II/III |
| BB-001 | HPV | Combination | ADXS11-001 + Pemetrexed | Non-Small Cell Lung Cancer (NSCLC) | II |
| | TLR9 | Monotherapy | | Chronic Lymphocytic Leukemia (CLL)/Small Cell Lymphocytic Lymphoma (SLL) - NHL | Development |
| bb2121 | CAR-T, HER2/neu or ErbB-2, Stem Cells, T lymphocytes | Monotherapy | | Brain Cancer (malignant glioma; AA and GBM) | I |
| | CAR-T, HER2/neu or ErbB-2, Stem Cells, T lymphocytes | Monotherapy | | Multiple Myeloma (MM) | Preclinical |
| | CAR-T, HER2/neu or ErbB-2, Stem Cells, T lymphocytes | Monotherapy | | Multiple Myeloma (MM) | I |
| Bexidem | Stem Cells | Monotherapy | | Bladder Cancer | II/III |
| | Stem Cells | Monotherapy | | Bladder Cancer | II/III |
| BGB-A317 | PD-1/PD-L1 and PD-L2 | Monotherapy | | Cancer | I |
| BiovaxID Vaccine | Stem Cells | Monotherapy | | Indolent Non-Hodgkin's Lymphoma - NHL | III |
| | Stem Cells | Monotherapy | | Indolent Non-Hodgkin's Lymphoma - NHL | II |
| | Stem Cells | Combination | | Mantle Cell Lymphoma - NHL | II |
| BMS-936559 | PD-1/PD-L1 and PD-L2 | Monotherapy | | Solid Tumors | I |
| | PD-1/PD-L1 and PD-L2 | Monotherapy | | Hematologic Cancer | I |
| | PD-1/PD-L1 and PD-L2 | Monotherapy | | Melanoma | I |
| BMS-98016 | LAG3/CD223 | Monotherapy and Combo Therapy | | Cancer | I |
| | LAG3/CD223 | Monotherapy | | Cancer | I |

TABLE D-continued

| Name | Target | Therapy Type | Combination | Indication | Phase |
|---|---|---|---|---|---|
| BPX-101 | CD40, PSMA, Stem Cells | Monotherapy | BP-GMAX-CD1 as 5 or 8 ID injections; at 24 hours after each vaccination, AP1903 at a 0.4 mg/kg via IV infusion over 2 hours. | Prostate Cancer | I/II |
| BPX-201 | CD40, PSMA, Stem Cells, TLR Family | Combination | BPX-201 vaccine + AP1903 | Prostate Cancer | I |
| BPX-601 | CAR-T, Stem Cells, T lymphocytes | Monotherapy | | Pancreatic Cancer | Preclinical |
| CA-170 | PD-1/PD-L1 and PD-L2, VISTA | Monotherapy | | Cancer | Preclinical |
| CA-4948 | IRAK4 | Monotherapy | | Cancer | Preclinical |
| Canvaxin | Immune system | Monotherapy | | Melanoma | III |
| | Immune system | Monotherapy | | Melanoma | I |
| | Immune system | Monotherapy | | Melanoma | II/III |
| CAR-T CD19 | CAR-T, CD19, Stem Cells | Monotherapy | | Acute Lymphocytic Leukemia (ALL) | I |
| CAR-T CD20 | CAR-T, CD20, Stem Cells | Monotherapy | | Diffuse Large B-Cell Lymphoma (DLBCL) - NHL | I/II |
| CAR-T CD30 | CAR-T, CD30/TNFRSF8, Stem Cells | Monotherapy | | Hodgkin's Lymphoma | I/II |
| CAR-T EGFR (HER1) | CAR-T, EGFR, Stem Cells | Monotherapy | | Non-Small Cell Lung Cancer (NSCLC) | I/II |
| CART123 | CAR-T, IL-3/CD123, Stem Cells, T lymphocytes | Monotherapy | | Hematologic Cancer | Preclinical |
| CART-meso | CAR-T, Mesothelin, Stem Cells, T lymphocytes | Monotherapy | | Solid Tumors | I |
| | CAR-T, Mesothelin, Stem Cells, T lymphocytes | Monotherapy | | Solid Tumors | I |
| CAR-TNK | CAR-T, Mesothelin, Stem Cells, T lymphocytes | Monotherapy | | Cancer | Preclinical |
| Cavatak (intratumoral) | ICAM-1, Tumor Cells | Monotherapy | | Melanoma | I |
| | ICAM-1, Tumor Cells | Monotherapy | | Melanoma | II |
| | ICAM-1, Tumor Cells | Monotherapy | | Melanoma | II |
| | ICAM-1, Tumor Cells | Monotherapy | | Melanoma | Preclinical |
| | ICAM-1, Tumor Cells | Monotherapy | | Head and Neck Cancer | I |
| | ICAM-1, Tumor Cells | Monotherapy | | Melanoma | I |
| | ICAM-1, Tumor Cells | Monotherapy and Combo Therapy | CAVATAK and ipilimumab | Solid Tumors | I |
| Cavatak (IV) | ICAM-1, Tumor Cells | Monotherapy | (Stage 2) Cavatak + KEYTRUDA | Solid Tumors | I |
| | ICAM-1, Tumor Cells | Monotherapy | | Solid Tumors | Preclinical |
| | ICAM-1, Tumor Cells | Monotherapy | | Non-Small Cell Lung Cancer (NSCLC) | Preclinical |
| | ICAM-1, Tumor Cells | Monotherapy and Combo Therapy | | Bladder Cancer | I |
| CC-122 | Angiogenesis | Monotherapy | | Solid Tumors | I |
| | Angiogenesis | Monotherapy | | Chronic Lymphocytic Leukemia (CLL)/Small Cell Lymphocytic Lymphoma (SLL) - NHL | I |
| | Angiogenesis | Monotherapy | | Multiple Myeloma (MM) | I |
| | Angiogenesis | Combination | | Diffuse Large B-Cell Lymphoma (DLBCL) - NHL | I |
| | Angiogenesis | Monotherapy and Combo Therapy | CC-122 + Ibrutinib, CC-122 + Obinutuzumab, CC-122 + Rituximab | Chronic Lymphocytic Leukemia (CLL)/Small Cell Lymphocytic Lymphoma (SLL) - NHL | I/II |
| | Angiogenesis | Combination | CC-122 + Obinutuzumab | Diffuse Large B-Cell Lymphoma (DLBCL) - NHL | I |
| | Angiogenesis | Combination | CC-122 + Fixed-dose Sorafenib | Hepatocellular (Liver) Cancer (HCC) (including secondary metastases) | I |
| CD19 CAR (Takara) | CAR-T, CD19, Stem Cells, T lymphocytes | Monotherapy | | Non-Hodgkin's Lymphoma (NHL) | I/II |
| CDX-1307 | hCG | Combination | Gemcitabine and Cisplatin combination chemotherapy with CDX-1307 + surgery | Bladder Cancer | II |

TABLE D-continued

| | | | | | |
|---|---|---|---|---|---|
| CDX-1401 | NY-ESO-1 | Combination | CDX-1401 + Resquimod and/or Hiltonal | Melanoma | I/II |
| | NY-ESO-1 | Combination | CDX-1401 + CDX-301 | Melanoma | II |
| | NY-ESO-1 | Monotherapy | | Ovarian Cancer | I/II |
| CGEN-15027 | CD28/ICOS and B7RP-1 | Monotherapy | | Cancer | Preclinical |
| CGEN-15049 | Immune system | Monotherapy | | Solid Tumors | Preclinical |
| CGEN-15052 | Immune system | Monotherapy | | Cancer | Preclinical |
| CLBS20 | Stem Cells | Monotherapy | | Melanoma | III |
| | Stem Cells | Monotherapy | | Melanoma | II |
| | Stem Cells | Monotherapy | | Hepatocellular (Liver) Cancer (HCC) (including secondary metastases) | I |
| | Stem Cells | Monotherapy | | Ovarian Cancer | II |
| | Stem Cells | Monotherapy | | Melanoma | II |
| | Stem Cells | Monotherapy | | Melanoma | Preclinical |
| CMB305 | NY-ESO-1 | Monotherapy | | Solid Tumors | I |
| | NY-ESO-1 | Combination | CMB305 + atezolizumab | Sarcoma | II |
| CM-CS1 | CAR-T, NKG2D/NKG2D Ligands, Stem Cells | Monotherapy | | Hematologic Cancer | I/II |
| CMP-001 | TLR Family | Combination | CMP-001 + pembrolizumab | Melanoma | I |
| ColoAd1 | Tumor Cells | Combination | Chemotherapy plus ColoAd1 | Colorectal Cancer (CRC) | I/II |
| | Tumor Cells | Monotherapy | | Ovarian Cancer | I/II |
| | Tumor Cells | Monotherapy | | Ovarian Cancer | Preclinical |
| Contego | Stem Cells, T lymphocytes | Combination | Young TIL + Vemurafenib + Cyclophosphamide + Fludarabine + Aldesleukin | Melanoma | I |
| | Stem Cells, T lymphocytes | Combination | Tumor Infiltrating Lymphocytes + Ipilimumab + Lymphodepletion + Cyclophosphamide + Fludarabine + High Dose IL-2 | Melanoma | I |
| | Stem Cells, T lymphocytes | Combination | TIL + Chemotherapy + 12 Gy Irradiation + 12 Gy Irradiation | Melanoma | II |
| | Stem Cells, T lymphocytes | Combination | TIL + Nivolumab | Melanoma | I |
| | Stem Cells, T lymphocytes | Combination | | Melanoma | II |
| CRS-207 | Mesothelin | Combination | GVAX Pancreas + Cyclophosphamide + CRS-207 | Pancreatic Cancer | II |
| | Mesothelin | Combination | With pemetrexed and cisplatin | Mesothelioma | I |
| | Mesothelin | Monotherapy | | Pancreatic Cancer | IIb |
| | Mesothelin | Combination | CRS-207 + GVAX Pancreas Vaccine +/– Nivolumab | Pancreatic Cancer | II |
| | Mesothelin | Combination | CRS-207 + Epacadostat | Ovarian Cancer | I/II |
| CTL019 | CAR-T, CD19, Stem Cells, T lymphocytes | Monotherapy | | Chronic Lymphocytic Leukemia (CLO/Small Cell Lymphocytic Lymphoma (SLL) - NHL | I |
| | CAR-T, CD19, Stem Cells, T lymphocytes | Monotherapy | | Chronic Lymphocytic Leukemia (CLL)/Small Cell Lymphocytic Lymphoma (SLL) - NHL | II |
| | CAR-T, CD19, Stem Cells, T lymphocytes | Monotherapy | | Acute Lymphocytic Leukemia (ALL) | I/II |
| | CAR-T, CD19, Stem Cells, T lymphocytes | Monotherapy | | Acute Lymphocytic Leukemia (ALL) | I |
| | CAR-T, CD19, Stem Cells, T lymphocytes | Monotherapy | | Chronic Lymphocytic Leukemia (CLL)/Small Cell Lymphocytic Lymphoma (SLL) - NHL | I |
| | CAR-T, CD19, Stem Cells, T lymphocytes | Monotherapy | | Acute Lymphocytic Leukemia (ALL) | II |
| | CAR-T, CD19, Stem Cells, T lymphocytes | Monotherapy | | Acute Lymphocytic Leukemia (ALL) | II |
| | CAR-T, CD19, Stem Cells, T lymphocytes | Monotherapy | | Diffuse Large B-Cell Lymphoma (DLBCL) - NHL | II |
| | CAR-T, CD19, Stem Cells, T lymphocytes | Combination | CTL019 with auto-SCT | Multiple Myeloma (MM) | I |

TABLE D-continued

| Name | Target | Type | Details | Indication | Phase |
|---|---|---|---|---|---|
| | CAR-T, CD19, Stem Cells, T lymphocytes | Monotherapy | | Diffuse Large B-Cell Lymphoma (DLBCL) - NHL | II |
| | CAR-T, CD19, Stem Cells, T lymphocytes | Monotherapy | | Acute Lymphocytic Leukemia (ALL) | II |
| | CAR-T, CD19, Stem Cells, T lymphocytes | Monotherapy | | Chronic Lymphocytic Leukemia (CLL)/Small Cell Lymphocytic Lymphoma (SLL) - NHL | II |
| CV-301 | CEA, MUC-1 | Combination | Docetaxel + Familimarev + Inalimarev + Sagramostim | Breast Cancer | II |
| | CEA, MUC-1 | Monotherapy | | Ovarian Cancer | I |
| | CEA, MUC-1 | Monotherapy | | Pancreatic Cancer | III |
| | CEA, MUC-1 | Monotherapy | | Colorectal Cancer (CRC) | II |
| | CEA, MUC-1 | Combination | PANVAC + TICE *Bacillus* Calmette-Guerin (BCG) | Bladder Cancer | II |
| CV9104 | Immune system | Monotherapy | | Prostate Cancer | I/II |
| | Immune system | Monotherapy | | Prostate Cancer | I/II |
| CV9201 | Tumor Cells | Monotherapy | | Non-Small Cell Lung Cancer (NSCLC) | I/II |
| | Tumor Cells | Monotherapy | | Non-Small Cell Lung Cancer (NSCLC) | I |
| CVac | Stem Cells | Monotherapy | | Ovarian Cancer | II |
| | Stem Cells | Monotherapy | | Ovarian Cancer | IIb |
| | Stem Cells | Monotherapy | | Ovarian Cancer | II/III |
| | Stem Cells | Monotherapy | | Ovarian Cancer | II |
| | Stem Cells | Monotherapy | | Pancreatic Cancer | II |
| CYT004-MelQbG10 | Immune system | Monotherapy | | Melanoma | II |
| CYT004-MelQbG10 | Immune system | Monotherapy | | Melanoma | II |
| Cytokine-Induced Killer Cells | Immune system | Monotherapy | | Hepatocellular (Liver) Cancer (HCC) (including secondary metastases) | III |
| | Immune system | Monotherapy | | Hepatocellular (Liver) Cancer (HCC) (including secondary metastases) | III |
| DC Vaccines | Stem Cells | Monotherapy | | Acute Myelogenous Leukemia (AML) | I/II |
| | Stem Cells | Monotherapy | | Prostate Cancer | I/II |
| | Stem Cells | Monotherapy | | Acute Myelogenous Leukemia (AML) | Preclinical |
| | Stem Cells | Monotherapy | | Acute Myelogenous Leukemia (AML) | I/II |
| DC-AdGM-CAIX | Carbonic Anhydrase, Stem Cells | Monotherapy | | Renal Cell Cancer (RCC) | Preclinical |
| dCellVax | IDO, Stem Cells | Monotherapy | | Breast Cancer | Preclinical |
| | IDO, Stem Cells | Monotherapy | | Breast Cancer | I/II |
| DCP-001 | Stem Cells | Monotherapy | | Acute Myelogenous Leukemia (AML) | I/II |
| DCVAC/LuCa | Stem Cells | Combination | DCVAC/LuCa added to standard first line chemotherapy with carboplatin and paclitaxel +/− immune enhancers | Non-Small Cell Lung Cancer (NSCLC) | I/II |
| | Stem Cells | Combination | DCVAC/OvCa Added to Standard Chemotherapy | Ovarian Cancer | II |
| | Stem Cells | Combination | DCVAC/OvCa with chemotherapy | Ovarian Cancer | II |
| | Stem Cells | Combination | DCVAC/OvCa in parallel with chemo (SoC) | Ovarian Cancer | II |
| | Stem Cells | Monotherapy | | Prostate Cancer | II |
| | Stem Cells | Combination | DCVAC + hormone therapy | Prostate Cancer | II |
| | Stem Cells | Monotherapy | | Prostate Cancer | II |
| | Stem Cells | Monotherapy | | Prostate Cancer | II |
| | Stem Cells | Monotherapy | | Prostate Cancer | III |
| DCVax-Brain | Immune system | Combination | Standard of care, including radiation and Temodar therapy and DCVax-Brain | Brain Cancer (malignant glioma; AA and GBM) | III |
| | Immune system | Monotherapy | | Brain Cancer (malignant glioma; AA and GBM) | I |
| | Immune system | Monotherapy | | Brain Cancer (malignant glioma; AA and GBM) | I |
| | Immune system | Monotherapy | | Brain Cancer (malignant glioma; AA and GBM) | III |
| DCVax-Colon | Immune system | Monotherapy | | Colorectal Cancer (CRC) | I/II |
| | Immune system | Monotherapy | | Colorectal Cancer (CRC) | Preclinical |

TABLE D-continued

| | | | | |
|---|---|---|---|---|
| DCVax-Head & Neck | Immune system | Monotherapy | | Head and Neck Cancer | I/II |
| | Immune system | Monotherapy | | Head and Neck Cancer | Preclinical |
| DCVax-Liver | Immune system | Monotherapy | | Hepatocellular (Liver) Cancer (HCC) (including secondary metastases) | I/II |
| | Immune system | Monotherapy | | Hepatocellular (Liver) Cancer (HCC) (including secondary metastases) | Preclinical |
| DCVax-Lung | Immune system | Monotherapy | | Non-Small Cell Lung Cancer (NSCLC) | I/II |
| | Immune system | Monotherapy | | Non-Small Cell Lung Cancer (NSCLC) | Preclinical |
| DCVax-Pancreas | Immune system | Monotherapy | | Pancreatic Cancer | I/II |
| | Immune system | Monotherapy | | Pancreatic Cancer | Preclinical |
| DCVax-Prostate | Immune system | Monotherapy | | Prostate Cancer | III |
| Denenicokin | IL-21 | Monotherapy | | Melanoma | II |
| | IL-21 | Combination | IL-21 with Nexavar | Renal Cell Cancer (RCC) | I/II |
| | IL-21 | Combination | IL-21 plus Caelyx | Ovarian Cancer | II |
| | IL-21 | Monotherapy | | Melanoma | II |
| Denenicokin | IL-21 | Combination | | Melanoma | IIb |
| | IL-21 | Monotherapy | | Solid Tumors | I |
| | IL-21 | Combination | | Renal Cell Cancer (RCC) | I |
| DN24-02 | HER2/neu or ErbB-2 | Monotherapy | | Bladder Cancer | II |
| DPX-0907 | Abi-2, Bap31, EDDR1, ITGB8, JUP/Gamma-Catenin, TACE/ADAM17, Topoisomerase II | Monotherapy | | Solid Tumors | I |
| DPX-Survivac | Survivin | Monotherapy | | Ovarian Cancer | I/II |
| | Survivin | Monotherapy | | Brain Cancer (malignant glioma; AA and GBM) | II |
| | Survivin | Combination | DPX-Survivac + Low Dose Oral Cyclophosphamide | Ovarian Cancer | II |
| | Survivin | Monotherapy | | Solid Tumors | Preclinical |
| | Survivin | Combination | DPX-Survivac + cyclophosphamide | Diffuse Large B-Cell Lymphoma (DLBCL) - NHL | II |
| | Survivin | Monotherapy | | Ovarian Cancer | Preclinical |
| | Survivin | Combination | DPX-Survivac, epacadostat and low dose oral cyclophosphamide | Ovarian Cancer | I |
| DSP-7888 | WT1 | Monotherapy | | Myelodysplastic Syndrome (MDS) | I/II |
| | WT1 | Monotherapy | | Myelodysplastic Syndrome (MDS) | I |
| Durvalumab | PD-1/PD-L1 and PD-L2 | Monotherapy | | Solid Tumors | I/II |
| | PD-1/PD-L1 and PD-L2 | Monotherapy | | Solid Tumors | I |
| | PD-1/PD-L1 and PD-L2 | Combination | MEDI4736 + Trametinib +/− Dabrafenib | Melanoma | I/II |
| | PD-1/PD-L1 and PD-L2 | Combination | MEDI4736 + Tremelimumab | Non-Small Cell Lung Cancer (NSCLC) | I |
| | PD-1/PD-L1 and PD-L2 | Monotherapy | | Solid Tumors | I |
| | PD-1/PD-L1 and PD-L2 | Combination | MEDI4736 + Tremelimumab | Myelodysplastic Syndrome (MDS) | I |
| | PD-1/PD-L1 and PD-L2 | Monotherapy | | Non-Small Cell Lung Cancer (NSCLC) | II |
| | PD-1/PD-L1 and PD-L2 | Monotherapy | | Non-Small Cell Lung Cancer (NSCLC) | III |
| | PD-1/PD-L1 and PD-L2 | Combination | MEDI4736 + INCB024360 | Solid Tumors | I/II |
| | PD-1/PD-L1 and PD-L2 | Monotherapy and Combo Therapy | MEDI4736 + tremelimumab | Non-Small Cell Lung Cancer (NSCLC) | III |
| | PD-1/PD-L1 and PD-L2 | Monotherapy | | Non-Small Cell Lung Cancer (NSCLC) | III |
| | PD-1/PD-L1 and PD-L2 | Monotherapy | | Non-Small Cell Lung Cancer (NSCLC) | II/III |
| | PD-1/PD-L1 and PD-L2 | Monotherapy and Combo Therapy | MEDI4736 + ADXS-HPV | Cervical Cancer | I/II |
| | PD-1/PD-L1 and PD-L2 | Monotherapy and Combo Therapy | ADXS11-001 + MEDI4736 | Head and Neck Cancer | I/II |
| | PD-1/PD-L1 and PD-L2 | Combination | MEDI4736 + Mogamulizumab, Tremelimumab + Mogamulizumab | Solid Tumors | I |

TABLE D-continued

| | | | | |
|---|---|---|---|---|
| PD-1/PD-L1 and PD-L2 | Combination | MEDI4736 + Gefitinib | Non-Small Cell Lung Cancer (NSCLC) | I |
| PD-1/PD-L1 and PD-L2 | Monotherapy | | Non-Small Cell Lung Cancer (NSCLC) | I/II |
| PD-1/PD-L1 and PD-L2 | Monotherapy | | Solid Tumors | 1 |
| PD-1/PD-L1 and PD-L2 | Combination | Imbruvica + MEDI4736 | Solid Tumors | I/II |
| PD-1/PD-L1 and PD-L2 | Monotherapy | | Head and Neck Cancer | II |
| PD-1/PD-L1 and PD-L2 | Combination | MEDI4736 + Tremelimumab | Solid Tumors | I |
| PD-1/PD-L1 and PD-L2 | Combination | MEDI4736 + tremelimumab | Head and Neck Cancer | I |
| PD-1/PD-L1 and PD-L2 | Combination | AZD9291 + AZD6094, AZD9291 + MEDI4736, AZD9291 + selumetinib | Non-Small Cell Lung Cancer (NSCLC) | I |
| PD-1/PD-L1 and PD-L2 | Combination | MEDI4736 + Tremelimumab | Solid Tumors | I |
| PD-1/PD-L1 and PD-L2 | Monotherapy and Combo Therapy | MEDI4736 + Tremelimumab | Head and Neck Cancer | II |
| PD-1/PD-L1 and PD-L2 | Monotherapy and Combo Therapy | | Head and Neck Cancer | III |
| PD-1/PD-L1 and PD-L2 | Combination | MEDI4736 + Zydelig | Solid Tumors | I/II |
| PD-1/PD-L1 and PD-L2 | Combination | MEDI4736 + Zydelig | Non-Hodgkin's Lymphoma (NHL) | I/II |
| PD-1/PD-L1 and PD-L2 | Monotherapy and Combo Therapy | MEDI4736 + Tremelimumab combination therapy or MEDI4736 monotherapy. | Non-Small Cell Lung Cancer (NSCLC) | III |
| PD-1/PD-L1 and PD-L2 | Combination | Ramucirumab + MEDI-4736 | Solid Tumors | I |
| PD-1/PD-L1 and PD-L2 | Monotherapy | | Ovarian Cancer | I/II |
| PD-1/PD-L1 and PD-L2 | Monotherapy and Combo Therapy | MEDI4736 + Tremelimumab | Gastric Cancer | I/II |
| PD-1/PD-L1 and PD-L2 | Combination | MEDI4736 + Tremelimumab | Pancreatic Cancer | I |
| PD-1/PD-L1 and PD-L2 | Combination | MEDI4736 + mocetinostat | Non-Small Cell Lung Cancer (NSCLC) | I/II |
| PD-1/PD-L1 and PD-L2 | Monotherapy and Combo Therapy | MEDI4736 + Tremelimumab | Bladder Cancer | III |
| PD-1/PD-L1 and PD-L2 | Monotherapy and Combo Therapy | MEDI4736 + Tremelimumab | Hepatocellular (Liver) Cancer (HCC) (including secondary metastases) | II |
| PD-1/PD-L1 and PD-L2 | Combination | AZD5069 + MEDI4736, AZD9150 + MEDI4736 | Head and Neck Cancer | I/II |
| PD-1/PD-L1 and PD-L2 | Monotherapy | | Solid Tumors | II |
| PD-1/PD-L1 and PD-L2 | Combination | Durvalumab + Tremelimumab | Non-Small Cell Lung Cancer (NSCLC) | III |
| PD-1/PD-L1 and PD-L2 | Combination | Chemotherapy + Durvalumab | Non-Small Cell Lung Cancer (NSCLC) | III |
| PD-1/PD-L1 and PD-L2 | Combination | MEDI4736 + olaparib or MEDI4736 + cediranib | Solid Tumors | I/II |
| PD-1/PD-L1 and PD-L2 | Monotherapy and Combo Therapy | | Non-Small Cell Lung Cancer (NSCLC) | III |
| PD-1/PD-L1 and PD-L2 | Combination | MEDI4736 + nab-paclitaxel + gemcitabine<BR> MEDI4736 + AZD5069 | Pancreatic Cancer | I/II |
| PD-1/PD-L1 and PD-L2 | Monotherapy | | Head and Neck Cancer | III |
| PD-1/PD-L1 and PD-L2 | Monotherapy and Combo Therapy | | Pancreatic Cancer | II |
| PD-1/PD-L1 and PD-L2 | Monotherapy and Combo Therapy | | Multiple Myeloma (MM) | I |
| PD-1/PD-L1 and PD-L2 | Monotherapy and Combo Therapy | | Non-Hodgkin's Lymphoma (NHL) | I/II |
| PD-1/PD-L1 and PD-L2 | Combination | TIL + Durvalumab | Myelodysplastic Syndrome (MDS) | I |
| PD-1/PD-L1 and PD-L2 | Combination | TIL + Durvalumab | Myelodysplastic Syndrome (MDS) | I |
| PD-1/PD-L1 and PD-L2 | Combination | IMCgp100 + MEDI4736 +/− Tremelimumab | Head and Neck Cancer | II |
| PD-1/PD-L1 and PD-L2 | Combination | | Melanoma | II |
| PD-1/PD-L1 and PD-L2 | Monotherapy and Combo Therapy | | Melanoma | I/II |

TABLE D-continued

| | | | | |
|---|---|---|---|---|
| | PD-1/PD-L1 and PD-L2 | Monotherapy | | Non-Small Cell Lung Cancer (NSCLC) | II |
| | PD-1/PD-L1 and PD-L2 | Combination | Dexamethasone + Durvalumab + Lenalidomide, Durvalumab + Lenalidomide | Multiple Myeloma (MM) | I/II |
| EBV-CTL | EBV, T lymphocytes | Monotherapy | | Hematologic Cancer | II |
| | EBV, T lymphocytes | Monotherapy | | Hematologic Cancer | I/II |
| EC17 | Immune system | Combination | | Solid Tumors | II |
| EGFRvIII CAR | CAR-T, EGFR, Stem Cells, T lymphocytes | Combination | Anti-EGFRvIII CAR + Aldesleukin + Cyclophosphamide + Fludarabine | Brain Cancer (malignant glioma; AA and GBM) | I/II |
| ETBX-011 | CEA | Monotherapy | | Colorectal Cancer (CRC) | I |
| Folate Receptor | FOLR1 | Monotherapy | | Breast Cancer | I |
| Peptide Vaccine | FOLR1 | Monotherapy | | Ovarian Cancer | I |
| | FOLR1 | Monotherapy | | Ovarian Cancer | I |
| | FOLR1 | Monotherapy | | Ovarian Cancer | II |
| | FOLR1 | Monotherapy | | Breast Cancer | II |
| FPI-01 | WT1 | Monotherapy | | Acute Myelogenous Leukemia (AML) | II |
| | WT1 | Monotherapy | | Acute Lymphocytic Leukemia (ALL) | II |
| | WT1 | Combination | WT1-vaccine + Montanide + GM-CSF | Mesothelioma | III |
| G17DT | G17, Protein synthesis | Combination | G17DT Immunogen + Chemotherapy | Pancreatic Cancer | III |
| | G17, Protein synthesis | Monotherapy | | Gastric Cancer | II |
| | G17, Protein synthesis | Monotherapy | | Pancreatic Cancer | II |
| GALE-301 | Folate Binding Protein | Monotherapy | | Ovarian Cancer | I/II |
| | Folate Binding Protein | Monotherapy | | Uterine (Endometrial) Cancer | I/II |
| GALE-301/302 | Folate Binding Protein | Monotherapy | | Breast Cancer | I |
| | Folate Binding Protein | Monotherapy | | Ovarian Cancer | I |
| Galinpepimut-S | CD4 | Monotherapy | | Acute Myelogenous Leukemia (AML) | II |
| | CD4 | Monotherapy | | Acute Myelogenous Leukemia (AML) | I |
| | CD4 | Monotherapy | | Mesothelioma | II |
| | CD4 | Combination | WT1 with GM-CSF and lenalidomide | Multiple Myeloma (MM) | I/II |
| Galiximab | CTLA4 | Monotherapy | | Indolent Non-Hodgkin's Lymphoma - NHL | I/II |
| | CTLA4 | Combination | Galiximab with Rituxan | Indolent Non-Hodgkin's Lymphoma - NHL | II |
| | CTLA4 | Combination | With Rituxan | Indolent Non-Hodgkin's Lymphoma - NHL | II |
| | CTLA4 | Combination | Galiximab + Rituxan | Indolent Non-Hodgkin's Lymphoma - NHL | III |
| | CTLA4 | Combination | Rituximab + galiximab | Indolent Non-Hodgkin's Lymphoma - NHL | II |
| | Immune system | Monotherapy | | Brain Cancer (malignant glioma; AA and GBM) | Preclinical |
| GBR 1302 | CD3, HER2/neu or ErbB-2 | Monotherapy | | Cancer | I/II |
| GCT-NK | Stem Cells | Monotherapy | | Acute Myelogenous Leukemia (AML) | Preclinical |
| GI-4000 | Ras | Combination | GI-4000 combined with gemcitabine | Pancreatic Cancer | I |
| | Ras | Combination | GI-4000 w/bevacizumab alone or + FOLFOX/FOLFIRI | Colorectal Cancer (CRC) | IIb |
| | Ras | Monotherapy | | Non-Small Cell Lung Cancer (NSCLC) | II |
| GI-6207 | CEA | Monotherapy | | Thyroid Cancer | I |
| | CEA | Monotherapy | | Thyroid Cancer | II |
| GI-6301 | Brachyury, Tumor Cells | Monotherapy | | Bone Cancer | I |
| | Brachyury, Tumor Cells | Monotherapy | | Bone Cancer | II |
| GL-0817 | MAGE | Monotherapy | | Multiple Myeloma (MM) | II |
| GMK | Immune system | Combination | GMK with high-dose alpha-interferon | Melanoma | III |
| | Immune system | Monotherapy | | Melanoma | III |
| GRN-1201 | HLA-A | Monotherapy | | Melanoma | I |
| GV1001 | Telomerase | Monotherapy | | Pancreatic Cancer | III |
| | Telomerase | Combination | GV1001 plus GM-CSF | Pancreatic Cancer | III |
| | Telomerase | Monotherapy | W/gemcitabine and capecitabine | Hepatocellular (Liver) Cancer (HCC) (including secondary metastases) | II |

TABLE D-continued

| Name | Target | Type | Description | Cancer | Phase |
|---|---|---|---|---|---|
| GVAX Leukemia Vaccine | Telomerase | Monotherapy | | Non-Small Cell Lung Cancer (NSCLC) | II |
| | Telomerase | Monotherapy | | Non-Small Cell Lung Cancer (NSCLC) | I/II |
| | Telomerase | Monotherapy | | Non-Small Cell Lung Cancer (NSCLC) | III |
| | Immune system | Combination | Successful response to chemotherapy and stem cell transplantation followed with GVAX vaccine | Acute Myelogenous Leukemia (AML) | II |
| GVAX Leukemia Vaccine | Immune system | Combination | | Chronic Myelogenous Leukemia (CML) | II |
| GVAX Melanoma Vaccine | Stem Cells | Monotherapy and Combo Therapy | Melanoma GVAX + Cyclophosphamide | Melanoma | I |
| GVAX Pancreatic Vaccine | GM-CSFR/CD116, Stem Cells | Combination | | Pancreatic Cancer | II |
| | GM-CSFR/CD116, Stem Cells | Combination | GVAX pancreatic cancer vaccine + cyclophosphamide | Pancreatic Cancer | II |
| | GM-CSFR/CD116, Stem Cells | Combination | GVAX pancreatic vaccine + Erbitux (cetuximab) + cyclophosphamide | Pancreatic Cancer | II |
| | GM-CSFR/CD116, Stem Cells | Monotherapy and Combo Therapy | GVAX Pancreas + Cyclophosphamide + CRS-207 | Pancreatic Cancer | II |
| | GM-CSFR/CD116, Stem Cells | Combination | Ipilimumab + PANC 10.05 pcDNA-1/GM-Neo and PANC 6.03 pcDNA-1 neo vaccine | Pancreatic Cancer | I |
| | GM-CSFR/CD116, Stem Cells | Monotherapy | CRS-207 + GVAX Pancreas Vaccine +/- Nivolumab | Pancreatic Cancer | IIb |
| | GM-CSFR/CD116, Stem Cells | Combination | | Pancreatic Cancer | II |
| GVAX Prostate Cancer Vaccine | GM-CSFR/CD116, Stem Cells | Monotherapy | | Prostate Cancer | I/II |
| | GM-CSFR/CD116, Stem Cells | Monotherapy | GVAX vaccine plus Taxotere | Prostate Cancer | III |
| | GM-CSFR/CD116, Stem Cells | Combination | | Prostate Cancer | I/II |
| | GM-CSFR/CD116, Stem Cells | Monotherapy | | Prostate Cancer | I/II |
| | GM-CSFR/CD116, Stem Cells | Monotherapy | | Prostate Cancer | I/II |
| | GM-CSFR/CD116, Stem Cells | Combination | GVAX and ipilimumab | Prostate Cancer | I/II |
| Hi-8 MEL | Immune system | Monotherapy | Hi-8 MEL and placebo | Melanoma | II |
| HLA-DR/CD5 Platform | CD5, HLA-DR | Monotherapy | | Cancer | Preclinical |
| HS-120 | OX40/CD134 and OX40L, Stem Cells | Monotherapy | | Non-Small Cell Lung Cancer (NSCLC) | Preclinical |
| Hu5F9-G4 | CD47 | Monotherapy | | Solid Tumors | I |
| | CD47 | Monotherapy | | Acute Myelogenous Leukemia (AML) | I |
| | CD47 | Monotherapy | | Acute Myelogenous Leukemia (AML) | Preclinical |
| | CD47 | Monotherapy | | Solid Tumors | Preclinical |
| HyperAcute Lung | Stem Cells | Monotherapy | | Non-Small Cell Lung Cancer (NSCLC) | I/II |
| | Stem Cells | Monotherapy | | Non-Small Cell Lung Cancer (NSCLC) | II |
| | Stem Cells | Combination | HyperAcute-Lung + Docetaxel + Gemcitabine + Pemetrexed | Non-Small Cell Lung Cancer (NSCLC) | II/III |
| HyperAcute Melanoma | Stem Cells | Monotherapy | | Non-Small Cell Lung Cancer (NSCLC) | IIb |
| | Stem Cells | Combination | HyperAcute vaccine + Pegylated Interferon-Alpha 2b | Melanoma | II |
| | Stem Cells | Monotherapy | | Melanoma | I/II |
| | Stem Cells | Monotherapy and Combo Therapy | HyperAcute-Melanoma (HAM) Immunotherapy + Ipilimumab | Melanoma | II |
| HyperAcute Pancreas | Stem Cells | Combination | With adjuvant standard of care (gemcitabine alone or with 5-FU chemoradiation) | Pancreatic Cancer | III |
| | Stem Cells | Combination | With chemotherapy and chemoradiation | Pancreatic Cancer | II |
| | Stem Cells | Monotherapy and Combo Therapy | With or without chemotherapy and chemoradiation | Pancreatic Cancer | II |
| | Stem Cells | Combination | FOLFIRINOX w/ algenpantucel-L | Pancreatic Cancer | III |

TABLE D-continued

| | | | | |
|---|---|---|---|---|
| HyperAcute Prostate | Immune system | Monotherapy | | Prostate Cancer | I/II |
| HyperAcute Renal | Immune system | Monotherapy | | Renal Cell Cancer (RCC) | I |
| IAB22M2C | Immune system | Monotherapy | | Cancer - Imaging | Preclinical |
| ICT-107 | AIM-2, gp100, HER2/neu or ErbB-2, IL-13R, MAGE, Stem Cells, TRP2 | Monotherapy | | Brain Cancer (malignant glioma; AA and GBM) | IIb |
| ICT-107 | AIM-2, gp100, HER2/neu or ErbB-2, IL-13R, MAGE, Stem Cells, TRP2 | Combination | With surgery, radiation and chemotherapy | Brain Cancer (malignant glioma; AA and GBM) | I |
| ICT-121 | AIM-2, gp100, HER2/neu or ErbB-2, IL-13R, MAGE, Stem Cells, TRP2 | Combination | ICT-107 in combination with the standard of care, temozolomide (TMZ) | Brain Cancer (malignant glioma; AA and GBM) | III |
| ICT-121 | CD133/PROM1, Stem Cells | Monotherapy | | Brain Cancer (malignant glioma; AA and GBM) | Preclinical |
| ID-G100 | CD133/PROM1, Stem Cells | Monotherapy | | Brain Cancer (malignant glioma; AA and GBM) | I |
| | TLR4 | Monotherapy | | Merkel Cell Carcinoma | I |
| | TLR4 | Monotherapy | | Sarcoma | I |
| | TLR4 | Combination | G100 + Keytruda | Non-Hodgkin's Lymphoma (NHL) | I/II |
| | TLR4 | Monotherapy | | Non-Hodgkin's Lymphoma (NHL) | I/II |
| | TLR4 | Monotherapy | | Non-Hodgkin's Lymphoma (NHL) | Preclinical |
| | TLR4 | Monotherapy | | Merkel Cell Carcinoma | Preclinical |
| ID-LV305 | NY-ESO-1 | Monotherapy | | Solid Tumors | I |
| | NY-ESO-1 | Combination | ID-G100 + Keytruda | Melanoma | I |
| IL-33 DNA Vaccine | IL-33, IL-33 Receptor | Monotherapy | | Solid Tumors | Preclinical |
| IMA901 | Immune system | Combination | IMA901 + GM-CSF | Renal Cell Cancer (RCC) | II |
| | Immune system | Combination | | Renal Cell Cancer (RCC) | III |
| IMA910 | Tumor Cells | Combination | | Colorectal Cancer (CRC) | I/II |
| IMA950 | Tumor Cells | Combination | | Brain Cancer (malignant glioma; AA and GBM) | I/II |
| | Tumor Cells | Monotherapy | | Brain Cancer (malignant glioma; AA and GBM) | I |
| Imlygic | GM-CSFR/CD116 | Combination | | Colorectal Cancer (CRC) | II |
| | GM-CSFR/CD116 | Monotherapy | | Melanoma | II |
| | GM-CSFR/CD116 | Combination | | Melanoma | III |
| | GM-CSFR/CD116 | Combination | With or without chemoradiation | Head and Neck Cancer | I/II |
| | GM-CSFR/CD116 | Combination | OncoVEX GM-CSF + chemotherapy | Head and Neck Cancer | I/II |
| | GM-CSFR/CD116 | Monotherapy | | Melanoma | I/II |
| | GM-CSFR/CD116 | Combination | Keytruda + T-VEC | Melanoma | II |
| | GM-CSFR/CD116 | Combination | Keytruda + T-VEC | Head and Neck Cancer | I |
| IMM-101 | Immune system | Monotherapy and Combo Therapy | | Melanoma | III |
| | Immune system | Combination | IMM-101 + Gemcitabine | Pancreatic Cancer | II |
| | Immune system | Monotherapy | | Colorectal Cancer (CRC) | II |
| | Immune system | Monotherapy | | Melanoma | I/II |
| ImMucin | MUC-1 | Monotherapy | | Multiple Myeloma (MM) | I/II |
| | MUC-1 | Monotherapy | | Multiple Myeloma (MM) | Preclinical |
| | MUC-1 | Monotherapy | | Multiple Myeloma (MM) | I/II |
| | MUC-1 | Monotherapy | | Breast Cancer | I/II |
| ImmuFact IMP321 | LAG3/CD223 | Combination | IMP321 + paclitaxel | Breast Cancer | I/II |
| | LAG3/CD223 | Combination | IMP321 + Paclitaxel | Breast Cancer | IIb |
| | LAG3/CD223 | Combination | | Melanoma | I |
| | LAG3/CD223 | Combination | | Melanoma | I/II |

TABLE D-continued

| | | | | | |
|---|---|---|---|---|---|
| IMP701 | LAG3/CD223 | | LAG525 and PDR001 | Combination | Cancer | I/II |
| Imprime PGG | Complement Proteins | | Imprime PGG in combination with Erbitux (cetuximab) with and without irinotecan | Combination | Colorectal Cancer (CRC) | I/II |
| | Complement Proteins | | Imprime PGG + Avastin + paclitaxel/carboplatin | Combination | Colorectal Cancer (CRC) | II |
| | Complement Proteins | | Imprime PGG + cetuximab + paclitaxel/carboplatin | Combination | Non-Small Cell Lung Cancer (NSCLC) | IIb |
| | Complement Proteins | | Imprime PGG + Rituximab + Alemtuzumab | Combination | Non-Small Cell Lung Cancer (NSCLC) | IIb |
| | Complement Proteins | | | Combination | Chronic Lymphocytic Leukemia (CLL)/Small Cell Lymphocytic Lymphoma (SLL) - NHL | I/II |
| | Complement Proteins | | Imprime PGG + cetuximab | Combination | Colorectal Cancer (CRC) | III |
| | Complement Proteins | | | Monotherapy | Pancreatic Cancer | Preclinical |
| | Complement Proteins | | | Monotherapy | Colorectal Cancer (CRC) | Preclinical |
| | Complement Proteins | | | Monotherapy | Non-Small Cell Lung Cancer (NSCLC) | Preclinical |
| | Complement Proteins | | | Monotherapy | Chronic Lymphocytic Leukemia (CLL)/Small Cell Lymphocytic Lymphoma (SLL) - NHL | Preclinical |
| | Complement Proteins | | | Monotherapy | Melanoma | Preclinical |
| | Complement Proteins | | | Monotherapy | Pancreatic Cancer | I |
| | Complement Proteins | | Imprime PGG in combination with pembrolizumab | Combination | Indolent Non-Hodgkin's Lymphoma - NHL | Preclinical |
| | Complement Proteins | | | Combination | Non-Small Cell Lung Cancer (NSCLC) | I/II |
| | Complement Proteins | | | Monotherapy | Non-Small Cell Lung Cancer (NSCLC) | I |
| | Complement Proteins | | | Monotherapy | Non-Small Cell Lung Cancer (NSCLC) | I |
| Indoximod | IDO | | 1-methyl-D-tryptophan + Ad.p53 DC vaccine | Monotherapy | Solid Tumors | I |
| | IDO | | 1-methyl-D-tryptophan + Docetaxel | Combination | Solid Tumors | I/II |
| | IDO | | Provenge + indoximod | Combination | Prostate Cancer | I |
| | IDO | | Docetaxel + Indoximod | Combination | Breast Cancer | II |
| | IDO | | | Combination | Brain Cancer (malignant glioma; AA and GBM) | II |
| | IDO | | | Monotherapy | Melanoma | I/II |
| | IDO | | | Monotherapy | Solid Tumors | I/II |
| | IDO | | Indoximod + Gemcitabine + Nab-paclitaxel | Combination | Pancreatic Cancer | Preclinical |
| | IDO | | Indoximod + Temozolomide | Combination | Brain Cancer (malignant glioma; AA and GBM) | I/II |
| | IDO | | | Monotherapy | Melanoma | I |
| INO-1400 | Telomerase | | INO-1400 + INO-9012 | Monotherapy and Combo Therapy | Solid Tumors | Preclinical |
| INO-3106 | Telomerase | | INO-3106 alone or in combination with INO-9012 | Monotherapy and Combo Therapy | Solid Tumors | Preclinical |
| INO-3112 | HPV | | | Monotherapy | Head and Neck Cancer | I |
| | HPV | | INO-3112 (VGX-3100 + DNA-based IL-12) | Monotherapy | Head and Neck Cancer | I/II |
| | HPV | | INO-3112 vaccine + Radiotherapy (External beam radiotherapy + brachytherapy) + Cisplatin chemotherapy | Combination | Cervical Cancer | I/II |
| | HPV | | | Combination | Cervical Cancer | II |
| INO-5150 | PSA, PSMA | | INO-5150 + INO-9012 | Monotherapy | Prostate Cancer | Preclinical |
| | PSA, PSMA | | | Monotherapy and Combo Therapy | Prostate Cancer | I |
| INVAC-1 | Telomerase | | | Monotherapy | Solid Tumors | I |
| IPH 2101 | KIR | | | Monotherapy | Multiple Myeloma (MM) | II |
| IPH 2101 | KIR | | IPH2101 + lenalinomide | Combination | Multiple Myeloma (MM) | I/II |
| | KIR | | | Monotherapy | Multiple Myeloma (MM) | II |
| | KIR | | | Monotherapy | Multiple Myeloma (MM) | II |
| IPH 2102 | KIR | | | Monotherapy | Acute Myelogenous Leukemia (AML) | I |
| | KIR | | | Monotherapy | Solid Tumors | I |
| | KIR | | | Monotherapy | Solid Tumors | I |
| | KIR | | | Monotherapy | Non-Hodgkin's Lymphoma (NHL) | Preclinical |
| | KIR | | | Monotherapy | Multiple Myeloma (MM) | I |

TABLE D-continued

| Drug | Target | Therapy | Combination | Indication | Phase |
|---|---|---|---|---|---|
| | KIR | Monotherapy | | Multiple Myeloma (MM) | Preclinical |
| | KIR | Combination | Lirilumab + Rituximab | Chronic Lymphocytic Leukemia (CLL)/Small Cell Lymphocytic Lymphoma (SLL) - NHL | II |
| | KIR | Monotherapy | | Myelodysplastic Syndrome (MDS) | II |
| IPH2201 | KIR | Monotherapy | | Head and Neck Cancer | I/II |
| | KIR | Combination | IPH2201 + Cetuximab | Head and Neck Cancer | II |
| | KIR | Combination | IPH2201 + Ibrutinib | Chronic Lymphocytic Leukemia (CLL)/Small Cell Lymphocytic Lymphoma (SLL) - NHL | I/II |
| | KIR | Monotherapy | | Ovarian Cancer | I/II |
| | KIR | Combination | Durvalumab + IPH2201 | Solid Tumors | I |
| IPH41 | KIR | Monotherapy | | Non-Hodgkin's Lymphoma (NHL) | Preclinical |
| IPH4102 | KIR | Monotherapy | | Cutaneous T-Cell Lymphoma (CTCL) - NHL | Preclinical |
| | KIR | Monotherapy | | Cutaneous T-Cell Lymphoma (CTCL) - NHL | I |
| IRX-2 | Immune system | Combination | | Head and Neck Cancer | II |
| | Immune system | Combination | IRX-2 + Cyclophosphamide + Indomethacin + Zinc-containing multivitamin + Omeprazole | Head and Neck Cancer | II |
| ISA101 | Immune system | Combination | | Cervical Cancer | I |
| | Immune system | Monotherapy and Combo Therapy | ISA101 + Carboplatin/Paclitaxel +/− pegylated interferon | Cervical Cancer | I/II |
| | Immune system | Monotherapy | | Cervical Cancer | Preclinical |
| ISA102 | Immune system | Combination | | Solid Tumors | II |
| ISF35 | p53 | Monotherapy | ISA101 + Nivolumab | Ovarian Cancer | II |
| | CD40 | Monotherapy | | Chronic Lymphocytic Leukemia (CLL)/Small Cell Lymphocytic Lymphoma (SLL) - NHL | II |
| | CD40 | Monotherapy | | Diffuse Large B-Cell Lymphoma (DLBCL) - NHL | II |
| | CD40 | Monotherapy | | Mantle Cell Lymphoma - NHL | II |
| | CD40 | Monotherapy | | Indolent Non-Hodgkin's Lymphoma - NHL | II |
| | CD40 | Monotherapy | | Chronic Lymphocytic Leukemia (CLL)/Small Cell Lymphocytic Lymphoma (SLL) - NHL | II |
| ITK-1 | HLA-A | Monotherapy | | Prostate Cancer | III |
| | HLA-A | Combination | ITK-1 + estramustine phosphate (EMP) | Prostate Cancer | I |
| JCAR014 | CAR-T, CD19, Stem Cells, T lymphocytes | Monotherapy | | Hematologic Cancer | I/II |
| JCAR015 | CAR-T, CD19, Stem Cells, T lymphocytes | Monotherapy | | Acute Lymphocytic Leukemia (ALL) | I |
| JCAR015 | CAR-T, CD19, Stem Cells, T lymphocytes | Monotherapy | | Diffuse Large B-Cell Lymphoma (DLBCL) - NHL | I |
| JCAR017 | CAR-T, CD19, Stem Cells, T lymphocytes | Monotherapy | | Acute Lymphocytic Leukemia (ALL) | II |
| | CAR-T, CD19, Stem Cells, T lymphocytes | Monotherapy | Patient Derived CD19 specific CART cells also expressing an EGFRt | Acute Lymphocytic Leukemia (ALL) | I/II |
| JCAR018 | CAR-T, CD19, Stem Cells, T lymphocytes | Monotherapy | | Non-Hodgkin's Lymphoma (NHL) | I |
| | CAR-T, CD19, Stem Cells, T lymphocytes | Monotherapy | | Non-Hodgkin's Lymphoma (NHL) | I |
| | CAR-T, CD19, Stem Cells, T lymphocytes | Monotherapy | | Acute Lymphocytic Leukemia (ALL) | I |
| JCAR023 | CAR-T, CD19, Stem Cells, T lymphocytes | Monotherapy | | Neuroendocrine Tumors (NET) | I |

TABLE D-continued

| | | | | |
|---|---|---|---|---|
| J-HER | HER2/neu or ErbB-2 | Monotherapy | | Breast Cancer | Preclinical |
| JTCR016 | Stem Cells, TCR, WT1 | Monotherapy | | Acute Myelogenous Leukemia (AML) | I/II |
| | Stem Cells, TCR, WT1 | Combination | Aldesleukin + Autologous WT1-TCRc4 Gene-transduced CD8-positive Tcm/Tn Lymphocytes + Cyclophosphamide, or + Therapeutic Conventional Surgery | Non-Small Cell Lung Cancer (NSCLC) | I/II |
| JX-929 | EGFR | Monotherapy | | Solid Tumors | I |
| KAHR-102 | CTLA4, FasR)/CD95/Apo-1/TNFRSf6 | Monotherapy | | Cancer | I/II |
| Keytruda | PD-1/PD-L1 and PD-L2 | Monotherapy | | Melanoma | I |
| | PD-1/PD-L1 and PD-L2 | Monotherapy | | Melanoma | II |
| | PD-1/PD-L1 and PD-L2 | Monotherapy | | Non-Small Cell Lung Cancer (NSCLC) | I |
| | PD-1/PD-L1 and PD-L2 | Monotherapy | | Solid Tumors | I |
| | PD-1/PD-L1 and PD-L2 | Monotherapy | | Melanoma | III |
| | PD-1/PD-L1 and PD-L2 | Monotherapy and Combo Therapy | | Non-Small Cell Lung Cancer (NSCLC) | I |
| | PD-1/PD-L1 and PD-L2 | Monotherapy | | Non-Small Cell Lung Cancer (NSCLC) | II/III |
| | PD-1/PD-L1 and PD-L2 | Monotherapy | | Hodgkin's Lymphoma | I |
| | PD-1/PD-L1 and PD-L2 | Monotherapy | | Colorectal Cancer (CRC) | II |
| | PD-1/PD-L1 and PD-L2 | Monotherapy | | Solid Tumors | II |
| | PD-1/PD-L1 and PD-L2 | Monotherapy and Combo Therapy | MK-3475 + Pazopanib | Renal Cell Cancer (RCC) | I/II |
| | PD-1/PD-L1 and PD-L2 | Monotherapy | | Non-Small Cell Lung Cancer (NSCLC) | I |
| | PD-1/PD-L1 and PD-L2 | Monotherapy | | Multiple Myeloma (MM) | I |
| | PD-1/PD-L1 and PD-L2 | Combination | Pembrolizumab with paclitaxel/carboplatin, paclitaxel/carboplatin/bevacizumab, carboplatin/pemetrexed, ipilimumab, erlotinib, paclitaxel/carboplatin | Non-Small Cell Lung Cancer (NSCLC) | I/II |
| | PD-1/PD-L1 and PD-L2 | Monotherapy | | Solid Tumors | I |
| | PD-1/PD-L1 and PD-L2 | Combination | Axitinib + MK-3475 | Renal Cell Cancer (RCC) | I |
| | PD-1/PD-L1 and PD-L2 | Monotherapy | | Solid Tumors | I/II |
| | PD-1/PD-L1 and PD-L2 | Monotherapy | | Melanoma | III |
| | PD-1/PD-L1 and PD-L2 | Monotherapy | | Multiple Myeloma (MM) | Preclinical |
| | PD-1/PD-L1 and PD-L2 | Monotherapy | | Solid Tumors | Preclinical |
| | PD-1/PD-L1 and PD-L2 | Monotherapy | | Melanoma | I/II |
| | PD-1/PD-L1 and PD-L2 | Monotherapy | | Melanoma | I/II |
| | PD-1/PD-L1 and PD-L2 | Monotherapy | | Non-Small Cell Lung Cancer (NSCLC) | III |
| | PD-1/PD-L1 and PD-L2 | Monotherapy | | Head and Neck Cancer | III |
| | PD-1/PD-L1 and PD-L2 | Monotherapy | | Non-Small Cell Lung Cancer (NSCLC) | III |
| | PD-1/PD-L1 and PD-L2 | Monotherapy | | Head and Neck Cancer | I |
| | PD-1/PD-L1 and PD-L2 | Monotherapy and Combo Therapy | Pembrolizumab + Ipilimumab, Pembrolizumab + PegIFN-2b | Melanoma | I/II |
| | PD-1/PD-L1 and PD-L2 | Monotherapy and Combo Therapy | | Renal Cell Cancer (RCC) | I |
| | PD-1/PD-L1 and PD-L2 | Monotherapy | | Gastric Cancer | I |
| | PD-1/PD-L1 and PD-L2 | Monotherapy | | Bladder Cancer | I |
| | PD-1/PD-L1 and PD-L2 | Monotherapy | | Bladder Cancer | III |
| | PD-1/PD-L1 and PD-L2 | Monotherapy | | Head and Neck Cancer | II |
| | PD-1/PD-L1 and PD-L2 | Monotherapy | | Breast Cancer | I |
| | PD-1/PD-L1 and PD-L2 | Monotherapy | | Breast Cancer | I/II |
| | PD-1/PD-L1 and PD-L2 | Monotherapy and Combo Therapy | Pembrolizumab + cisplatin and 5-Fluorouracil (5-FU) | Gastric Cancer | II |
| | PD-1/PD-L1 and PD-L2 | Monotherapy | | Bladder Cancer | II |
| | PD-1/PD-L1 and PD-L2 | Combination | ADXS31-142 + Pembrolizumab (MK-3475) | Prostate Cancer | I/II |

TABLE D-continued

| Target | Type | Drug | Cancer | Phase |
|---|---|---|---|---|
| PD-1/PD-L1 and PD-L2 | Monotherapy | | Multiple Myeloma (MM) | I |
| PD-1/PD-L1 and PD-L2 | Monotherapy and Combo Therapy | | Head and Neck Cancer | III |
| PD-1/PD-L1 and PD-L2 | Monotherapy | | Melanoma | III |
| PD-1/PD-L1 and PD-L2 | Monotherapy | | Gastric Cancer | III |
| PD-1/PD-L1 and PD-L2 | Combination | pembrolizumab + lenvatinib | Solid Tumors | I/II |
| PD-1/PD-L1 and PD-L2 | Combination | pembrolizumab + eribulin | Breast Cancer | I/II |
| PD-1/PD-L1 and PD-L2 | Monotherapy | | Mesothelioma | I |
| PD-1/PD-L1 and PD-L2 | Combination | Keytruda + PLX3397 | Melanoma | I/II |
| PD-1/PD-L1 and PD-L2 | Monotherapy | | Ovarian Cancer | I |
| PD-1/PD-L1 and PD-L2 | Monotherapy | | Breast Cancer | II |
| PD-1/PD-L1 and PD-L2 | Monotherapy | | Hodgkin's Lymphoma | II |
| PD-1/PD-L1 and PD-L2 | Combination | Keytruda + T-VEC | Head and Neck Cancer | I |
| PD-1/PD-L1 and PD-L2 | Combination | Niraparib + Pembrolizumab | Ovarian Cancer | I/II |
| PD-1/PD-L1 and PD-L2 | Combination | Niraparib + Pembrolizumab | Breast Cancer | I/II |
| PD-1/PD-L1 and PD-L2 | Monotherapy and Combo Therapy | Pembrolizumab + Ipilimumab, Pembrolizumab + PegIFN2b | Renal Cell Cancer (RCC) | I/II |
| PD-1/PD-L1 and PD-L2 | Monotherapy | | Small Cell Lung Cancer (SCLC) | I |
| PD-1/PD-L1 and PD-L2 | Monotherapy | | Colorectal Cancer (CRC) | II |
| PD-1/PD-L1 and PD-L2 | Combination | SD-101 + pembrolizumab | Melanoma | I/II |
| PD-1/PD-L1 and PD-L2 | Monotherapy and Combo Therapy | Pembrolizumab + cisplatin + 5-fluorouracil (5-FU) or capecitabine | Gastric Cancer | III |
| PD-1/PD-L1 and PD-L2 | Combination | G100 + Keytruda | Non-Hodgkin's Lymphoma (NHL) | I/II |
| PD-1/PD-L1 and PD-L2 | Monotherapy and Combo Therapy | ACP-196 + pembrolizumab | Ovarian Cancer | II |
| PD-1/PD-L1 and PD-L2 | Combination | ublituximab + Pembrolizumab + TGR-1202 | Chronic Lymphocytic Leukemia (CLL)/Small Cell Lymphocytic Lymphoma (SLL) - NHL | I/II |
| PD-1/PD-L1 and PD-L2 | Combination | CC-486 + Pembrolizumab | Non-Small Cell Lung Cancer (NSCLC) | II |
| PD-1/PD-L1 and PD-L2 | Monotherapy | | Anal Cancer | I |
| PD-1/PD-L1 and PD-L2 | Monotherapy | | Colorectal Cancer (CRC) | I |
| PD-1/PD-L1 and PD-L2 | Monotherapy | | Biliary Tract Cancer | I |
| PD-1/PD-L1 and PD-L2 | Monotherapy | | Melanoma | I |
| PD-1/PD-L1 and PD-L2 | Monotherapy | | Breast Cancer | III |
| PD-1/PD-L1 and PD-L2 | Monotherapy | | Esophageal Cancer | II |
| PD-1/PD-L1 and PD-L2 | Monotherapy | | Head and Neck Cancer | I |
| PD-1/PD-L1 and PD-L2 | Monotherapy | | Merkel Cell Carcinoma | II |
| PD-1/PD-L1 and PD-L2 | Combination | Keytruda + Entinostat | Non-Small Cell Lung Cancer (NSCLC) | I/II |
| PD-1/PD-L1 and PD-L2 | Combination | entinostat + pembrolizumab | Melanoma | I/II |
| PD-1/PD-L1 and PD-L2 | Monotherapy | | Esophageal Cancer | III |
| PD-1/PD-L1 and PD-L2 | Combination | Pembrolizumab + Pomalidomide + Dexamethasone | Multiple Myeloma (MM) | III |
| PD-1/PD-L1 and PD-L2 | Combination | Pembrolizumab + Carboplatin + Cisplatin + Pemetrexed | Non-Small Cell Lung Cancer (NSCLC) | III |
| PD-1/PD-L1 and PD-L2 | Combination | margetuximab + pembrolizumab | Gastric Cancer | I/II |
| PD-1/PD-L1 and PD-L2 | Combination | Pembrolizumab + lenalidomide + dexamethasone | Multiple Myeloma (MM) | III |
| PD-1/PD-L1 and PD-L2 | Monotherapy | | Colorectal Cancer (CRC) | III |
| PD-1/PD-L1 and PD-L2 | Combination | | Breast Cancer | I |
| PD-1/PD-L1 and PD-L2 | Combination | | Solid Tumors | I/II |
| PD-1/PD-L1 and PD-L2 | Combination | Pomalidomide + Dexamethasone + MK-3475 | Diffuse Large B-Cell Lymphoma (DLBCL) - NHL | III |
| PD-1/PD-L1 and PD-L2 | Combination | | Multiple Myeloma (MM) | III |
| PD-1/PD-L1 and PD-L2 | Combination | | Non-Small Cell Lung Cancer (NSCLC) | I |
| PD-1/PD-L1 and PD-L2 | Combination | | Non-Small Cell Lung Cancer (NSCLC) | I |
| PD-1/PD-L1 and PD-L2 | Monotherapy | | Non-Small Cell Lung Cancer (NSCLC) | I |

TABLE D-continued

| | | | | |
|---|---|---|---|---|
| | PD-1/PD-L1 and PD-L2 | Combination | | Gastric Cancer | I |
| | PD-1/PD-L1 and PD-L2 | Combination | | Bladder Cancer | I |
| | PD-1/PD-L1 and PD-L2 | Monotherapy | | Chronic Lymphocytic Leukemia (CLL)/Small Cell Lymphocytic Lymphoma (SLL) - NHL | II |
| | PD-1/PD-L1 and PD-L2 | Combination | Pembrolizumab + Neoadjuvant Chemoradiation | Solid Tumors | I/II |
| | PD-1/PD-L1 and PD-L2 | Monotherapy | | Ovarian Cancer | II |
| | PD-1/PD-L1 and PD-L2 | Combination | | Solid Tumors | I |
| | PD-1/PD-L1 and PD-L2 | Monotherapy | | Hodgkin's Lymphoma | III |
| | PD-1/PD-L1 and PD-L2 | Combination | pembrolizumab + dinaciclib | Hematologic Cancer | I |
| | PD-1/PD-L1 and PD-L2 | Combination | Pembrolizumab + Best Supportive Care | Hepatocellular (Liver) Cancer (HCC) (including secondary metastases) | III |
| | PD-1/PD-L1 and PD-L2 | Monotherapy | | Hepatocellular (Liver) Cancer (HCC) (including secondary metastases) | II |
| KTE-C19 | CAR-T, CD19, Stem Cells, T lymphocytes | Monotherapy | | Acute Lymphocytic Leukemia (ALL) | I |
| | CAR-T, CD19, Stem Cells, T lymphocytes | Combination | Anti-CD19-CAR PBL + Fludarabine + Cyclophosphamide | Chronic Lymphocytic Leukemia (CLL)/Small Cell Lymphocytic Lymphoma (SLL) - NHL | I |
| | CAR-T, CD19, Stem Cells, T lymphocytes | Combination | Anti-CD19-CAR PBL + Fludarabine + Cyclophosphamide | Mantle Cell Lymphoma - NHL | I |
| | CAR-T, CD19, Stem Cells, T lymphocytes | Combination | Cyclophosphamide + Fludarabine + Anti-CD19-CAR PBL | Diffuse Large B-Cell Lymphoma (DLBCL) - NHL | I/II |
| | CAR-T, CD19, Stem Cells, T lymphocytes | Combination | Cyclophosphamide + Fludarabine + Anti-CD19-CAR PBL | Acute Lymphocytic Leukemia (ALL) | I |
| | CAR-T, CD19, Stem Cells, T lymphocytes | Monotherapy | | Diffuse Large B-Cell Lymphoma (DLBCL) - NHL | I |
| | CAR-T, CD19, Stem Cells, T lymphocytes | Monotherapy | | Mantle Cell Lymphoma - NHL | I |
| | CAR-T, CD19, Stem Cells, T lymphocytes | Monotherapy | | Chronic Lymphocytic Leukemia (CLL)/Small Cell Lymphocytic Lymphoma (SLL) - NHL | I |
| | CAR-T, CD19, Stem Cells, T lymphocytes | Monotherapy | | Acute Lymphocytic Leukemia (ALL) | I |
| | CAR-T, CD19, Stem Cells, T lymphocytes | Combination | Cyclophosphamide + Pentostatin + Anti-CD19-chimeric-antigenreceptor-traduced T cell | Chronic Lymphocytic Leukemia (CLL)/Small Cell Lymphocytic Lymphoma (SLL) - NHL | I |
| | CAR-T, CD19, Stem Cells, T lymphocytes | Combination | Cyclophosphamide + Pentostatin + Anti-CD19-chimeric-antigenreceptor-traduced T cell | Mantle Cell Lymphoma - NHL | I |
| | CAR-T, CD19, Stem Cells, T lymphocytes | Combination | Cyclophosphamide + Pentostatin + Anti-CD19-chimeric-antigenreceptor-traduced T cell | Diffuse Large B-Cell Lymphoma (DLBCL) - NHL | I |
| | CAR-T, CD19, Stem Cells, T lymphocytes | Monotherapy | | Chronic Lymphocytic Leukemia (CLL)/Small Cell Lymphocytic Lymphoma (SLL) - NHL | I/II |
| | CAR-T, CD19, Stem Cells, T lymphocytes | Monotherapy | | Diffuse Large B-Cell Lymphoma (DLBCL) - NHL | I/II |
| | CAR-T, CD19, Stem Cells, T lymphocytes | Monotherapy | | Indolent Non-Hodgkin's Lymphoma - NHL | I/II |
| | CAR-T, CD19, Stem Cells, T lymphocytes | Monotherapy | | Mantle Cell Lymphoma - NHL | II |
| | CAR-T, CD19, Stem Cells, T lymphocytes | Monotherapy | | Acute Lymphocytic Leukemia (ALL) | I/II |
| | CAR-T, CD19, Stem Cells, T lymphocytes | Monotherapy | | Acute Lymphocytic Leukemia (ALL) | I/II |
| | CAR-T, CD19, Stem Cells, T lymphocytes | Combination | | Non-Hodgkin's Lymphoma (NHL) | I/II |

TABLE D-continued

| | | | | |
|---|---|---|---|---|
| LAG-3 Antibody | LAG3/CD223 | Monotherapy | | Solid Tumors | Preclinical |
| Limtop | Immune system | Monotherapy | | Skin Cancer - Basal Cell Carcinoma (BCC) | I |
| Lipo-MERIT | Immune system | Monotherapy | | Melanoma | I |
| LN-145 | HPV, Stem Cells, T lymphocytes | Combination | | Cervical Cancer | II |
| | HPV, Stem Cells, T lymphocytes | Combination | TIL + Durvalumab | Melanoma | II |
| | HPV, Stem Cells, T lymphocytes | Combination | TIL + Durvalumab | Head and Neck Cancer | II |
| LOAd703 | CD40L/gp39 | Combination | LOAd703 + Gemcitabine + nab-paclitaxel | Pancreatic Cancer | I/II |
| LTX-315/GV1001 | Cell Membrane, Telomerase | Monotherapy | | Cancer | I |
| Lucanix | TGF-beta and Superfamily | Monotherapy | | Non-Small Cell Lung Cancer (NSCLC) | III |
| | TGF-beta and Superfamily | Monotherapy | | Non-Small Cell Lung Cancer (NSCLC) | II |
| Lumiliximab | CD23/Fc epsilon RII | Combination | Lumiliximab + fludarabine, cyclophosphamide, and Rituxan (FCR) vs FCR alone | Chronic Lymphocytic Leukemia (CLL)/Small Cell Lymphocytic Lymphoma (SLL) - NHL | II/III |
| | CD23)/Fc epsilon RII | Monotherapy | w/FCR | Chronic Lymphocytic Leukemia (CLL)/Small Cell Lymphocytic Lymphoma (SLL) - NHL | I/II |
| L-Vax | Stem Cells | Monotherapy | | Non-Small Cell Lung Cancer (NSCLC) | I/II |
| M7824 | Immune system | Monotherapy | | Solid Tumors | I |
| MabVax Neuroblastoma Vaccine | Ganglioside GD2, Ganglioside GD3 | Monotherapy | | Neuroendocrine Tumors (NET) | I/II |
| mAbXcite | Immune system | Monotherapy | | Cancer | Preclinical |
| MAGE A3 TCR | MAGE, Stem Cells, T lymphocytes | Combination | Anti-MAGE-A3 HLAA 01-restricted TCR + Aldesleukin + Cyclophosphamide + Fludarabine | Cancer | I/II |
| MAGE A3/A6 TCR | (MAGE, Stem Cells, T lymphocytes | Combination | Anti-MAGE-A3-DP4 TCR + Aldesleukin + Cyclophosphamide + Fludarabine | Cancer | I/II |
| MAGE-A10 T | Stem Cells, Tumor Cells | Monotherapy | | Non-Small Cell Lung Cancer (NSCLC) | I/II |
| | Stem Cells, Tumor Cells | Monotherapy | | Non-Small Cell Lung Cancer (NSCLC) | Preclinical |
| MAGE-A3 | MAGE | Monotherapy | | Non-Small Cell Lung Cancer (NSCLC) | IIb |
| | MAGE | Monotherapy | | Non-Small Cell Lung Cancer (NSCLC) | III |
| | MAGE | Combination | MAGE-A3 protein combined with either AS15 or AS02B | Melanoma | II |
| | MAGE | Monotherapy | | Melanoma | II |
| | MAGE | Combination | GSK1572932A in combination with dacarbazine | Melanoma | III |
| | MAGE | Monotherapy | | Melanoma | II |
| | MAGE | Monotherapy | | Multiple Myeloma (MM) | I |
| | MAGE | Monotherapy | | Melanoma | II |
| | MAGE | Monotherapy and Combo Therapy | recMAGE-A3 Protein plus AS15 Adjuvant | Non-Small Cell Lung Cancer (NSCLC) | I |
| | MAGE | Monotherapy | | Bladder Cancer | II |
| | MAGE | Monotherapy | | Bladder Cancer | I |
| | MAGE | Monotherapy | | Melanoma | III |
| MCNA | Tumor Cells | Monotherapy | | Bladder Cancer | II |
| | Tumor Cells | Monotherapy | | Bladder Cancer | III |
| | Tumor Cells | Monotherapy | | Bladder Cancer | I/II |
| MDX-1379 | HLA-A | Monotherapy and Combo Therapy | MDX-010 in combination with MDX-1379 | Melanoma | III |
| | HLA-A | Combination | MDX-010 and MDX-1379 | Melanoma | II |
| MEDI0680 | PD-1/PD-L1 and PD-L2 | Monotherapy | | Solid Tumors | I |
| | PD-1/PD-L1 and PD-L2 | Combination | MEDI0680 + MEDI4736 | Solid Tumors | I |
| | PD-1/PD-L1 and PD-L2 | Combination | MEDI-551 and MEDI0680 | Diffuse Large B-Cell Lymphoma (DLBCL) - NHL | I/II |
| MEDI6383 | OX40/CD134 and OX40L | Monotherapy | | Solid Tumors | I |
| | OX40/CD134 and OX40L | Monotherapy | | Solid Tumors | Preclinical |

TABLE D-continued

| Name | Target | Type | Detail | Indication | Phase |
|---|---|---|---|---|---|
| MEDI6469 | OX40/CD134 and OX40L | Monotherapy | | Melanoma | II |
| | OX40/CD134 and OX40L | Combination | | Melanoma | I/II |
| | OX40/CD134 and OX40L | Combination | Anti-OX40 + Cyclophosphamide + Radiation | Prostate Cancer | I/II |
| | OX40/CD134 and OX40L | Monotherapy | | Breast Cancer | I/II |
| | OX40/CD134 and OX40L | Monotherapy | | Solid Tumors | I |
| MEDI9197 | TLR7, TLR8 | Monotherapy | | Breast Cancer | I/II |
| MelCancerVac | MAGE, Stem Cells | Monotherapy | | Solid Tumors | I |
| | MAGE, Stem Cells | Monotherapy | | Colorectal Cancer (CRC) | II |
| | MAGE, Stem Cells | Monotherapy | | Colorectal Cancer (CRC) | II |
| | MAGE, Stem Cells | Combination | MelCancerVac + Celecoxib | Non-Small Cell Lung Cancer (NSCLC) | II |
| MGD006 | CD3 | Monotherapy | | Colorectal Cancer (CRC) | III |
| | CD3 | Monotherapy | | Acute Myelogenous Leukemia (AML) | Preclinical |
| MGD007 | CD3, gpA33 | Monotherapy | | Acute Myelogenous Leukemia (AML) | I |
| | CD3, gpA33 | Monotherapy | | Colorectal Cancer (CRC) | Preclinical |
| MGN1601 | TLR9 | Monotherapy | | Colorectal Cancer (CRC) | I |
| Mifamurtide | Immune system | Monotherapy and Combo Therapy | | Renal Cell Cancer (RCC) | I/II |
| | Immune system | Monotherapy and Combo Therapy | | Bone Cancer | III |
| MKC1106-MT | Immune system | Monotherapy | | Bone Cancer | II |
| | Immune system | Monotherapy | | Melanoma | II |
| Mobilan | TLR5 | Monotherapy | | Prostate Cancer | I |
| Modi-1 | Vimentin | Monotherapy | | Solid Tumors | Preclinical |
| Multiferon | Immune system | Combination | Multiferon with dacarbazine | Melanoma | III |
| Multikine | Immune system | Monotherapy | | Head and Neck Cancer | II |
| | Immune system | Combination | With low-dose cyclophosphamide (once before the Multikine injection schedule begins) and low-dose indomethacin | Head and Neck Cancer | III |
| MVA-BN Brachyury | Brachyury | Monotherapy | | Solid Tumors | I |
| MVA-BN HER2 | HER2/neu or ErbB-2 | Monotherapy | | Breast Cancer | Preclinical |
| | HER2/neu or ErbB-2 | Monotherapy | | Breast Cancer | I |
| MVA-BN PRO | PSA | Monotherapy | | Prostate Cancer | I/II |
| M-Vax | Immune system | Combination | M-Vax followed by CY and with BCG; then low dose IL-2 | Melanoma | III |
| | Immune system | Monotherapy | | Melanoma | I/II |
| MX-225 | Immune system, p53 | Monotherapy | | Small Cell Lung Cancer (SCLC) | I/II |
| | Immune system, p53 | Combination | Ad.p53-DC vaccines + ATRA + Second Line Chemo | Small Cell Lung Cancer (SCLC) | I/II |
| MyVax | Immune system | Monotherapy | Granulocyte-Macrophage Colony-Stimulating Factor (GM-CSF) with GTOP-99 | Indolent Non-Hodgkin's Lymphoma - NHL | II |
| | Immune system | Monotherapy | | Indolent Non-Hodgkin's Lymphoma - NHL | II |
| | Immune system | Monotherapy | | Indolent Non-Hodgkin's Lymphoma - NHL | III |
| | Immune system | Monotherapy | | Indolent Non-Hodgkin's Lymphoma - NHL | III |
| Neukoplast | Stem Cells | Monotherapy | | Acute Myelogenous Leukemia (AML) | I |
| | Stem Cells | Monotherapy | | Acute Myelogenous Leukemia (AML) | I |
| NeuVax | GM-CSFR/CD116, HER2/neu or ErbB-2 | Combination | With standard of care | Breast Cancer | I/II |
| | GM-CSFR/CD116, HER2/neu or ErbB-2 | Combination | With standard of care | Breast Cancer | I/II |
| | GM-CSFR/CD116, HER2/neu or ErbB-2 | Monotherapy and Combo Therapy | With SoC | Breast Cancer | III |
| | GM-CSFR/CD116, HER2/neu or ErbB-2 | Combination | Herceptin + NeuVax vaccine | Breast Cancer | IIb |

TABLE D-continued

| Name | Target | Therapy | Combination/Detail | Indication | Phase |
|---|---|---|---|---|---|
| | GM-CSFR/CD116, HER2/neu or ErbB-2 | Combination | NeuVax + GM-CSF (granulocyte macrophage-colony stimulating factor) + trastuzumab or trastuzumab + GM-CSF | Breast Cancer | II |
| | GM-CSFR/CD116, HER2/neu or ErbB-2 | Monotherapy | | Gastric Cancer | II |
| | GM-CSFR/CD116, HER2/neu or ErbB-2 | Monotherapy | | Breast Cancer | II |
| NK Cell Cancer Immunotherapy Program | Tumor Cells | Monotherapy | | Cancer | Preclinical |
| NKR-2 | CAR-T | Monotherapy | | Acute Myelogenous Leukemia (AML) | I/II |
| | CAR-T | Monotherapy | | Multiple Myeloma (MM) | I/II |
| Non-Viral CAR-T Program | CAR-T | Monotherapy | | Hematologic Cancer | Preclinical |
| Non-Viral CAR-T Program | CAR-T | Combination | | Hematologic Cancer | I |
| | CAR-T | Monotherapy and Combo Therapy | | Hematologic Cancer | I |
| NR2F6 T Cell Immunotherapy Program | CAR-T | Monotherapy | | Solid Tumors | Preclinical |
| | TRs | Monotherapy | | Cancer | Preclinical |
| NY-ESO-1 Vaccine | NY-ESO-1 | Monotherapy | | Solid Tumors | I |
| OBI-822 | Immune system | Monotherapy | | Breast Cancer | II/III |
| | Immune system | Monotherapy | NY-ESO-1 vaccine + Rapamycin | Ovarian Cancer | II |
| OCV-501 | WT1 | Monotherapy | | Acute Myelogenous Leukemia (AML) | I |
| | WT1 | Monotherapy | | Acute Myelogenous Leukemia (AML) | II |
| | WT1 | Monotherapy | | Acute Myelogenous Leukemia (AML) | II |
| Oncophage | Tumor Cells | Monotherapy | | Renal Cell Cancer (RCC) | II |
| | Tumor Cells | Monotherapy | | Renal Cell Cancer (RCC) | III |
| | Tumor Cells | Monotherapy | | Renal Cell Cancer (RCC) | III |
| Oncoquest-L Vaccine | IL-2 | Monotherapy | | Chronic Lymphocytic Leukemia (CLL)/Small Cell Lymphocytic Lymphoma (SLL) - NHL | I |
| | IL-2 | Monotherapy | | Indolent Non-Hodgkin's Lymphoma - NHL | II |
| ONCOS-102 | RB | Combination | CGTG-102 + Cyclophosphamide | Sarcoma | I |
| | RB | Monotherapy | | Mesothelioma | I |
| | RB | Monotherapy | | Mesothelioma | I/II |
| | RB | Combination | ONCOS-102 + Pemetrexed + Cisplatin | Colorectal Cancer (CRC) | III |
| OncoVAX | Stem Cell | Monotherapy | | Colorectal Cancer (CRC) | III |
| | Stem Cells | Monotherapy | | Hepatocellular (Liver) Cancer (HCC) (including secondary metastases) | I |
| ONO-7268MX1 | Immune system | Monotherapy | | Hepatocellular (Liver) Cancer (HCC) (including secondary metastases) | I |
| ONO-7268MX2 | Immune system | Monotherapy | | Solid Tumors | I |
| ONT-10 | MUC-1, TLR4 | Monotherapy | | Solid Tumors | I |
| | MUC-1, TLR4 | Monotherapy | | Solid Tumors | I |
| | MUC-1, TLR4 | Combination | ONT-10 + Varlilumab | Renal Cell Cancer (RCC) | II |
| Opdivo | PD-1/PD-L1 and PD-L2 | Monotherapy | | Non-Small Cell Lung Cancer (NSCLC) | I |
| | PD-1/PD-L1 and PD-L2 | Combination | Nivolumab (BMS-936558) in Combination With Gemcitabine/Cisplatin, Pemetrexed/Cisplatin, Carboplatin/Paclitaxel, Bevacizumab Maintenance, Erlotinib, Ipilimumab or as Monotherapy in First-Line or in Switch Maintenance | | |
| | PD-1/PD-L1 and PD-L2 | Monotherapy | | Melanoma | I |
| | PD-1/PD-L1 and PD-L2 | Monotherapy | | Melanoma | I |
| | PD-1/PD-L1 and PD-L2 | Combination | | Melanoma | I |
| | PD-1/PD-L1 and PD-L2 | Monotherapy | | Renal Cell Cancer (RCC) | I |

TABLE D-continued

| | | | | |
|---|---|---|---|---|
| PD-1/PD-L1 and PD-L2 | Combination | BMS-982470 + BMS-936558 | Solid Tumors | I |
| PD-1/PD-L1 and PD-L2 | Monotherapy | | Non-Small Cell Lung Cancer (NSCLC) | III |
| PD-1/PD-L1 and PD-L2 | Monotherapy | | Hepatocellular (Liver) Cancer (HCC) (including secondary metastases) | I/II |
| PD-1/PD-L1 and PD-L2 | Monotherapy | | Renal Cell Cancer (RCC) | III |
| PD-1/PD-L1 and PD-L2 | Monotherapy | | Non-Small Cell Lung Cancer (NSCLC) | III |
| PD-1/PD-L1 and PD-L2 | Monotherapy | | Melanoma | III |
| PD-1/PD-L1 and PD-L2 | Monotherapy | | Non-Small Cell Lung Cancer (NSCLC) | II |
| PD-1/PD-L1 and PD-L2 | Monotherapy | | Melanoma | III |
| PD-1/PD-L1 and PD-L2 | Monotherapy and Combo Therapy | Nivolumab + Ipilimumab + Lirilumab | Hodgkin's Lymphoma | I |
| PD-1/PD-L1 and PD-L2 | Monotherapy | | Non-Small Cell Lung Cancer (NSCLC) | I |
| PD-1/PD-L1 and PD-L2 | Combination | Nivolumab + Ipilimumab, Pazopanib or Sunitinib | Renal Cell Cancer (RCC) | I |
| PD-1/PD-L1 and PD-L2 | Monotherapy | | Renal Cell Cancer (RCC) | I |
| PD-1/PD-L1 and PD-L2 | Monotherapy | | Non-Small Cell Lung Cancer (NSCLC) | I |
| PD-1/PD-L1 and PD-L2 | Monotherapy | | Renal Cell Cancer (RCC) | I |
| PD-1/PD-L1 and PD-L2 | Monotherapy | | Colorectal Cancer (CRC) | I |
| PD-1/PD-L1 and PD-L2 | Monotherapy | | Prostate Cancer | I |
| PD-1/PD-L1 and PD-L2 | Monotherapy and Combo Therapy | Nivolumab +/- Ipilimumab | Melanoma | III |
| PD-1/PD-L1 and PD-L2 | Monotherapy | | Melanoma | II |
| PD-1/PD-L1 and PD-L2 | Monotherapy | | Melanoma | I/II |
| PD-1/PD-L1 and PD-L2 | Combination | Nivolumab + Ipilimumab | Melanoma | II |
| PD-1/PD-L1 and PD-L2 | Monotherapy and Combo Therapy | Nivolumab + Ipilimumab | Solid Tumors | I/II |
| PD-1/PD-L1 and PD-L2 | Monotherapy | | Melanoma | II |
| PD-1/PD-L1 and PD-L2 | Monotherapy | | Non-Small Cell Lung Cancer (NSCLC) | II |
| PD-1/PD-L1 and PD-L2 | Monotherapy and Combo Therapy | Nivolumab + Ipilimumab + Lirilumab | Brain Cancer (malignant glioma; AA and GBM) | III |
| PD-1/PD-L1 and PD-L2 | Monotherapy | | Non-Hodgkin's Lymphoma (NHL) | II |
| PD-1/PD-L1 and PD-L2 | Monotherapy | | Non-Hodgkin's Lymphoma (NHL) | II |
| PD-1/PD-L1 and PD-L2 | Monotherapy | | Non-Small Cell Lung Cancer (NSCLC) | III |
| PD-1/PD-L1 and PD-L2 | Monotherapy | | Esophageal Cancer | II |
| PD-1/PD-L1 and PD-L2 | Monotherapy and Combo Therapy | Nivolumab + Ipilimumab + Lirilumab | Non-Hodgkin's Lymphoma (NHL) | I |
| PD-1/PD-L1 and PD-L2 | Monotherapy | | Hodgkin's Lymphoma | II |
| PD-1/PD-L1 and PD-L2 | Combination | Opdivo + Zykadia | Non-Small Cell Lung Cancer (NSCLC) | I/II |
| PD-1/PD-L1 and PD-L2 | Combination | Opdivo + INC280 and Opdivo + EGF816. | Non-Small Cell Lung Cancer (NSCLC) | II |
| PD-1/PD-L1 and PD-L2 | Combination | Opdivo + Imbruvica | Non-Hodgkin's Lymphoma (NHL) | I/II |
| PD-1/PD-L1 and PD-L2 | Monotherapy | | Gastric Cancer | III |
| PD-1/PD-L1 and PD-L2 | Combination | Nivolumab + Ipilimumab | Head and Neck Cancer | III |
| PD-1/PD-L1 and PD-L2 | Monotherapy | | Renal Cell Cancer (RCC) | III |
| PD-1/PD-L1 and PD-L2 | Monotherapy | | Non-Small Cell Lung Cancer (NSCLC) | III |
| PD-1/PD-L1 and PD-L2 | Monotherapy | | Solid Tumors | I/II |
| PD-1/PD-L1 and PD-L2 | Combination | Ibrutinib + Nivolumab | Hematologic Cancer | I/II |
| PD-1/PD-L1 and PD-L2 | Combination | Nivolumab + Galunisertib | Solid Tumors | I/II |
| PD-1/PD-L1 and PD-L2 | Combination | Varlilumab + Nivolumab | Solid Tumors | I/II |
| PD-1/PD-L1 and PD-L2 | Combination | CRS-207 + GVAX Pancreas Vaccine +/- Nivolumab | Pancreatic Cancer | II |
| PD-1/PD-L1 and PD-L2 | Monotherapy | | Bladder Cancer | II |
| PD-1/PD-L1 and PD-L2 | Monotherapy | | Melanoma | III |
| PD-1/PD-L1 and PD-L2 | Combination | | Hepatocellular (Liver) Cancer (HCC) (including secondary metastases) | I/II |

TABLE D-continued

| | | | | | |
|---|---|---|---|---|---|
| | | PD-1/PD-L1 and PD-L2 | Monotherapy and Combo Therapy | | Small Cell Lung Cancer (SCLC) | I/II |
| | | PD-1/PD-L1 and PD-L2 | Monotherapy | Varlilumab + Nivolumab | Ovarian Cancer | I/II |
| | | PD-1/PD-L1 and PD-L2 | Combination | | Ovarian Cancer | I/II |
| | | PD-1/PD-L1 and PD-L2 | Monotherapy and Combo Therapy | Nivolumab + Ipilimumab; Nivolumab + Platinum doublet chemotherapy | Non-Small Cell Lung Cancer (NSCLC) | III |
| | | PD-1/PD-L1 and PD-L2 | Monotherapy | | Small Cell Lung Cancer (SCLC) | III |
| | | PD-1/PD-L1 and PD-L2 | Combination | Nivolumab + nab-Paclitaxel +/− Gemcitabine +/− Carboplatin | Breast Cancer | I |
| | | PD-1/PD-L1 and PD-L2 | Combination | Nivolumab + nab-Paclitaxel +/− Gemcitabine +/− Carboplatin | Pancreatic Cancer | I |
| | | PD-1/PD-L1 and PD-L2 | Monotherapy | Nivolumab + nab-Paclitaxel +/− Gemcitabine +/− Carboplatin | Non-Small Cell Lung Cancer (NSCLC) | I |
| | | PD-1/PD-L1 and PD-L2 | Monotherapy | | Melanoma | II |
| | | PD-1/PD-L1 and PD-L2 | Monotherapy and Combo Therapy | Nivolumab in Combination With Ipilimumab | Melanoma | I |
| | | PD-1/PD-L1 and PD-L2 | Monotherapy and Combo Therapy | | Melanoma | II |
| | | PD-1/PD-L1 and PD-L2 | Monotherapy and Combo Therapy | Nivolumab + Ipilimumab | Colorectal Cancer (CRC) | I/II |
| | | PD-1/PD-L1 and PD-L2 | Combination | Mogamulizumab + Nivolumab | Solid Tumors | I |
| | | PD-1/PD-L1 and PD-L2 | Monotherapy and Combo Therapy | | Small Cell Lung Cancer (SCLC) | III |
| | | PD-1/PD-L1 and PD-L2 | Combination | FPA008 and nivolumab IV infusions | Solid Tumors | I |
| | | PD-1/PD-L1 and PD-L2 | Monotherapy | | Esophageal Cancer | III |
| | | PD-1/PD-L1 and PD-L2 | Monotherapy and Combo Therapy | Nivolumab + SOC maintenance therapy or Erlotinib or Crizotinib | Non-Small Cell Lung Cancer (NSCLC) | I/II |
| | | PD-1/PD-L1 and PD-L2 | Combination | Nivolumab + Brentuximab Vedotin | Non-Hodgkin's Lymphoma (NHL) | I/II |
| | | PD-1/PD-L1 and PD-L2 | Combination | Brentuximab Vedotin + Nivolumab | Hodgkin's Lymphoma | I/II |
| | | PD-1/PD-L1 and PD-L2 | Monotherapy | | Hepatocellular (Liver) Cancer (HCC) (including secondary metastases) | III |
| | | PD-1/PD-L1 and PD-L2 | Combination | Nivolumab + Radiotherapy Arm | Brain Cancer (malignant glioma; AA and GBM) | III |
| | | PD-1/PD-L1 and PD-L2 | Monotherapy | | Bladder Cancer | III |
| | | PD-1/PD-L1 and PD-L2 | Monotherapy | | Non-Small Cell Lung Cancer (NSCLC) | III |
| | | PD-1/PD-L1 and PD-L2 | Monotherapy | | Melanoma | III |
| OVax Vaccine | | Immune system | Monotherapy | | Ovarian Cancer | I/II |
| p.DOM-WT1-126 | | WT1 | Monotherapy | | Chronic Myelogenous Leukemia (CML) | II |
| | | WT1 | Monotherapy | | Acute Myelogenous Leukemia (AML) | II |
| p.DOM-WT1-37 | | WT1 | Monotherapy | | Chronic Myelogenous Leukemia (CML) | II |
| | | WT1 | Monotherapy | | Acute Myelogenous Leukemia (AML) | II |
| PCI for Vaccination | | Endosomes, Tumor Cells | Monotherapy | | Solid Tumors | Preclinical |
| PDR001 | | PD-1/PD-L1 and PD-L2 | Monotherapy | | Solid Tumors | I/II |
| | | PD-1/PD-L1 and PD-L2 | Monotherapy and Combo Therapy | LAG525 + PDR001 | Solid Tumors | I/II |
| | | PD-1/PD-L1 and PD-L2 | Monotherapy | MBG453 + PDR001 | Solid Tumors | I/II |
| PDS0101 | | HPV | Monotherapy | | Cervical Cancer | I |
| | | HPV | Monotherapy | | Cervical Dysplasia | I |
| | | HPV | Monotherapy | | Cervical Dysplasia | Preclinical |

TABLE D-continued

| | | | | |
|---|---|---|---|---|
| Pexa-Vec | GM-CSFR/CD116 | Combination | | Hepatocellular (Liver) Cancer (HCC) (including secondary metastases) | II |
| | GM-CSFR/CD116 | Monotherapy | | Hepatocellular (Liver) Cancer (HCC) (including secondary metastases) | II |
| | GM-CSFR/CD116 | Monotherapy | | Melanoma | I/II |
| Pexa-Vec | GM-CSFR/CD116 | Monotherapy and Combo Therapy | JX-594 plus best supportive care as needed | Hepatocellular (Liver) Cancer (HCC) (including secondary metastases) | IIb |
| | GM-CSFR/CD116 | Monotherapy | | Colorectal Cancer (CRC) | II |
| | GM-CSFR/CD116 | Monotherapy | | Colorectal Cancer (CRC) | I |
| | GM-CSFR/CD116 | Monotherapy and Combo Therapy | JX-594 +/− irinotecan | Colorectal Cancer (CRC) | I/II |
| | GM-CSFR/CD116 | Monotherapy | | Hepatocellular (Liver) Cancer (HCC) (including secondary metastases) | II |
| | GM-CSFR/CD116 | Monotherapy | | Hepatocellular (Liver) Cancer (HCC) (including secondary metastases) | Preclinical |
| | GM-CSFR/CD116 | Monotherapy | | Colorectal Cancer (CRC) | Preclinical |
| | GM-CSFR/CD116 | Monotherapy | | Melanoma | Preclinical |
| | GM-CSFR/CD116 | Combination | Pexa-Vec + metronomic cyclophosphamide | Solid Tumors | I/II |
| | GM-CSFR/CD116 | Monotherapy and Combo Therapy | Pexa-Vec + Sorafenib | Hepatocellular (Liver) Cancer (HCC) (including secondary metastases) | III |
| | GM-CSFR/CD116 | Monotherapy | | Solid Tumors | I |
| Pidilizumab | T lymphocytes | Monotherapy | | Diffuse Large B-Cell Lymphoma (DLBCL) - NHL | II |
| | T lymphocytes | Combination | CT-011 + Rituximab | Indolent Non-Hodgkin's Lymphoma - NHL | II |
| | T lymphocytes | Combination | With FOLFOX | Colorectal Cancer (CRC) | II |
| | T lymphocytes | Monotherapy | | Hepatocellular (Liver) Cancer (HCC) (including secondary metastases) | I/II |
| | T lymphocytes | Combination | CT-011 + DC AML Vaccine | Acute Myelogenous Leukemia (AML) | II |
| | T lymphocytes | Monotherapy | | Melanoma | II |
| | T lymphocytes | Monotherapy | | Multiple Myeloma (MM) | I/II |
| | T lymphocytes | Monotherapy | | Diffuse Large B-Cell Lymphoma (DLBCL) - NHL | II |
| | G17 | Combination | G17DT Immunogen in Combination w/ Cisplatin and 5-FU | Pancreatic Cancer | III |
| | G17 | Combination | | Gastric Cancer | III |
| Polyclonal Antibody Stimulator | G17 | Monotherapy | | Colorectal Cancer (CRC) | II |
| | G17 | Combination | Vaccine + OPT-821 adjuvant | Ovarian Cancer | II |
| Polyvalent Antigen-KLH Conjugate Vaccine | Immune system | Combination | PV-KLH Conjugate vaccine + Avastin (bevacizumab) + OPT-821 | Ovarian Cancer | I |
| PRAME Antigen Specific Cancer Immunotherapeutic (ASCI) | PRAME/MAPE/OIP4 | Monotherapy | | Non-Small Cell Lung Cancer (NSCLC) | I |
| | PRAME/MAPE/OIP4 | Monotherapy | | Non-Small Cell Lung Cancer (NSCLC) | II |
| Prophage | Immune system | Monotherapy | | Melanoma | II |
| | Immune system | Monotherapy | | Melanoma | III |
| | Immune system | Monotherapy | | Brain Cancer (malignant glioma; AA and GBM) | I/II |
| | Immune system | Combination | Oncophage (vitespen) + temozolomide and adjuvant therapy | Brain Cancer (malignant glioma; AA and GBM) | II |
| | Immune system | Combination | HSPPC-96 + bevacizumab | Brain Cancer (malignant glioma; AA and GBM) | II |
| | Immune system | Combination | Prophage + Yervoy +/− cyclophosphamide | Melanoma | II |
| Prostvac | PSA | Combination | PROSTVAC-VF/TRICOM co-administered with GM-CSF | Prostate Cancer | II |
| | PSA | Monotherapy and Combo Therapy | PROSTVAC + GM-CSF | Prostate Cancer | III |
| Prostvac | PSA | Combination | With docetaxel and prednisone | Prostate Cancer | II |
| | PSA | Combination | (153)Sm-EDTMP + PROSTVAC V or F/TRICOM | Prostate Cancer | II |
| | PSA | Combination | Sargramostim + MDX-010 (ipilimumab) + PROSTVAC | Prostate Cancer | I |

TABLE D-continued

| | | | | |
|---|---|---|---|---|
| Provenge | PSA | Monotherapy | PSA-TRICOM vaccine + GM-CSF | Prostate Cancer | II |
| | PSA | Monotherapy | | Prostate Cancer | I/II |
| | PSA | Monotherapy | | Prostate Cancer | II |
| | PAP, Stem Cells | Monotherapy | | Prostate Cancer | III |
| | PAP, Stem Cells | Combination | Provenge plus Avastin | Prostate Cancer | II |
| | PAP, Stem Cells | Monotherapy | | Prostate Cancer | III |
| | PAP, Stem Cells | Combination | w/ LHRH agonists | Prostate Cancer | III |
| | PAP, Stem Cells | Monotherapy | | Prostate Cancer | II |
| | PAP, Stem Cells | Combination | Provenge + PA2024 antigen | Prostate Cancer | II |
| | PAP, Stem Cells | Combination | Sipuleucel-T followed by ADT | Prostate Cancer | II |
| | PAP, Stem Cells | Combination | Sipuleucel-T concurrent or sequential with abiraterone acetate plus prednisone | Prostate Cancer | II |
| | PAP, Stem Cells | Monotherapy | | Prostate Cancer | II |
| | PAP, Stem Cells | Monotherapy | | Prostate Cancer | II |
| | PAP, Stem Cells | Monotherapy | | Prostate Cancer | IV |
| | PAP, Stem Cells | Monotherapy | | Prostate Cancer | IV |
| | PAP, Stem Cells | Combination | Sipuleucel-T with enzalutamide (Xtandi) | Prostate Cancer | II |
| PV-10 | Immune system | Monotherapy | | Melanoma | II |
| | Immune system | Monotherapy | | Melanoma | III |
| | Immune system | Monotherapy | | Hepatocellular (Liver) Cancer (HCC) (including secondary metastases) | I |
| | Immune system | Monotherapy | | Melanoma | Preclinical |
| | Immune system | Monotherapy | | Melanoma | I |
| | Immune system | Monotherapy | | Hepatocellular (Liver) Cancer (HCC) (including secondary metastases) | I/II |
| | Immune system | Monotherapy | | Breast Cancer | Preclinical |
| | Immune system | Monotherapy | | Cancer | I |
| | Immune system | Combination | PV-10 + Pembrolizumab | Melanoma | I/II |
| | Immune system | Monotherapy | | Colorectal Cancer (CRC) | Preclinical |
| | Immune system | Monotherapy | | Neuroendocrine Tumors (NET) | I |
| PVSRIPO | Tumor Cells | Monotherapy | | Brain Cancer (malignant glioma; AA and GBM) | I |
| PVX-410 | CS1/SLAMF7 | Combination | PVX-410 + Hiltonol | Multiple Myeloma (MM) | I |
| | CS1/SLAMF7 | Monotherapy | | Multiple Myeloma (MM) | Preclinical |
| RBL001/RBL002 | Tumor Cells | Monotherapy | | Melanoma | I |
| | Tumor Cells | Monotherapy | | Melanoma | I |
| Revlimid | Angiogenesis, E3 ubiquitin ligase | Monotherapy | | Myelodysplastic Syndrome (MDS) | II |
| | Angiogenesis, E3 ubiquitin ligase | Monotherapy | | Myelofibrosis (MF) | II |
| | Angiogenesis, E3 ubiquitin ligase | Combination | Lenalidomide + prednisone | Multiple Myeloma (MM) | II |
| | Angiogenesis, E3 ubiquitin ligase | Combination | REVLIMID plus dexamethasone with low dose (81 mg) aspirin | | |
| | Angiogenesis, E3 ubiquitin ligase | Combination | REVLIMID and high-dose dexamethasone | Multiple Myeloma (MM) | III |
| | Angiogenesis, E3 ubiquitin ligase | Monotherapy | | Myelodysplastic Syndrome (MDS) | III |
| | Angiogenesis, E3 ubiquitin ligase | Combination | REVLIMID and high-dose dexamethasone | Multiple Myeloma (MM) | III |
| | Angiogenesis, E3 ubiquitin ligase | Monotherapy and Combo Therapy | Lenalidomide + Rituximab | Chronic Lymphocytic Leukemia (CLL)/Small Cell Lymphocytic Lymphoma (SLL) - NHL | II |
| Revlimid | Angiogenesis, E3 ubiquitin ligase | Monotherapy | | Myelodysplastic Syndrome (MDS) | I/II |
| | Angiogenesis, E3 ubiquitin ligase | Monotherapy | | Multiple Myeloma (MM) | I |
| | Angiogenesis, E3 ubiquitin ligase | Monotherapy | | Multiple Myeloma (MM) | I |
| | Angiogenesis, E3 ubiquitin ligase | Monotherapy | | Myelodysplastic Syndrome (MDS) | III |
| | Angiogenesis, E3 ubiquitin ligase | Monotherapy | | Renal Cell Cancer (RCC) | II |
| | Angiogenesis, E3 ubiquitin ligase | Monotherapy | | Diffuse Large B-Cell Lymphoma (DLBCL) - NHL | II |

TABLE D-continued

| | | | | |
|---|---|---|---|---|
| Angiogenesis, E3 ubiquitin ligase | Combination | Dexamethasone and lenalidomide compared to dexamethasone alone | Multiple Myeloma (MM) | III |
| Angiogenesis, E3 ubiquitin ligase | Monotherapy | | Multiple Myeloma (MM) | II |
| Angiogenesis, E3 ubiquitin ligase | Monotherapy | | Cutaneous T-Cell Lymphoma (CTCL) - NHL | II |
| Angiogenesis, E3 ubiquitin ligase | Combination | Revlimid plus melphalan and prednisone | Multiple Myeloma (MM) | II |
| Angiogenesis, E3 ubiquitin ligase | Monotherapy | | Chronic Lymphocytic Leukemia (CLL)/Small Cell Lymphocytic Lymphoma (SLL) - NHL | I/II |
| Angiogenesis, E3 ubiquitin ligase | Combination | 45 pts Revlimid and Rituxan IV | Indolent Non-Hodgkin's Lymphoma - NHL | II |
| Angiogenesis, E3 ubiquitin ligase | Combination | Lenalidomide + radiation therapy | Brain Cancer (malignant glioma; AA and GBM) | II |
| Angiogenesis, E3 ubiquitin ligase | Combination | Revlimid plus dexamethasone (Dex) | Multiple Myeloma (MM) | III |
| Angiogenesis, E3 ubiquitin ligase | Monotherapy | | Diffuse Large B-Cell Lymphoma (DLBCL) - NHL | II |
| Angiogenesis, E3 ubiquitin ligase | Combination | Lenalidomide + MP | Multiple Myeloma (MM) | III |
| Angiogenesis, E3 ubiquitin ligase | Combination | Lenalidomide plus low-dose dexamethasone | Multiple Myeloma (MM) | III |
| Angiogenesis, E3 ubiquitin ligase | Monotherapy | Revlimid | Chronic Lymphocytic Leukemia (CLL)/Small Cell Lymphocytic Lymphoma (SLL) - NHL | II |
| Angiogenesis, E3 ubiquitin ligase | Monotherapy | | Myelodysplastic Syndrome (MDS) | III |
| Angiogenesis, E3 ubiquitin ligase | Monotherapy and Combo Therapy | Revlimid or Revlimid + dexamethasone | Hodgkin's Lymphoma | II |
| Angiogenesis, E3 ubiquitin ligase | Monotherapy | | Hodgkin's Lymphoma | II |
| Angiogenesis, E3 ubiquitin ligase | Combination | Revlimid plus melphalan | Multiple Myeloma (MM) | II |
| Angiogenesis, E3 ubiquitin ligase | Combination | Revlimid, low dose dexamethasone with cyclophosphamid (aspirin as thromboprophylaxis) | Multiple Myeloma (MM) | II |
| Angiogenesis, E3 ubiquitin ligase | Combination | Revlimid with Velcade + dexamethasone | Multiple Myeloma (MM) | II |
| Angiogenesis, E3 ubiquitin ligase | Monotherapy | | Chronic Lymphocytic Leukemia (CLL)/Small Cell Lymphocytic Lymphoma (SLL) - NHL | II |
| Angiogenesis, E3 ubiquitin ligase | Monotherapy | | Peripheral T-Cell Lymphoma (PTCL) - NHL | II |
| Angiogenesis, E3 ubiquitin ligase | Monotherapy | | Chronic Lymphocytic Leukemia (CLL)/Small Cell Lymphocytic Lymphoma (SLL) - NHL | II |
| Angiogenesis, E3 ubiquitin ligase | Monotherapy | | Acute Myelogenous Leukemia (AML) | II |
| Angiogenesis, E3 ubiquitin ligase | Monotherapy | | Myelodysplastic Syndrome (MDS) | II |
| Angiogenesis, E3 ubiquitin ligase | Monotherapy | | Acute Myelogenous Leukemia (AML) | II |
| Angiogenesis, E3 ubiquitin ligase | Monotherapy | | Myelodysplastic Syndrome (MDS) | II |
| Angiogenesis, E3 ubiquitin ligase | Monotherapy | | Diffuse Large B-Cell Lymphoma (DLBCL) - NHL | II |
| Angiogenesis, E3 ubiquitin ligase | Monotherapy | | Renal Cell Cancer (RCC) | III |
| Angiogenesis, E3 ubiquitin ligase | Monotherapy | | Melanoma | II/III |
| Angiogenesis, E3 ubiquitin ligase | Combination | Velcade + Revlimid + dexamethasone | Melanoma | III |
| Angiogenesis, E3 ubiquitin ligase | Monotherapy | | Multiple Myeloma (MM) | III |
| Angiogenesis, E3 ubiquitin ligase | Monotherapy and Combo Therapy | Concomitant dex permitted in patients with disease progression or stable disease | Multiple Myeloma (MM) | I/II |
| Angiogenesis, E3 ubiquitin ligase | Monotherapy | | Multiple Myeloma (MM) | II |
| Angiogenesis, E3 ubiquitin ligase | Combination | Revlimid + Rituxan | Indolent Non-Hodgkin's Lymphoma - NHL | II |
| Angiogenesis, E3 ubiquitin ligase | Combination | Lenalidomide + Dexamethasone | Indolent Non-Hodgkin's Lymphoma - NHL | II |
| Angiogenesis, E3 ubiquitin ligase | Monotherapy | | Diffuse Large B-Cell Lymphoma (DLBCL) - NHL | III |
| Angiogenesis, E3 ubiquitin ligase | Monotherapy | | Chronic Lymphocytic Leukemia(CLL)/Small Cell Lymphocytic Lymphoma (SLL) - NHL | |
| Angiogenesis, E3 ubiquitin ligase | Monotherapy | | Mantle Cell Lymphoma - NHL | II |
| Angiogenesis, E3 ubiquitin ligase | Monotherapy | With Melphalan + Prednisone | Multiple Myeloma (MM) | III |
| Angiogenesis, E3 ubiquitin ligase | Combination | dexamethasone, lenalidomide, bortezomib | Multiple Myeloma (MM) | III |
| Angiogenesis, E3 ubiquitin ligase | Monotherapy | Rituxan + R-CHOP | Diffuse Large B-Cell Lymphoma (DLBCL) - NHL | III |
| Angiogenesis, E3 ubiquitin ligase | Monotherapy | | Chronic Lymphocytic Leukemia (CLL)/Small Cell Lymphocytic Lymphoma (SLL) - NHL | III |

TABLE D-continued

| | | | | |
|---|---|---|---|---|
| Angiogenesis, E3 ubiquitin ligase | Monotherapy | | Myelofibrosis (MF) | II |
| Angiogenesis, E3 ubiquitin ligase | Monotherapy | | Prostate Cancer | I/II |
| Angiogenesis, E3 ubiquitin ligase | Monotherapy | | Mantle Cell Lymphoma - NHL | II |
| Angiogenesis, E3 ubiquitin ligase | Combination | Lenalidomide + Dexamethasone | Multiple Myeloma (MM) | III |
| Angiogenesis, E3 ubiquitin ligase | Monotherapy | | Acute Myelogenous Leukemia (AML) | II |
| Angiogenesis, E3 ubiquitin ligase | Monotherapy | | Myelodysplastic Syndrome (MDS) | III |
| Angiogenesis, E3 ubiquitin ligase | Combination | Lenalidomide + Dexamethasone | Multiple Myeloma (MM) | II |
| Angiogenesis, E3 ubiquitin ligase | Combination | Gemcitabine in combination with lenalidomide | Pancreatic Cancer | II |
| Angiogenesis, E3 ubiquitin ligase | Monotherapy | | Acute Myelogenous Leukemia (AML) | II |
| Angiogenesis, E3 ubiquitin ligase | Combination | Revlimid + Rituxan | Chronic Lymphocytic Leukemia (CLL)/Small Cell Lymphocytic Lymphoma (SLL) - NHL | II |
| Angiogenesis, E3 ubiquitin ligase | Combination | Lenalidomide + Dexamethasone | Multiple Myeloma (MM) | II |
| Angiogenesis, E3 ubiquitin ligase | Combination | Revlimid + Velcade + Dexamethasone + Doxil | Multiple Myeloma (MM) | II |
| Angiogenesis, E3 ubiquitin ligase | Combination | <U>Induction</u>: Bortezomib + Pegylated-liposomal-doxorubicin + Dexamethasone; <BR><U>Autologous transplantation</u>: Melphalan + stem-cell support; <BR><U>Consolidation</u>: Lenalidomide + Prednisone followed by Lenalidomide alone | Multiple Myeloma (MM) | I/II |
| Angiogenesis, E3 ubiquitin ligase | Combination | | Multiple Myeloma (MM) | II |
| Angiogenesis, E3 ubiquitin ligase | Combination | With Rituxan + CHOP (RCHOP) | Diffuse Large B-Cell Lymphoma (DLBCL) - NHL | I/II |
| Angiogenesis, E3 ubiquitin ligase | Combination | With Rituxan (rituximab) | Indolent Non-Hodgkin's Lymphoma - NHL | II |
| Angiogenesis, E3 ubiquitin ligase | Combination | Lenalidomide + Rituximab | Mantle Cell Lymphoma - NHL | I/II |
| Angiogenesis, E3 ubiquitin ligase | Combination | Revlimid + docetaxel + prednisone | Prostate Cancer | III |
| Angiogenesis, E3 ubiquitin ligase | Monotherapy | Revlimid (lenalidomide), melphalan and prednisone | Multiple Myeloma (MM) | III |
| Angiogenesis, E3 ubiquitin ligase | Monotherapy | | Mantle Cell Lymphoma - NHL | II |
| Angiogenesis, E3 ubiquitin ligase | Monotherapy and Combo Therapy | Lenalidomide + Cetuximab | Colorectal Cancer (CRC) | II |
| Angiogenesis, E3 ubiquitin ligase | Combination | Lenalidomide + Sunitinib | Renal Cell Cancer (RCC) | I/II |
| Angiogenesis, E3 ubiquitin ligase | Monotherapy | Clarithromycin + Lenalidomide + Dexamethasone | Multiple Myeloma (MM) | II |
| Angiogenesis, E3 ubiquitin ligase | Monotherapy | | Cutaneous T-Cell Lymphoma (CTCL) - NHL | II |
| Angiogenesis, E3 ubiquitin ligase | Monotherapy | | Chronic Lymphocytic Leukemia (CLL)/Small Cell Lymphocytic Lymphoma (SLL) - NHL | II |
| Angiogenesis, E3 ubiquitin ligase | Monotherapy | | Diffuse Large B-Cell Lymphoma (DLBCL) - NHL | II/III |
| Angiogenesis, E3 ubiquitin ligase | Combination | Lenalidomide + cyclophosphamide + prednisone | Multiple Myeloma (MM) | II |
| Angiogenesis, E3 ubiquitin ligase | Monotherapy | | Myelodysplastic Syndrome (MDS) | III |
| Angiogenesis, E3 ubiquitin ligase | Monotherapy | | Chronic Lymphocytic Leukemia (CLL)/Small Cell Lymphocytic Lymphoma (SLL) - NHL | II |
| Angiogenesis, E3 ubiquitin ligase | Combination | | Chronic Lymphocytic Leukemia (CLL)/Small Cell Lymphocytic Lymphoma (SLL) - NHL | II |
| Angiogenesis, E3 ubiquitin ligase | Combination | With low dose dexamethasone plus rituximab | Indolent Non-Hodgkin's Lymphoma - NHL | II |
| Angiogenesis, E3 ubiquitin ligase | Combination | Bevacizumab + Lenalidomide + Docetaxel + Prednisone | Prostate Cancer | II |
| Angiogenesis, E3 ubiquitin ligase | Combination | Temsirolimus + Lenalidomide | Multiple Myeloma (MM) | L |
| Angiogenesis, E3 ubiquitin ligase | Monotherapy and Combo Therapy | Azacitidine + Lenalidomide | Acute Myelogenous Leukemia (AML) | II |
| Angiogenesis, E3 ubiquitin ligase | Combination | Lenalidomide + Rituximab | Indolent Non-Hodgkin's Lymphoma - NHL | III |
| Angiogenesis, E3 ubiquitin ligase | Combination | Lenalidomide + Dexamethasone | Multiple Myeloma (MM) | II |
| Angiogenesis, E3 ubiquitin ligase | Combination | With Rituxan + CHOP (RCHOP) | Indolent Non-Hodgkin's Lymphoma - NHL | I/II |
| Angiogenesis, E3 ubiquitin ligase | Monotherapy | | Mantle Cell Lymphoma - NHL | II |
| Angiogenesis, E3 ubiquitin ligase | Monotherapy | | Peripheral T-Cell Lymphoma (PTCL) - NHL | II |
| Angiogenesis, E3 ubiquitin ligase | Monotherapy | | Mantle Cell Lymphoma - NHL | II |
| Angiogenesis, E3 ubiquitin ligase | Monotherapy | | Indolent Non-Hodgkin's Lymphoma - NHL | II |
| Angiogenesis, E3 ubiquitin ligase | Monotherapy | | Peripheral T-Cell Lymphoma (PTCL) - NHL | II |

TABLE D-continued

| | | | | |
|---|---|---|---|---|
| | Angiogenesis, E3 ubiquitin ligase | Combination | Rituximab + Cyclophosphamide + Doxorubicin + Vincristine + Prednisone + Revlimid | Diffuse Large B-Cell Lymphoma (DLBCL) - NHL | II |
| | Angiogenesis, E3 ubiquitin ligase | Combination | Lenalidomide + Thalidomide + Dexamethasone | Multiple Myeloma (MM) | I/II |
| | Angiogenesis, E3 ubiquitin ligase | Monotherapy | | Chronic Lymphocytic Leukemia (CLL)/Small Cell Lymphocytic Lymphoma (SLL) - NHL | I/II |
| | Angiogenesis, E3 ubiquitin ligase | Monotherapy | | Multiple Myeloma (MM) | II |
| | Angiogenesis, E3 ubiquitin ligase | Combination | Lenalidomide + Azacitidine | Acute Myelogenous Leukemia (AML) | I/II |
| | Angiogenesis, E3 ubiquitin ligase | Combination | lenalidomide + ofatumumab | Indolent Non-Hodgkin's Lymphoma - NHL | I/II |
| | Angiogenesis, E3 ubiquitin ligase | Monotherapy | | Diffuse Large B-Cell Lymphoma (DLBCL) - NHL | II |
| | Angiogenesis, E3 ubiquitin ligase | Monotherapy | | Ovarian Cancer | I/II |
| | Angiogenesis, E3 ubiquitin ligase | Monotherapy | | Ovarian Cancer | I/II |
| | Angiogenesis, E3 ubiquitin ligase | Combination | Lenalidomide + Liposomal Doxorubicin + Bevacizumab | Ovarian Cancer | I |
| | Angiogenesis, E3 ubiquitin ligase | Monotherapy | | Myelodysplastic Syndrome (MDS) | II |
| | Angiogenesis, E3 ubiquitin ligase | Combination | Lenalidomide + rituximab | Indolent Non-Hodgkin's Lymphoma - NHL | II |
| | Angiogenesis, E3 ubiquitin ligase | Monotherapy | | PrimaryCentral NervousSystem Lymphoma (PCNSL) - NHL | I |
| | Angiogenesis, E3 ubiquitin ligase | Combination | Lenalidomide + Dexamethasone; <BR> Lenalidomide + Dexamethasone + Elotuzumab | Multiple Myeloma (MM) | III |
| | Angiogenesis, E3 ubiquitin ligase | Monotherapy | | Brain Cancer (malignant glioma; AA and GBM) | I/II |
| | Angiogenesis, E3 ubiquitin ligase | Combination | lenalidomide and CC-292. | Diffuse Large B-Cell Lymphoma (DLBCL) - NHL | I |
| | Angiogenesis, E3 ubiquitin ligase | Combination | CC-292 + lenalidomide | Mantle Cell Lymphoma - NHL | I |
| | Angiogenesis, E3 ubiquitin ligase | Combination | CC-292 + lenalidomide | Indolent Non-Hodgkin's Lymphoma - NHL | I |
| | Angiogenesis, E3 ubiquitin ligase | Monotherapy and Combo Therapy | | Indolent Non-Hodgkin's Lymphoma - NHL | III |
| | Angiogenesis, E3 ubiquitin ligase | Monotherapy | Induction with melphalan/prednisone/bortezomib(VMP)for 6-9 cycles, followed by Revlimid or Placebo. | Multiple Myeloma (MM) | III |
| | Angiogenesis, E3 ubiquitin ligase | Monotherapy and Combo Therapy | Revlimid (10-20 mg) and Rituximab | Indolent Non-Hodgkin's Lymphoma - NHL | III |
| | Angiogenesis, E3 ubiquitin ligase | Combination | Lenalidomide and Rituximab, Induction and Maintenance Phases | Diffuse Large B-Cell Lymphoma (DLBCL) - NHL | III |
| | Angiogenesis, E3 ubiquitin ligase | Monotherapy | | Mantle Cell Lymphoma - NHL | II |
| | Angiogenesis, E3 ubiquitin ligase | Combination | cyclophosphamide 300 mg/m2 on day 1, 8, and 15, lenalidomide 25 mg on d 1-21 and prednisone 100 mg every other day in a 28-d cycle | Multiple Myeloma (MM) | I/II |
| | Angiogenesis, E3 ubiquitin ligase | Combination | dexamethasone, carfilzomib, lenalidomide | Multiple Myeloma (MM) | II |
| | Angiogenesis, E3 ubiquitin ligase | Combination | Lenalidomide + Rituximab | Marginal Zone Lymphoma - NHL | III |
| | Angiogenesis, E3 ubiquitin ligase | Monotherapy and Combo Therapy | | Marginal Zone Lymphoma - NHL | III |
| | Angiogenesis, E3 ubiquitin ligase | Monotherapy | | Acute Myelogenous Leukemia (AML) | II |
| | Angiogenesis, E3 ubiquitin ligase | Combination | Cyclophosphamide + Dexamethasone + Lenalidomide | Multiple Myeloma (MM) | III |
| | Angiogenesis, E3 ubiquitin ligase | Combination | | Peripheral T-Cell Lymphoma (PTCL) - NHL | I |
| | Angiogenesis, E3 ubiquitin ligase | Monotherapy | | Multiple Myeloma (MM) | II |
| RG7888 | OX40/CD134 and OX40L | Combination | MOXR0916 + MPDL3280A | Solid Tumors | I |
| | OX40/CD134 and OX40L | Monotherapy | | Solid Tumors | I |
| Rintega | EGFR | Combination | Standard of care plus CDX-110 | Brain Cancer (malignant glioma; AA and GBM) | II |
| | EGFR | Combination | TMZ + CDX-110 | Brain Cancer (malignant glioma; AA and GBM) | IIb |
| | EGFR | Combination | | Brain Cancer (malignant glioma; AA and GBM) | II |
| | EGFR | Combination | | Brain Cancer (malignant glioma; AA and GBM) | II |
| | EGFR | Combination | Rindopepimut/GM-CSF plus Temozolomide | Brain Cancer (malignant glioma; AA and GBM) | III |
| | EGFR | Monotherapy and Combo Therapy | Rindopepimut w/GM-CSF + Avastin | Brain Cancer (malignant glioma; AA and GBM) | II |

TABLE D-continued

| | | | | | |
|---|---|---|---|---|---|
| S-288310 | | Immune system | Monotherapy | | Bladder Cancer | I/II |
| S-588410 | | Immune system | Monotherapy | | Esophageal Cancer | I/II |
| SB-313 | | Immune system | Combination | GRm13Z40-2 therapeutic allogeneic lymphocytes + Aldesleukin | Bladder Cancer | II |
| | | | | | Brain Cancer (malignant glioma; AA and GBM) | I |
| SCIB1 | | TRP2 | Monotherapy | | Melanoma | I/II |
| SCIB2 | | TRP2 | Monotherapy and Combo Therapy | | Melanoma | Preclinical |
| Seprehvir | | NY-ESO-1 | Monotherapy | | Cancer | Preclinical |
| | | Immune system | Monotherapy | | Mesothelioma | I/II |
| | | Immune system | Monotherapy | | Solid Tumors | I |
| | | Immune system | Monotherapy | | Hepatocellular (Liver) Cancer (HCC) (including secondary metastases) | Preclinical |
| | | Immune system | Monotherapy | | Brain Cancer (malignant glioma; AA and GBM) | I |
| | | Immune system | Monotherapy | | Brain Cancer (malignant glioma; AA and GBM) | I |
| | | Immune system | Monotherapy | | Brain Cancer (malignant glioma; AA and GBM) | I |
| Seviprotimut | | Immune system | Monotherapy | | Melanoma | III |
| Seviprotimut | | Immune system | Monotherapy | | Melanoma | II |
| | | Immune system | Monotherapy | | Melanoma | II |
| SHR-1210 | | PD-1/PD-L1 and PD-L2 | Monotherapy | | Solid Tumors | I |
| | | PD-1/PD-L1 and PD-L2 | Monotherapy | | Solid Tumors | I |
| SL-701 | | EphA2, IL-13, Stem Cells, Survivin | Combination | GAA/TT-peptide vaccine and poly-ICLC | Brain Cancer (malignant glioma; AA and GBM) | I/II |
| | | EphA2, IL-13, Stem Cells, Survivin | Combination | GAA/TT-peptide vaccine and poly-ICLC | Brain Cancer (malignant glioma; AA and GBM) | I/II |
| | | EphA2, IL-13, Stem Cells, Survivin | Monotherapy | | Brain Cancer (malignant glioma; AA and GBM) | I/II |
| | | EphA2, IL-13, Stem Cells, Survivin | Monotherapy | | Brain Cancer (malignant glioma; AA and GBM) | I/II |
| Specifid | | Immune system | Monotherapy and Combo Therapy | | Indolent Non-Hodgkin's Lymphoma - NHL | II |
| | | Immune system | Combination | Favid + Leukine | Indolent Non-Hodgkin's Lymphoma - NHL | III |
| | | Immune system | Monotherapy | | Indolent Non-Hodgkin's Lymphoma - NHL | II |
| | | Immune system | Monotherapy | | Indolent Non-Hodgkin's Lymphoma - NHL | II |
| | | Immune system | Combination | with Rituxan | Indolent Non-Hodgkin's Lymphoma - NHL | II |
| | | Immune system | Combination | Rituximab plus FavID and GM-CSF | Indolent Non-Hodgkin's Lymphoma - NHL | II |
| STI-A1010 | | PD-1/PD-L1 and PD-L2 | Monotherapy | | Cancer | Preclinical |
| STI-A1110 | | PD-1/PD-L1 and PD-L2 | Monotherapy | | Cancer | Preclinical |
| Stingvax | | Stem Cells | Monotherapy | | Prostate Cancer | Preclinical |
| SurVaxM | | Survivin | Combination | Montanide ISA-51/survivin peptide vaccine SC followed by sargramostimSC | Brain Cancer (malignant glioma; AA and GBM) | I |
| | | Survivin | Combination | SurVaxM, temozolomide | Brain Cancer (malignant glioma; AA and GBM) | II |
| | | Survivin | Combination | SVN53-67/M57-KLH peptide vaccine in Montanide ISA 51 SC and sargramostim SC | Multiple Myeloma (MM) | I |
| Talactoferrin | | Immune system | Combination | With paclitaxel + carboplatin | Non-Small Cell Lung Cancer (NSCLC) | III |
| | | Immune system | Monotherapy | | Non-Small Cell Lung Cancer (NSCLC) | III |
| | | Immune system | Combination | With C/P | Non-Small Cell Lung Cancer (NSCLC) | III |
| | | Immune system | Monotherapy | | Non-Small Cell Lung Cancer (NSCLC) | II |
| | | Immune system | Combination | With standard supportive care | Non-Small Cell Lung Cancer (NSCLC) | II |
| TDO/IDO Inhibitors | | IDO, TDO | Monotherapy | | Cancer | Preclinical |
| Tecemotide | | MUC-1 | Combination | Cyclophosphamide three days prior to the first vaccination of L-BLP25 | Non-Small Cell Lung Cancer (NSCLC) | II |
| | | MUC-1 | Monotherapy | | Non-Small Cell Lung Cancer (NSCLC) | II |
| | | MUC-1 | Combination | | Prostate Cancer | II |
| | | MUC-1 | Monotherapy | | Non-Small Cell Lung Cancer (NSCLC) | III |
| | | MUC-1 | Combination | Stimuvax (L-BLP25), cyclophosphamide, sodium chloride | Breast Cancer | III |
| | | MUC-1 | Combination | Cyclophosphamide + L-BLP25 + BLP25 | Non-Small Cell Lung Cancer (NSCLC) | III |
| | | MUC-1 | Combination | L-BLP25 + Androgen Deprivation Therapy (ADT) | Prostate Cancer | II |

TABLE D-continued

| | | | | | |
|---|---|---|---|---|---|
| | MUC-1 | Combination | L-BLP25 + Cyclophosphamide + Chemoradiation therapy; or L-BLP25 + Chemoradiation therapy | Colorectal Cancer (CRC) | II |
| | MUC-1 | Monotherapy and Combo Therapy | L-BLP25 + cyclophosphamide | Multiple Myeloma (MM) | II |
| | MUC-1 | Combination | Paclitaxel, Carboplatin, Cyclophosphamide, Bevacizumab, BLP25 liposome vaccine | Non-Small Cell Lung Cancer (NSCLC) | II |
| | MUC-1 | Monotherapy | EMD531444 + cyclophosphamide + BSC | Non-Small Cell Lung Cancer (NSCLC) | I/II |
| Tedopi | MUC-1 | Combination | Tecemotide + Cyclophosphamide | Non-Small Cell Lung Cancer (NSCLC) | III |
| | Immune system | Monotherapy | | Non-Small Cell Lung Cancer (NSCLC) | II |
| | Immune system | Monotherapy | | Non-Small Cell Lung Cancer (NSCLC) | III |
| Telekin | IL-2 | Combination | F16-IL2 + Paclitaxel | Breast Cancer | I/II |
| | IL-2 | Combination | F16IL2 + Doxorubicin | Breast Cancer | I/II |
| | IL-2 | Combination | F16IL2 + paclitaxel | Merkel Cell Carcinoma | II |
| TG01 | Ras | Monotherapy | | Pancreatic Cancer | I/II |
| TG4001 | HPV | Monotherapy | | Cervical Dysplasia | II |
| | HPV | Monotherapy | | Cervical Dysplasia | IIb |
| | HPV | Combination | TG4001 + chemo-radiotherapy | Head and Neck Cancer | IIb |
| TG4010 | IL-2, MUC-1 | Combination | Muc1-IL2 + cisplatin/vinorelbine-based chemotherapy | Non-Small Cell Lung Cancer (NSCLC) | II |
| | IL-2, MUC-1 | Combination | TG4010 + cisplatin and gemcitabine | Non-Small Cell Lung Cancer (NSCLC) | II |
| | IL-2, MUC-1 | Combination | TG4010 + standard of care | Non-Small Cell Lung Cancer (NSCLC) | II/III |
| Theratope | STn | Monotherapy | | Breast Cancer | III |
| Thymoglobulin | Immune system | Monotherapy | | Bone Marrow Transplant and Stem Cell Transplant | II |
| | Immune system | Monotherapy | Thymoglobulin + fludarabine + busulfex | Bone Marrow Transplant and Stem Cell Transplant | II |
| | Immune system | Combination | With busulfan, melphalan, and fludarabine | Bone Marrow Transplant and Stem Cell Transplant | II |
| | Immune system | Monotherapy | | Bone Marrow Transplant and Stem Cell Transplant | III |
| TLPLDC | Immune system | Monotherapy | | Melanoma | II |
| | Immune system | Monotherapy | | Melanoma | I/II |
| Tremelimumab | CTLA4 | Monotherapy | | Melanoma | III |
| | CTLA4 | Monotherapy | | Melanoma | I/II |
| | CTLA4 | Monotherapy | | Colorectal Cancer (CRC) | II |
| | CTLA4 | Monotherapy | | Non-Small Cell Lung Cancer (NSCLC) | II |
| | CTLA4 | Combination | with HDI | Melanoma | II |
| | CTLA4 | Monotherapy | | Mesothelioma | IIb |
| | CTLA4 | Monotherapy | | Hepatocellular (Liver) Cancer (HCC) (including secondary metastases) | II |
| | CTLA4 | Monotherapy | | Melanoma | II |
| | CTLA4 | Monotherapy | | Pancreatic Cancer | I |
| | CTLA4 | Monotherapy | | Melanoma | II |
| | CTLA4 | Monotherapy | | Mesothelioma | I |
| | CTLA4 | Monotherapy | | Solid Tumors | I |
| | CTLA4 | Combination | MEDI4736 + Mogamulizumab, Tremelimumab + Mogamulizumab | Solid Tumors | I |
| | CTLA4 | Combination | MEDI4736 + Tremelimumab | Solid Tumors | I |
| | CTLA4 | Monotherapy and Combo Therapy | MEDI4736 + tremelimumab | Head and Neck Cancer | I |
| | CTLA4 | Combination | MEDI4736 + Tremelimumab | Solid Tumors | I |
| | CTLA4 | Monotherapy and Combo Therapy | MEDI4736 + Tremelimumab | Head and Neck Cancer | II |

TABLE D-continued

| | | | | |
|---|---|---|---|---|
| | CTLA4 | Monotherapy and Combo Therapy | MEDI4736 + tremelimumab | Solid Tumors | II |
| | CTLA4 | Monotherapy and Combo Therapy | | Hepatocellular (Liver) Cancer (HCC) (including secondary metastases) | II |
| | CTLA4 | Monotherapy and Combo Therapy | Olaparib + Tremelimumab | Ovarian Cancer | I/II |
| Trivalent Ganglioside Vaccine | GD2, GD3, GM2 | Monotherapy | | Sarcoma | II |
| TroVax | 5T4 tumor antigen | Monotherapy | Trovax alongside first-line 5FU/LV and irinotecan (IFL) | Colorectal Cancer (CRC) | II |
| | 5T4 tumor antigen | Combination | Trovax alongside first-line 5FU/LV and oxaliplatin (FOLFOX) | Colorectal Cancer (CRC) | II |
| | 5T4 tumor antigen | Combination | | Colorectal Cancer (CRC) | II |
| | 5T4 tumor antigen | Combination | Trovax with subcutaneous low dose IL-2 | Renal Cell Cancer (RCC) | II |
| | 5T4 tumor antigen | Combination | Trovax w/high-dose IL-2 | Renal Cell Cancer (RCC) | II |
| | 5T4 tumor antigen | Combination | Trovax alone versus TroVax alongside GM-CSF | Prostate Cancer | II |
| | 5T4 tumor antigen | Monotherapy | | Breast Cancer | II |
| | 5T4 tumor antigen | Combination | with Sutent (standard of care) | Renal Cell Cancer (RCC) | III |
| | 5T4 tumor antigen | Combination | TroVax with adjuvant chemotherapy | Colorectal Cancer (CRC) | III |
| | 5T4 tumor antigen | Monotherapy and Combo Therapy | TroVax alone or in combination with IFNa | Renal Cell Cancer (RCC) | III |
| | 5T4 tumor antigen | Combination | | Colorectal Cancer (CRC) | III |
| | 5T4 tumor antigen | Combination | TroVax + Docetaxel | Prostate Cancer | II |
| | 5T4 tumor antigen | Combination | TroVax + Docetaxel | Prostate Cancer | II |
| | 5T4 tumor antigen | Monotherapy | | Colorectal Cancer (CRC) | II |
| | 5T4 tumor antigen | Monotherapy | | Mesothelioma | II |
| | 5T4 tumor antigen | Monotherapy | | Ovarian Cancer | III |
| TT10 EB-VST | EBV | Combination | autologous EBV specific Cytotoxic T Lymphocytes + IV gemcitabine + IV carboplatin | Head and Neck Cancer | III |
| TT12 HP-VST | HPV | Monotherapy | | Cervical Cancer | I |
| TVI-Brain-1 | Stem Cells, T lymphocytes | Monotherapy | | Brain Cancer (malignant glioma; AA and GBM) | I/II |
| | Stem Cells, T lymphocytes | Monotherapy | | Brain Cancer (malignant glioma; AA and GBM) | II |
| UCART123 | CAR-T, IL-3 Receptor/CD123, Stem Cells, T lymphocytes | Monotherapy | | Acute Myelogenous Leukemia (AML) | Preclinical |
| UCART19 | CAR-T, CD19, Stem Cells, T lymphocytes | Monotherapy | | Acute Lymphocytic Leukemia (ALL) | Preclinical |
| UCARTCS1 | CAR-T, CS1/SLAMF7, Stem Cells | Monotherapy | | Multiple Myeloma (MM) | Preclinical |
| Urelumab | CD 137 | Monotherapy | | Melanoma | II |
| | CD 137 | Monotherapy | | Non-Hodgkin's Lymphoma (NHL) | I |
| | CD 137 | Combination | Urelumab + Rituxan | Chronic Lymphocytic Leukemia (CLL)/Small Cell Lymphocytic Lymphoma (SLL) - NHL | I |
| | CD 137 | Combination | Urelumab + Rituxan | Non-Hodgkin's Lymphoma (NHL) | I |
| Uvidem | Stem Cells | Monotherapy | | Melanoma | II |
| | Stem Cells | Monotherapy and Combo Therapy | either Uvidem alone or Uvidem combined with peginterferon alpha-2b | Melanoma | II |
| | Stem Cells | Combination | UVIDEM + low-dose cyclophosphamide | Melanoma | II |
| V934/V935 | Telomerase | Monotherapy | | Solid Tumors | I |
| ValloVax | Stem Cells | Monotherapy | | Non-Small Cell Lung Cancer (NSCLC) | Preclinical |
| VaxImmune (Adjuvant) | TLR9 | Monotherapy | | Non-Small Cell Lung Cancer (NSCLC) | III |
| Vesigenurtacel-L | Stem Cells | Monotherapy and Combo Therapy | | Bladder Cancer | I/II |
| VGX-3100 | HPV | Monotherapy | | Cervical Dysplasia | IIb |
| | HPV | Monotherapy | | Cervical Dysplasia | I |

TABLE D-continued

| | | | | |
|---|---|---|---|---|
| Viagenpumatucel-L | Stem Cells | Combination | With erlotinib | Non-Small Cell Lung Cancer (NSCLC) | II |
| | Stem Cells | Monotherapy and Combo Therapy | HS-110 + Cyclophosphamide | Non-Small Cell Lung Cancer (NSCLC) | II |
| | Stem Cells | Monotherapy | | Non-Small Cell Lung Cancer (NSCLC) | I |
| | Stem Cells | Monotherapy | Viagenpumatucel-L +/- High-flow Oxygen +/- Theophylline | Non-Small Cell Lung Cancer (NSCLC) | Preclinical |
| | Stem Cells | Monotherapy | HS-110 plus nivolumab | Non-Small Cell Lung Cancer (NSCLC) | I |
| | Stem Cells | Combination | | Non-Small Cell Lung Cancer (NSCLC) | I |
| Vigil Vaccine | Furin, Stem Cells | Monotherapy | | Ovarian Cancer | II |
| | Furin, Stem Cells | Monotherapy | | Melanoma | II |
| | Furin, Stem Cells | Monotherapy | | Colorectal Cancer (CRC) | II |
| | Furin, Stem Cells | Monotherapy | | Ovarian Cancer | III |
| | Furin, Stem Cells | Monotherapy | | Sarcoma | II |
| | Furin, Stem Cells | Monotherapy | | Melanoma | I |
| Virexxa | Progesterone Receptor | Combination | Sodium cridanimod in combination with megestrol acetate or medroxyprogesterone acetate | Uterine (Endometrial) Cancer | II |
| Virulizin | Immune system | Combination | Virulizin combined with Gemzar | Pancreatic Cancer | III |
| | Immune system | Monotherapy | | Pancreatic Cancer | I/II |
| | Immune system | Monotherapy | | Pancreatic Cancer | I/II |
| VM206 | HER2/neu or ErbB-2 | Monotherapy | | Breast Cancer | I |
| WDVAX | Stem Cells, Tumor Cells | Monotherapy | | Melanoma | I |
| WT1 Antigen Specific Cancer Immunotherapeutic (ASCI) | Immune system | Monotherapy | | Breast Cancer | II |
| WT1-CTL | T lymphocytes, WT1 | Combination | Busulfan, melphalan, fludarabine, and anti-thymocyte globulin (ATG), and a T cell depleted stem cell transplant from a histocompatible related or unrelated donor | Multiple Myeloma (MM) | I |
| WT2725 | T lymphocytes, WT1 | Monotherapy | | Hematologic Cancer | I |
| | WT1 | Monotherapy | | Solid Tumors | I |
| | WT1 | Monotherapy | | Solid Tumors | I |
| WT4869 | WT1 | Monotherapy | | Myelodysplastic Syndrome (MDS) | I |
| | WT1 | Monotherapy | | Solid Tumors | I |
| XmAb (Amgen) | CD3, CD38 | Monotherapy | | Multiple Myeloma (MM) | Preclinical |
| Yervoy | CTLA4 | Monotherapy and Combo Therapy | MDX-010 in combination with MDX-1379 | Melanoma | III |
| | CTLA4 | Combination | MDX-010 + MDX-1379 | Melanoma | II |
| | CTLA4 | Combination | MDX-010 and high-dose IL-2 therapy | Melanoma | I/II |
| | CTLA4 | Monotherapy | | Melanoma | II |
| | CTLA4 | Monotherapy | | Melanoma | II |
| | CTLA4 | Monotherapy | | Prostate Cancer | II |
| | CTLA4 | Combination | Ipilimumab with dacarbazine | Melanoma | I/II |
| | CTLA4 | Monotherapy and Combo Therapy | Ipilimumab with prophylactic oral budesonide | Melanoma | III |
| | CTLA4 | Monotherapy | | Melanoma | II |
| | CTLA4 | Monotherapy | | Melanoma | II |

TABLE D-continued

| | | | | |
|---|---|---|---|---|
| CTLA4 | Combination | Ipilimumab and Taxol and Paraplatin | Non-Small Cell Lung Cancer (NSCLC) | II |
| CTLA4 | Combination | Ipilimumab and Taxol and Paraplatin | Small Cell Lung Cancer (SCLC) | II |
| CTLA4 | Monotherapy and Combo Therapy | MDX-010 ± dacarbazine (DTIC) | Melanoma | II |
| CTLA4 | Monotherapy | | Melanoma | III |
| CTLA4 | Combination | Radiotherapy with or without ipilimumab | Prostate Cancer | III |
| CTLA4 | Combination | | Prostate Cancer | I/II |
| CTLA4 | Combination | Lupron + Casodex + MDX-010 | Prostate Cancer | II |
| CTLA4 | Monotherapy and Combo Therapy | Ipilimumab +/− steroids | Melanoma | II |
| CTLA4 | Monotherapy | | Melanoma | II |
| CTLA4 | Monotherapy | | Prostate Cancer | III |
| CTLA4 | Combination | Ipilimumab IV over 90 minutes on weeks 1, 4, 7, and 10 + Bevacizumab IV on weeks 1, 4, 7, and 10 then 3 weeks thereafter | Melanoma | |
| CTLA4 | Combination | Ipilimumab + Vemurafenib | Melanoma | I/II |
| CTLA4 | Combination | Ipilimumab + Paclitaxel + Carboplatin | Non-Small Cell Lung Cancer (NSCLC) | III |
| CTLA4 | Combination | Ipilimumab + Etoposide + Cisplatin/Carboplatin | Small Cell Lung Cancer (SCLC) | III |
| CTLA4 | Monotherapy | | Melanoma | III |
| CTLA4 | Monotherapy | | Gastric Cancer | II |
| CTLA4 | Monotherapy | | Ovarian Cancer | IV |
| CTLA4 | Combination | Ipilimumab + Dacarbazine | Melanoma | II |
| CTLA4 | Monotherapy | | Melanoma | II |
| CTLA4 | Monotherapy | | Melanoma | II |
| CTLA4 | Combination | Ipilimumab & Cryoablation (procedure) | Breast Cancer | II |
| CTLA4 | Combination | Ipilimumab and gemcitabine | Pancreatic Cancer | Preclinical |
| CTLA4 | Monotherapy | | Melanoma | I |
| CTLA4 | Monotherapy and Combo Therapy | With or without sargramostim | Melanoma | II |
| CTLA4 | Monotherapy | | Non-Small Cell Lung Cancer (NSCLC) | II |
| CTLA4 | Monotherapy | | Melanoma | II |
| CTLA4 | Combination | ipilimumab + recombinant interferon alfa-2b | Melanoma | II |
| CTLA4 | Monotherapy | | Melanoma | I |
| CTLA4 | Combination | Sargramostim + MDX-010 (ipilimumab) + PROSTVAC | Prostate Cancer | I |
| CTLA4 | Monotherapy | | Merkel Cell Carcinoma | II |
| CTLA4 | Monotherapy | | Melanoma | III |

TABLE D-continued

| | Monotherapy Combination | | |
|---|---|---|---|
| Z-100 | Immune system | | Cervical Cancer | III |
| Zadaxin | Immune system | DTIC chemotherapy and randomly assigned either Zadaxin, interferon, or Zadaxin plus interferon | Melanoma | II |
| | Immune system | Combination | Hepatocellular (Liver) Cancer (HCC) (including secondary metastases) | II |

ABBREVIATIONS FOR TABLE D

| | |
|---|---|
| Abi-2, Abelson Interactor 2 | |
| Bap31, B-cell receptor-associated protein 31 | |
| CAR-T, Chimeric Antigen Receptor T-cells | IL-2, Interleukin-2 Receptor | PSA, Prostate-Specific Antigen |
| CEA, Carcinoembryonic antigen | IL-3, Interleukin-3 Receptor | PSMA, Prostate-specific Membrane Antigen |
| CD3, Cluster of Differentiation 3 | IL-13R, IL-13 Receptor | RB, Retinoblastoma |
| CD4, Cluster of Differentiation 4 | IL-21, Interleukin-21 | STn, Sialyl Tn |
| CTLA4, Cytotoxic T-Lymphocyte Antigen 4 | IL-33, IL-33 Receptor | TCR, T-Cell Receptor |
| EBV, Epstein Barr Virus | IRAK4, Interleukin-1 receptor-associated kinase 4 | TDO, Tryptophan 2,3-dioxygenase |
| CD5, Cluster of Differentiation 5 | EDDR1, Epithelial Discoidin Domain Receptor ITGB8, Integrin Beta-8 | TGF-beta, Transforming Growth Factor-beta |
| CD19, Cluster of Differentiation 19 | EGFR, Epidermal Growth Factor Receptor | KIR, Killer Immunoglobulin-like Receptors | TLR3, Toll-like receptor 3 |
| CD20, Cluster of Differentiation 20 | EphA2, Ephrin Receptor | LAG3, Lymphocyte-Activation Gene 3 | TLR4, Toll-like receptor 4 |
| CD22, Cluster of Differentiation 22 | FasR, Fas receptor | MAGE, Melanoma antigen-encoding gene | TLR5, Toll-like receptor 5 |
| CD23, Cluster of Differentiation 23 | FOLR1, Folate Receptor | MUC-1, Mucin 1 | TLR7, Toll-like receptor 7 |
| CD28, Cluster of Differentiation 28 | G17, gastrin1-17 | NY-ESO-1 (Cancer-testis antigen) | TLR8, Toll-like receptor 8 |
| CD30, Cluster of Differentiation 30 | GM-CSFR, Granulocyte Macrophage Colony-Stimulating Factor Receptor | PAPm Prostatic Acid Phosphatase | TLR9, Toll-like receptor 9 |
| CD38, Cluster of Differentiation 38 | HPV, Human Papillomavirus | PD-1, Programmed Cell Death Protein-1 | TRP2, Tyrosinase-Related Protein 2 |
| CD40, Cluster of Differentiation 40 | ICAM-1, Intercellular Adhesion Molecule-1 | PD-L1, Programmed Death-Ligand 1 (or Programmed Cell Death Ligand-1) | VISTA, V-domain immunoglobulin-containing suppressor of T-cell activation |
| CF40L, CD40 Ligand | IDO, Indoleamine 2,3-dioxygenase | PD-L2, Programmed Death-Ligand 2 (or Programmed Cell Death Ligand-2) | WT1, Wilms' Tumor Protein 1 |

TABLE E

IO Agents Approved for Clinical Treatment or in Clinical Trials

| Generic Name | Other Name | Target | Indications | Dosage | Notes |
|---|---|---|---|---|---|
| nivolumab | OPDIVO | PD-1 | Melanoma | OPDIVO 240 mg every 2 weeks. OPDIVO with ipilimumab: OPDIVO 1 mg/kg every 3 weeks × 4 doses, then OPDIVO 240 mg every 2 weeks. | Marketed (CheckMate 067, NCT01844505) |
| nivolumab | OPDIVO | PD-1 | Non-Small Cell Lung Cancer | OPDIVO 240 mg every 2 weeks. | Marketed (CheckMate 227, NCT02477826) |
| nivolumab | OPDIVO | PD-1 | Renal Cell Carcinoma | OPDIVO 240 mg every 2 weeks. | Marketed (CheckMate 025, NCT01668784) |
| nivolumab | OPDIVO | PD-1 | Classical Hodgkin Lymphoma | OPDIVO 3 mg/kg every 2 weeks. | Marketed (CheckMate 205, NCT02181738) |
| nivolumab | OPDIVO | PD-1 | Squamous Cell Carcinoma of the Head and Neck | OPDIVO 3 mg/kg every 2 weeks. | Marketed (CheckMate 141, NCT02105636) |
| nivolumab | OPDIVO | PD-1 | Bladder Cancer | OPDIVO 240 mg every 2 weeks. | Marketed (CheckMate 274, NCT02632409) |
| nivolumab | OPDIVO | PD-1 | Small Cell Lung Cancer | | Ph 3 (CheckMate 451, NCT02538666) |
| nivolumab | OPDIVO | PD-1 | Brain Cancer (Malignant Glioma; AA and GBM) | nivolumab 1 mg/kg every 3 weeks × 4 doses, then nivolumab 3 mg/kg every 2 weeks. nivolumab 3 mg/kg every 3 weeks for 4 doses, then nivolumab 3 mg/kg every 2 weeks. nivolumab 3 mg/kg every 2 weeks. | Ph 3 (CheckMate 143, NCT02017717, CheckMate 498, NCT02617589, Checkmate 548, NCT02667587) |
| nivolumab | OPDIVO | PD-1 | Hepatocellular Cancer | | Ph 3 (CheckMate 459, NCT02617589, CheckMate 040, NCT01658878) |
| nivolumab | OPDIVO | PD-1 | Esophageal Cancer | nivolumab 240 mg every 2 weeks. | Ph 3 (CheckMate 473, NCT02569242, CheckMate 577, NCT02743494) |
| nivolumab | OPDIVO | PD-1 | Gastric Cancer | | Ph 3 (CheckMate 649, NCT02872116) |
| nivolumab | OPDIVO | PD-1 | Mesothelioma | | Ph 3 (CheckMate 743, NCT02899299) |
| nivolumab | OPDIVO | PD-1 | Multiple Myeloma | | Ph 3 (CheckMate 602, NCT02726581) |
| pembrolizumab | KEYTRUDA | PD-1 | Melanoma | KEYTRUDA 2 mg/kg every 3 weeks. | Marketed (KEYNOTE 006, NCT01866319) |
| pembrolizumab | KEYTRUDA | PD-1 | Non-Small Cell Lung Cancer | KEYTRUDA 200 mg every 3 weeks. | Marketed (KEYNOTE 010, KEYNOTE 024,) NCT02142738 |
| pembrolizumab | KEYTRUDA | PD-1 | Classical Hodgkin Lymphoma) | KEYTRUDA 200 mg every 3 weeks for adults. KEYTRUDA 2 mg/kg (up to 200 mg) every 3 weeks for pediatrics. | Marketed (KEYNOTE 087, NCT02453594) |
| pembrolizumab | KEYTRUDA | PD-1 | Squamous Cell Carcinoma of the Head and Neck | KEYTRUDA 200 mg every 3 weeks. | Marketed (KEYNOTE 048, NCT02358031) |
| pembrolizumab | KEYTRUDA | PD-1 | Gastric Cancer | pembrolizumab 200 mg every 3 weeks. | Ph 3 (KEYNOTE 062, NCT02494583) |
| pembrolizumab | KEYTRUDA | PD-1 | Breast Cancer | pembrolizumab 200 mg every 3 weeks. | Ph 3 (KEYNOTE 522, NCT03036488) |
| pembrolizumab | KEYTRUDA | PD-1 | Bladder Cancer | pembrolizumab 200 mg every 3 weeks. | Ph 3 (KEYNOTE 361, NCT02853305) |
| pembrolizumab | KEYTRUDA | PD-1 | Solid Tumors | | Ph 2 (KEYNOTE 158, NCT02628067) |
| pembrolizumab | KEYTRUDA | PD-1 | Colorectal Cancer | pembrolizumab 200 mg every 3 weeks. | Ph 3 (KEYNOTE 177, NCT02563002) |
| pembrolizumab | KEYTRUDA | PD-1 | Renal Cell Carcinoma | pembrolizumab 200 mg every 3 weeks. | Ph 3 (KEYNOTE 426, NCT02853331) |
| pembrolizumab | KEYTRUDA | PD-1 | Multiple Myeloma | pembrolizumab 200 mg every 3 weeks. | Ph 3 (KEYNOTE 183, NCT02576977, KEYNOTE 185, NCT02579863) |
| pembrolizumab | KEYTRUDA | PD-1 | Esophageal Cancer | pembrolizumab 200 mg every 3 weeks. | Ph 3 (KEYNOTE 181, NCT02564263) |
| pembrolizumab | KEYTRUDA | PD-1 | Hepatocellular Cancer | pembrolizumab 200 mg every 3 weeks. | Ph 3 (KEYNOTE 240, NCT02702401) |
| atezolizumab | TECENTRIQ MPDL3280A | PD-L1 | Bladder Cancer | TECENTRIQ 1200 mg every 3 weeks. | Marketed (IMvigor210 trial, NCT02108652) |
| atezolizumab | TECENTRIQ MPDL3280A | PD-L1 | Non-Small Cell Lung Cancer | TECENTRIQ 1200 mg every 3 weeks. | Marketed (OAK trial, NCT02008227, POPLAR trial, NCT01903993) |

TABLE E-continued

IO Agents Approved for Clinical Treatment or in Clinical Trials

| Generic Name | Other Name | Target | Indications | Dosage | Notes |
|---|---|---|---|---|---|
| atezolizumab | TECENTRIQ MPDL3280A | PD-L1 | Renal Cell Carcinoma | atezolizumab 1200 mg every 3 weeks. | Ph 3 (IMmotion 151, NCT03024996) |
| atezolizumab | TECENTRIQ MPDL3280A | PD-L1 | Colorectal Cancer | atezolizumab 840 mg on Day 1 and Day 15 in a 28-day cycle, or 1200 mg on Day 1 in a 21-day cycle. | Ph 3 (COTEZO trial, NCT02788279) |
| atezolizumab | TECENTRIQ MPDL3280A | PD-L1 | Prostate Cancer | atezolizumab 1200 mg every 3 weeks. | Ph 3 (IMbassador 250, NCT03016312) |
| atezolizumab | TECENTRIQ MPDL3280A | PD-L1 | Melanoma |  | Ph 3 (NCT02908672) |
| atezolizumab | TECENTRIQ MPDL3280A | PD-L1 | Breast Cancer |  | Ph 3 (Impassion 130, NCT02425891) |
| atezolizumab | TECENTRIQ MPDL3280A | PD-L1 | Ovarian Cancer | atezolizumab 1200 mg every 3 weeks. | Ph 3 (NCT03038100) |
| atezolizumab | TECENTRIQ MPDL3280A | PD-L1 | Small Cell Lung Cancer | atezolizumab 1200 mg every 3 weeks. | Ph 3 (IMpower 133, NCT02763579) |
| avelumab | BAVENCIO | PD-L1 | Metastatic Merkel Cell Carcinoma | BAVENCIO 10 mg/kg every 2 weeks. | Marketed (JAVELIN Merkel 200, NCT02155647) |
| avelumab | BAVENCIO | PD-L1 | Non-Small Cell Lung Cancer | BAVENCIO 10 mg/kg every 2 weeks. | Ph 3 (JAVELIN Lung 200, NCT02395172) |
| avelumab | BAVENCIO | PD-L1 | Ovarian Cancer | avelumab 10 mg/kg every 2 weeks. | Ph 3 (JAVELIN Ovarian 200, NCT02580058) |
| avelumab | BAVENCIO | PD-L1 | Gastric Cancer | avelumab 10 mg/kg every 2 weeks. | Ph 3 (JAVELIN Gastric 100, NCT02625610, JAVELIN Gastric 300, NCT02625623) |
| avelumab | BAVENCIO | PD-L1 | Bladder Cancer | avelumab 10 mg/kg every 2 weeks. | Accelerated Approval Ph 3 (JAVELIN Bladder 100, NCT02603432) |
| avelumab | BAVENCIO | PD-L1 | Renal Cell Carcinoma | avelumab 10 mg/kg every 2 weeks. | Ph 3 (JAVELIN Renal 101, NCT02684006) |
| avelumab | BAVENCIO | PD-L1 | Diffuse Large B-Cell Lymphoma (DLBCL)-NHL |  | Ph 3 (JAVELIN DLBCL, NCT01741792) |
| avelumab | BAVENCIO | PD-L1 | Head & Neck Cancer | avelumab 10 mg/kg on Day 1 of the Lead-in Phase; Days 8, 25, and 39 of the CRT Phase; and every 2 weeks during the Maintenance Phase. | Ph 3 (JAVELIN Head and Neck 100, NCT02952586) |
| durvalumab | MEDI4736 | PD-L1 | Non-Small Cell Lung Cancer | durvalumab 10 mg/kg every 2 weeks. | Ph 3 (ARCTIC trial, NCT02352948, MYSTIC trial, NCT02453282) |
| durvalumab | MEDI4736 | PD-L1 | Head & Neck Carcinoma |  | Ph 3 (EAGLE trial, NCT02369874) |
| durvalumab | MEDI4736 | PD-L1 | Bladder Cancer |  | Ph 3 (DANUBE trial, NCT02516241) |
| durvalumab | MEDI4736 | PD-L1 | Small Cell Lung Cancer |  | Ph 3 (NCT03043872) |
| cemiplimab | REGN2810 | PD-1 | Non-Small Cell Lung Cancer |  | Ph 3 (NCT03088540) |
| PDR001 |  | PD-1 | Melanoma |  | Ph 3 (NCT02967692) |
| CBT-501 |  | PD-1 | Solid Tumors |  | Ph 1 (NCT03053466) |
| CX-072 |  | PD-L1 | Solid Tumors or Lymphomas |  | Ph 1 (NCT03013491) |
| LY-3300054 |  | PD-L1 | Solid Tumors |  | Ph 1 NCT03099109 |
| ipilimumab | YERVOY MDX-010 | CTLA-4 | Unresectable or Metastatic Melanoma | YERVOY 3 mg/kg every 3 weeks for a total of 4 doses. | Marketed (MDX010-020, NCT00094653) |
| ipilimumab | YERVOY MDX-010 | CTLA-4 | Adjuvant Melanoma | YERVOY 10 mg/kg every 3 weeks × 4 doses, followed by 10 mg/kg every 12 weeks. | Marketed (CA184-029, NCT00636168) |
| tremelimumab | AZD9150 | CTLA-4 | Melanoma | tremelimumab 15 mg/kg every 3 months. | Ph 3 (NCT00257205) |
| racotumomab |  | N-glycolil-GM3 ganglioside | Non-Small Cell Lung Cancer |  | Ph 3 (RANIDO trial, NCT01460472) |
| AGS-003 |  | Individualized based on tumor antigens | Renal Cell Carcinoma |  | Ph 3 (ADAPT trial, NCT01582672) |
| MED10562 |  | OX40 | Advanced Solid Tumors |  | Ph 1 (NCT02318394) |
| GSK3174998 |  | OX40 | Advanced Solid Tumors |  | Ph 1 (ENGAGE-1 trial, NCT02528357) |

TABLE E-continued

IO Agents Approved for Clinical Treatment or in Clinical Trials

| Generic Name | Other Name | Target | Indications | Dosage | Notes |
|---|---|---|---|---|---|
| Urelumab | BMS-663513 | 4-1BB | Melanoma | | Ph 2 (NCT00612664) |
| Utomilumab | PF-05082566 | 4-1BB | Diffuse Large B-Cell Lymphoma | | Ph 3 (NCT02951156) |
| BMS-986016 | | LAG-3 | Solid Tumors | | Ph 1/2a (NCT01968109) |
| LAG525 | | LAG-3 | Solid Tumors | | Ph 1 (NCT02460224) |
| JNJ-61610588 | | VISTA | Solid Tumors | | Ph 1 (NCT02671955) |
| TSR-022 | | TIM-3 | Solid Tumors | | Ph 1 (NCT02817633) |
| MBG453 | | TIM-3 | Solid Tumors | | Ph 1 (NCT02608268) |
| MEDI1873 | | GITR | Solid Tumors | | Ph 1 (NCT02583165) |
| INCAGN01876 | | GITR | Solid Tumors | | Ph 1/2 (NCT02697591) |

TABLE F

Blocking Antibodies to CTLA-4, PD-1 and PD-L1 and Functional Assays

| Target | Representative Generic Name | Representative Brand Name | U.S. Patents | Teaching |
|---|---|---|---|---|
| CTLA-4 | Ipilimumab | Yervoy ® | 6,984,720 | Antibodies to CTLA-4 defined by sequences; quantitative and qualitative properties |
| | | | 7,605,238 | Antibodies to CTLA-4 defined by binding affinity, including inhibitory and competitive binding assays; sequences |
| | | | 8,318,916 | Nucleic acids for antibodies to CTLA-4 defined by CDR3 sequences |
| | | | 8,784,815 | Increase immune responses and treat cancer with CTLA-4 antibodies |
| | | | 8,017,114 | defined by CDR3 sequences and affinity, or competition with reference antibody and affinity |
| | Tremelimumab | | 6,682,736 | Antibodies to CTLA-4 (preferably human and primate) defined by VH genes and aa substitutions therein; binding affinity, quantitative properties, antibody competition |
| | | | 7,109,003 | Expressing antibodies to CTLA-4, defined by quantitative binding properties or VL genes; affinity, antibody competition |
| | | | 7,132,281 | Host cells, expressing and purifying antibodies to CTLA-4, defined by antibody competition (e.g., deposited antibody) and VL genes, quantitative binding properties, 90%, 95% sequence identity |
| | | | 7,411,057 | Nucleic acids, host cells and expressing antibodies to CTLA-4, defined by CDR sequences and deposited antibody |
| | | | 7,807,797 | Antibodies to CTLA-4, defined by heavy or light chain sequences |
| | | | 7,824,679 | (chain-shuffling) or CDRs, single chains and bispecifics, and |
| | | | 8,143,379 | treating cancer |
| | | | 8,491,895 | |
| | | | 8,883,984 | |
| PD-1 | Nivolumab | Opdivo ® | 8,008,449 | Antibodies to PD-1 that compete for binding with reference |
| | | | 8,779,105 | antibody; immunoconjugates; bispecifics; quantitative and |
| | | | 9,387,247 | qualitative properties |
| | | | 9,492,539 | Antibodies to PD-1 that compete for binding with reference |
| | | | 9,492,540 | antibody, 80%, 85%, 90%, 95%, 96%, 97%, 98% or 99%, framework sequence identity, and treating cancer |
| | | | 8,728,474 | Treating tumors with antibodies to PD-1, including chimeric, humanized and human |
| | | | 9,067,999 | Treating lung cancer with antibodies to PD-1 including combinations |
| | | | 9,073,994 | Treating melanoma with antibodies to PD-1 including combinations |
| | | | 7,595,048 | Treating PD-L1 or PD-L2 over-expressing cancers with human anti-PD-1 antibodies, including chemotherapy combinations |
| | Pembrolizumab | Keytruda ® | 8,354,509 | Competitive binding antibodies to PD-1; quantitative and qualitative properties |
| | | | 8,900,587 | Antibodies to PD-1 defined by CDRs or certain sequences |
| | | | 8,952,136 | Antibodies to PD-1 defined by CDRs or certain sequences |
| | Cemiplimab | REGN2810 | prosecuting; 14/603,776 | Antibodies to PD-1 defined by CDRs or certain sequences |
| | CBT-501 | | not yet prosecuting | Antibodies to PD-1 defined by CDRs or certain sequences |
| PD-L1 | Durvalumab | [MEDI4736] | 8,779,108 | Antibodies to PD-L1 (B7-H1) that compete with deposited antibody for binding to known epitope or have 90% identity to heavy and light chain variable domains; competition assays for mutational analyses |
| | | | 9,493,565 | Antibodies to PD-L1 (B7-H1) defined by CDRs or sequences |
| | Atezolizumab | Tecentriq ® | 8,217,149 | Heavy chain variable regions and antibodies that bind to PD-L1 defined by CDRs with sequence variants, including effector-less Fc mutations and aglycosylation; chemotherapy, anti-viral and vaccine combinations |

TABLE F-continued

Blocking Antibodies to CTLA-4, PD-1 and PD-L1 and Functional Assays

| Target | Representative Generic Name | Representative Brand Name | U.S. Patents | Teaching |
|---|---|---|---|---|
| | CX-072 | | not yet prosecuting 15/069,622 | Antibodies to PD-1 defined by CDRs or certain sequences and activity |
| | LY300054 | | not yet prosecuting 15/239,959 | Antibodies to PD-1 defined by CDRs or certain sequences |
| Combos | | | 9,084,776 [8,728,474] [9,067,999] [9,073,994] | Treating tumors with antibodies to PD-1 and CTLA-4 |
| | | | 9,358,289 | Treating tumors with antibodies to PD-1 and CTLA-4, including sub-therapeutic doses and PD-L1 negative tumors |
| | | | 9,393,301 [9,402,899] | Treating tumors with antibodies to PD-L1 and CTLA-4 |

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example I

Generation and Characterization of Bavituximab

The present example summarizes the generation and initial characterization of the murine PS-targeting antibody termed 3G4, and the generation of chimeric versions of the 3G4 antibody, including the mouse-human chimeric antibody (ch3G4), now called bavituximab.
A. Generation of the 3G4 Antibody
The 3G4 antibody was produced by immunizing mice with autologous, PS-positive endothelial cells, as reported in Ran et al., 2005. The 3G4 antibody was tested for binding to PS in a standard ELISA in the presence and absence of serum, and was initially characterized as being "serum-independent", i.e., an antibody that binds to PS in the absence of serum. It was determined that the 3G4 antibody bound to PS, CL, PI (phosphatidylinositol), PA (phosphatidic acid) and PG (phosphatidylglycerol). In keeping with the model for targeting PS differentially expressed in tumors, the 3G4 antibody did not react with the neutral phospholipids, PC and SM.

The 3G4 antibody was purified to apparent homogeneity from the supernatant of the cultured hybridoma using a standard Protein A procedure. Early pre-clinical experience showed some of the anti-tumor effects of the 3G4 antibody in syngeneic and xenogeneic tumor models, again reported in Ran et al., 2005 (e.g., see FIG. 4 in Ran et al., 2005). The 3G4 antibody caused tumor vascular injury, localized thrombosis, tumor necrosis and retarded tumor growth, with no evidence of toxicity.

The full sequences of the heavy and light chain variable regions of the 3G4 antibody were determined, which together include the six complementarity determining regions (CDRs), followed by the generation of chimeric versions of the 3G4 antibody, including the mouse-human chimeric antibody (ch3G4), now called bavituximab. The nucleic acid and amino acid sequences of the variable region of the heavy chain (Vh) of the 3G4 antibody are represented by SEQ ID NO:35 and SEQ ID NO:36, respectively. The heavy chain variable region sequence encompasses VH CDR1, VH CDR2 and VH CDR3, at locations predictable by Rabat (Rabat et al., 1991).

SEQ ID NO:35 and SEQ ID NO:36 include part of the mouse leader sequence and constant chain sequences, as shown in FIG. 1A. The leader sequence is represented by amino acids 1 through 19 of SEQ ID NO:36, and the mature protein begins as shown by the arrow in FIG. 1A. Sufficient variable region and CDR sequence information is included by the sequence of the mature protein up to the sequence portion concluding VSS, after which the amino acids are not essential for antigen binding. As such, the BstEII site in the nucleic acid sequence can be used as a convenient site to prepare a functional mouse variable region, e.g., for use in grafting onto a human constant region (FIG. 1A).

In practice, the 3G4-2BVH sequence has been grafted onto a human γ1 constant region at the BstEII site using a Lonza pEE vector. The resultant product contains the mouse leader sequence and its VH is joined to the human CHI sequence in the manner shown in FIG. 1A, wherein ASTLGPSVFPLAPSSRSTSG (SEQ ID NO:39) represents the first part of the human CHI sequence.

The nucleic acid and amino acid sequences of the variable region of the light chain (Vκ) of the 3G4 antibody are represented by SEQ ID NO:37 and SEQ ID NO:38, respectively. The light chain variable region sequence encompasses VL CDR1, VL CDR2 and VL CDR3, at locations predictable by Rabat (Rabat et al., 1991).

SEQ ID NO:37 and SEQ ID NO:38 again include part of the mouse leader sequence and constant chain sequences, as shown in FIG. 1B. The leader sequence is amino acids 1 through 22 of SEQ ID NO:38, and the mature protein begins as shown by the arrow in FIG. 1B. Sufficient variable region and CDR sequence information is included by the sequence of the mature protein up to the sequence portion concluding TVF, after which the amino acids are not essential for antigen binding. As such, the BbsI site in the nucleic acid sequence can be used as a convenient site to prepare a functional mouse variable region, e.g., for use in grafting onto a human constant region (FIG. 1B).

In practice, the 3G4-2BVL sequence has been grafted onto a human K constant region at the BbsI site using a Lonza pEE vector. The resultant product contains the mouse leader sequence and its VL is joined within the human CL1 sequence in the manner shown in FIG. 1B, wherein IFPPSDEQLKSGTAS (SEQ ID NO:40) represents the first part of the human κ constant region sequence.

B. Generation of the Mouse Chimeric Antibody, 2aG4

As described immediately below, the human chimera of the murine 3G4 antibody (ch3G4) is a human IgG$_1$ isotype (hIgG$_1$). The murine IgG homolog of ch3G4 corresponds to a mouse IgG$_{2a}$ isotype (mIgG$_{2a}$). This construct was made and tested, and shown to behave essentially the same as the original mouse IgG$_3$ antibody.

Briefly, the 3G4 light chain coding sequence was amplified by RT-PCR from total RNA isolated from the 3G4 hybridoma cell line. RT-PCR primers were designed such that the amplified fragment contained XmaI and EcoRI restriction enzyme sites on either end of the amplified product for cloning into the Lonza expression vector, pEE12.4 vector. The variable region of the 3G4 heavy chain was amplified by RT-PCR from total RNA isolated from the 3G4 hybridoma cell line. Primers were designed such that the amplified fragment contained HindIII and XmaI restriction enzyme sites on either end of the amplified product for cloning into the Lonza expression vector, pEE6.4 vector.

The murine IgG2a constant region was amplified by PCR from a plasmid vector provided by Dr. Shozo Izui. PCR primers were designed with BstII and EcoRI restriction enzyme sites at either end of the amplification product for cloning into the pEE6.4+3G4VH vector. The BstEII site was designed to be in-frame with the 3G4 VH variable region sequence upstream. The heavy and light chain constructs were combined into a single double gene vector (12.4 3G4 IgG2a) by cutting both vectors with SaiI and NotI. The heavy and light chain coding regions were verified by sequencing.

The 12.4 3G4 IgG2a vector was transfected into NS0 cells by electroporation. Following transfection, the NS0 cells were diluted and plated into 96-well plates in media lacking glutamine. Only cells transfected with the construct (which contains the glutamine synthease gene for positive selection) can grow in the absence of glutamine. Transfectants were identified and screened for antibody secretion using the same standard ELISA as originally used to test the 3G4 antibody and those transfectants secreting the highest amounts of antibody were grown in large culture to generate purified antibody.

The resultant 2aG4 antibodies were purified to apparent homogeneity and shown to have essentially the same affinity and binding profile as the 3G4 antibody.

C. Generation of the Human Chimeric Antibody, ch3G4 (Bavituximab)

The chimeric construct containing the murine variable regions and the human constant regions has been produced (ch3G4) and shown to have essentially the same characteristics as the original murine antibody.

The murine 3G4 antibody was converted into a human-mouse chimeric antibody. The murine VH was cloned and grafted onto the human γ$_1$ constant region at the BstEII site of the Lonza 2BVH vector. The murine Vκ was cloned and grafted onto the human κ constant region at the BbsI site of the Lonza 2BVL vector. The sequences were verified. The entire construct was expressed in CHO cells (Chinese hamster ovary) and the antibody purified. This is the antibody now called bavituximab.

The resultant ch3G4 bound at least as well as the murine 3G4 to phospholipid-coated ELISA plates using the same standard ELISA as originally used to test the 3G4 antibody. The in vitro binding profile of chimeric 3G4 to the panel of phospholipids, PS, PA, CL, PI and PG, was shown to be the same as 3G4. The binding was antigen-specific, since no binding was observed with control antibodies of irrelevant specificity. In vivo, ch3G4 was also shown to localize to tumor vascular endothelium and to exert anti-tumor effects and anti-viral effects in a wide range of studies.

D. The 3G4 Antibody and Bavituximab Target PS in a β2GPI-Dependent Manner

When the chimeric 3G4 construct was expressed in CHO cells under serum-free conditions, and the purified antibody tested for binding to PS in an ELISA in the absence of serum, binding to PS was lost. Data were generated to resolve the apparent discrepancy in the PS binding profiles of the 3G4 antibody from the original hybridoma and the chimeric antibody expressed in CHO cells. In so doing, it was demonstrated that the interaction between the 3G4 antibody and PS is dependent on the plasma protein, $2-glycoprotein I (β2GPI).

The data demonstrated that the interaction between the 3G4 (and bavituximab) antibodies and PS is dependent on the plasma protein, β2GPI. 3G4 was shown to bind to β2GPI at domain II, which is not linked to pathogenic antibodies isolated from patients with Anti-Phospholipid Syndrome (APS), which commonly recognize β2GPI domain I. The data showed that divalent 3G4/β2GPI complexes are required for enhanced PS binding, including to PS-positive cells, since 3G4 Fab' fragments do not have this activity. In cell binding assays, it was shown that the ch3G4 antibody and hβ2GPI must be present simultaneously to bind ABAE cells with exposed PS, suggesting the ch3G4 antibody enhances the affinity of β2GPI for PS (Luster et al., 2006).

In summary, it was shown that the 3G4 antibody binds to β2GPI at domain II and that the lipid binding region of β2GPI domain V is required for co-binding of 3G4 (and ch3G4) and β2GPI to PS exposed on cells. In addition, it was demonstrated that antibody divalency is required for such co-binding of 3G4 (and ch3G4) and β2GPI to exposed PS. Accordingly, antibody and β2GPI co-bind to PS exposed on the outer surfaces of membranes, such as occurs on activated endothelial cells, tumor vascular endothelial cells and tumor cells, as well as on virally infected cells.

E. Pre-Clinical Modelling of the Interactions Between Bavituximab and β2GPI

Pre-clinical data concerning interactions between the bavituximab family of antibodies, β2GPI and PS showed that relatively low levels of β2GPI, markedly below the typical amounts in the human population, are sufficient for effective binding of bavituximab to PS.

In early studies in mice, it was calculated that molar ratios of β2GPI to antibody of between 0.12 and 0.25 were effective for anti-tumor activity, thus showing that high levels of β2GPI are not necessary for anti-tumor activity.

In analyzing the β2GPI levels required for binding of 3G4-β2GPI complexes to PS on cells, the maximum relative binding in a first study occurred at an antibody concentration of 80 nM, which is a β2GPI to antibody ratio of only 0.5. It was concluded that optimal antibody binding occurs at a molar ratio of β2GPI to antibody of between 0.125, 0.5 and 2. The first in vitro study therefore also showed that low levels of β2GPI effectively support bavituximab binding to cells with exposed PS.

In a follow-on study, the binding of the 2aG4 antibody to PS was tested in an ELISA in the presence of varying concentrations of human β2GPI. This study showed that 2aG4 antibody binding to PS started to plateau at a molar ratio of β2GPI to antibody of about 1. More precisely, a molar ratio of β2GPI to antibody of 0.93 was shown to be effective in supporting antibody binding to plates coated with PS.

A series of related studies were conducted testing the binding of bavituximab to PS in ELISAs in the presence of varying concentrations of human β2GPI in ovalbumin. Both bavituximab and β2GPI titrations were conducted. These studies also showed that low levels of β2GPI, including down to concentrations of 0.5 µg/ml, were effective in supporting a range of antibody concentrations in binding to plates coated with PS.

Another series of studies was conducted to test the binding and functions of bavituximab to PS in varying dilutions of human sera. These included binding to PS in ELISAs, FACS analyses using PS-positive cells and functional assays in the form of an NFAT surrogate ADCC bioassay (Larson et al., 2013).

Exemplary results from the ELISA assay showed that bavituximab binding to PS was already at saturation at the concentration of β2GPI in 1% human sera, which is a molar ratio of β2GPI to antibody of 2.86. Even at 0.5% human sera, bavituximab binding to PS is approaching the plateau, and this corresponds to a molar ratio of β2GPI to antibody of 1.43. Results from the NFAT surrogate ADCC bioassay also indicated that molar ratios of β2GPI to antibody in this general range were effective to support bavituximab function. For example, although the study was not designed to identify optimal ratios for bavituximab activity, a molar ratio of (bovine) β2GPI to antibody of 1.9 was shown to effectively support bavituximab activity in the NFAT assay.

In summary, it was shown that molar ratios of β2GPI to antibody from as low as 0.12 to 2.86 support antibody binding to PS and PS-positive cells, facilitate activity in functional assays and permit effective treatment of mice with tumors. In light of all the above data, and taking a precautionary approach, it was deduced that to maximize bavituximab binding and function, a molar ratio of β2GPI to antibody should be about 2.86, but that it does not need to be higher than about 3.

Example II

Pharmacokinetics of Bavituximab in Clinical Studies

This example concerns pharmacokinetics of bavituximab when administered to human subjects having diseases in which PS is a marker, particularly cancer and viral infections. The clinical experience is shown to be consistent with the pre-clinical modelling, as described above.

A. Initial Phase I Study

A Phase I, multicenter, open-label, dose escalation study was conducted to evaluate the safety, tolerability and pharmacokinetics (PK) of bavituximab when administered intravenously (bavituximab monotherapy) to 26 patients with refractory advanced solid tumors. Patients were enrolled into four sequential dose-escalation cohorts (0.1, 0.3, 1 or 3 mg/kg bavituximab weekly) with two dosing schedules. In the 0.1 mg/kg and 0.3 mg/kg cohorts, patients received bavituximab on days 0, 28, 35 and 42; and in the 1 mg/kg and 3 mg/kg cohorts, patients were administered bavituximab on days 0, 7, 14 and 21.

The upper dose of 3 mg/kg weekly was selected based on preclinical modeling (Example I, E) and experience in other patient populations. In extensive animal model studies subsequent to those of Example I and Ran et al., 2005, maximal efficacy was achieved at antibody doses of 0.5 mg/kg 3 times weekly, yielding a $C_{max}$ of 5.5 µg/mL with a half-life of 48 hours and a simulated average blood concentration of 2 µg/mL over the course of treatment. Beyond such a dose, PS binding by bavituximab was presumably saturated, based on observations of the concentration at which binding of bavituximab to PS-positive cells becomes saturated in vitro (Example I, E).

Samples were collected from patients in the 0.1 and 0.3 mg/kg dose cohorts before the study, on days 0, 1, 2, 4, 7, 10, 14, and every 7 days from days 21 to 70. Samples were collected from patients in the 1 and 3 mg/kg dose cohorts before the study, on days 0, 1, 2, 4, 7, 14, 21, 22, 23, 25, and every 7 days from days 28 to 56. Bavituximab blood levels were determined by a validated ELISA.

Table 1 presents a summary of the mean (coefficient of variation, CV) PK parameters of bavituximab following single-dose administration (day 0) and multiple-dose administration (day 21) in this Phase I trial, including maximum concentration ($C_{max}$), clearance (CL), half-life ($t_{1/2}$) and area under plasma concentration-time curve from time zero to infinity ($AUC_{inf}$).

TABLE 1

Pharmacokinetic Parameters of Bavituximab in Phase I Trial

| Day 0 | | | | | |
|---|---|---|---|---|---|
| Dose | | Mean (CV %) | | | |
| (mg/kg) | N= | $C_{max}$ (µg/mL) | CL (mL/h/kg) | $t_{1/2}$ (h) | $AUC_{inf}$ (d µg/mL) |
| 0.1 | 8 | 2.11 (27.3) | 1.10 (48.7) | 43.9 (48.5) | 113 (50.1) |
| 0.3 | 6 | 5.13 (42.4) | 1.39 (34.3) | 39.8 (34.1) | 241 (39.8) |
| 1.0 | 6 | 16.6 (30.9) | 1.14 (36.7) | 40.3 (20.2) | 966 (30.0) |
| 3.0 | 6 | 56.4 (25.8) | 1.34 (72.2) | 37.2 (34.5) | 3,017 (50.3) |
| Day 21 (for 1 and 3 mg/kg) | | | | | |
| Dose | | Mean (CV %) | | | |
| (mg/kg) | N= | $C_{max}$ (µg/mL) | CL (mL/kg/d) | $t_{1/2}$ (h) | $AUC_{inf}$ (d µg/mL) |
| 1.0 | 6 | 18.7 (31.8) | 1.12 (52.1) | 46.8 (38.4) | 1,053 (38.0) |
| 3.0 | 4 | 59.6 (27.6) | 1.51 (61.4) | 46.0 (44.4) | 2,672 (63.4) |

As shown in Table 1, following single-dose administration, it was determined that the mean half-life of bavituximab ranged from 37.2 to 43.9 hours. On day 0, the mean maximum serum concentration ($C_{max}$) ranged from 2.11 to 56.4 µg/mL (depending on dose) at the median time after administration when the maximum serum concentration was reached ($T_{max}$) (values ranging from 2.04 to 3.73 hours). For bavituximab administered at 3 mg/kg, the maximum serum concentration was 56.4 µg/mL. For the study overall, the bavituximab half-life ranged from 37 to 47 hours. No maximum tolerated dose was reached in this study.

Bavituximab exhibited linear single-dose (day 0) and multiple-dose (days 21 or 42) PK characteristics. Bavituximab did not exhibit appreciable accumulation or time-dependent PK differences following multiple-dose administration. In summary, this study showed that bavituximab was well tolerated at doses ranging up to 3 mg/kg weekly and the pharmacokinetics support a weekly dosing regimen. In particular, it was determined that at the dose of 1 mg/kg, the bavituximab concentration remained above 2 µg/mL, the predicted therapeutic threshold based on preclinical modeling, for 6 days; and at the dose of 3 mg/kg, the bavituximab concentration remained above this 2 µg/mL for 7 days. The dose of 3 mg/kg weekly was therefore selected for future use in oncology.

B. Further Pharmacokinetic Studies

In addition to the above Phase I trial, the PK of bavituximab given as a single dose, weekly or twice weekly infusion (60-90 minutes) has now been evaluated in over 120 patients across several other clinical studies in patients with cancer or viral infections. It was confirmed that bavituximab exhibits linear single-dose and multiple-dose PK characteristics at doses ranging from 0.1 to 6 mg/kg, with no evidence of appreciable accumulation of bavituximab or time-dependent PK differences. The median $T_{max}$ was shown to occur within the first 2 to 3 hours following the end of the infusion. Serum bavituximab concentrations decline in an apparent mono-exponential or bi-exponential first-order manner. The more rapid distribution phase, where observed, is essentially complete within 6 hours and the terminal elimination half-life is approximately 1 to 2 days (21.9 to 46.8 hours).

1. PK in Viral Infections

Bavituximab PK characteristics are generally similar in patients with cancer and chronic viral infections, as tested in patients chronically infected with HCV, with and without HIV.

A Phase I, open-label, single center, dose escalation study evaluated a single intravenous infusion of bavituximab in patients chronically infected with HCV (Example III, A). As shown in Table 2, it was found that the observed concentrations of bavituximab were very consistent with the predictions from the PK modeling data.

TABLE 2

Predicted and Measured Bavituximab Concentrations

| Parameters | Values | | | | |
|---|---|---|---|---|---|
| Doses (mg/kg) | 0.1 | 0.3 | 1 | 3 | 6 |
| Predicted $C_{max}$ (µg/mL) | 2.2 | 6.5 | 21.8 | 65.4 | 130.8 |
| Observed $C_{max}$ (µg/mL) | 2.5 | 5.7 | 24.3 | 75.8 | 135.0 |

In the corresponding Phase Ib, multi-center, open-label, non-randomized, escalating repeat-dose study in patients with chronic HCV, analysis of the PK data showed linear single-dose PK characteristics on day 0 and linear multiple-dose characteristics on day 10 at all dose levels, with no evidence of accumulation of bavituximab or time-dependent PK differences after 2 weeks dosing.

In the Phase Ib study in patients co-infected with chronic HCV and HIV (Example III, C), bavituximab exhibited linear single-dose PK characteristics on day 0 and linear multiple-dose PK characteristics on day 49 following once weekly administration at doses ranging from 0.3 to 6 mg/kg. Bavituximab did not exhibit time-dependent PK differences or accumulation following multiple-dose administration once weekly for 8 weeks.

2. PK in Combination Therapies

Importantly, when bavituximab and other drugs (particularly chemotherapeutic agents) were given in combination, there did not appear to be any clinically relevant pharmacokinetic interactions for either of the drugs. This includes when bavituximab and docetaxel were given in combination.

In this regard, a Phase Ib, multi-center, open-label, non-randomized study first evaluated the safety, tolerability and PK of weekly intravenous administration of 3 mg/kg bavituximab when used in combination with gemcitabine, paclitaxel plus carboplatin or docetaxel in patients with refractory advanced solid tumors. It was determined that there were no significant differences in any measurable parameter among the three treatment groups following a single-dose (day 0) or multiple-dose bavituximab administration (day 21). Evaluation of $C_{max}$ and AUC indicated that no accumulation of bavituximab following multiple-dose administration once weekly for eight weeks.

Within a Phase II, randomized, double-blind, placebo-controlled study evaluating bavituximab plus docetaxel in patients with previously treated locally advanced or metastatic non-squamous NSCLC (Example IX), a subset of the overall study population (6 patients per arm) also participated in a PK sub-study to investigate any drug-drug interactions between bavituximab and docetaxel. Additional blood draws were performed for these patients during cycles 1 and 2 at specified time points. No clinically relevant pharmacokinetic drug-drug interaction was observed for bavituximab with docetaxel. In addition, docetaxel exhibited similar pharmacokinetic characteristics with or without the administration of bavituximab. Thus, no clinically relevant pharmacokinetic drug-drug interaction was observed for docetaxel with bavituximab in these patients.

Example III

Treating Viral Infections in Patients Using Bavituximab

In this example, data are presented to exemplify some of the clinical experience in treating viral infections in patients using bavituximab, including bavituximab in combination with ribavirin. Data are also presented to show that, at the selected clinical dose, administration of bavituximab does not appreciably reduce β2GPI levels in human subjects.

A. Phase I Studies in HCV Patients

Bavituximab was first evaluated in Phase I, open-label, dose escalation studies and Phase Ib, open-label, escalating repeat-dose studies in patients chronically infected with hepatitis C virus (HCV). These studies concerned the safety, tolerability, PK profile, viral kinetics, maximum tolerated dose (MTD) and maximum effective dose (MED) of bavituximab. Doses of 0.1, 0.3, 1, 3 and 6 mg/kg were administered in Phase I (30 patients; successive cohorts of 6 patients), and doses of 0.3, 1, 3 and 6 mg/kg were administered in Phase Ib (24 patients; four cohorts of 6 patients).

In the Phase I and Phase Ib studies in HCV patients, all dose levels of bavituximab were well tolerated. In Phase I, transient reductions in viral load suggestive of anti-viral activity were observed at all dose levels. In Phase Ib, small decreases in viral load resulted after treatment with bavituximab at doses of 0.3, 1 and 6 mg/kg; those decreases were often transient, but at least one patient in each cohort had a sustained decrease in viral load. Notably, at doses of bavituximab of 3 mg/kg, consistent decreases in HCV were demonstrated throughout study treatment and follow-up.

B. Bavituximab does not Deplete β2GPI

The Phase Ib study described above also measured levels of β2GPI in the patients, to determine whether administration of bavituximab altered β2GPI levels in these human subjects. In patients receiving 1 mg/kg bavituximab, β2GPI levels were virtually unchanged. A transient reduction (20 to 25%) in serum levels of β2GPI was observed in patients receiving 3 mg/kg bavituximab. However, such a reduction was not statistically significantly changed from the pre-dose levels. Indeed, at the 3 mg/kg bavituximab dose, β2GPI levels remained within the normal range and returned to the pre-treatment level within 24 hours. In contrast, in patients receiving 6 mg/kg bavituximab, β2GPI levels were significantly reduced (p<0.02). At the 6 mg/kg dose, β2GPI levels fell by 40% relative to the pretreatment levels, to approximately the lower limit of the normal range. Nonetheless, even in human subjects treated with bavituximab at 6 mg/kg, β2GPI recovered to baseline levels in 3 days.

These data therefore validated the selection of the 3 mg/kg dose of bavituximab for use in humans. This dose was determined to be the maximal dose at which bavituximab and β2GPI were present together at concentrations effective to allow the bavituximab-β2GPI complex to form and bind to PS exposed on cells in the disease site without depleting plasma β2GPI levels. However, the data also show that any reductions in β2GPI during bavituximab treatment are only temporary and that β2GPI levels are restored within 3 days.

C. Phase I Study in HCV-HIV Patients

A separate Phase Ib, multi-center, open-label, non-randomized, dose-escalating, repeat-dose study was conducted to evaluate bavituximab in patients co-infected with chronic HCV (majority of HCV genotype 1) and human immunodeficiency virus (HIV). The primary objectives were to determine the safety, tolerability, PK profile, viral kinetics, MTD and/or MED. The study involved 16 scheduled visits over approximately 16 weeks. Bavituximab was administered to successive cohorts of patients at the following doses: 0.3 mg/kg, six patients; 1 mg/kg, six patients; 3 mg/kg, nine patients; and 6 mg/kg, six patients. Patients received intravenous bavituximab weekly for 8 weeks. Dose escalation proceeded after all patients in the cohort had completed the first 4 weeks of dosing with no thrombotic events classified as serious adverse events (SAEs).

The median baseline HCV viral load was 6.76 $\log_{10}$ and the median baseline for HIV was 3.99 $\log_{10}$. Plasma viral loads of HCV and HIV were measured at specific time points during the study. When treated with bavituximab at all dose levels, several patients in each treatment group exhibited transient antiviral activity (maximum reduction in HCV and/or HIV viral load of ≥0.5 $\log_{10}$ from baseline).

D. Phase II Study in HCV Patients

A Phase II, multi-center, randomized, active-control study was conducted to evaluate bavituximab in combination with ribavirin for the initial treatment of chronic HCV (genotype 1) infection. The primary endpoint was the proportion of patients who showed an early virological response (EVR) at Study Week 12, with an EVR being defined as equal to or greater than a 2-$\log_{10}$ international unit (IU) reduction in HCV RNA level. Safety was included amongst the secondary endpoints.

Patients underwent a screening/washout period of up to 28 days followed by randomization (in a 1:1:1 ratio) to receive 0.3 or 3 mg/kg weekly bavituximab infusion or pegylated interferon alpha-2a (pegylated interferon, also referred to as PEG-IFNα-2a) subcutaneous injection for 12 weeks, all with twice-daily oral ribavirin 1000 mg (weight <75 kg) or 1200 mg (weight ≥75 kg). Patients who showed an EVR after 12 weeks received off-study treatment with pegylated interferon plus ribavirin up to a 48 week course.

A total of 66 patients (38 males and 28 females) with a mean age of 39.1 years were enrolled to the study. Twenty-two patients each received 0.3 mg/kg bavituximab, 3 mg/kg bavituximab and pegylated interferon. The median number of 0.3 and 3 mg/kg bavituximab doses received was 12 doses each, and the mean duration of treatment was 78 and 75 days, respectively.

In this study, a gradual viral reduction over 12 weeks was seen in some patients treated with bavituximab plus ribavirin. Interestingly, an EVR was seen in twice as many patients treated with the lower dose of bavituximab (0.3 mg/kg), as opposed to the higher dose of 3 mg/kg bavituximab (18% vs. 9%). Although the EVR rate was higher in patients receiving pegylated interferon than bavituximab at either dose, bavituximab displayed a more favorable safety profile; almost twice as many patients in the pegylated interferon arm reported AEs compared to either bavituximab-containing arms.

Example IV

Treating Breast Cancer Patients with Bavituximab and Paclitaxel

Turning to clinical cancer treatment, the present example provides data from the treatment of patients with HER2-negative metastatic breast cancer using bavituximab in combination with the taxane, paclitaxel.

In a single-center, investigator-sponsored study, 14 patients with HER2-negative metastatic breast cancer received bavituximab at 3 mg/kg weekly in combination with paclitaxel (80 mg/m$^2$) given on days 1, 8 and 15 in 4-week cycles. Bone pain, fatigue, headache and neutropenia were the most common adverse events (AEs). Manageable infusion-related reactions were the most common AE related to bavituximab. Bavituximab showed no evidence for increased thrombogenicity. Treatment resulted in an overall response rate (ORR) of 85%, with 2 patients having a complete response, and a median progression-free survival (PFS) of 7.3 months (95% CI: 2.8, 10.8).

In summary, this study showed that bavituximab in combination with paclitaxel is well tolerated for the treatment of patients with metastatic breast cancer, with promising results observed in terms of clinical response rates (RRs) and PFS.

Example V

Treating Breast Cancer Patients with Bavituximab and Paclitaxel-Carboplatin

This example reports results from a Phase II, open-label, single arm study evaluating the safety and efficacy of bavituximab plus paclitaxel and carboplatin in patients with locally advanced or metastatic breast cancer, unrestricted by hormone or HER2 status.

This Phase II study utilized a Simon 2-stage design. Fifteen patients were enrolled into Stage A and the trial was expanded to an additional 31 patients in Stage B, for a total of 46 patients. The primary objective was to determine the overall response rate (ORR), defined as complete response (CR) plus partial response (PR), CR+PR. Secondary objectives included time to tumor progression, duration of response (DOR or DR), overall survival (OS) and safety.

Bavituximab (3 mg/kg) was given weekly until disease progression, in combination with carboplatin (at a dose of AUC=2) and paclitaxel 100 mg/m$^2$ on days 1, 8, and 15 of a 28-day cycle for up to 6 cycles. Sixteen of the 46 patients (34.8%) were treatment naïve.

The most common Grade 4 treatment-emergent adverse event (TEAE) was neutropenia (12 patients, 26.1%), which is the expected incidence in patients treated with the chemotherapies used in this study. The most common Grade 3 TEAEs were leukopenia (11 patients, 23.9%), neutropenia (9 patients, 19.6%), and anemia (5 patients, 10.9%). These are also the expected incidences in patients treated with the chemotherapies used in this study.

An objective response per Response Evaluation Criteria in Solid Tumors (RECIST) occurred in 34 of 46 patients (73.9%); 5 of 46 patients (10.9%) had a CR and 29 patients (63.0%) had a PR. The median duration of response (DOR) was 3.7 months (95% confidence interval [CI]: 3.1, 5.8) and the median PFS was 6.9 months (95% CI: 5.6, 7.7). At study closure, the median OS was determined to be 23.2 months (95 CI: 553 days to 'not determined'). These results are very encouraging for the ongoing development of bavituximab, particularly in combination therapies.

Example VI

Treating Breast Cancer Patients with Bavituximab and Docetaxel

The present example reports results from another Phase II, open-label, single arm study evaluating the safety and efficacy of bavituximab, this time in combination with docetaxel in patients with locally advanced or metastatic breast cancer.

This trial was also a Phase II, multicenter trial utilizing a Simon 2-stage design. Fifteen patients were enrolled into Stage A and the trial was expanded to an additional 31 patients in Stage B, for a total of 46 patients. The primary objective was to determine the ORR (CR+PR). Secondary objectives included time to tumor progression, DOR, OS and safety.

Bavituximab (3 mg/kg) was given weekly until progression, in combination with docetaxel (35 mg/m$^2$), given on days 1, 8, and 15 of planned 4-week cycles for up to 6 cycles. All patients received one prior chemotherapy regimen. Of the most common TEAEs reported, only fatigue, headache, back pain and hypertension were Grade ≥3.

In this study, it was determined that an objective response occurred in 28 of 46 patients (60.9%); 5 of 46 patients (10.9%) had a CR and 23 of 46 patients (50.0%) had a PR. The median DOR of 6.1 months (95% CI: 5.7, 7.5) and median PFS of 7.4 (95% CI: 6.1, 9.1) months. At the time of final analysis, median OS was approximately 20.7 months (95% CI: 16.1 months to 'not determined'). These data provide strong support for the further development of bavituximab, including in combination therapies with docetaxel.

Example VII

Treating Liver Cancer Patients with Bavituximab and Sorafenib

In this example, data are presented from the treatment of patients with advanced hepatocellular carcinoma (HCC) using bavituximab in combination with sorafenib.

A Phase II, single institution study of bavituximab and sorafenib in advanced hepatocellular carcinoma (HCC) was conducted. Patients received weekly bavituximab at 3 mg/kg intravenously (IV) and 400 mg sorafenib by mouth, two times per day (PO BID) until radiologic progression. Secondary endpoints included overall survival (OS), disease specific survival, 4 month progression free survival, safety and response rate. The study accrued 38 patients.

In related translational data from six patients in this study, it was determined that half of the patients evaluated had an increase in tumor fighting immune cells following one cycle of bavituximab treatment, similar to what has been shown for related PS-targeting antibodies in multiple preclinical cancer models. In addition, the increase in immune response was associated with patients that remained on study treatment for longer time periods, suggestive of a clinically meaningful anti-tumor immune response. Three of the six patients evaluated had increased infiltration of activated tumor-fighting T-cells (CD8) into the tumor microenvironment, which correlated with a prolonged time to disease progression. In addition, these responding patients initially expressed lower levels of PD-1 positive cells, an established marker of T-cell activation and disease outcome, prior to the initiation of therapy that was followed by a measurable rise post bavituximab treatment.

Clinically, there were no grade 4 or 5 adverse events recorded. The most common all grade events were diarrhea (32%), fatigue (26%) and anorexia (24%). The median OS (mOS) was 6.2 months. Two patients achieved partial response and the four month PFS was 61%.

These results demonstrated that bavituximab and sorafenib were well tolerated in patients with advanced HCC, with no indications of autoimmune adverse events that have been seen with other checkpoint immunotherapies. The clinical outcomes of time to progression, disease control rate and 4-month progression-free survival are encouraging, especially in this heavily pretreated patient cohort with very poor prognosis due to their unfavorable disease biology including a high rate of macrovascular invasion.

Example VIII

Treating Pancreatic Cancer Patients with Bavituximab and Gemcitabine

In the present example, data are presented from the treatment of patients with previously untreated stage IV pancreatic cancer using gemcitabine in combination with bavituximab.

This study (PPHM 1002) was a Phase II, randomized, open-label study to evaluate gemcitabine when administered with or without bavituximab in patients with previously untreated stage IV pancreatic cancer. The primary objective was to compare the OS of patients among the treatment arms. Secondary objectives included comparing PFS, ORR, DR and safety.

Enrolled patients were randomized in a 1:1 ratio to receive study treatment of gemcitabine alone or gemcitabine with weekly 3 mg/kg bavituximab. Gemcitabine (1000 mg/m$^2$) was given on days 1, 8, and 15 of each 28-day cycle (4 weeks) until disease progression or unacceptable toxicities. A total of 70 patients were enrolled to the study. In general, the patient population had very extensive disease burden, which may have reduced the response in both arms.

The most common TEAEs for the bavituximab plus gemcitabine treatment group were nausea (44.1%), anemia (35.3%), and fatigue, constipation and anorexia (each occurring in 32.4% of patients). Three (9.1%) patients randomized to gemcitabine only had Grade 5 (fatal) events (sudden death [1 patient], liver abscess [1 patient], and cardiac arrest [1 patient]). None of the Grade 5 (fatal) events occurred in the gemcitabine plus bavituximab group.

Although most efficacy endpoints were comparable across treatment groups, there was a numerically higher response rate and survival probability at 1 year in the bavituximab and gemcitabine group. At study closure, the median overall survival (95% CI) was 5.2 (4.0 to 6.3) months in the gemcitabine only treatment group and 5.6 (4.7 to 7.0) months in the bavituximab plus gemcitabine treatment group. These outcomes for the addition of bavituximab are encouraging, particularly in this patient population with very extensive disease burden.

After the Phase III trial of Example X, and the functional β2GPI analyses of Example XIII, showing that functional β2GPI levels correlate with treatment outcomes, stored samples from the present Phase II trial were also tested for functional β2GPI. Results from these analyses, as reported in Example XIV, strengthen the finding that levels of functional β2GPI are a biomarker for successful bavituximab treatment.

Example IX

Phase II Trial of Bavituximab and Docetaxel in NSCLC Patients

Building on the Phase I and single arm Phase II experience, the present example concerns a Phase II trial testing bavituximab plus docetaxel in patients with previously-treated Stage IIIb/IV non-squamous non-small cell lung cancer (NSCLC).

This study (PPHM 0902) was a Phase II, randomized, double-blind, placebo-controlled trial evaluating bavituximab plus docetaxel in patients with previously treated locally advanced or metastatic non-squamous NSCLC. The primary objective of this study was to compare the ORR (CR+PR) among the treatment arms. Secondary objectives included comparing PFS, DR, OS, safety and PK.

Patients were randomized in a 1:1:1 ratio to receive docetaxel plus placebo, docetaxel plus bavituximab at 1 mg/kg, or docetaxel plus bavituximab at 3 mg/kg. Docetaxel 75 mg/m$^2$ was given on day 1 of each 21-day cycle for up to 6 cycles, and placebo or the assigned dose of bavituximab was given weekly. Patients continued to receive assigned blinded treatment (placebo, 1 mg/kg bavituximab or 3 mg/kg bavituximab) weekly until progression or toxicity.

A subset of the overall study population (6 patients per arm) participated in a PK sub-study to investigate the drug-drug interaction between bavituximab and docetaxel. Additional blood draws were performed for these patients during Cycles 1 and 2 at specified time points.

A total of 121 patients (76 males and 45 females) with a mean age of 60.0 years were enrolled in the study. Study treatment was unblinded following an Independent Data Monitoring Committee (IDMC) meeting, in which it was determined that the primary endpoint of ORR had been reached and unblinding of study treatment was thus recommended. Additionally, no safety concerns or issues were identified by the IDMC.

After study unblinding, a labeling error by the package and labeling vendor was discovered involving the placebo and 1 mg/kg arms. An investigation summary was submitted to the Food and Drug Administration (FDA) and data from patients dosed with placebo or 1 mg/kg bavituximab were pooled to form a combined control arm for exploratory analyses and comparison to the 3 mg/kg bavituximab group.

Overall, no significant difference was observed in the incidence of AEs by toxicity grade between the treatment groups. No notable differences were observed in SAEs between treatment groups. Three patients (3.8%) in the combined control group and 2 patients (5.0%) in the 3 mg/kg bavituximab with docetaxel group had Grade 5 (fatal) events. The combined control patients with fatal events included 1 patient with sepsis, 1 patient with a cerebrovascular accident, and 1 patient experiencing both pneumonia and pseudomonil sepsis. In the 3 mg/kg bavituximab plus docetaxel group, 1 patient had fatal sepsis unrelated to bavituximab, and 1 patient had an event of failure to thrive, also unrelated to bavituximab.

A summary of efficacy endpoints is presented in Table 3, in which the analyses are based on the Intend-To-Treat (ITT) population and central review data. All endpoints (ORR, PFS, and OS) demonstrated trends towards superiority for bavituximab 3 mg/kg, compared to the combined control arm (placebo or 1 mg/kg bavituximab). The ORR was approximately 50% greater for bavituximab 3 mg/kg compared to the combined group. Although median PFS was similar between the combined groups and the 3 mg/kg bavituximab group, median OS was approximately 60% longer for patients receiving bavituximab 3 mg/kg. In particular, the patients treated with 3 mg/kg bavituximab plus docetaxel had a mOS of 11.7 months vs. only 7.3 months mOS for the patients in the combined arm (HR=0.66).

TABLE 3

Summary of Efficacy Analysis Based in Phase II Trial

| Efficacy Measure N= | Placebo + Bavituximab 1 mg/kg 80 | Bavituximab 3 mg/kg 41 |
|---|---|---|
| Overall Response Rate (CR + PR) | | |
| N (%) | 9 (11.3) | 7 (17.1) |
| 95% CI | (4.3, 18.2) | (5.6, 28.6) |
| Progression-Free Survival | | |
| Median in Days (Months) | 119 (3.9) | 127 (4.2) |
| 95% CI (Days) | (79, 126) | (82, 197) |
| Overall Survival | | |
| Number of Deaths (%) | 60 (75.0) | 22 (53.7) |
| Median in Days (Months) | 221 (7.3) | 355 (11.7) |
| 95% CI (Days) | (169, 367) | (157, 525) |

Subsequent to the Phase III trial of Example X, and the analyses of functional β2GPI in Example XIII, which showed that functional β2GPI levels correlate with treatment outcomes, stored samples from the present Phase II trial were also tested for functional β2GPI. Results from these analyses, which are described in Example XIV, further validate that levels of functional β2GPI are a biomarker for successful bavituximab treatment.

Example X

Phase III Trial of Bavituximab and Docetaxel in NSCLC Patients

As reported in the previous examples, the overall results from Phase I and Phase II studies have demonstrated a clinically meaningful treatment effect of bavituximab. Based on such results, and particularly on the double-blind Phase II trial described above, a Phase III trial was undertaken and the present example describes the Phase III trial and the resulting data.

The Phase III trial was a randomized, double-blind, placebo-controlled multicenter trial of bavituximab plus docetaxel in patients with previously-treated Stage IIIb/IV non-squamous non-small cell lung cancer (NSCLC). This global, double-blind Phase III trial was initiated in 2012. Selection criteria were for patients with Stage IIIb/IV non-squamous NSCLC who progressed on platinum-doublet chemotherapy (should have progressed on appropriate targeted therapy if known EGFR or ALK mutation), with ECOG PS 0-1 and prior immunotherapy allowed (ECOG is the performance status scale defined by the Eastern Cooperative Oncology Group). The trial accrued 597 such patients in a 1:1 ratio to receive up to six 21-day cycles of docetaxel (D) in combination with either weekly 3 mg/kg bavituximab (bavituximab plus docetaxel, B+D) or placebo (docetaxel alone, D) until progression or toxicity. The primary endpoint was overall survival (OS) and secondary endpoints included objective response rate (Independent Central Review, ICR), progression-free survival (ICR), safety, PK, Quality of Life (LCSS) and exploratory biomarkers, including immune correlates. The baseline characteristics of the selected patients are shown in Table 4, in which the 'Placebo' column refers to patients treated with docetaxel alone and the 'Bavituximab' column refers to patients treated with bavituximab plus docetaxel.

TABLE 4

Baseline Characteristics of Patients in Phase III Trial

|  | Placebo n = 300 | Bavituximab n = 297 |
|---|---|---|
| Median Age, yrs (Range) | 62 (30-82) | 63 (37-85) |
| >75 (%) | 5 | 8 |
| Male/Female % | 60/40 | 60/40 |
| Disease stage % |  |  |
| Stage IIIb | 5 | 5 |
| Stage IV | 95 | 95 |
| Current/former smoker % | 75 | 78 |
| Genetic mutation % |  |  |
| EGFR/ALK | 9 | 12 |
| Other | 14 | 9 |
| None | 51 | 52 |
| Unknown or not tested | 27 | 28 |
| Performance status % |  |  |
| 0 | 29 | 32 |
| 1 | 70 | 66 |
| Prior therapy % |  |  |
| Maintenance and/or targeted therapy | 57 | 57 |
| Immunotherapy | 4 | 2 |

A. Safety

With 70% of the targeted OS events reached, the median OS (mOS) was assessed (see below). At this point, it was determined that the safety profile was generally similar between groups. Thus, the safety profile of the combination of bavituximab with docetaxel is similar to placebo plus docetaxel.

B. Efficacy

With 70% of the targeted OS events reached, the mOS was 10.7 months (95% confidence interval [CI], 8.6-11.5) among 297 patients in the bavituximab plus docetaxel group and 10.8 months (95% CI, 9.2-12.6) among 300 patients in the docetaxel alone group (hazard ratio (HR) for death, 1.10 (0.89, 1.37)). Subsequent immunotherapy was received by about 15% of the patients in the study, evenly distributed between the bavituximab plus docetaxel arm and the docetaxel alone arm (see Example XVI).

Progression-free survival (PFS) was also similar in the two arms when 70% of the targeted OS events were reached, with a median PFS of 4.1 months for the bavituximab plus docetaxel group and 3.9 months for the docetaxel alone group. Analyses of the objective response rate (ITT) and duration of response (DOR) at this stage are listed in Table 5, in which the P-value is based on the two-sided stratified Cochran-Mantel-Haenszel exact method. Stratification factors include disease stage (IIIB vs. IV), geographic region (North America, Europe, Rest of World), previous maintenance and/or targeted therapy (Yes vs. No).

TABLE 5

Phase III Trial, Objective Response Rate

|  | Placebo + Docetaxel n = 300 | Bavituximab + Docetaxel n = 297 |
|---|---|---|
| ORR % (95% CI) | 11 (8-15) | 13 (10-18) |
| P-value |  | 0.53 |
| Best overall response % |  |  |
| Complete response | <1 | 0 |
| Partial response | 11 | 13 |
| Stable disease | 53 | 54 |
| Progressive disease | 20 | 17 |
| Unable to determine | 16 | 16 |
| Median DOR months (range) | 3.9 (0.03+ to 11.6) | 3.7 (0.03+ to 21.0) |
| Median time to response | 2.6 (1.3-6.2) | 2.7 (1.2-10.6) |

With 12 months follow-up from the last patient randomized and about 85% of the targeted OS events reached, the median OS is 10.5 months (95% confidence interval [CI], 8.4-11.9) among 297 patients in the bavituximab plus docetaxel group and 10.9 months (95% CI, 9.2-12.1) among 300 patients in the docetaxel alone group (HR, 1.06; P=0.533). PFS at this stage was 4.2 months (95% CI, 3.9-4.6) in the bavituximab plus docetaxel group and 4.1 months (95% CI, 3.2-4.8) in the docetaxel alone group (HR, 1.02; P=0.876). The ORR at this stage was 15% in the bavituximab plus docetaxel group vs. 11% in the docetaxel alone group (odds ratio, 0.7; P=0.15). The safety profile at this stage was similar between the groups. Grade 3 or higher adverse events occurred in 68% of patients in the bavituximab plus docetaxel group and 60% of those in the docetaxel alone group.

These results in median OS are unexpectedly different from the Phase II data described above in Example IX and the assumed mOS used for study powering, the latter of which were 9.1 months mOS for bavituximab plus docetaxel vs. 7.0 months mOS for docetaxel alone (473 OS events to provide 80% power and 1-sided 2.5% level of significance, assuming 9.1 vs 7.0 months mOS; HR 0.77).

Retrospective VeriStrat® proteomic testing demonstrated a VS Good signature in 80% of the bavituximab plus docetaxel group and 84% of the docetaxel alone group (Example XI). Although this Phase III trial in patients with previously treated non-squamous NSCLC did not meet the primary objective of superior OS in the bavituximab plus docetaxel arm, this outcome may be impacted by the higher than expected proportion of VS Good signature overall, and particularly in the docetaxel alone group.

Example XI

Initial Biomarker Analyses of the Bavituximab Phase III Trial

In connection with the Phase III trial described above, biomarker analyses were conducted with a view to identifying one or more biomarkers, or a pattern of biomarkers (a bavituximab "signature"), for patients who receive the most benefit from a bavituximab-containing therapeutic regimen. The present example concerns proteomic signature analyses and their application in the biomarker-guided ongoing clinical development of bavituximab.

A. Sample Collection

The Phase III trial was designed, and informed consent was obtained, for the collection of patient blood samples. Patient blood specimens were obtained using proper phlebotomy techniques. A tourniquet was placed 7 to 10 cm above the venipuncture site, but tourniquet application for preliminary vein selection was not permitted to exceed one minute. The patients were requested to close, but not pump, their first and the venipuncture site was cleaned with a 70% isopropyl alcohol pad using a circular motion from the center to the periphery and allow to air dry.

Using a 21 gauge needle, patient blood was collected in a 5.0 mL gold top Serum Separator Tube (SST). The tourniquet was released as soon as possible after the blood began to flow and the tube permitted to fill completely. The tube was immediately inverted 5 times after collection and allowed to clot for at least 30 minutes. To separate the serum, the tube was centrifuged within 30 to 60 minutes of collection at 1,000 to 1,300 g for 15 minutes. A pipette was used to transfer approximately 1.25 mL of serum into 3.6 mL cryovial tubes ×2 and those samples were frozen.

The frozen vials were placed into a specimen bag and sealed tightly. The bottom of a dry ice shipper was layered with dry ice and the specimen bag placed in the box. Dry ice was added until the box was full, the lid was secured in place, and the samples were shipped to Central Lab for storage at −70° degrees Celsius.

The Central Lab prepared the vials for sub-aliquotting by thawing the samples. Using a pipette at least 250 µl of serum was transferred into 2 ml natural cap cryovial tubes ×4 and refrozen at −70° Celsius. Repeating the same shipping directions, the sub-aliquoted samples were shipped frozen on dry ice to the testing labs for biomarker for testing.

B. VeriStrat® Analyses

Understanding the multi-dimensional characteristics of cancer is important to patient selection and treatment planning. The VeriStrat® test is a commercially available, blood-based predictive and prognostic proteomic test for patients with advanced NSCLC. In addition to being prognostic, VeriStrat is predictive of differential treatment benefit when selecting between single-agent treatment options. VeriStrat was retrospectively performed on patient samples from the Phase III trial. Separate proteomic approaches are also being explored specifically for bavituximab.

Pre-treatment serum samples from patients in the Phase III trial were tested for protein expression using mass spectrometry, classifying patients as VeriStrat (VS) Poor (VS-P), which correlates with a more aggressive disease, or VS Good (VS-G), which correlates with a more favorable prognosis. OS was analyzed by VeriStrat subgroups using Kaplan-Meier statistical methods.

VeriStrat classification was available for 569 patients of the 597 randomized patients. In the bavituximab plus docetaxel group, 80% were VS Good and 20% were VS Poor. In the docetaxel alone group, 84% were VS Good and 16% were VS Poor. The VeriStrat Good/Poor signature was thus largely balanced between the treatment groups in the Phase III trial.

The median overall survival (mOS) in all VS Good is 11.5 months (95% confidence interval [CI], 10.6-12.9) and 5.7 (95% CI, 4.2-7.2) in all VS Poor; p<0.0001, Hazard Ratio [HR] OS (VS-G vs. VS-P) 0.49 (95% CI 0.37-0.64); p<0.001. These VeriStrat results are consistent with PROSE Trial (Gregorc et al., 2014) and are overall prognostic for PFS and OS.

Among VS Good patients, mOS of the bavituximab plus docetaxel arm is 11.2 months (95% CI, 10.2-12.8) and 11.8 months (95% CI, 10.4-13.5) in the docetaxel alone group; p=0.38. Among VS Poor patients, mOS of the bavituximab plus docetaxel arm is 5.8 months (95% CI, 5.0-11.3) and 4.7 months (95% CI, 3.4-7.2) in the docetaxel alone group; p=0.27. The ability of bavituximab to improve OS in VS Poor patients is important, given the limited treatment options for this group of patients.

In conclusion, the VeriStrat results in the Phase III trial are overall prognostic for PFS and OS, but not predictive for bavituximab treatment response. The unexpected OS result in the docetaxel arm may have been impacted by the relatively high overall proportion of VeriStrat Good patients. In particular, the percentage of VeriStrat Good patients in this Phase III trial (greater than 80%) is higher than previously reported (approximately 67%), indicating that patients had better prognosis overall, thus partially explaining the better than expected performance of the docetaxel arm.

C. Bavituximab Immune Biomarkers

Aside from the foregoing VeriStrat analyses, the development of a unique immune biomarker signature for bavituximab is underway. Firstly, analyses of survival based on interferon gamma (IFNγ) levels show that IFNγ is a biomarker for successful treatment with bavituximab. In particular, patients with low levels of (peripheral) IFNγ, pre-treatment perform better on bavituximab treatment (Example XVII). IFNγ levels can also be measured in the tumor microenvironment.

Secondly, PD-L1 expression was explored as a prognostic biomarker. Baseline PD-L1 expression in a subset of patients demonstrated that negative PD-L1 expression (TC0) is associated with a significantly prolonged OS compared to positive PD-L1 expression (TC1/2/3) in bavituximab-treated patients (Example XV).

Together, these observations are consistent with bavituximab demonstrating more effect in PD-L1 negative, "immune cold" tumors. These and related testing of immune correlatives are designed for use in patient selection in future clinical studies.

Example XII

Assay for Functional β2GPI

The present example concerns the development of a β2GPI assay explicitly designed for the detection of functional (active) β2GPI in fluid samples. This test method is uniquely adapted to detect and quantify functional β2GPI, meaning β2GPI that is able to bind to both PS and to bavituximab. The present example thus provides a previously unavailable tool required for further meaningful biomarker analyses in connection with bavituximab treatment.

A. Materials and Methods

1. Materials and Equipment

The following particular materials and equipment were used in the assay to generate the Results presented in this example under Sections B1 and B2. Materials: 96-well medium binding flat bottom plates (Greiner BioOne, cat #655001); 96-well non-binding round bottom plates (Costar, cat #3605); hexane (Sigma, cat #32293); PS antigen (Sigma, cat #P6641); ovalbumin (Sigma, cat #A5503); chromogenic substrate, tetramethylbenzidine (TMB), (KPL, cat #50-76-00); 2M $H_2SO_4$ (Fisher, Cat #SA818-4); plate covers (Fisher 015-027-11); adhesive plate sealer (VWR 232701); reagent reservoirs (VistaLab Cat #3054-1000). 1.5 mL microcentrifuge tubes, 50 mL conical tubes and 15 mL conical tubes were also utilized.

Equipment: vortex (Scientific Industries); timer (VWR 62344-64); pipettors from 10 to 1,000 µL (Rainin); multi-channel pipettors from 100 to 300 µL (Rainin); plate reader at 450 and 650 nm (EN1835). A scale, stir bar and 37° C. incubator were also utilized. The SoftMax® Pro Software was used with the assay.

2. Buffers and Techniques

The Wash Buffer is 1X phosphate-buffered saline (PBS) and the Blocking Buffer is 2% Ovalbumin in 1X PBS.

Throughout the assay, subtractive pipetting was utilized when working with large volumes (e.g., ≥500 μL). The full amount of diluent was first pipetted. An equivalent volume of diluent was removed prior to adding additional reagents. All potentially hazardous vapors were handled in a fume hood.

3. Bavituximab-HRP

The bavituximab antibody was conjugated to horseradish peroxidase (HRP) to prepare a bavituximab-HRP detection agent for use in the assay. The conjugation was performed using EZ-Link® Plus Activated Peroxidase (Thermo Scientific, Cat #31487) following the procedure for conjugating activated peroxidase to an antibody at pH 7.2 provided by the manufacturer. Briefly, 1 mg of bavituximab was diluted to 1 mg/mL in PBS, pH 7.2. This was added to 1 mg of lyophilized EZ-Link Plus activated peroxidase to reconstitute. Immediately following reconstitution, 10 μL of 5M sodium cyanoborohydride solution was added to the reaction and incubated for 1 hour at room temperature. Once incubation was completed, 20 μL of quenching buffer was added and incubated for 15 minutes at room temperature. Conjugated bavituximab-HRP (1 mg/mL) was stored at 4° C. for up to 4 weeks.

1 mL of β2GPI Substock A at 10 μg/mL was prepared in Blocking Buffer;

1 mL of β2GPI Substock B at 1,000 ng/mL was prepared in Blocking Buffer by subtractive pipetting 100 μL from Substock A;

1 mL of β2GPI standard at 250 ng/mL was prepared in Blocking Buffer by subtractive pipetting 250 μL from Substock B; and control samples at 200 ng/mL, 75 ng/mL, 30 ng/mL and 5 ng/mL were prepared from the 1000 ng/mL substock using subtractive pipetting.

The unknown samples were prepared for testing as follows: unknown samples were prepared in Blocking Buffer with a final dilution of 1:4000 and 1:8000; a 1:100 dilution of the unknown sample was prepared first; a 1:40 dilution was prepared from the 1:100 dilution to achieve a 1:4000 dilution; and a 1:80 dilution was prepared from the 1:100 dilution to achieve a 1:8000 dilution.

The non-binding plate preparation was performed as follows: 75 μL of Blocking Buffer was added to columns 1-3 of rows B-H; 150 μL of 250 ng/mL standard was added to 25 columns 1-3, row A; using a multichannel pipette, 75 μL from columns 1-3 was serially diluted from row A through row G; 75 μL of positive controls and samples was added to the designated wells; and 75 μL of Blocking Buffer was added to any blank wells. The plate setup is shown in Table 6.

TABLE 6

Plate Setup for Functional β2GPI Assay

| | 1 | 2 | 3 | 4 | 5 | 6 | 7 | 8 | 9 | 10 | 11 | 12 |
|---|---|---|---|---|---|---|---|---|---|---|---|---|
| A | 250 ng/mL STD | | | (+) Control 200 ng/mL | | | Sample 3 Dilution 1 | | | Sample 7 Dilution 1 | | |
| B | 125 ng/mL STD | | | (+) Control 75 ng/mL | | | Sample 3 Dilution 2 | | | Sample 7 Dilution 2 | | |
| C | 62.5 ng/mL STD | | | (+) Control 30 ng/mL | | | Sample 4 Dilution 1 | | | Sample 8 Dilution 1 | | |
| D | 31.3 ng/mL STD | | | (+) Control 5 ng/mL | | | Sample 4 Dilution 2 | | | Sample 8 Dilution 2 | | |
| E | 15.6 ng/mL STD | | | Sample 1 Dilution 1 | | | Sample 5 Dilution 1 | | | Sample 9 Dilution 1 | | |
| F | 7.8 ng/mL STD | | | Sample 1 Dilution 2 | | | Sample 5 Dilution 2 | | | Sample 9 Dilution 2 | | |
| G | 3.9 ng/mL STD | | | Sample 2 Dilution 1 | | | Sample 6 Dilution 1 | | | Sample 10 Dilution 1 | | |
| H | 0 ng/mL STD | | | Sample 2 Dilution 2 | | | Sample 6 Dilution 2 | | | Sample 10 Dilution 2 | | |

4. Coating

The ELISA plates were coated with the PS antigen as follows: 5 μg/mL PS antigen was prepared and diluted into 6 mL of hexane in a fume hood with the blower off. 50 μL of PS solution was added to each well using a 12-channel pipette. The fume hood blower was turned back on and the hexane allowed to evaporate for 30-45 minutes, typically 30 minutes.

5. Blocking

The PS-coated ELISA plates were blocked as follows: 100 mL per plate of the Blocking Buffer (2% Ovalbumin in 1X PBS) was prepared. 200 μL of Blocking Buffer was added to each well using a 12-channel pipette. The blocked ELISA plates were incubated at 37° C. for 120 minutes (±10 minutes, which did not alter the performance of the assay).

6. Sample Preparations

The standard, positive control and sample preparations for the assay were performed as described below.

The β2GPI standards for the positive control were obtained from Haematologic Technologies, Inc. (HTI; cat #B2G1-0001-C; 1.0 mg/ml) in a buffer of 0.2 M Glycine, 0.15 M NaCl, pH 7.4. A vial of β2GPI was thawed and the standard and positive control preparation was performed as follows:

7. Detection

Prior to finish of the block, 6 mL of 300 ng/mL bavituximab-HRP was prepared in Blocking Buffer. The assay plate was washed with 1×PBS by pipetting 250 μL into each well and this was repeated 2 more times. A plate washer may be used, in which case, the plate is washed once with 1×PBS. It was ensured that the plate was as dry as possible.

50 μL of 300 ng/mL bavituximab-HRP was added to all wells of the assay plate. 50 μL was added from each corresponding well of the non-binding plate. Incubation was conducted at 37° C. for 90 minutes.

8. Development

The TMB peroxidase substrate and TMB peroxidase Solution B was removed from the refrigerator at least 1 hour before use. The assay plate was washed with 1×PBS by pipetting 250 μL into each well and this was repeated 2 more times. A plate washer may be used, in which case, the plate is washed once with 1×PBS. It was ensured that the plate was as dry as possible.

12 mL of TMB mixture was prepared by mixing 6 mL of TMB peroxidase substrate with 6 mL of TMB solution B. 100 μL of TMB solution was added to each well of the assay plate and allowed to develop for 5-6 minutes. Development was stopped by adding 100 µL of 2M H$_2$SO$_4$ to each well of the assay plate. The assay plate was read and optical density (OD) determined at 450 nm within 30 minutes of stopping the reaction. The microplate reader was used in conjunction with the SoftMaxPro plate data and analysis template, which provides a printout of assay data.

9. Preparation of Nicked β2GPI

Samples of β2GPI purified from human plasma and recombinant human β2GPI were both treated with plasmin (enzyme hydrolysis) to prepare samples that contained a majority of nicked β2GPI. The nicked β2GPI was not purified to homogeneity for initial studies, but nicked β2GPI was determined to be present in excess over the non-nicked, or "intact" β2GPI.

10. Assay for Total β2GPI

An assay was designed that should detect total β2GPI, based on the manufacturer's specifications for the antibodies used. This is an assay using commercially available antibodies from US Biological, in which plates are coated with a capture antibody against β2GPI and any bound β2GPI is detected using an anti-β2GPI-HRP conjugate as a detection antibody. The antibody catalog numbers are: Capture Antibody, US Biological #A2299-81A, affinity-purified anti-β2GPI and Detecting Antibody, US Biological #A2299-81B, peroxidase-conjugated anti-β2GPI.

A 1:100 dilution of the capture antibody was prepared in carbonate buffer (50 mM Sodium Bicarbonate) at pH 9.6. 100 µL was added to each well of the ELISA plate and incubated at room temperature. The plate was washed with 1×PBS buffer containing Tween-20, then blocked with 200 µL/well of assay diluent containing 1% BSA and incubated at 37° C. Purified β2GPI was used to prepare a two-fold dilution standard curve starting at 500 ng/mL in assay diluent. Samples were diluted in assay diluent to achieve a concentration within the linear region of the standard curve. After the blocking incubation, the plate was washed, followed by the addition of 100 µL/well of the standard curve and samples in either duplicate or triplicate. After the addition of the standard curve and samples, the plate was incubated at 37° C. The detection antibody was diluted 1:400 in assay diluent. After incubating the samples and standard curve, the plate was washed, followed by the addition of 100 µL/well of the detection antibody. The plate was incubated at 37° C. After the secondary antibody incubation, the plate was washed, then developed with TMB. The plate was read on a plate reader at 450 nm and the sample concentrations determined from the standard curve.

B. Results

1. Distinguishing Functional from Nicked β2GPI

β2GPI purified from human plasma ("human") or following recombinant expression ("recombinant") was treated with plasmin to prepare β2GPI test samples that contained a majority of plasmin-cleaved (nicked) β2GPI, which does not bind to PS. Those samples were tested alongside plasmin-free (intact) β2GPI, and a 50:50 mixture of each, in the present assay (Table 7B) and using an assay designed to detect total β2GPI using commercially available capture and detection antibodies (Table 7A). The results are shown below.

TABLE 7A

Testing Nicked and Functional β2GPI in Total β2GPI Assay

| Sample | | Conc. (ng/mL) |
|---|---|---|
| Human | Plasmin-treated β2GPI | 104.12 |
|  | 50:50 Mix | 119.77 |
|  | Plasmin-free β2GPI | 140.90 |

TABLE 7A-continued

Testing Nicked and Functional β2GPI in Total β2GPI Assay

| Sample | | Conc. (ng/mL) |
|---|---|---|
| Recombinant | Plasmin-treated β2GPI | 141.35 |
|  | 50:50 Mix | 134.51 |
|  | Plasmin-free β2GPI | 140.90 |

TABLE 7B

Testing Nicked and Functional β2GPI in Functional β2GPI Assay

| Sample | | Conc. (ng/mL) |
|---|---|---|
| Human | Plasmin-treated β2GPI | 32.95 |
|  | 50:50 Mix | 80.86 |
|  | Plasmin-free β2GPI | 136.42 |
| Recombinant | Plasmin-treated β2GPI | 33.26 |
|  | 50:50 Mix | 88.29 |
|  | Plasmin-free β2GPI | 136.42 |

It can first be seen that the so-called "total β2GPI assay" using commercially available antibodies (Table 7A), and the present, "functional β2GPI assay" (Table 7B), both read out similar concentrations of β2GPI (approximately 141 ng/mL and 136 ng/mL). Using the total β2GPI assay, there is essentially no difference in detecting plasmin-treated recombinant β2GPI, and only a moderate reduction in detection as the amounts of plasmin-treated β2GPI from human plasma are increased (141 to 104 ng/mL). In contrast, using the functional β2GPI assay, increasing amounts of plasmin-treated β2GPI, either recombinant or plasma-derived, result in a significant reduction in binding (136 to 33 ng/mL).

Consistent with the design of the assay, these results therefore show that the present assay is able to effectively detect functional β2GPI, i.e., β2GPI that binds to both PS and to bavituximab, as opposed to nicked β2GPI. This distinguishes the present, functional β2GPI assay from commercially available assay kits (and assays using commercially available anti-β2GPI antibodies), which detect nicked β2GPI (non PS-binding) along with β2GPI that does bind to PS.

2. Quantifying Functional β2GPI

The assay is able to successfully determine the amount of functional β2GPI in fluid samples, which is β2GPI that binds to both PS and to bavituximab. This assay has now been routinely performed to prepare reproducible β2GPI standard curves. In this regard, a Four-Parameter Logistic Fit is used, which is a statistical equation used for non-linear regression analysis. The Four-Parameter Fit Equation is:

$$y = \frac{(A-D)}{\left(1+\left(\frac{X}{C}\right)^B\right)} + D$$

Where:
A is the Y-value corresponding to the asymptote (i.e. the flat part of the curve) for the low values of the X-axis;
B is the coefficient that describes how rapidly the curve makes its transition from asymptotes in the center of the curve, and is commonly called as the slope factor;
C is the X value corresponding to the midpoint between A and D; commonly called the EC50; and D is the Y-value corresponding to the asymptote for the high values of the X-axis.

A standard curve for functional β2GPI is generated and the concentrations of functional β2GPI in human blood samples, such as plasma or serum samples, can be determined from such a standard curve. Mainly for accuracy, but also for economy of sample preparation, the standard curve is prepared in ng/ml (nanogram/ml). As the average levels of β2GPI in the normal human population are about 200 μg/ml (microgram/ml) (Mehdi et al., 1999; Miyakis et al., 2004), the standard curve is prepared in expectation that the test samples will be diluted before analysis in the assay. Diluted plasma or serum test samples are run in the assay and the concentration of β2GPI in the patient then calculated by adjusting for the dilution factor.

This assay has now been used to determine the levels of functional β2GPI in the patients from the above Phase III trial, the results of which are presented in Example XIII, below, and in Example XIV and Example XVII.

3. Alternative, Equivalent Assay Components and Steps

In addition to the particular materials, equipment and assay steps described in this example under Sections A1-A8, variations in the components and method steps can be made and executed without departing from the concept of the assay to detect and quantify functional β2GPI. The following results show that related agents may be substituted for the agents described in Sections A1-A8 and essentially the same results achieved.

Certain preferred ELISA plates are those optimized for lipid adsorption, which may be used to replace the ELISA plates in Section A1, above. ELISA plates are known that are optimized for lipid adsorption, which have surface chemistries providing better lipid (PS) binding. One such ELISA plate is the ThermoFisher PolySorp® plate, which has been used in a new assay format.

The hexane-based PS coating method in Section A4, above, may preferably be replaced with an isopropanol-based PS coating method, which can provide certain safety benefits to the user (by avoiding the use of hexane). In using isopropanol as a coating buffer in a new assay format, the ELISA plates are coated with PS antigen using 10 μg/mL PS antigen diluted in isopropanol and the incubation time is 90 min.

To produce an effective β2GPI calibration curve, any known method of obtaining β2GPI may be employed. For example, as purchased from a commercial vendor, such as HTI (Section A6, above). Alternative β2GPI preparations may also be developed for defined, reproducible calibration control. One such preferred method is to express β2GPI in CHO cells and purify the expressed β2GPI.

A preferred purification of β2GPI from CHO cells includes: a harvest clarification, chromatin extraction step, which removes contaminants and allows the clarified harvest to pass through a 0.2 μm filter; use of a tangential flow filtration (TFF) system, to buffer-exchange the clarified harvest and decrease its conductivity without increasing the volume; a Capto Adhere (GE Life Sciences) step in anion flow through mode, to remove further contaminants; a strong cation step using Nuvia™ S to remove aggregates and other contaminants, concentrate the eluate and facilitate any buffer exchange step; and, optionally, use of a TFF system to buffer exchange and concentrate the purified β2GPI. β2GPI has been expressed and purified in this way and used in a new assay format.

In addition to Section A3, above, certain preferred bavituximab-HRP detection agents are conjugates crosslinked using either of two commonly-used, non-proprietary cross-linkers, SMCC (succinimidyl 4-(N-maleimidomethyl)cyclohexane-1-carboxylate) or SATA (N-succinimidyl S-acetylthioacetate). Other preferred bavituximab-HRP detection agents are conjugates in which the number of HRP is in excess to the bavituximab antibody, particularly those resulting in an HRP:bavituximab ratio of 2:1 or 3:1, with essentially no free (unconjugated) antibody. Such conjugates are purified by an S-300 sizing column to remove unreacted reaction components. Bavituximab-HRP detection agents with each of these constituents and properties have been obtained from Columbia Biosciences, 4985 Winchester Blvd., Frederick, Md., 21703, and used at 600 ng/mL in a new assay format.

Whilst one or more of the above alternative components and assay steps may be preferred, even the combined use of all such alternatives provides a functional β2GPI assay that gives essentially the same results as the assay originally described in this example, i.e., under Sections A1-A8. Such comparative results are shown below in Table 8, which presents the functional β2GPI levels measured in the two different assay formats using four random human samples (Donor) obtained from the San Diego Blood Bank.

TABLE 8

Comparable Performance of Functional β2GPI Assays

| | β2GPI Concentration (μg/mL) | | | |
|---|---|---|---|---|
| | Assay Format, Example XII, A1-A8 | | Assay Format, Example XII, B9 | |
| Donor | Mean | SD | Mean | SD |
| 1 | 214 | 21 | 214 | 20 |
| 2 | 276 | 20 | 281 | 33 |
| 3 | 224 | 22 | 226 | 22 |
| 4 | 223 | 21 | 219 | 23 |

Example XIII

β2GPI Biomarker Analyses in the Bavituximab Phase III Trial

Utilizing the functional β2GPI assay described above, the present example reports the levels of pre-treatment functional β2GPI in the patients of the Phase III trial of Example X. By correlating the levels of functional β2GPI with treatment outcomes, the present example also concerns functional β2GPI as a biomarker for successful bavituximab treatment, such as in NSCLC patients treated with bavituximab and docetaxel.

A. Functional β2GPI Levels in Patients

The Phase III trial described above accrued 597 patients. The collection of blood samples from the patients in the Phase III trial is described in Example XI, A. At the time of the present analyses, there were 592 patient samples evaluable for functional β2GPI. Sub-aliquots of those 592 patient blood samples were tested for functional β2GPI, using the assay described in the example immediately above.

The levels of pre-treatment functional β2GPI in μg/ml and a summary of the statistics are presented in Table 9, in which the 'Bavituximab' row refers to patients treated with bavituximab plus docetaxel and the 'Placebo' row refers to patients treated with docetaxel alone.

TABLE 9

Functional β2GPI Levels in Phase III Patients

|  | N | Mean (SD) | Min | Q1 | Median | Q3 | Max |
|---|---|---|---|---|---|---|---|
| Bavituximab | 294 | 202 (57.3) | 22 | 162 | 207 | 240 | 365 |
| Placebo | 298 | 195 (59.7) | 0.5 | 159 | 199 | 238 | 402 |
| All | 592 | 198 (58.6) | 0.5 | 161 | 203 | 239 | 402 |

The levels of pre-treatment functional β2GPI ranged from 0.5 to 402 µg/ml. Within the patients treated with bavituximab plus docetaxel, functional β2GPI ranged from 22 to 365 µg/ml. The distribution of functional β2GPI in the patients treated with docetaxel alone covers the full range for the study (0.5 to 402 µg/ml).

For each treatment group (202 and 195 µg/ml), and for the study overall (198 µg/ml), the levels of pre-treatment functional β2GPI are consistent with the average of 200 µg/ml reported in the literature (20 mg/dl by Mehdi et al., 1999 and 200 mg/l by Miyakis et al., 2004).

It was determined that the percentage of patients with levels of pre-treatment functional β2GPI of equal to or greater than 200 µg/ml was 56% for patients treated with bavituximab plus docetaxel, and 49% for patients treated with docetaxel alone.

B. Initial β2GPI Biomarker Analyses

Sub-group analyses performed to evaluate functional β2GPI as a predictor of response in patients receiving bavituximab plus docetaxel therapy demonstrated trends for prolonged survival.

A single cutoff method was first used to assess the patient β2GPI data. In searching for the optimal cutoff in this manner, step 1 is to search for significant OS separation of a High β2GPI vs. Low β2GPI group for patients in the bavituximab plus docetaxel group; step 2 is to search for significant OS separation of the bavituximab plus docetaxel group vs. the docetaxel alone group (placebo) for those High β2GPI patients.

Initial analyses of functional β2GPI as a possible biomarker by applying the single cutoff method to 578 evaluable patients surprisingly indicated that in patients with high β2GPI, the mOS was 11.9 months (95% CI, 9.0-14.7) among 167 patients in the bavituximab plus docetaxel group and 9.4 months (95% CI, 7.7-11.7) among 141 patients in the docetaxel alone group (HR for death, 0.77; P=0.1). In these initial analyses, "high β2GPI" is defined as pre-treatment levels of functional β2GPI of equal to or higher than 200 µg/mL (≥200 µg/mL). As these analyses are based on a single cutoff, patients not having "high β2GPI" have functional β2GPI of less than 200 µg/mL (<200 µg/mL).

The single cutoff analyses were then extended to the 592 evaluable patients. Although not statistically significant, these analyses also demonstrated a surprising trend for prolonged survival in the bavituximab plus docetaxel group when patients had pre-treatment levels of functional β2GPI of equal to or greater than 200 µg/mL. These results are represented by the Kaplan-Meier survival curves for functional β2GPI of ≥200 µg/mL in FIG. 3. Of the 592 evaluable patients, in patients with pre-treatment levels of functional β2GPI≥200 µg/mL, the mOS was 11.9 months (95% CI, 9.0-14.7) among 167 patients in the bavituximab plus docetaxel group and 10.1 months (95% CI, 8.5-11.7) among 146 patients in the docetaxel alone group (HR for death, 0.81; P=0.155 with CI (0.60, 1.09)).

C. Detailed β2GPI Biomarker Analyses

The initial analyses described above prompted further, extensive analyses of the data in 592 evaluable patients. These analyses used a two cutoff method (Klein & Moeschberger, 2003). In the two cutoff method, Step 1 is to search for significant OS separation of "Within Range" vs. "Outside of Range" for patients treated with bavituximab (plus docetaxel), and Step 2 is to search for significant OS separation of the bavituximab vs. placebo arms for patients "Within Range".

These detailed sub-group analyses using the two cutoff method in 592 evaluable patients produced the surprising finding that pre-treatment levels of functional β2GPI within the range of 200-240 µg/mL are predictive of benefit in overall survival in patients treated with bavituximab plus docetaxel vs. those treated with docetaxel alone. These results are represented by the Kaplan-Meier survival curves for the functional β2GPI range of 200-240 µg/mL (FIG. 4).

Summarizing the results in FIG. 4, in patients with functional β2GPI in the range of 200-240 µg/mL ("200, 240" or "200<=β2GPI<=240"), the mOS is 13.2 months (95% CI, 9.0-17.9) among 94 patients in the bavituximab plus docetaxel group and 7.7 months (95% CI, 6.6-12.1) among 77 patients in the docetaxel alone group (HR for death, 0.67 with CI (0.44, 1.00); log-rank p-value=0.049). Thus, patients in the bavituximab group who possessed pre-treatment β2GPI levels between 200 and 240 µg/mL (about 30% of the study population) experienced a statistically significant, 5.5-month improvement in mOS as compared to patients in the control group with the same range of β2GPI levels.

There is no suggestion in the literature that pre-treatment levels of functional β2GPI of equal to or greater than 200 µg/mL would indicate a trend for prolonged survival on bavituximab treatment, and no suggestion that pre-treatment levels of functional β2GPI of 200-240 µg/mL would be predictive of benefit in overall survival in patients treated with bavituximab. Indeed, there is nothing in the significant prior clinical experience with bavituximab to suggest such outcomes. Moreover, such findings are very much at odds with the data from extensive pre-clinical modelling, which indicated that varying levels of serum β2GPI would not significantly impact treatment outcomes for bavituximab. The pre-clinical experience, in particular, rather indicated that quite low levels of serum β2GPI, such as on the order of 10-20 to 50-60 µg/mL or so, would be sufficient to support bavituximab binding and activity (Example I, E).

In particular, using different assays, Example I, E reports that molar ratios of β2GPI to antibody of 0.12 to 0.25; 0.125, 0.5 to 2; 0.93; and 1.43 to 2.86 are effective in supporting binding of bavituximab to PS. Considering several different binding and functional test systems, including pre-clinical data indicating that bavituximab is effective at molar ratios of β2GPI to antibody of about 2.86, a molar ratio of β2GPI to antibody of above 3 should not be needed. In using a dose of 3 mg/kg of bavituximab in the present Phase III trial, such ratios are achieved at β2GPI levels below 60 µg/mL (FIG. 5). For reference, the amounts of β2GPI, antibody and comparable β2GPI-antibody ratios for the Phase III trial are shown in Table 10, where N=the number of patients (from the 592 evaluable patients) having levels of functional β2GPI within each defined increment.

TABLE 10

β2GPI and Antibody Levels and Ratios in Phase III Patients

| Bavi (mg/kg) | Cmax (µg/ml) | Bavi (µM) | β2GPI (µg/ml) | N = | β2GPI (µM) | Molar Ratio β2GPI to Ab |
|---|---|---|---|---|---|---|
| 3 | 56.4 | 0.389 | 10 | 3 | 0.2 | 0.514 |
| 3 | 56.4 | 0.389 | 20 |  | 0.4 | 1.028 |
| 3 | 56.4 | 0.389 | 30 | 1 | 0.6 | 1.542 |
| 3 | 56.4 | 0.389 | 40 |  | 0.8 | 2.057 |
| 3 | 56.4 | 0.389 | 50 | 0 | 1.0 | 2.571 |

TABLE 10-continued

β2GPI and Antibody Levels and Ratios in Phase III Patients

| Bavi (mg/kg) | Cmax (μg/ml) | Bavi (μM) | β2GPI (μg/ml) | N = | β2GPI (μM) | Molar Ratio β2GPI to Ab |
|---|---|---|---|---|---|---|
| 3 | 56.4 | 0.389 | 60  |     | 1.2 | 3.085 |
| 3 | 56.4 | 0.389 | 80  | 9   | 1.6 | 4.113 |
| 3 | 56.4 | 0.389 | 100 | 26  | 2.0 | 5.141 |
| 3 | 56.4 | 0.389 | 120 | 28  | 2.4 | 6.170 |
| 3 | 56.4 | 0.389 | 140 | 43  | 2.8 | 7.198 |
| 3 | 56.4 | 0.389 | 160 | 36  | 3.2 | 8.226 |
| 3 | 56.4 | 0.389 | 180 | 43  | 3.6 | 9.254 |
| 3 | 56.4 | 0.389 | 200 | 90  | 4.0 | 10.283 |
| 3 | 56.4 | 0.389 | 220 | 101 | 4.4 | 11.311 |
| 3 | 56.4 | 0.389 | 240 | 70  | 4.8 | 12.339 |
| 3 | 56.4 | 0.389 | 260 | 62  | 5.2 | 13.368 |
| 3 | 56.4 | 0.389 | 280 | 44  | 5.6 | 14.396 |
| 3 | 56.4 | 0.389 | 300 | 23  | 6.0 | 15.424 |
| 3 | 56.4 | 0.389 | 320 | 7   | 6.4 | 16.452 |
| 3 | 56.4 | 0.389 | 340 | 2   | 6.8 | 17.481 |
| 3 | 56.4 | 0.389 | 360 | 1   | 7.2 | 18.509 |
| 3 | 56.4 | 0.389 | 380 | 1   | 7.6 | 19.537 |
| 3 | 56.4 | 0.389 | 402 | 2   | 8.0 | 20.566 |

In comparing Table 10 to the data used for modelling (Example I, E), it can be seen that the vast majority of patients in the Phase III trial had levels of functional β2GPI that equated to β2GPI to antibody molar ratios that were more than sufficient to saturate bavituximab binding (≥2.86), i.e., starting from 60 μg/ml or 1.2 μM (Table 10; FIG. 5), even when bavituximab was at its maximum concentration in the blood (Cmax of 56.4 μg/ml; Example II; Gerber et al., 2011). In fact, only 4 out of 592 evaluable patients (0.68%) had pre-treatment levels of functional β2GPI of less than 60 μg/ml. Moreover, as the levels of functional β2GPI increase, which was the case for the majority of patients in the trial, the molar ratios of β2GPI to bavituximab are much higher than 2 or 3, such as being over 10 at 200 μg/ml and being over 12 at 240 μg/ml. Nothing in the prior pre-clinical modelling or clinical experience pointed towards such β2GPI levels or ratios being beneficial for bavituximab therapy. Rather, as shown in FIG. 5, pre-clinical data indicated that low levels of serum β2GPI, starting at about 10 μg/mL or even less (β2GPI at 5 μg/mL has a β2GPI:Ab molar ratio of 0.257), and comfortably at about 60 μg/mL, would be sufficient to support bavituximab binding and activity (Example I, E).

Although unexpected, these detailed analyses of the pre-treatment levels of functional β2GPI as a possible biomarker for bavituximab outcomes are highly encouraging. Measuring pre-treatment concentrations of functional β2GPI in patients thus provides a strategy to predict response to bavituximab therapy, i.e., to select patients who are more, and most, likely to benefit from treatment with bavituximab. This was first observed in the use of bavituximab with docetaxel, particularly in NSCLC. However, as the mechanisms of bavituximab binding in a complex with functional β2GPI and PS, and the immune activating mechanisms of bavituximab overall, are common to all bavituximab therapies, the selection of patients based on pre-treatment levels of functional β2GPI of equal to or greater than 200 μg/mL, such as pre-treatment functional β2GPI in the range of 200-240 μg/mL, can therefore be included in all future trials and therapies using bavituximab with a well-founded expectation that this will improve the treatment outcomes. Indeed, further evidence supporting this is provided in Example XIV and Example XVII.

Example XIV

β2GPI Biomarker Analyses in Further Bavituximab Clinical Trials

Following the identification of functional β2GPI as a biomarker for successful bavituximab treatment in Example XIII, the present example extends the use of the functional β2GPI assay to samples from earlier bavituximab clinical trials. The following results show that the same levels of functional β2GPI also correlate with successful treatment outcomes for bavituximab, thus confirming functional β2GPI as a biomarker for bavituximab.

A. Phase II Trial of Example IX

Samples from the NSCLC Phase II trial of Example IX (PPHM 0902) were tested using the functional β2GPI assay of Example XII. There were 119 patient samples in which levels of pre-treatment functional β2GPI were evaluable, of which 40 patients were in the bavituximab 3 mg/kg arm and 79 patients were in the combined control arm (placebo or 1 mg/kg bavituximab).

The levels of pre-treatment functional β2GPI ranged from 0.5 to 266 μg/ml for all patients. Within the patients treated with bavituximab 3 mg/kg plus docetaxel, functional β2GPI ranged from 0.5 to 266 μg/ml. The distribution of functional β2GPI in the patients in the combined control arm was 0.5 to 257.4 μg/ml. For each treatment group (169.4 μg/ml for bavituximab 3 mg/kg, and 171.8 μg/ml for combined control arm), and for the study overall (171.0 μg/ml), the levels of pre-treatment functional β2GPI are consistent with the average reported in the literature.

Using a cut-off of "high β2GPI" being defined as pre-treatment levels of functional β2GPI of equal to or higher than 200 μg/mL (≥200 μg/mL), it was determined that β2GPI≥200 μg/mL trended with increased overall survival in the bavituximab 3 mg/kg arm, but not in the other arm. For example, for patients treated with bavituximab 3 mg/kg, those with functional β2GPI of equal to or higher than 200 μg/mL had a mOS of 16.8 months, vs. only 9.4 months for "low β2GPI" of less than 200 μg/mL. Also, in patients with functional β2GPI≥200 μg/mL, the 16.8 months mOS for patients treated with bavituximab 3 mg/kg exceeded that of only 8.7 months mOS for patients in the combined control arm.

B. Phase II Trial of Example VIII

Samples from the Phase II pancreatic cancer trial of Example VIII (PPHM 1002) were tested using the functional β2GPI assay of Example XII. There were 31 patient samples in which levels of pre-treatment functional β2GPI were evaluable. The levels of pre-treatment functional β2GPI ranged from 82.5 to 343.2 μg/ml for all patients. For these 31 patients, the mean level of pre-treatment functional β2GPI (219.2 μg/ml) was consistent with the average reported in the literature.

Although the sample size is small, and the disease is very aggressive, using a cut-off of "high β2GPI" of functional β2GPI of equal to or higher than 200 μg/mL (≥200 μg/mL), it was determined that β2GPI≥200 μg/mL trended with increased overall survival for bavituximab. Patients treated with bavituximab having functional β2GPI of equal to or higher than 200 μg/mL had a mOS of 7.4 months, vs. 5.3 months for "low β2GPI" of less than 200 μg/mL.

C. Phase II Trial of Bavituximab and Paclitaxel/Carboplatin in NSCLC

A randomized, open-label, Phase II trial (PPHM 1001) of paclitaxel/carboplatin with or without bavituximab was conducted in patients with previously untreated locally advanced or metastatic non-squamous NSCLC. Samples from this trial were tested using the functional β2GPI assay of Example XII. There were 84 patient samples in which levels of pre-treatment functional β2GPI were evaluable, of which 44 patients were in the bavituximab arm and 40 patients were in the paclitaxel/carboplatin arm.

The levels of pre-treatment functional β2GPI ranged from 0.5 to 326 μg/ml for all patients. Within the patients treated with bavituximab, functional β2GPI ranged from 0.5 to 326 μg/ml. Functional β2GPI in the patients in the paclitaxel/carboplatin arm ranged from 88.8 to 292.7 μg/ml. For each treatment group (187.9 μg/ml for bavituximab, and 186.4 μg/ml for the paclitaxel/carboplatin arm), and for the study overall (187.2 μg/ml), the levels of pre-treatment functional β2GPI are again consistent with the average reported in the literature.

Using the same cut-off of "high β2GPI" as being pre-treatment levels of functional β2GPI of equal to or higher than 200 μg/mL (≥200 μg/mL), it was determined that β2GPI≥200 μg/mL again trended with increased overall survival in the bavituximab arm, but not in the control (paclitaxel/carboplatin) arm. For example, for patients treated with bavituximab, those with functional β2GPI of equal to or higher than 200 μg/mL had a mOS of 17.0 months, vs. 14.2 months for "low β2GPI" of less than 200 μg/mL. Also, in patients with functional β2GPI≥200 μg/mL, the 17.0 months mOS for patients treated with bavituximab exceeded that of only 13.2 months mOS for patients in the control arm.

In conclusion, the data in Example XIII and Example XIV, from four separate clinical trials, consistently show that functional β2GPI levels correlate with treatment outcomes, thus validating functional β2GPI levels as a biomarker for successful bavituximab treatment.

Example XV

PD-L1 Expression as a Prognostic Biomarker for Bavituximab

The present example concerns analyses of pre-treatment PD-L1 expression in the patients of the Phase III trial of Example X. These studies show that negative PD-L1 expression, characterized as TC0, is associated with a significantly prolonged OS compared to positive PD-L1 expression, characterized as TC1/2/3, in patients receiving bavituximab.

A. Methods

Archival tissue obtained at the time of diagnosis was requested, but not required, in the Phase III trial of Example X. Formalin-fixed paraffin-embedded (FFPE) slides were stained with antibodies for a panel of lymphoid (or tumor) cell markers, as described in Feng et al., 2015: CD3+, CD8+, FoxP3+, PD-L1+, CD163+ and CK+ (cytokeratin, an epithelial carcinoma marker) using a mutliplex (6-plex) quantitative immunohistochemistry (IHC) assay (OPAL®, PerkinElmer, Waltham, Mass., USA) and using DAPI. The PD-L1 antibody used was the rabbit anti-PD-L1 antibody termed E1L3N® XP® (Cell Signaling Technology, (CST), Danvers, Mass., Catalogue #13684; Mahoney et al., 2015). Baseline PD-L1 expression was retrospectively scored on tumor cells (TC, i.e., CK+) and PD-L1 expressing tumor cells were classified according to their percentage within the total number of tumor cells using established assays and classifications (Fehrenbacher et al., 2016), as follows: TC3≥50%; TC2≥5% and ≤50%; TC1≥1% and <5%; and TC0<1%. Cox regression models for PD-L1 IHC subgroup populations were used for correlation with OS.

B. Results

Figure 8A:
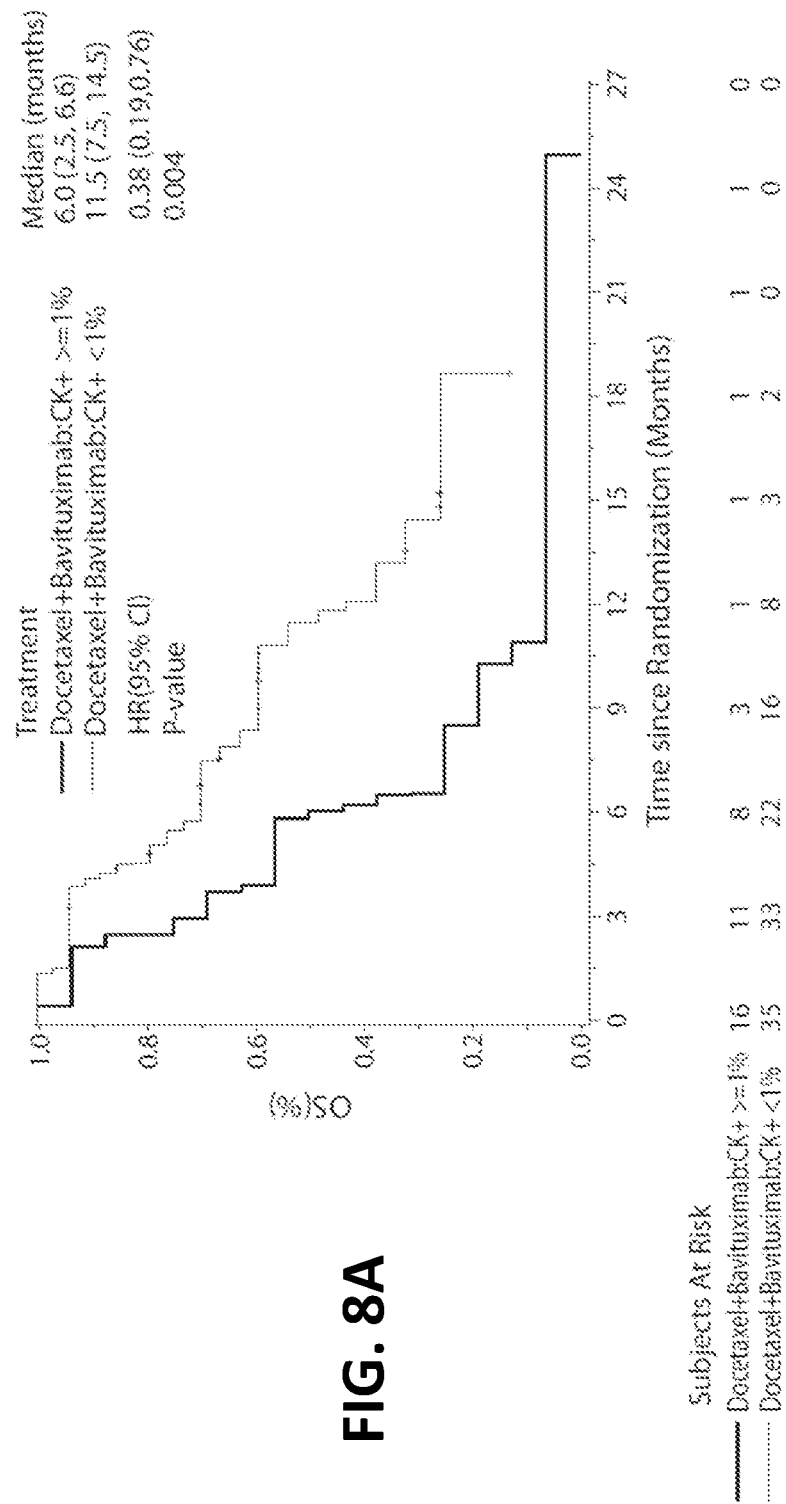
FIG. 8A and FIG. 8B. Kaplan-Meier survival curves showing that NSCLC patients treated with bavituximab have a statistically significant better mOS when they have negative pre-treatment PD-L1 expression (TC0, <1%).
Figure 8B:
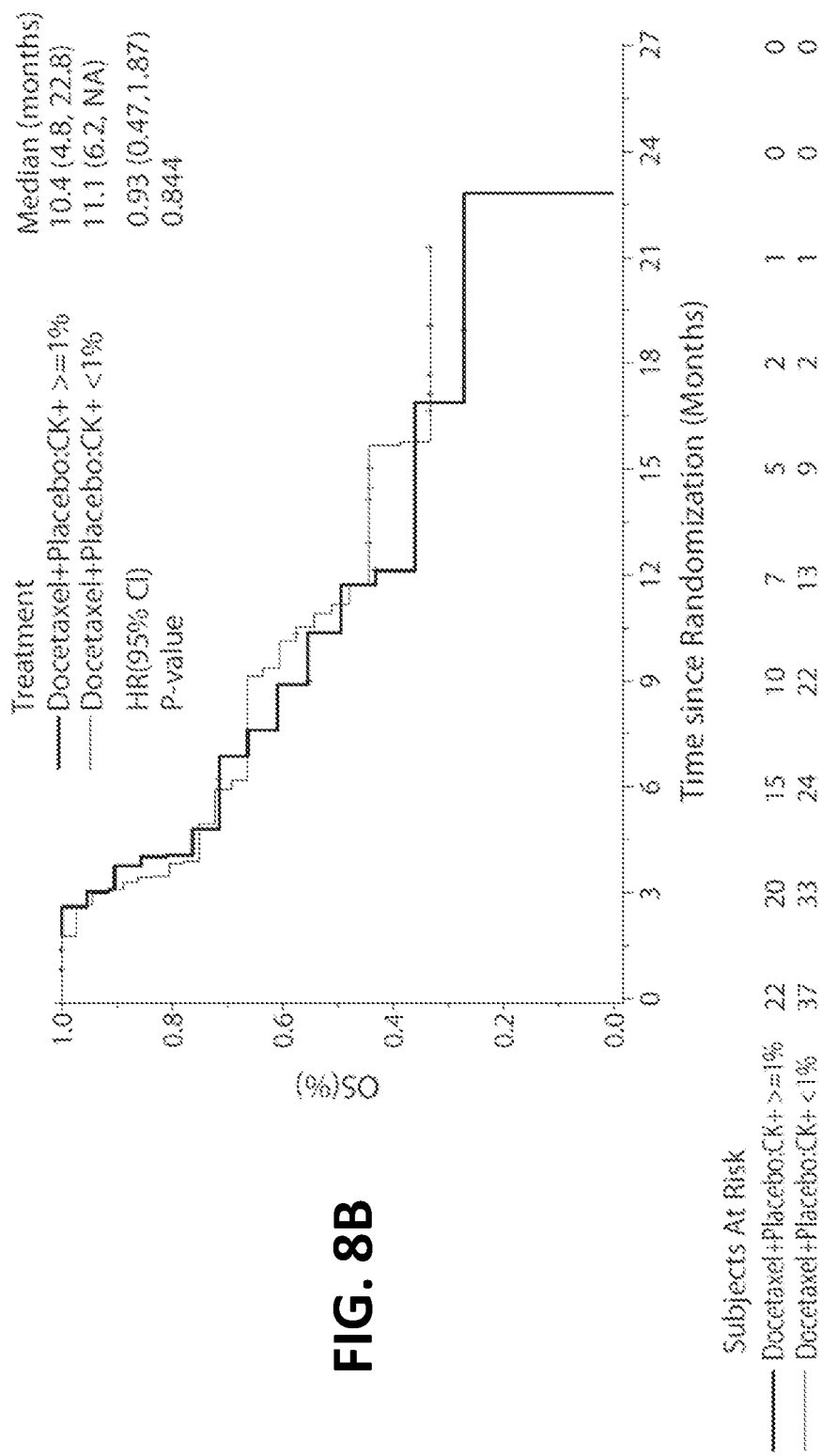

In the subset of patients with available diagnostic biopsies (110 out of 597 randomized patients), the prevalence of PD-L1 expression was 5.45% for TC3; 18.2% for TC2/3; 34.5% for TC1/2/3; and 65.5% for TC0. mOS for the patients in the bavituximab plus docetaxel group was 11.5 months for those with negative PD-L1 expression (TC0, <1%; "CK+<1%"), as compared to only 6.0 months for those with higher PD-L1 expression (TC 1/2/3, ≥1%, "CK+ >=1%") with HR 0.38 (95% CI, 0.19-0.76); p-value=0.004 (FIG. 8A). mOS of the patients in the docetaxel alone group was 11.1 months for negative PD-L1 (TC0, <1%; "CK+ <1%") and 10.4 months for higher PD-L1 (TC 1/2/3, ≥1%; "CK+>=1%") with HR 0.93 (95% CI, 0.47-1.87); p value=0.844 (FIG. 8B).

Thus, baseline PD-L1 expression in a subset of patients from the Phase III trial demonstrated that negative PD-L1 expression (TC0) is associated with a significantly prolonged OS compared to positive PD-L1 expression (TC 1/2/3) in patients receiving bavituximab plus docetaxel. No significant difference in OS was observed in the patients in the docetaxel alone group by PD-L1 expression. Contrast the clear separation of the curves in FIG. 8A (for the bavituximab patients) with the super-imposed curves in FIG. 8B (for the control patients). These observations are also consistent with the bavituximab demonstrating more effect in PD-L1 negative, "immune cold" tumors.

Example XVI

Survival Benefit for Bavituximab in Combination with Subsequent Immunotherapy

Although the initial analyses of the Phase III trial of Example X did not show superior OS in the bavituximab plus docetaxel arm as compared to the docetaxel alone group, ongoing studies were conducted with a view to identifying other possible indicators of a therapeutic benefit to bavituximab treatment. The present example shows that patients treated with bavituximab and docetaxel followed by subsequent immunotherapy (SACT-IO) have a statistically significant better mOS as opposed to patients treated with docetaxel alone followed by subsequent immunotherapy.

Following treatment with either bavituximab and docetaxel, or docetaxel alone, about 15% of the patients (91 out of 597) received subsequent anti-cancer therapy (SACT), in the form of subsequent immuno-oncology (IO) therapy (SACT-IO or subsequent IO). These 91 patients were evenly balanced between the treatment arms, with 45 patients receiving prior treatment with bavituximab and docetaxel, and 46 patients receiving prior treatment with docetaxel alone.

Surprisingly, it was determined that there was a dramatic increase in mOS for patients receiving prior treatment with bavituximab, as opposed to placebo, when treated with subsequent IO (FIG. 6). In particular, for patients receiving subsequent IO, mOS has yet to be reached for the bavituximab and docetaxel group (95% CI, 15.2-NA), whereas it was 12.6 months for the docetaxel alone group (95% CI, 10.4-17.8); HR=0.46 and p=0.006 (FIG. 6; Table 11). For patients who did not receive subsequent IO, mOS was 9.2 months in the bavituximab and docetaxel group and 10.2 months in the docetaxel alone group; HR=1.16 and p=0.172.

TABLE 11

Survival Benefit for Bavituximab in Combination with Subsequent Immunotherapy

| Treatment Groups | Parameters | Bavituximab + Docetaxel n = 46 | Placebo + Docetaxel n = 47 |
|---|---|---|---|
| Subsequent IO | Median Months (95% C1) | N/A-not yet reached (15.2-N/A) | 12.6 (10.4-17.8) |
| | HR (95% C1) | 0.46 (0.24-0.79) | |
| | P-value | 0.006 | |
| No Subsequent IO | Median Months (95% C1) | 9.2 (7.2-11.0) | 10.2 (8.9-11.9) |
| | HR (95% C1) | 1.16 (0.94-1.42) | |
| | P-value | 0.172 | |

Within the subsequent IO groups, the particular immunotherapy agents of the "first subsequent IO" were also identified. Within the 45 patients treated with bavituximab (and docetaxel) and subsequent IO, the immunotherapy agents are shown in Table 12, all of which are checkpoint inhibitor antibodies (immune checkpoint inhibitors) in the form of a blocking antibody that binds to CTLA-4, PD-1 or PDL-1. In particular, the blocking antibodies used were tremelimumab, a blocking antibody that binds to CTLA-4; nivolumab, a blocking antibody that binds to PD-1; and durvalumab (MEDI4736), a blocking antibody that binds to PD-L1.

TABLE 12

Bavituximab and Subsequent Immunotherapeutic Agents

| Bavituximab (+Docetaxel) Subsequent 10 | Number of Patients |
|---|---|
| Durvalumab (MEDI4736) | 4 |
| Nivolumab (Opdivo ®) | 40 |
| Tremelimumab | 2 |
| Nivolumab plus IL-10 | 1 |

It will be noted that four patients received more than one IO agent, i.e., their "first subsequent IO" therapy was itself an "IO combination", i.e., a first and second checkpoint inhibitor antibody. Therefore, in the "ITT" (Intent to Treat) analysis, there are 45 patients treated with bavituximab who received a first subsequent IO, but there are 47 subsequent IO agents in Table 12. This is because two patients received an "IO doublet". Overall, four patients received more than one subsequent IO, and each of these received a doublet of MEDI4736 (durvalumab) and tremelimumab. Out of these four subjects, two were in the bavituximab arm and two were in the placebo arm.

Within the 91 patients receiving subsequent IO, patients with prior treatment of docetaxel alone (placebo) also received tremelimumab, nivolumab or durvalumab (MEDI4736). In addition, two patients in the placebo arm received pembrolizumab (formerly MK-3475) and one patient in the placebo arm received REGN2810, which are both blocking antibodies that bind to PD-1. Overall, the first subsequent IO in the placebo arm was: tremelimumab (3), nivolumab (39), durvalumab (3), pembrolizumab (2) and REGN2810 (1), which is a total of 48 agents in 46 patients, with two patients receiving an IO doublet of MEDI4736-tremelimumab.

In conclusion, the data in the present example show, for the first time, that bavituximab enhances the activity of immunotherapy agents in human patients. These results therefore strongly support the ongoing and future treatment of cancer patients with bavituximab in combination with immunotherapy agents, particularly immune checkpoint inhibitors.

Example XVII

β2GPI Biomarker Analyses for Bavituximab and Subsequent Immunotherapy

As shown in Example XVI, patients treated with bavituximab (plus docetaxel) and subsequent IO have a markedly better mOS than patients treated with docetaxel alone and subsequent IO. The present example further validates the use of functional β2GPI as a bavituximab biomarker, showing that the same levels of functional β2GPI also correlate with successful treatment by bavituximab in combination with immunotherapy.

Using the assay of Example XII, functional β2GPI levels of 200 µg/mL or higher are shown to correlate with successful bavituximab treatment, including in the Phase III trial (Example XIII). Based on the same cut-off of "high β2GPI" as being pre-treatment levels of functional β2GPI of equal to or higher than 200 µg/mL (≥200 µg/mL), it was again determined that β2GPI≥200 µg/mL correlated with increased overall survival in patients treated with bavituximab and subsequent IO, but not in control patients who received subsequent IO (FIG. 7A and FIG. 7B).

Figure 7A:
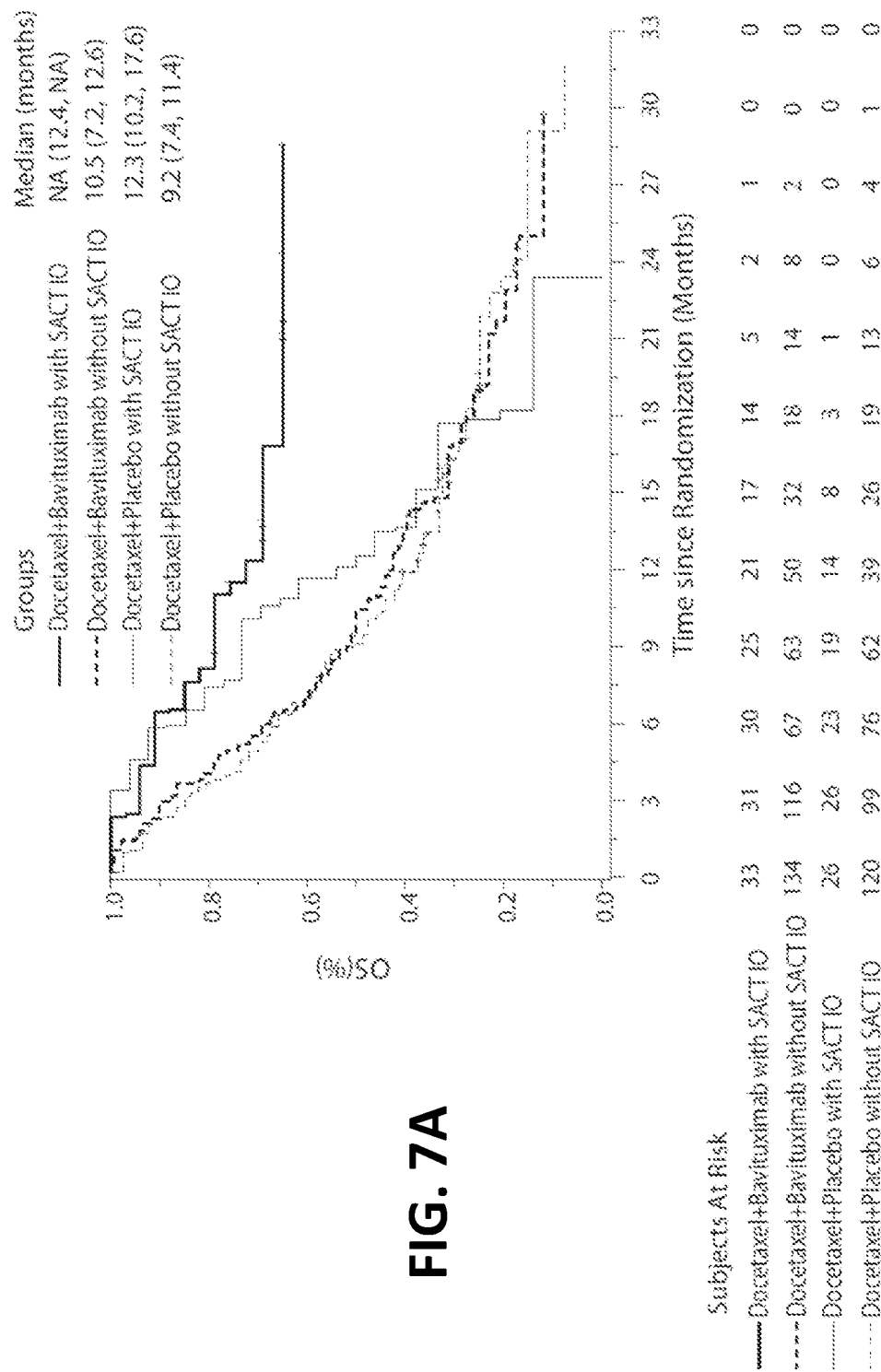
FIG. 7A and FIG. 7B. Kaplan-Meier survival curves showing that NSCLC patients having functional β2GPI levels of equal to or greater than 200 μg/mL have a statistically significant better mOS when treated with bavituximab followed by subsequent immunotherapy ("SACT-IO").
Figure 7B:
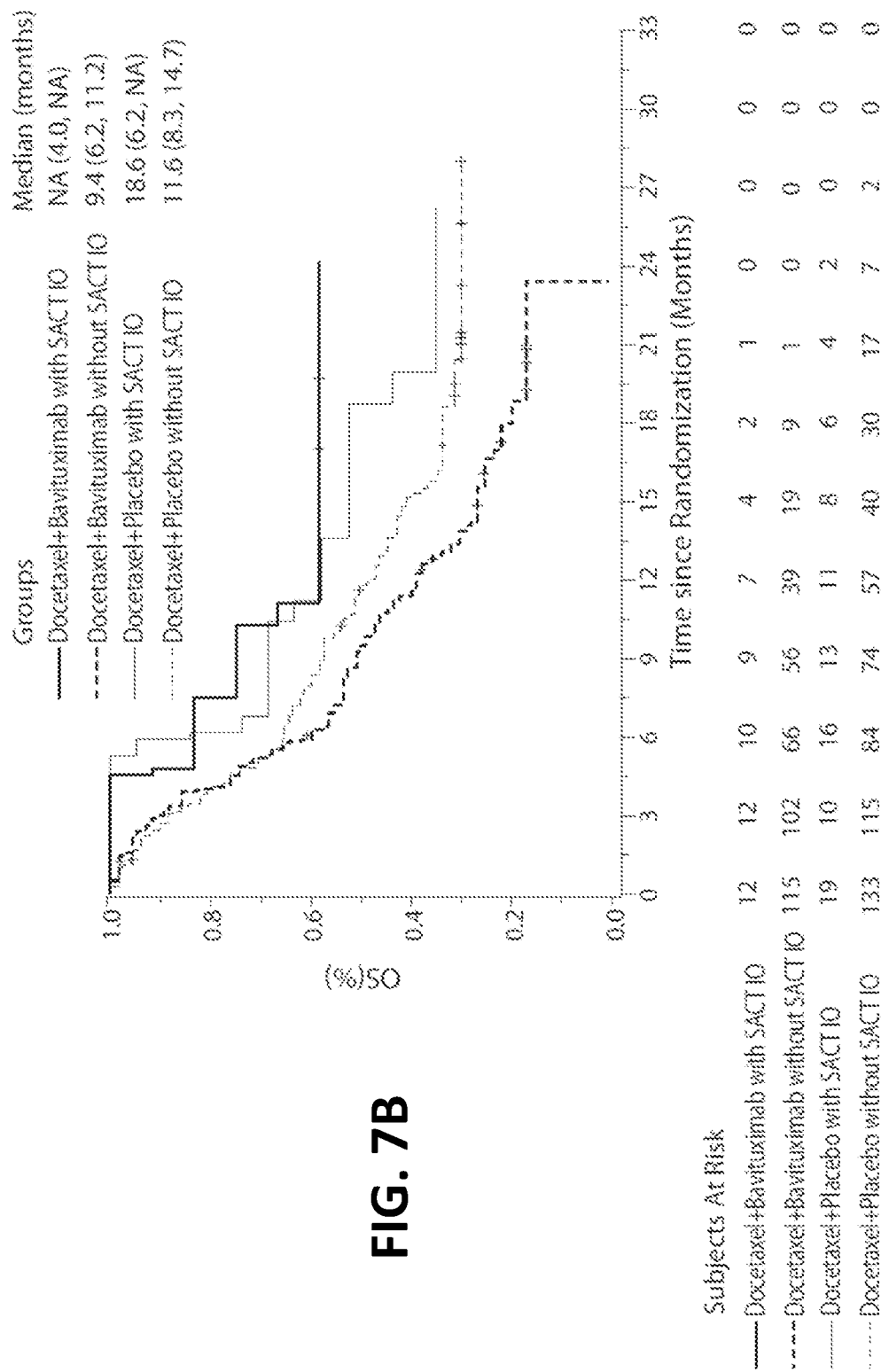

In particular, for patients with functional β2GPI of equal to or higher than 200 µg/mL, mOS has yet to be reached for patients treated with bavituximab and subsequent IO, whereas mOS was 12.3 months (10.2-17.6) for patients treated with docetaxel and subsequent IO (FIG. 7A; p=0.002). As predicted by the data in Example XIII, in patients without subsequent IO, β2GPI≥200 µg/mL still trended with increased overall survival in patients treated with bavituximab (10.5 months), as compared to control (9.2 months), although the separation of the curves is not as pronounced as observed for the subsequent IO patients (FIG. 7A). Comparing FIG. 7A to FIG. 7B shows that, in contrast to bavituximab treatment, there is a trend for patients in the control arm to survive longer when β2GPI is less than 200 µg/mL, both for those with subsequent IO (18.6 vs. 12.3 months) and without subsequent IO (11.6 vs. 9.2 months). Further detailed analyses of the data in FIG. 7B, are hampered by the relatively small number of patients treated with bavituximab and subsequent IO in the β2GPI<200 µg/mL group (n=12).

These clinical data therefore show that functional β2GPI is a biomarker for successful treatment with bavituximab in combination with immunotherapy, particularly in combination with immune checkpoint inhibitors such as tremelimumab, nivolumab, pembrolizumab, durvalumab and atezolizumab.

Example XVIII

Low Interferon-gamma (IFNγ) as a Biomarker for Bavituximab

The present example concerns measurements of pre-treatment IFNγ in blood and tissue from the patients of the Phase III trial of Example X and analyses of IFNγ as a potential biomarker for bavituximab. A statistically significant separation in OS was observed in patients treated with bavituximab and docetaxel in favor of low pre-treatment serum IFNγ, while no difference in OS was observed in the docetaxel alone (placebo) group.

A. Methods

In the Phase III trial of Example X, pre-treatment archival biopsies were optional and mainly collected for mutliplex-IHC. Where possible, immune gene expression in remainder tumor specimens, including intratumoral IFNγ, was analysed using the Fluidigm®-based gene expression platform (Sirona DX, Lake Oswego, Oreg., USA).

Serum was isolated at screening from all randomized NSCLC patients in the Phase III trial, as well as periodically during treatment and at disease progression. EFNγ levels in the serum samples were evaluated using the Simoa® (Quanterix) assay (Myriad RBM, Austin, Tex., USA). Pre-treatment serum samples from 582 out of 597 randomized patients were available for correlation with OS.

Kaplan-Meier statistical methods and Cox proportional hazard models were utilized to evaluate and contrast the correlation of peripheral (and intratumoral) IFNγ levels with OS based on a data cut from the Phase III trial (Example X) dated Feb. 28, 2017. OS by IFNγ classification was also correlated with or without subsequent anticancer therapy with immune checkpoint inhibitors (SACT-IO), as described in Example XVI.

B. Results

With the limited intratumoral IFNγ gene expression data (n=33), statistical correlations were not possible for tumoral IFNγ.

For serum IFNγ, the median pre-treatment serum IFNγ value in the bavituximab and docetaxel group was determined to be 0.093 μg/mL. Each patient in either arm was classified to be pre-treatment serum "IFNγ high" (≥cut-off) or "IFNγ low" (<cut-off) using the median IFNγ of 0.093 μg/mL as the cut-off.

A statistically significant increase in OS was observed for patients treated with bavituximab and docetaxel in the IFNγ low group, while no difference in OS was observed for patients treated with docetaxel alone. In particular, in the bavituximab and docetaxel group, mOS was 11.9 months for IFNγ low vs. 9.2 months for IFNγ high; p=0.046. In contrast, for the docetaxel alone group, mOS was 11.1 months for IFNγ low vs. 10.6 months for IFNγ high.

For patients with low pretreatment IFNγ who received subsequent IO (Example XVI), mOS in the bavituximab and docetaxel group was not reached; mOS was 12.1 months in the corresponding docetaxel alone group; HR=0.24 and p<0.001. For patients with IFNγ low who did not receive subsequent 10, mOS in the bavituximab and docetaxel group was 10.5 months; mOS was 10.8 months in the corresponding docetaxel alone group; HR=1.17 and p=0.328. For patients with high pretreatment IFNγ who received subsequent IO, mOS in the bavituximab and docetaxel was 13.9 months; mOS was 13.5 months in the corresponding docetaxel alone group; HR=1.0 and p=0.998. For patients with IFNγ high who did not receive subsequent IO, mOS in the bavituximab and docetaxel group was 9.0 months; mOS was 9.2 months in the corresponding docetaxel alone group; HR=1.14 and p=0.375.

To summarize, analysis by both IFNγ and SACT-IO classifications confirmed a statistically significant difference in OS favoring the bavituximab and docetaxel group among patients with low pretreatment IFNγ who received subsequent IO (HR=0.24, p<0.001). No OS difference was observed between bavituximab and placebo for patients with high pretreatment IFNγ regardless of subsequent IO.

Overall, these clinical data support the mechanistic observations that bavituximab modulates immune response to enhance the activity of immunotherapy agents. Together with the data in Example XVI, these results support further clinical treatment of cancer patients using bavituximab in combination with immunotherapy agents such as checkpoint inhibitors.

Example XIX

Treating Cancer with Bavituximab in Combination with CBT-501

As shown in Example XVI, treating patients with bavituximab and docetaxel followed by immunotherapy (SACT-IO) has a statistically significant better mOS as opposed to patients first treated with placebo and docetaxel followed by subsequent immunotherapy. The present example concerns the use of bavituximab to enhance the activity of IO agents in humans, and particularly concerns treating cancer patients with bavituximab in combination with CBT-501.

The present example describes an Open-Label, Phase II Trial of CBT-501 with Bavituximab in Patients with Previously Treated Metastatic Non-Small Cell Lung Cancer (NSCLC), conducted at approximately 10 centers worldwide, including in the United States. It is designed for approximately 12 months accrual (n=42) or 18 months accrual (n=64), with 12 months estimated follow-up. Thus, enrollment is a total sample size of 42 or 64 patients. Stage 1 enrolls 42 patients. During Stage 2, an additional 22 patients are enrolled in for a total of 64 patients.

The Test Product, Dose, and Mode of Administration are as follows: Bavituximab is supplied as a sterile, preservative-free solution with 10 mM acetate at pH 5.0, and Water for Injection. Bavituximab is administered as an intravenous (IV) infusion at least 3 mg/kg body weight weekly, or as a flat dose, according to the clinical protocol. CBT-501 is administered as an IV infusion.

The Objectives are as follows: Primary Objectives, to evaluate the anti-tumor activity as determined by the objective response rate (ORR); and to characterize the safety and tolerability of the combination of bavituximab and CBT-501; Secondary Objectives, to evaluate clinical benefit response rate (CR+PR+SD lasting ≥16 weeks); to evaluate overall survival (OS), progression-free survival (PFS) and duration of response (DOR); to evaluate ORR by baseline β2GP1 levels and/or IFNγ and/or PD-L1 expression; Exploratory/Correlative Objectives, to assess immune changes in patients treated with bavituximab in combination with atezolizumab; and to correlate the level of PD-L1 expression on tumor and immune cells with clinical outcomes.

Figure 9:
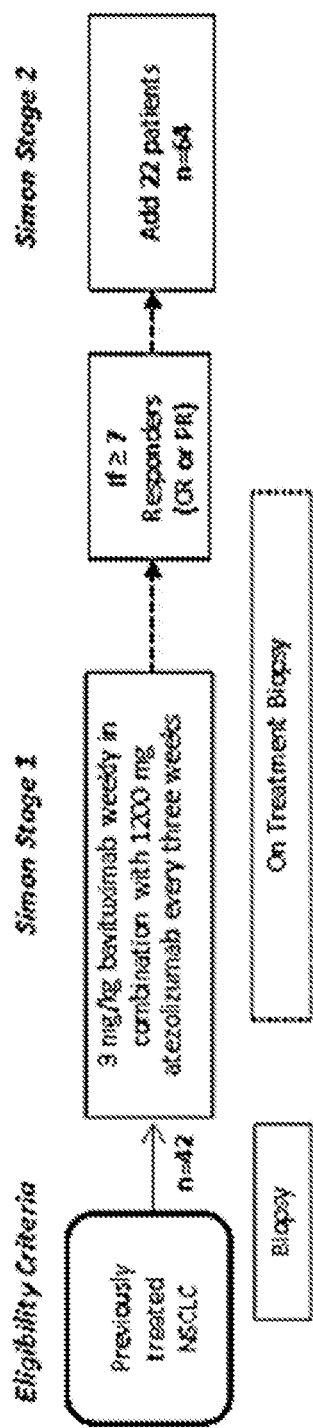
FIG. 9 shows a schematic representation of the Study Design for Example XIX.

The Study Design is an open-label, Phase II trial of CBT-501 plus bavituximab in patients with previously treated NSCLC. In the Treatment Phase, a Simon's two-stage MinMax design is employed to evaluate the objective response rate (ORR) for patients receiving bavituximab in combination with CBT-501. In Stage 1, up to 42 patients receive at least 3 mg/kg bavituximab weekly, or a flat dose, in combination with CBT-501, until disease progression or unacceptable toxicity. Seven or more responses are observed, and 22 additional patients are recruited and enrolled in Stage 2. The Treatment Phase for each patient begins on C1D1. Patients will continue study treatment until disease progression, discontinuation due to toxicity, withdrawal of consent, or the study ends. A schematic of the Study Design is shown in FIG. 9.

In the Post Treatment Follow-up Phase, patients who discontinue all study treatment but have not experienced disease progression or initiated subsequent anti-cancer therapy continue to undergo tumor and correlative assessments according to the study schedule until disease progression or the start of subsequent anti-cancer therapy.

In the Survival Follow-Up Phase, patients who are no longer receiving any study treatment and experience disease progression or initiated subsequent anti-cancer therapy entersurvival follow-up. Survival follow-up information is collected approximately every 3 months until death, loss to follow-up, withdrawal of consent, or study termination.

The Diagnosis and Main Inclusion/Exclusion Criteria are:

Inclusion Criteria
1. Able to understand and sign an Institutional Review Board/Independent Ethics Committee-approved informed consent form prior to any study-specific evaluation.
2. Target Population
   a) Male or female at least 18 years of age on day of signing informed consent.
   b) Histologically documented, metastatic non-small cell lung cancer with prior progression on a platinum-based regimen (maintenance therapy such as pemetrexed is considered a component for a first-line regimen). Patients with known EGFR-activating mutations or ALK translocations should have progressed after appropriate targeted treatment (or not tolerated appropriate targeted therapy).
   c) Tumor tissue (or archival tissue) or baseline research biopsy must be available for biomarker evaluation.
3. Measurable disease on cross sectional imaging per RECIST 1.1 criteria. Target tumor lesions may be in a previously irradiated area if progression has been demonstrated in such lesions.
4. Eastern Cooperative Oncology Group (ECOG) Performance Status 0 or 1.
5. Laboratory Requirements demonstrating adequate organ function:
   a) Hematology:
   Absolute Neutrophil Count [ANC]≥1,000 cells/µL
   Platelets ≥100,000 cells/µL
   Hemoglobin ≥9 g/dL
   b) Renal
   Serum creatinine ≤1.5×ULN-OR-Measured or calculated creatinine >60 mL/min if serum creatinine >1.5×ULN; creatinine clearance may be calculated using the institutional/laboratory standard
   c) Hepatic
   Total bilirubin ≤1.5×ULN-OR-Direct bilirubin <ULN for patients with total bilirubin >1.5×ULN
   AST and ALT≤2.5×ULN; ALT and/or AST may be ≤5×ULN in patients with liver metastases
   d) Coagulation [under consideration]
   INR or PT<1.5×ULN unless patient is receiving anticoagulant therapy as long as INR or PT is not greater than the recommended range for the intended use of the anticoagulant
   aPTT<1.5×ULN unless patient is receiving anticoagulant therapy as long as aPTT is not greater than the recommended range for the intended use of the anticoagulant
6. Reproductive Status
   a) Female patients must have a negative serum human chorionic gonadotropin (hcG) test within 1 week of Day 1 (pregnancy test not required for patients with bilateral oophorectomy and/or hysterectomy or to those patients who are >1 year postmenopausal).
   b) All patients of reproductive potential (i.e., not surgically sterile or postmenopausal) must agree to use a highly effective method of contraception, as determined by the investigator, during and for 5 months after the last dose of study treatment.

Exclusion Criteria
1. Treatment with another anti-cancer therapy or investigational drug within 2 weeks prior to study day 1 (C1D1)
2. Prior anti-PD-1, anti-PD-L1, or anti-PD-L2 therapy [under consideration]
3. Persistent >Grade 1 adverse event related to prior therapy Exceptions: Grade 2 neuropathy and alopecia due to prior therapy are allowed
4. History of prior malignancy except:
   Curatively treated non-melanoma skin cancer
   Solid tumor treated curatively more than 5 years previously without evidence of recurrence
   History of other malignancy that in the Investigator's opinion would not affect the determination of study treatment effect
5. Transfusion of blood products (including platelets or red blood cells) or administration of colony stimulating factors (including G-CSF, GM-CSF or recombinant erythropoietin) within 4 weeks prior to study day 1 (C1D1)
6. Known active central nervous system (CNS) metastases and/or carcinomatous meningitis
   Note: Patients with previously treated brain metastases may participate provided they are stable (without evidence of progression by imaging [using identical imaging modality for each assessment, either MRI or CT scan] for at least four weeks prior to the first dose of study treatment and any neurologic symptoms have returned to baseline), have no evidence of new or enlarging brain metastases, and are not using steroid for at least 7 days prior to study treatment. This exception does not include carcinomatous meningitis which is excluded regardless of clinical stability
7. Diagnosis of immunodeficiency or receiving systemic steroid therapy within 7 days prior to study day 1. Known history of HIV; known active Hepatitis B or Hepatitis C.
8. Active autoimmune disease that has required systemic treatment within past 2 years (i.e. with use of disease modifying agents, corticosteroids or immunosuppressive drugs). Replacement therapy (e.g., thyroxine, insulin, or physiologic corticosteroid replacement therapy for adrenal or pituitary insufficiency, etc.) is not considered a form of systemic treatment.
   Use of topical corticosteroids or eye drops containing corticosteroids is acceptable.
   Inhaled steroids are excluded.
   Use of physiologic doses of corticosteroids may be approved after consultation with the Sponsor
9. Active infection requiring systemic therapy.
10. Current evidence of non-infectious pneumonitis.
11. History of interstitial lung disease.
12. Any other comorbid illness that would place the patient at risk, per investigator discretion
13. Pregnant or breast-feeding or expecting to conceive or father a child within the projected duration of the trial, including 90 days following the last dose of atezolizumab and 30 days after the last dose of bavituximab
14. Live-virus vaccination within 30 days of study Day 1; seasonal flu vaccines that do not contain live virus are permitted
15. History of hypersensitivity to bavituximab, atezolizumab or any of their excipients.

16. Serious non-healing wound, including wound healing by secondary intention.
17. Major surgery within 4 weeks prior to CID 1.
18. Prior therapy with bavituximab.

The Criteria for Evaluation are as follows:

Safety:
Adverse events (AEs).
Laboratory measurements: hematology (complete blood count with platelets and differential), biochemistry (including renal, liver), thyroid function tests, and anti-drug antibodies (ADA).
Other safety evaluations including vital signs assessments (heart rate, systolic and diastolic blood pressure), ECOG performance status, and physical examinations.

Efficacy:
ORR: percentage of patients whose best overall response is complete response (CR) or partial response (PR).
DOR: duration of response (DOR): number of days from first CR or PR (whichever is first recorded) until the first documented tumor progression (per RECIST 1.1) or death due to any cause, whichever occurs first
PFS: number of days from first dose of study treatment until the first documented tumor progression (per RECIST 1.1) or death due to any cause, whichever occurs first.
OS: number of days from the first dose of study medication until death due to any cause.

Exploratory:
Immune correlates, such as IFNγ and PD-L1 status
Serum levels of β2-GP1

Statistical Considerations:
Sample Size:
Employing a Simon two-stage MinMax design, 42 or 64 patients will be enrolled depending on whether the study proceeds through Stage 2.

Data Analysis:
Efficacy:
ORR will be reported with 95% confidence intervals (CIs), using the Clopper Pearson exact method. Time-to-event endpoints, including PFS, DOR, and OS, will be summarized using Kaplan-Meier product-limit methods and displayed graphically.

Safety:
Safety evaluations will be performed using data from all patients who receive any amount of study treatment (bavituximab and/or atezolizumab). AE evaluations will focus on treatment-emergent events. The overall safety profile will be characterized by the type, frequency, severity, timing of onset, duration, and relationship to study treatment of any AEs or abnormalities of laboratory tests. Enumeration and description of any serious adverse events (SAEs), or AEs leading to discontinuation of study treatment will occur. Immunogenicity will also be assessed. Tabulations will be provided for AEs (including those considered serious), laboratory results, and anti-drug antibody (ADA) data.

Exploratory/Correlative:
Immune effects will be assessed, including correlation of PD-L1 expression on clinical outcomes.

Example XX

As shown in Example XVI, treating patients with bavituximab and docetaxel followed by immunotherapy (SACT-IO) has a statistically significant better mOS as opposed to patients first treated with placebo and docetaxel followed by subsequent immunotherapy. The present example concerns the use of bavituximab to enhance the activity of IO agents in humans, and particularly concerns treating cancer patients with bavituximab in combination with an anti-PD-1 or an anti-PD-L1 antibody.

The present example describes an Open-Label, Phase II Trial of Bavituximab with Investigator's choice of an anti-PD-1 or an anti-PD-L1 antibody in patients that have progressed on an anti-PD-1 or an anti-PD-L1 therapy in metastatic Non-Small Cell Lung Cancer (NSCLC), or metastatic gastroesphogeal cancer. The Trial is conducted at approximately 10 centers world-wide, including the U S. The goals of the Trial are to see a clinically meaningful improvement from the combination treatment compared to historical results with anti-PD-1 or an anti-PD-L1 monotherapy and to see if there is a biomarker subgroup in which whose response to the combination therapy that is statistically significant over other biomarker subgroups.

The Test Product, Dose, and Mode of Administration are as follows: Bavituximab is supplied as a sterile, preservative-free solution with 10 mM acetate at pH 5.0, and Water for Injection. Bavituximab is administered as an intravenous (IV) infusion at least 3 mg/kg and no more than 10 mg/kg body weight, or as a flat dose, weekly or less frequently, according to the clinical protocol. The anti-PD-1 or anti-PD-L1 therapies are administered according to their label or in a regimen established via a combination dose finding study.

The Trial is conducted by stratifying patients according to biomarker status. The biomarkers include, but are not limited to, baseline P2GP1 levels and/or IFNγ and/or PD-L1 expression; to assess baseline immune status of patients.

Example XXI

The present example concerns the use of bavituximab to enhance the activity of 10 agents in humans, and particularly concerns treating cancer patients with bavituximab in combination with an anti-PD-1 or an anti-PD-L1 antibody.

The present example describes an Open-Label, Phase II Trial of bavituximab with pembrolizumab in patients with recurrent/metastatic squamous cell head and neck cancer (HNSCC) who progressed on a PD-1 inhibitor. The Trial is conducted in the US. The goal of the Trial is to determine if bavituximab could potentially synergize with PD-1 inhibitor therapy to generate an effective anti-tumor immune response in patients with recurrent/metastatic squamous cell head and neck cancer (HNSCC) who progressed on a PD-1 inhibitor.

The Test Product, Dose, and Mode of Administration are as follows: Bavituximab is supplied as a sterile, preservative-free solution with 10 mM acetate at pH 5.0, and Water for Injection. Bavituximab is administered as an intravenous (IV) infusion at least 3 mg/kg and no more than 10 mg/kg body weight, or as a flat dose, weekly or less frequently, according to the clinical protocol. Pembrolizumab is administered according to its label.

Exploratory correlatives are used to determine biomarkers related to response to therapy. Blood is collected for PD analyses at baseline and during cycles 1, 2, 4 and at end of study. Fresh biopsy tissue is submitted for analyses and if feasible a repeat tumor core biopsy is obtained during week 4-6 after the start of therapy. The following correlative studies are performed:
β2-GP1—blood samples are collected to evaluate PS expression.
PD-L1 expression pre and post treatment—This is assessed on tumor tissue.

Automated immunohistochemical staining including: β2m, B7H3, B7H4, CSF1R, HLA-ABC, HLA-DR/DQ/DP, HLA-DR, IDO1, and TIM3

HPV status is obtained as per clinical standard. If this data is available in the medical record repeat testing is not necessary.

Somatic genomic analysis is considered for select patients.

Additional immune related analyses is considered on banked material depending on study results and material availability, including gene expression profiling to evaluate immune-related gene expression profiles.

Example XXII

The present example concerns the use of bavituximab to enhance the activity of 10 agents in humans, and particularly concerns treating cancer patients with bavituximab in combination with an anti-PD-1 antibody.

The present example describes an Open-Label, Phase II Trial of Bavituximab with pembrolizumab in patients with advanced Hepatocellular Carcinoma (HCC). The Trial is conducted in the US. The goal of the Trial is to determine the overall response rate (ORR) of combination pembrolizumab and bavituximab in patients with advanced HCC.

The Test Product, Dose, and Mode of Administration are as follows: Bavituximab is supplied as a sterile, preservative-free solution with 10 mM acetate at pH 5.0, and Water for Injection. Bavituximab is administered as an intravenous (IV) infusion at least 3 mg/kg and no more than 10 mg/kg body weight, or as a flat dose, weekly or less frequently, according to the clinical protocol. Pembrolizumab is administered according to its label.

In this study all patients potentially undergo up to two image-guided (either CT or Ultrasound) core needle biopsy of a single site of HCC at baseline (for clinical care) and between five and six weeks after the initiation of study drug (research only). Pre-treatment biopsies are used to evaluate potential markers of durable response. This includes the analysis of tumor-infiltrating lymphocytes, monocytes, and natural killer cells within tumors by immunohistochemistry. In addition, PD-L1 expression is analyzed at baseline and analyzed for associated measures of outcome. In parallel, RNA profiling is employed to delineate baseline features of tumor tissue including the local tumor microenvironment if there is sufficient material. The molecular features of the tumor from RNA profiling are analyzed for association with ORR and other clinical features of disease to explore markers of response. Post-treatment biopsies are used to determine the effect of pembrolizumab and bavituximab on tumor markers, and for RNA profiling. Clinical outcome is correlated with markers of response. Plasma, serum, and whole blood samples are collected at baseline and every 9-12 weeks while on treatment. The blood samples are used to measure circulating tumor DNA or other features of tumor burden and are correlated with disease response.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Agostinis et al., "In vivo distribution of β2GPI under pathophysiologic conditions", Blood 118(15):4231-4238, 2011.

An et al., "Exosomes serve as tumour markers for personalized diagnostics owing to their important role in cancer metastasis", J. Extracell. Vesicles, 4:27522, 2015; http://dx.doi.org/10.3402/jev.v4.27522.

Balasubramanian et al., "Estimation of plasma beta-2-glycoprotein levels by competitive ELISA", Thromb. Res., 92:91-97, 1998.

Beck et al., "Combination of a monoclonal anti-phosphatidylserine antibody with gemcitabine strongly inhibits the growth and metastasis of orthotopic pancreatic tumors in mice", Int. J. Cancer, 118:2639-2643, 2006.

Best, "Viruses play dead to TAMe interferon responses", Cell Host & Microbe, 14(2): 117-8, 2013.

Bhattacharyya et al., "Enveloped viruses disable innate immune responses in dendritic cells by direct activation of TAM receptors", Cell Host & Microbe, 14(2): 136-147, 2013.

Birge et al., "Phosphatidylserine is a global immunosuppressive signal in efferocytosis, infectious disease, and cancer", Cell Death Differ., 23(6):962-78, 2016.

Brahmer et al., "Nivolumab versus docetaxel in advanced squamous-cell non-small-cell lung cancer", N. Engl. J. Med, 373(2):123-135, 2015.

Chalasani et al., "A Phase I Clinical Trial of Bavituximab and Paclitaxel in Patients with HER2 Negative Metastatic Breast Cancer", Cancer Medicine, 4(7):1051-1059, 2015.

Chen et al., "Phosphatidylserine Vesicles Enable Efficient En Bloc Transmission of Enteroviruses", Cell, 160:619-630, 2015.

Cheng et al., "Antibody-Mediated Blockade of Phosphatidylserine Enhances the Antitumor Effect of Sorafenib in Hepatocellular Carcinomas Xenografts", Ann. Surg. Oncol., 5107-5, DOI 10.1245/s10434-016-5107-5, 2016.

Clayson et al., "Release of Simian Virus 40 Virions from Epithelial Cells is Polarized and Occurs without Cell Lysis", J. Virology, 63(5):2278-2288, 1989.

Czuczman et al., "Listeria monocytogenes exploits efferocytosis to promote cell-to-cell spread", Nature, 509:230-234, 2014.

DaMatta et al., "Trypanosoma cruzi exposes phosphatidyl serine as an evasion mechanism", FEMS Microbiol. Lett., 266:29-33, 2007.

Davra et al., "Ligand Activation of TAM Family Receptors-Implications for Tumor Biology and Therapeutic Response", Cancers, 8:107-120, 2016.

de Laat, Derksen, Urbanus, de Groot, "IgG antibodies that recognize epitope Gly40-Arg43 in domain I of β$_2$-glycoprotein I cause LAC, and their presence correlates strongly with thrombosis", Blood, 105(4):1540-5, 2005.

de Laat, Derksen, van Lummel, Pennings, de Groot, "Pathogenic anti-β$_2$-glycoprotein I antibodies recognize domain I of β₂-glycoprotein I only after a conformational change", *Blood*, 107(5): 1916-24, 2006.

DeRose et al., "Development of bavituximab, a vascular targeting agent with immune-modulating properties, for lung cancer treatment", *Immunotherapy*, 3(8):933-944, 2011.

Digumarti et al., "Bavituximab Plus Paclitaxel and Carboplatin for the Treatment of Advanced Non-Small-Cell Lung Cancer", *Lung Cancer*, 86:231-236, 2014.

Eda & Sherman, "Cytoadherence of Malaria-Infected Red Blood Cells Involves Exposure of Phosphatidylserine", *Cell Physiol. Biochem.*, 12:373-384, 2002.

Fehrenbacher et al., "Atezolizumab versus docetaxel for patients with previously treated non-small-cell lung cancer (POPLAR): a multicentre, open-label, phase 2 randomised controlled trial", *The Lancet*, 387(10030): 1837-1846, 2016.

Feng et al., "Multispectral imaging of formalin-fixed tissue predicts ability to generate tumor-infiltrating lymphocytes from melanoma", *J. ImmunoTher. Cancer*, 3:47, 2015.

Francis et al., "*Mycobacterium tuberculosis* ESAT-6 is a leukocidin causing Ca2+ influx, necrosis and neutrophil extracellular trap formation", *Cell Death and Disease*, 5:e1474; doi:10.1038/cddis.2014.394, 2014.

Freimark et al., "Antibody-Mediated Phosphatidylserine Blockade Enhances the Antitumor Responses to CTLA-4 and PD-1 Antibodies in Melanoma", *Cancer Immunol. Res.*, 4(6):531-40, 2016.

Garon et al., "Pembrolizumab for the treatment of non-small-cell lung cancer", *N. Engl. J. Med.*, 372(21):2018-2028, 2015.

Gaule et al., "A quantitative comparison of antibodies to programmed cell death 1 ligand 1", *JAMA Oncol*, 3(2): 256-259, 2017.

Gerber et al., "Phase I Safety and Pharmacokinetic Study of Bavituximab, a Chimeric Phosphatidylserine-Targeting Monoclonal Antibody, in Patients with Advanced Solid Tumors", *Clin. Cancer Res.*, 17(21):1-9, 2011.

Gerber et al., "Docetaxel Combined with Bavituximab in Previously Treated, Advanced Nonsquamous Non-Small-Cell Lung Cancer", *Clinical Lung Cancer*, 17(3): 169-176, 2016.

Gong et al., "Measuring Response to Therapy by Near-Infrared Imaging of Tumors Using a Phosphatidylserine-Targeting Antibody Fragment", *Molecular Imaging*, 12(4):244-256, 2013.

Goth & Stephens, "Rapid, Transient Phosphatidyl serine Externalization Induced in Host Cells by Infection with *Chlamydia* spp", *Infect. Immun.*, 69(2): 1109-1119, 2001.

Gray el al., "Phosphatidylserine-targeting antibodies augment the anti-tumorigenic activity of anti-PD-1 therapy by enhancing immune activation and downregulating pro-oncogenic factors induced by T-cell checkpoint inhibition in murine triple-negative breast cancers", *Breast Cancer Research*, 18(1):50, DOI 10.1186/s13058-016-0708-2, 2016a.

Gray et al., "LAG3 is an immunotherapeutic target in murine triple negative breast cancers whose activity is significantly enhanced in combination with phosphatidylserine targeting antibodies", Poster B019, CRI-CIMT-EATI-AACR International Cancer Immunotherapy Conference, New York, N.Y., Sep. 25-28, 2016b.

Gregorc et al., "Predictive value of a proteomic signature in patients with non-small-cell lung cancer treated with second-line erlotinib or chemotherapy (PROSE): a biomarker-stratified, randomised phase 3 trial", *Lancet Oncology*, 15(7):713-721, 2014.

Hagele et al., "*Legionella pneumophila* kills human phagocytes but not protozoan host cells by inducing apoptotic cell death", *FEMS Microbiol. Lett.*, 169(1):51-58, 1998.

He et al., "Radiation-enhanced vascular targeting of human lung cancers in mice with a monoclonal antibody that binds anionic phospholipids", *Clin. Cancer Res.*, 13(17): 5211-5218, 2007.

He et al., "Antiphosphatidylserine antibody combined with irradiation damages tumor blood vessels and induces tumor immunity in a rat model of glioblastoma", *Clin. Cancer Res.*, 15(22):6871-80, 2009.

Hogg et al., "Retargeting Adenoviral Vectors to Improve Gene Transfer into Tumors", *Cancer Gene Therapy*, 18:275-287, 2011.

Hotchkiss et al., "Inhibition of endothelial cell function in vitro and angiogenesis in vivo by docetaxel (Taxotere): association with impaired repositioning of the microtubule organizing center", *Mol. Cancer Ther.*, 1 (13): 1191-200, 2002.

Huang, Bennett, Thorpe, "A monoclonal antibody that binds anionic phospholipids on tumor blood vessels enhances the antitumor effect of docetaxel on human breast tumors in mice", *Cancer Res.*, 65(10):4408-4416, 2005.

Hunt, Simpson, Krilis, "Identification of a region of β₂-glycoprotein I critical for lipid-binding and anticardiolipin antibody cofactor activity", *Proc. Natl. Acad. Sci. USA*, 90:2141-2145, 1993.

Hunt and Krilis, "The fifth domain of β₂-glycoprotein I contains a phospholipid-binding site (Cys281-Cys288) and a region recognized by anti cardiolipin antibodies", *J. Immunol.*, 152:653-659, 1994.

Ioannou, Pericleous, Giles, Latchman, Isenberg, Rahman, "Binding of antiphospholipid antibodies to discontinuous epitopes on domain I of human β₂-glycoprotein I: mutation studies including residues R39 to R43", *Arthritis Rheum.*, 56(1):280-90, 2007.

Izquierdo-Useros et al., "HIV and mature dendritic cells: Trojan exosomes riding the Trojan horse?", *PLoS Pathog*, 6(3):e1000740, 2010.

Jennewein et al., "Vascular Imaging of Solid Tumors in Rats with a Radioactive Arsenic-Labeled Antibody that Binds Exposed Phosphatidylserine", *Clin. Cancer Res.*, 14(5): 1377-1385, 2008.

Jemielity et al., "TIM-Family Proteins Promote Infection of Multiple Enveloped Viruses through Virion-Associated Phosphatidylserine", *PLoS Pathogens*, 9(3):e1003232; 2013.

Judy et al., "Vascular Endothelial-Targeted Therapy Combined with Cytotoxic Chemotherapy Induces Inflammatory Intratumoral Infiltrates and Inhibits Tumor Relapses after Surgery", *Neoplasia*, 14:352-359, 2012.

Kabat et al., "*Sequences of Proteins of Immunological Interest*" 5th Ed. Public Health Service, National Institutes of Health, Bethesda, Md., 1991, pp 647-669 in particular.

Kamboh et al., "Genetic Studies of Human Apolipoproteins. IV. Structural Heterogeneity of Apolipoprotein H (β2-Glycoprotein I)", *Am. J. Hum. Genet.*, 42:452-457, 1988.

Kennedy et al., "Attenuating a sickle cell crisis with annexin V", Medical Hypotheses, http://dx.doi.Org/10.1016/j.mehy.2015.01.037, 2015.

Klein & Moeschberger, "Survival Analysis. Techniques for censored and truncated data", $2^{nd}$ Edition, New York, 2003 (ISBN-10: 038795399X; ISBN-13: 978-0387953991).

Larson, Iyengar, Kinjo, Pascual, Knauer, Chang, "Customization, Scale-Up and Qualification of an Antibody-dependent Cell-mediated Cytotoxicity (ADCC) Bioassay", *IBC's 23rd International Intensive Symposium Development, Validation and Maintenance of Biological Assays Conference*, Seattle, Wash., May 14-16, 2013; Poster Board #7.

Li et al., "Phosphatidylserine (PS) is Exposed in Choroidal Neovascular Endothelium: PS-Targeting Antibodies Inhibit Choroidal Angiogenesis In vivo and Ex Vivo", *Invest. Ophthalmol. Vis. Sci.*, 56:7137-7145, 2015.

Liang et al., "Targeting Mutant P53 Protein and the Tumor Vasculature: An Effective Combination Therapy for Advanced Breast Tumors", *Breast Cancer Res. Treat.*, 125:407-420, 2011.

Lonsdale et al., "Phosphatidylserine as a Therapeutic Target for the treatment of *Francisella tularensis* and *Yersinia pestis* infections", Chemical & Biological Defense Science & Technology Conference, 2011 Las Vegas, Nev. Abstract W15-048.

Luster et al., "Plasma Protein $\beta_2$-glycoprotein 1 Mediates Interaction between the Anti-tumor Monoclonal Antibody 3G4 and Anionic Phospholipids on Endothelial Cells", *J. Biol. Chem.,* 281(40):29863-29871, 2006.

Mahoney et al., "PD-L1 Antibodies to Its Cytoplasmic Domain Most Clearly Delineate Cell Membranes in Immunohistochemical Staining of Tumor Cells", *Cancer Immunol Res.,* 3(12): 1308-1315, 2015.

Mallat et al., "Shed Membrane Microparticles With Procoagulant Potential in Human Atherosclerotic Plaques", *Circulation,* 99:348-353, 1999.

Marconescu & Thorpe, "Coincident Exposure of Phsophatidylethanolamine and Anionic Phospholipids on the Surface of Irradiated Cells", *Biochemica et Biophysica Acta,* 1778(10):2217-2224, 2008.

McNeil, Simpson, Chesterman, Krilis, "Anti-phospholipid antibodies are directed against a complex antigen that includes a lipid-binding inhibitor of coagulation: $\beta_2$-glycoprotein I (apolipoprotein H)", *Proc. Natl. Acad. Sci. USA,* 87(11):4120-4124, 1990.

Meckes et al., "Human tumor virus utilizes exosomes for intercellular communication", *Proc. Natl. Acad. Sci. USA,* 107(47):20370-20375, 2010.

Meckes and Raab-Traub, "Microvesicles and Viral Infection", *J. Virology,* 85(24): 12844-12854, 2011.

Mehdi et al., "Genetic variation in the apolipoprotein H (β2-glycoprotein I) gene affects plasma apolipoprotein H concentrations", *Hum. Genet.,* 105:6371, 1999.

Meertens et al., "The TIM and TAM families of phosphatidylserine receptors mediate dengue virus entry", *Cell Host & Microbe,* 12(4):544-557, 2012.

Mercer and Helenius, "Vaccinia virus uses macropinocytosis and apoptotic mimicry to enter host cells", *Science,* 320:531-535, 2008.

Miyakis et al., "β2-glycoprotein I—function in health and disease", *Thromb. Res.,* 114:335-346, 2004.

Moller-Tank & Maury, "Phosphatidylserine receptors: Enhancers of enveloped virus entry and infection", *Virology,* 468-470 (2014) 565-580, 2014.

Moody et al., "Anti-phospholipid human monoclonal antibodies inhibit CCR5-tropic HIV-1 and induce β-chemokines", *J. Exp. Med.,* 207(4):763-776, 2010.

Morizono et al., "The soluble serum protein Gas6 bridges virion envelope phosphatidyl serine C254 to the TAM receptor tyrosine kinase Axl to mediate viral entry", *Cell Host Microbe,* 9:286-298. 2011.

Murata-Kamiya et al., "*Helicobacter pylori* Exploits Host Membrane Phosphatidylserine for Delivery, Localization, and Pathophysiological Action of the CagA Oncoprotein", *Cell Host Microbe,* 7:399-411, 2010.

Pattanapanyasat et al., "Febrile temperature but not proinflammatory cytokines promotes phosphatidylserine expression on *Plasmodium falciparum* malaria-infected red blood cells during parasite maturation", *Cytometry, Part A,* 77A:515-523, 2010.

Petersen & Krogfelt, "*Helicobacter pylori*: an invading microorganism? A review", *FEMS Immunol. Med. Microbiol.,* 36:117-126, 2003.

Prakasam and Thiagarajan, "P2-Glycoprotein I—A Protein in Search of Function", In *Antiphospholipid Syndrome*, Ed. Alena Bulikova, ISBN: 978-953-51-0526-8, InTech, Available from: http://www.intechopen.com/books/antiphospholipid-syndrome/beta2-glycoprotein-i-in-search-of-function, 2012.

Ran et al., "Antitumor effects of a monoclonal antibody that binds anionic phospholipids on the surface of tumor blood vessels in mice", *Clin. Cancer Res.,* 11:1551-1562, 2005.

Rebelatto et al., "Development of a programmed cell death ligand-1 immunohistochemical assay validated for analysis of non-small cell lung cancer and head and neck squamous cell carcinoma", *Diagnos. Pathol.,* 11(1):95, 2016.

Sabatier et al., "Type 1 And Type 2 Diabetic Patients Display Different Patterns of Cellular Microparticles", *Diabetes,* 51:2840-2845, 2002.

Saha et al., "An Orthotopic Lung Tumor Model for Image-Guided Microirradiation in Rats", *Radiat. Res.,* 174:62-71, 2010.

Schubert-Unkmeir et al., "Gene Expression Pattern in Human Brain Endothelial Cells in Response to *Neisseria meningitidis", Infect. Immun.,* 75(2):899-914, 2007.

Seabra et al., "*Toxoplasma gondii* exposes phosphatidylserine inducing a TGF-beta1 autocrine effect orchestrating macrophage evasion", *Biochem. Biophys. Res. Comm.,* 324(2):744-752, 2004.

Sheng et al., "Impaired Thrombin Generation in β2-Glycoprotein I Null Mice", *J. Biol. Chem.,* 276(17): 13817-13821, 2011.

Sims et al., "Neural stem cell-derived exosomes mediate viral entry", *Int. J. Nanomedicine,* 9:4893-4897, 2014.

Soares et al., "Targeting inside-out phosphatidylserine as a therapeutic strategy for viral diseases", *Nature Medicine,* 14(12):1357-1362, 2008.

Souza et al., "Microparticles: markers and mediators of sepsis-induced microvascular dysfunction, immunosuppression, and AKI", *Kidney Int*., doi: 10.1038/ki.2015.26, 2015.

Stafford & Thorpe, "Increased Exposure of Phosphatidylethanolamine on the Surface of Tumor Vascular Endothelium", *Neoplasia,* 13:299-308, 2011.

Stafford et al., "Highly Specific PET Imaging of Prostate Tumors in Mice with an Iodine-124-Labeled Antibody Fragment that Targets Phosphatidylserine", *PLoS ONE,* 8(12):e84864, 2013.

Steinkasserer et al., "Complete nucleotide and deduced amino acid sequence of human β2-glycoprotein I", *Biochem. J.,* 277:387-391, 1991.

Takeuchi et al., "Coagulation and fibrinolytic activities in 2 siblings with β2-glycoprotein I deficiency", *Blood,* 96:1594-1595, 2000.

U.S. Patent Application No. US 2016/0009805 A1.

U.S. Pat. No. 4,861,581

U.S. Pat. No. 5,019,368

U.S. Pat. No. 5,882,626

U.S. Pat. No. 7,247,303

U.S. Pat. No. 7,422,738
U.S. Pat. No. 7,455,833
U.S. Pat. No. 7,572,448
U.S. Pat. No. 7,611,704
U.S. Pat. No. 7,790,860
U.S. Pat. No. 7,906,115
U.S. Pat. No. 8,486,391
U.S. Pat. No. 8,956,616
van der Kleij et al., "A Novel Host-Parasite Lipid Cross-talk: schistosomal lyso-phosphatidylserine activates toll-like receptor 2 and affects immune polarization", *J. Biol. Chem.*, 277(50):48122-48129, 2002.
Walker et al., "Cytomegalovirus-infected human endothelial cells can stimulate allogeneic CD4+ memory T cells by releasing antigenic exosomes" *J Immunol.*, 182(3): 1548-1559, 2009.
Wanderley et al., "Cooperation between apoptotic and viable metacyclics enhances the pathogenesis of leishmaniasis", *PLoS One*, 4(5):e5733, 2009.
Wanderley et al., "Phosphatidylserine exposure on the surface of *Leishmania amazonensis* amastigotes modulates in vivo infection and dendritic cell function", *Parasite Immunology*, 35:109-119, 2013.
Wandler et al., "A Greasy Foothold for *Helicobacter pylori*", *Cell Host Microbe*, 7:338-339, 2010.
Weihua et al., "Apoptotic Cells Initiate Endothelial Cell Sprouting via Electrostatic Signaling", *Cancer Res.*, 65(24): 11529-11535, 2005.
Yin et al., "Phosphatidylserine-targeting antibody induces M1 macrophage polarization and promotes myeloid-derived suppressor cell differentiation", *Cancer Immunol. Res.*, 1(4):256-268, 2013.
Yuyama et al., "Sphingolipid-modulated Exosome Secretion Promotes Clearance of Amyloid-β by Microglia", *J. Biol. Chem.*, 287(14):10977-10989, 2012.
Zandbergen et al., "*Leishmania* disease development depends on the presence of apoptotic promastigotes in the virulent inoculum", *Proc. Natl. Acad Sci. USA.*, 103(37): 13837-13842, 2006.
Zhang et al., "Phosphatidylserine-Targeted Bimodal Liposomal Nanoparticles for in vivo Imaging of Breast Cancer in Mice", *J. Control. Release*, 183:114-123, 2014.
Zhao et al., "Near-Infrared Optical Imaging of Exposed Phosphatidylserine in a Mouse Glioma Model", *Translational Oncology*, 4:355-364, 2011.
Zhou et al., "Phosphatidylserine-Targeted Molecular Imaging of Tumor Vasculature by Magnetic Resonance Imaging", *J. Biomed Nanotechnol.*, 10:1-10, 2014.

What is claimed is:

1. A method for treating a tumor in a human subject in need thereof, comprising administering to said subject a therapeutically effective amount of (i) a phosphatidylserine (PS)-targeting antibody and (ii) an antibody that specifically binds to programmed cell death protein 1 (PD-1), wherein the subject is expected to have an increased survival as determined by the presence of less than about 1% of tumor cells expressing programmed cell death protein ligand 1 (PD-L1).

2. A method for treating a tumor in a human subject in need thereof, comprising
   (a) determining the expression level of PD-L1 in the subject's tumor cells; and,
   (b) administering to said subject a therapeutically effective amount of (i) a PS-targeting antibody and (ii) an antibody that specifically binds to PD-1,
   wherein the subject is expected to have an increased survival as determined by the presence of less than about 1% of tumor cells expressing PD-L1.

3. A method for treating a tumor in a human subject in need thereof, comprising administering to said subject if the subject is expected to have an increased survival as determined by the presence of less than about 1% of the tumor cells expressing PD-L1, a therapeutically effective amount of (i) a PS-targeting antibody and (ii) an antibody that specifically binds to PD-1, wherein the antibody that specifically binds to PD-1 comprises pembrolizumab or an antigen binding portion thereof.

4. The method of claim 3, wherein the PS-targeting antibody comprises bavituximab or an antigen binding portion thereof.

5. The method of claim 3, wherein the PS-targeting antibody is administered to the subject prior to, concurrently with, or after the administration of pembrolizumab or an antigen binding portion thereof.

6. The method of claim 3, wherein the PS-targeting antibody is administered weekly or once every two, three, four, five, or six weeks.

7. The method of claim 6, wherein the PS-targeting antibody is administered weekly.

8. The method of claim 3, wherein pembrolizumab is administered weekly or once every two, three, four, five, or six weeks.

9. The method of claim 8, wherein pembrolizumab is administered once every three weeks.

10. The method of claim 3, wherein the PS-targeting antibody is administered intravenously.

11. The method of claim 3, wherein pembrolizumab is administered intravenously.

12. The method of claim 3, wherein the PS-targeting antibody is administered to the subject in an amount of about 1 mg/kg, about 2 mg/kg, or about 3 mg/kg.

13. The method of claim 3, wherein pembrolizumab is administered to the subject in an amount of about 1 mg/kg, about 2 mg/kg, or about 3 mg/kg.

14. The method of claim 3, wherein the PS-targeting antibody is administered to the subject in an amount between about 100 mg and about 500 mg per dose.

15. The method of claim 3, wherein pembrolizumab is administered to the subject in an amount between about 100 mg and about 500 mg per dose.

16. The method of claim 3, wherein the PS-targeting antibody is administered to the subject at a flat dose of about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, about 300 mg, about 310 mg, about 320 mg, about 330 mg, about 340 mg, about 350 mg, about 360 mg, about 370 mg, about 380 mg, about 390 mg, or about 400 mg.

17. The method of claim 3, wherein pembrolizumab is administered to the subject at a flat dose of about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, about 300 mg, about 310 mg, about 320 mg, about 330 mg, about 340 mg, about 350 mg, about 360 mg, about 370 mg, about 380 mg, about 390 mg, or about 400 mg.

18. The method of claim 3, wherein the tumor is a lung cancer, ovarian cancer, gastric cancer, hepatocellular carcinoma, colorectal cancer, esophageal cancer, malignant glioma, pancreatic cancer, prostate cancer, Merkel cell carcinoma, head and neck cancer, renal cell carcinoma, bladder cancer, liver cancer, non-small cell lung cancer (NSCLC), metastatic gastroesophageal cancer, recurrent/metastatic squamous cell head and neck cancer (HNSCC), or hepatocellular carcinoma tumor.

19. The method of claim 3, wherein the subject is immunosuppressed.

20. A method for treating a tumor in a human subject in need thereof, comprising administering to said subject a therapeutically effective amount of (i) bavituximab or an antigen binding portion thereof, and (ii) pembrolizumab or an antigen binding portion thereof, wherein the tumor is NSCLC and the subject is expected to have an increased survival as determined by the presence of less than about 1% of tumor cells expressing PD-L1.

21. The method of claim 20, wherein bavituximab is administered to the subject in an amount of about 1 mg/kg, about 2 mg/kg, or about 3 mg/kg, and pembrolizumab is administered to the subject in an amount of about 200 mg.

22. The method of claim 21, wherein bavituximab is administered to the subject weekly, and pembrolizumab is administered to the subject once every three weeks.

* * * * *

SEQUENCE LISTING

```
<160> NUMBER OF SEQ ID NOS: 44

<210> SEQ ID NO 1
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
caggtgcagc tgcaggagtc gggcccagga ctggtgaagc cttcacagac cctgtccctc      60
acctgcactg tctctggtgg ctccatcagc agtggtgatt actactggag ttggatccgc     120
cagcccccag ggaagggtct ggagtggatt gggtacatct attacagtgg gagcacctac     180
tacaacccgt ccctcaagag tcgagttacc atatcagtag acacgtccaa gaaccagttc     240
tccctgaagc tgagctctgt gactgccgca gacacggccg tgtattactg tgccagatct     300
gagtggtccc tagcttttga tatctggggc caagggacaa tggtcaccgt ctcttca       357

<210> SEQ ID NO 2
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
cagcctgtgc tgactcagcc accctcagcg tctgggaccc ccgggcagag ggtcaccatc      60
ccttgttctg gaagcagctc caacatcgga ggtaatgatg tatactggta ccagcaagtc     120
ccaggaatgg cccccaaact cctcatctat cggaatcatc agcggccctc aggggtccct     180
gaccgattct ctggctccaa gtctggcacc tccgcctccc tggccatcag tgggctccgg     240
tccgaggatg aggctgatta ttattgtgca gcgtgggatg acagcctggg tggggtggtg     300
ttcggcggag ggaccaaggt caccgtccta                                      330
```

```
<210> SEQ ID NO 3
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Asp Tyr Tyr Trp Ser Trp Ile Arg Gln Pro Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Ser Glu Trp Ser Leu Ala Phe Asp Ile Trp Gly Gln Gly
            100                 105                 110

Thr Met Val Thr Val Ser Ser
        115

<210> SEQ ID NO 4
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Gln Pro Val Leu Thr Gln Pro Pro Ser Ala Ser Gly Thr Pro Gly Gln
1               5                   10                  15

Arg Val Thr Ile Pro Cys Ser Gly Ser Ser Ser Asn Ile Gly Gly Asn
            20                  25                  30

Asp Val Tyr Trp Tyr Gln Gln Val Pro Gly Met Ala Pro Lys Leu Leu
        35                  40                  45

Ile Tyr Arg Asn His Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Gly Gly Val Val Phe Gly Gly Gly Thr Lys Val Thr Val Leu
            100                 105                 110

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ser Gly Asp Tyr Tyr Trp Ser
1               5
```

```
<210> SEQ ID NO 6
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Tyr Ile Tyr Tyr Ser Gly Ser Thr Tyr Tyr Asn Pro Ser Leu Lys Ser
1               5                   10                  15

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ser Glu Trp Ser Leu Ala Phe Asp Ile
1               5

<210> SEQ ID NO 8
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ser Gly Ser Ser Ser Asn Ile Gly Gly Asn Asp Val Tyr
1               5                   10

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Arg Asn His Gln Arg Pro Ser
1               5

<210> SEQ ID NO 10
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Ala Ala Trp Asp Asp Ser Leu Gly Gly Val Val
1               5                   10

<210> SEQ ID NO 11
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 11

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser
            20                  25                  30

<210> SEQ ID NO 12
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Trp Ile Arg Gln Pro Pro Gly Lys Gly Leu Glu Trp Ile Gly
1               5                   10

<210> SEQ ID NO 13
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Arg Val Thr Ile Ser Val Asp Thr Ser Lys Asn Gln Phe Ser Leu Lys
1               5                   10                  15

Leu Ser Ser Val Thr Ala Ala Asp Thr Ala Val Tyr Tyr Cys Ala Arg
            20                  25                  30

<210> SEQ ID NO 14
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Trp Gly Gln Gly Thr Met Val Thr Val Ser Ser
1               5                   10

<210> SEQ ID NO 15
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gln Pro Val Leu Thr Gln Pro Pro Ser Ala Ser Gly Thr Pro Gly Gln
1               5                   10                  15

Arg Val Thr Ile Pro Cys
            20

<210> SEQ ID NO 16
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 16

Trp Tyr Gln Gln Val Pro Gly Met Ala Pro Lys Leu Leu Ile Tyr
1               5                   10                  15

<210> SEQ ID NO 17
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Gly Val Pro Asp Arg Phe Ser Gly Ser Lys Ser Gly Thr Ser Ala Ser
1               5                   10                  15

Leu Ala Ile Ser Gly Leu Arg Ser Glu Asp Glu Ala Asp Tyr Tyr Cys
            20                  25                  30

<210> SEQ ID NO 18
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Phe Gly Gly Gly Thr Lys Val Thr Val Leu
1               5                   10

<210> SEQ ID NO 19
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Lys Leu Ser Gly Ser Ala Ser Ala Pro Lys Leu Glu Glu Gly Glu Phe
1               5                   10                  15

Ser Glu Ala Arg Val
            20

<210> SEQ ID NO 20
<211> LENGTH: 750
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20
caggtgcagc tgcaggagtc gggcccagga ctggtgaagc cttcacagac cctgtccctc      60
acctgcactg tctctggtgg ctccatcagc agtggtgatt actactggag ttggatccgc     120
cagcccccag ggaagggtct ggagtggatt gggtacatct attacagtgg gagcacctac     180
tacaacccgt ccctcaagag tcgagttacc atatcagtag acacgtccaa gaaccagttc     240
tccctgaagc tgagctctgt gactgccgca gacacggccg tgtattactg tgccagatct     300
gagtggtccc tagctttttga tatctggggc caagggacaa tggtcaccgt ctcttcaaag    360 cttttcaggga gtgcatccgc cccaaaactt gaagaaggtg aatttcaga agcacgcgta     420 cagcctgtgc tgactcagcc accctcagcg tctgggaccc ccgggcagag ggtcaccatc     480
```

```
ccttgttctg gaagcagctc caacatcgga ggtaatgatg tatactggta ccagcaagtc    540
ccaggaatgg cccccaaact cctcatctat cggaatcatc agcggccctc agggggtccct   600 gaccgattct ctggctccaa gtctggcacc tccgcctccc tggccatcag tgggctccgg    660
tccgaggatg aggctgatta ttattgtgca gcgtgggatg acagcctggg tggggtggtg    720
ttcggcggag ggaccaaggt caccgtccta                                     750
```

<210> SEQ ID NO 21
<211> LENGTH: 250
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Ser Ile Ser Ser Gly
            20                  25                  30

Asp Tyr Tyr Trp Ser Trp Ile Arg Gln Pro Pro Gly Lys Gly Leu Glu
        35                  40                  45

Trp Ile Gly Tyr Ile Tyr Tyr Ser Gly Ser Thr Tyr Tyr Asn Pro Ser
50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
            85                  90                  95

Cys Ala Arg Ser Glu Trp Ser Leu Ala Phe Asp Ile Trp Gly Gln Gly
        100                 105                 110

Thr Met Val Thr Val Ser Ser Lys Leu Ser Gly Ser Ala Ser Ala Pro
    115                 120                 125

Lys Leu Glu Glu Gly Glu Phe Ser Glu Ala Arg Val Gln Pro Val Leu
130                 135                 140

Thr Gln Pro Pro Ser Ala Ser Gly Thr Pro Gly Gln Arg Val Thr Ile
145                 150                 155                 160

Pro Cys Ser Gly Ser Ser Ser Asn Ile Gly Gly Asn Asp Val Tyr Trp
                165                 170                 175

Tyr Gln Gln Val Pro Gly Met Ala Pro Lys Leu Leu Ile Tyr Arg Asn
            180                 185                 190

His Gln Arg Pro Ser Gly Val Pro Asp Arg Phe Ser Gly Ser Lys Ser
        195                 200                 205

Gly Thr Ser Ala Ser Leu Ala Ile Ser Gly Leu Arg Ser Glu Asp Glu
    210                 215                 220

Ala Asp Tyr Tyr Cys Ala Ala Trp Asp Asp Ser Leu Gly Gly Val Val
225                 230                 235                 240

Phe Gly Gly Gly Thr Lys Val Thr Val Leu
                245                 250
```

<210> SEQ ID NO 22
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 22

Gln Val Gln Leu Gln Glu Ser Gly Pro Gly Leu Val Lys Pro Ser Gln
1               5                   10                  15

Thr Leu Ser Leu Thr Cys Thr Val Ser Gly Ser Ile Ser Ser Gly
            20                  25                  30

Asp Tyr Tyr Trp Ser Trp Ile Arg Gln Pro Pro Gly Lys Gly Leu Glu
            35                  40                  45

Trp Ile Gly Tyr Ile Tyr Tyr Ser Gly Ser Thr Tyr Tyr Asn Pro Ser
        50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Ser Glu Trp Ser Leu Ala Phe Asp Ile Trp Gly Gln Gly
            100                 105                 110

Thr Met Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415
```

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 23
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Gln Pro Val Leu Thr Gln Pro Pro Ser Ala Ser Gly Thr Pro Gly Gln
1               5                   10                  15

Arg Val Thr Ile Pro Cys Ser Gly Ser Ser Ser Asn Ile Gly Gly Asn
            20                  25                  30

Asp Val Tyr Trp Tyr Gln Gln Val Pro Gly Met Ala Pro Lys Leu Leu
        35                  40                  45

Ile Tyr Arg Asn His Gln Arg Pro Ser Gly Val Pro Asp Arg Phe Ser
50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Gly Gly Val Val Phe Gly Gly Gly Thr Lys Val Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 24
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Ser Gly Ser Ser Ser Asn Ile Gly Ser Asn Thr Val Asn
1               5                   10

```
<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Ser Asn Asn Gln Arg Pro Ser
1               5

<210> SEQ ID NO 26
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Ala Ala Trp Asp Asp Ser Leu Asn Gly Pro Tyr Val
1               5                   10

<210> SEQ ID NO 27
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Gln Pro Gly Leu Thr Gln Pro Pro Ser Ala Ser Gly Thr Pro Gly Gln
1               5                   10                  15

Arg Val Thr Ile Ser Cys
            20

<210> SEQ ID NO 28
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Trp Tyr Gln Gln Leu Pro Gly Thr Ala Pro Lys Leu Leu Ile Tyr
1               5                   10                  15

<210> SEQ ID NO 29
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Gly Val Pro Asp Arg Phe Ser Gly Ser Lys Ser Gly Thr Ser Ala Ser
1               5                   10                  15

Leu Ala Ile Ser Gly Leu Gln Ser Glu Asp Glu Ala Asp Tyr Tyr Cys
            20                  25                  30
```

<210> SEQ ID NO 30
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Phe Gly Thr Gly Thr Lys Leu Thr Val Leu
1               5                   10

<210> SEQ ID NO 31
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 31
cagccagggc tgactcagcc accctcagcg tctgggaccc ccgggcagag ggtcaccatc      60
tcttgttctg gaagcagctc aacatcgga agtaatactg taaactggta ccagcagctc     120
ccaggaacgg cccccaaact cctcatctat agtaataatc agcggccctc aggggtccct    180
gaccgattct ctggctccaa gtctggcacc tcagcctccc tggccatcag tgggctccag    240
tctgaggatg aggctgatta ttactgtgca gcatgggatg acagcctgaa tggcccttat    300
gtcttcggaa ctgggaccaa gctcaccgtc cta                                 333

<210> SEQ ID NO 32
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Gln Pro Gly Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
                20                  25                  30

Thr Val Asn Trp Tyr Gln Gln Leu Pro Gly Thr Ala Pro Lys Leu Leu
            35                  40                  45

Ile Tyr Ser Asn Asn Gln Arg Pro Ser Gly Val Pro Asp Arg Phe Ser
        50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Pro Tyr Val Phe Gly Thr Gly Thr Lys Leu Thr Val Leu
            100                 105                 110

<210> SEQ ID NO 33
<211> LENGTH: 753
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 33

```
caggtgcagc tgcaggagtc gggcccagga ctggtgaagc cttcacagac cctgtccctc    60
acctgcactg tctctggtgg ctccatcagc agtggtgatt actactggag ttggatccgc   120
cagcccccag ggaagggtct ggagtggatt gggtacatct attacagtgg gagcacctac   180
tacaaccgt ccctcaagag tcgagttacc atatcagtag acacgtccaa gaaccagttc    240
tccctgaagc tgagctctgt gactgccgca gacacggccg tgtattactg tgccagatct   300
gagtggtccc tagcttttga tatctggggc caagggacaa tggtcaccgt ctcttcaaag   360
ctttcaggga gtgcatccgc cccaaaactt gaagaaggtg aattttcaga agcacgcgta   420
cagccagggc tgactcagcc accctcagcg tctgggaccc ccgggcagag ggtcaccatc   480
tcttgttctg gaagcagctc caacatcgga agtaatactg taaactggta ccagcagctc   540
ccaggaacgg cccccaaact cctcatctat agtaataatc agcggccctc aggggtccct   600
gaccgattct ctggctccaa gtctggcacc tcagcctccc tggccatcag tgggctccag   660
tctgaggatg aggctgatta ttactgtgca gcatgggatg acagcctgaa tggcccttat   720
gtcttcggaa ctgggaccaa gctcaccgtc cta                                 753
```

<210> SEQ ID NO 34
<211> LENGTH: 255
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 34

```
Met Ala Gln Val Gln Leu Gln Glu Ser Gly Pro Gly Leu Val Lys Pro
  1               5                  10                  15

Ser Gln Thr Leu Ser Leu Thr Cys Thr Val Ser Gly Gly Ser Ile Ser
             20                  25                  30

Ser Gly Asp Tyr Tyr Trp Ser Trp Ile Arg Gln Pro Pro Gly Lys Gly
         35                  40                  45

Leu Glu Trp Ile Gly Tyr Ile Tyr Tyr Ser Gly Ser Thr Tyr Tyr Asn
     50                  55                  60

Pro Ser Leu Lys Ser Arg Val Thr Ile Ser Val Asp Thr Ser Lys Asn
 65                  70                  75                  80

Gln Phe Ser Leu Lys Leu Ser Ser Val Thr Ala Ala Asp Thr Ala Val
                 85                  90                  95

Tyr Tyr Cys Ala Arg Ser Glu Trp Ser Leu Ala Phe Asp Ile Trp Gly
            100                 105                 110

Gln Gly Thr Met Val Thr Val Ser Ser Lys Leu Ser Gly Ser Ala Ser
        115                 120                 125

Ala Pro Lys Leu Glu Glu Gly Glu Phe Ser Ala Arg Val Gln Pro
    130                 135                 140

Gly Leu Thr Gln Pro Pro Ser Ala Ser Gly Thr Pro Gly Gln Arg Val
145                 150                 155                 160

Thr Ile Ser Cys Ser Gly Ser Ser Asn Ile Gly Ser Asn Thr Val
                165                 170                 175

Asn Trp Tyr Gln Gln Leu Pro Gly Thr Ala Pro Lys Leu Leu Ile Tyr
            180                 185                 190

Ser Asn Asn Gln Arg Pro Ser Gly Val Pro Asp Arg Phe Ser Gly Ser
        195                 200                 205
```

Lys Ser Gly Thr Ser Ala Ser Leu Ala Ile Ser Gly Leu Gln Ser Glu
         210                 215                 220

Asp Glu Ala Asp Tyr Tyr Cys Ala Ala Trp Asp Asp Ser Leu Asn Gly
225                 230                 235                 240

Pro Tyr Val Phe Gly Thr Gly Thr Lys Leu Thr Val Leu Ala Ala
                245                 250                 255

<210> SEQ ID NO 35
<211> LENGTH: 519
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(456)

<400> SEQUENCE: 35 atg gga tgg acc tgg atc ttt att tta atc ctg tca gta act aca ggt        48
Met Gly Trp Thr Trp Ile Phe Ile Leu Ile Leu Ser Val Thr Thr Gly
1               5                   10                  15 gtc cac tct gag gtc cag ctg cag cag tct gga cct gag ctg gag aag        96
Val His Ser Glu Val Gln Leu Gln Gln Ser Gly Pro Glu Leu Glu Lys
                20                  25                  30 cct ggc gct tca gtg aag cta tcc tgc aag gct tct ggt tac tca ttc       144
Pro Gly Ala Ser Val Lys Leu Ser Cys Lys Ala Ser Gly Tyr Ser Phe
            35                  40                  45 act ggc tac aac atg aac tgg gtg aaa cag agc cat gga aag agc ctt       192
Thr Gly Tyr Asn Met Asn Trp Val Lys Gln Ser His Gly Lys Ser Leu
        50                  55                  60 gaa tgg att gga cat att gat cct tac tat ggt gat act tcc tac aac       240
Glu Trp Ile Gly His Ile Asp Pro Tyr Tyr Gly Asp Thr Ser Tyr Asn
65                  70                  75                  80 cag aag ttc agg ggc aag gcc aca ttg act gta gac aaa tcc tcc agc       288
Gln Lys Phe Arg Gly Lys Ala Thr Leu Thr Val Asp Lys Ser Ser Ser
                85                  90                  95 aca gcc tac atg cag ctc aag agc ctg aca tct gag gac tct gca gtc       336
Thr Ala Tyr Met Gln Leu Lys Ser Leu Thr Ser Glu Asp Ser Ala Val
            100                 105                 110 tat tac tgt gta aag ggg ggt tac tac ggg cac tgg tac ttc gat gtc       384
Tyr Tyr Cys Val Lys Gly Gly Tyr Tyr Gly His Trp Tyr Phe Asp Val
        115                 120                 125 tgg ggc gca ggg acc acg gtc acc gtc tcc tca gct aca aca aca gcc       432
Trp Gly Ala Gly Thr Thr Val Thr Val Ser Ser Ala Thr Thr Thr Ala
    130                 135                 140 cca tct gtc tat ccc ttg gtc ccg ggcggatccc ccgggctgca ggaattcgat      486
Pro Ser Val Tyr Pro Leu Val Pro
145                 150 atcaagctta tcgataccgt cgacctcgag ggg                                  519

<210> SEQ ID NO 36
<211> LENGTH: 152
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

```
Met Gly Trp Thr Trp Ile Phe Ile Leu Ile Leu Ser Val Thr Thr Gly
1               5                   10                  15

Val His Ser Glu Val Gln Leu Gln Gln Ser Gly Pro Glu Leu Glu Lys
            20                  25                  30

Pro Gly Ala Ser Val Lys Leu Ser Cys Lys Ala Ser Gly Tyr Ser Phe
        35                  40                  45

Thr Gly Tyr Asn Met Asn Trp Val Lys Gln Ser His Gly Lys Ser Leu
    50                  55                  60

Glu Trp Ile Gly His Ile Asp Pro Tyr Tyr Gly Asp Thr Ser Tyr Asn
65                  70                  75                  80

Gln Lys Phe Arg Gly Lys Ala Thr Leu Thr Val Asp Lys Ser Ser Ser
                85                  90                  95

Thr Ala Tyr Met Gln Leu Lys Ser Leu Thr Ser Glu Asp Ser Ala Val
            100                 105                 110

Tyr Tyr Cys Val Lys Gly Gly Tyr Tyr Gly His Trp Tyr Phe Asp Val
        115                 120                 125

Trp Gly Ala Gly Thr Thr Val Thr Val Ser Ser Ala Thr Thr Thr Ala
    130                 135                 140

Pro Ser Val Tyr Pro Leu Val Pro
145                 150
```

<210> SEQ ID NO 37
<211> LENGTH: 435
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<221> NAME/KEY: CDS
<222> LOCATION: (1)..(432)

<400> SEQUENCE: 37

```
atg gac atg agg gct cct gca cag att ttg ggc ttc ttg ttg ctc ttg      48
Met Asp Met Arg Ala Pro Ala Gln Ile Leu Gly Phe Leu Leu Leu Leu
1               5                   10                  15 ttt cca ggt acc aga tgt gac atc cag atg acc cag tct cca tcc tcc      96
Phe Pro Gly Thr Arg Cys Asp Ile Gln Met Thr Gln Ser Pro Ser Ser
            20                  25                  30 tta tct gcc tct ctg gga gaa aga gtc agt ctc act tgt cgg gca agt     144
Leu Ser Ala Ser Leu Gly Glu Arg Val Ser Leu Thr Cys Arg Ala Ser
        35                  40                  45 cag gac att ggt agt agc tta aac tgg ctt cag cag gga cca gat gga     192
Gln Asp Ile Gly Ser Ser Leu Asn Trp Leu Gln Gln Gly Pro Asp Gly
    50                  55                  60 act att aaa cgc ctg atc tac gcc aca tcc agt tta gat tct ggt gtc     240
Thr Ile Lys Arg Leu Ile Tyr Ala Thr Ser Ser Leu Asp Ser Gly Val
65                  70                  75                  80 ccc aaa agg ttc agt ggc agt agg tct ggg tca gat tat tct ctc acc     288
Pro Lys Arg Phe Ser Gly Ser Arg Ser Gly Ser Asp Tyr Ser Leu Thr
                85                  90                  95 atc agc agc ctt gag tct gaa gat ttt gta gac tat tac tgt cta caa     336
Ile Ser Ser Leu Glu Ser Glu Asp Phe Val Asp Tyr Tyr Cys Leu Gln
            100                 105                 110 tat gtt agt tct cct ccc acg ttc ggt gct ggg acc aag ctg gag ctg     384
Tyr Val Ser Ser Pro Pro Thr Phe Gly Ala Gly Thr Lys Leu Glu Leu
        115                 120                 125
```

```
aaa cgg gct gat gct gca cca act gtc ttc atc ttc ggg cgg atc ccc    432
Lys Arg Ala Asp Ala Ala Pro Thr Val Phe Ile Phe Gly Arg Ile Pro
130                 135                 140 cgg                                                                435
```

```
<210> SEQ ID NO 38
<211> LENGTH: 144
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38
```

Met Asp Met Arg Ala Pro Ala Gln Ile Leu Gly Phe Leu Leu Leu Leu
1               5                   10                  15

Phe Pro Gly Thr Arg Cys Asp Ile Gln Met Thr Gln Ser Pro Ser Ser
            20                  25                  30

Leu Ser Ala Ser Leu Gly Glu Arg Val Ser Leu Thr Cys Arg Ala Ser
        35                  40                  45

Gln Asp Ile Gly Ser Ser Leu Asn Trp Leu Gln Gln Gly Pro Asp Gly
    50                  55                  60

Thr Ile Lys Arg Leu Ile Tyr Ala Thr Ser Ser Leu Asp Ser Gly Val
65                  70                  75                  80

Pro Lys Arg Phe Ser Gly Ser Arg Ser Gly Ser Asp Tyr Ser Leu Thr
                85                  90                  95

Ile Ser Ser Leu Glu Ser Glu Asp Phe Val Asp Tyr Tyr Cys Leu Gln
            100                 105                 110

Tyr Val Ser Ser Pro Pro Thr Phe Gly Ala Gly Thr Lys Leu Glu Leu
        115                 120                 125

Lys Arg Ala Asp Ala Ala Pro Thr Val Phe Ile Phe Gly Arg Ile Pro
    130                 135                 140

```
<210> SEQ ID NO 39
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39
```

Ala Ser Thr Leu Gly Pro Ser Val Phe Pro Leu Ala Pro Ser Ser Lys
1               5                   10                  15

Ser Thr Ser Gly
            20

```
<210> SEQ ID NO 40
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40
```

Ile Phe Pro Pro Ser Asp Glu Gln Leu Lys Ser Gly Thr Ala Ser
1               5                   10                  15

```
<210> SEQ ID NO 41
<211> LENGTH: 159
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Met Gly Trp Thr Trp Ile Phe Ile Leu Ile Leu Ser Val Thr Thr Gly
1               5                   10                  15

Val His Ser Glu Val Gln Leu Gln Gln Ser Gly Pro Glu Leu Glu Lys
            20                  25                  30

Pro Gly Ala Ser Val Lys Leu Ser Cys Lys Ala Ser Gly Tyr Ser Phe
        35                  40                  45

Thr Gly Tyr Asn Met Asn Trp Val Lys Gln Ser His Gly Lys Ser Leu
    50                  55                  60

Glu Trp Ile Gly His Ile Asp Pro Tyr Tyr Gly Asp Thr Ser Tyr Asn
65                  70                  75                  80

Gln Lys Phe Arg Gly Lys Ala Thr Leu Thr Val Asp Lys Ser Ser Ser
                85                  90                  95

Thr Ala Tyr Met Gln Leu Lys Ser Leu Thr Ser Glu Asp Ser Ala Val
            100                 105                 110

Tyr Tyr Cys Val Lys Gly Gly Tyr Tyr Gly His Trp Tyr Phe Asp Val
        115                 120                 125

Trp Gly Ala Gly Thr Thr Val Thr Val Ser Ser Ala Ser Thr Lys Gly
    130                 135                 140

Pro Ser Val Phe Pro Leu Ala Pro Ser Ser Lys Ser Thr Ser Gly
145                 150                 155

<210> SEQ ID NO 42
<211> LENGTH: 153
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Met Asp Met Arg Ala Pro Ala Gln Ile Leu Gly Phe Leu Leu Leu Leu
1               5                   10                  15

Phe Pro Gly Thr Arg Cys Asp Ile Gln Met Thr Gln Ser Pro Ser Ser
            20                  25                  30

Leu Ser Ala Ser Leu Gly Glu Arg Val Ser Leu Thr Cys Arg Ala Ser
        35                  40                  45

Gln Asp Ile Gly Ser Ser Leu Asn Trp Leu Gln Gln Gly Pro Asp Gly
    50                  55                  60

Thr Ile Lys Arg Leu Ile Tyr Ala Thr Ser Ser Leu Asp Ser Gly Val
65                  70                  75                  80

Pro Lys Arg Phe Ser Gly Ser Arg Ser Gly Ser Asp Tyr Ser Leu Thr
                85                  90                  95

Ile Ser Ser Leu Glu Ser Glu Asp Phe Val Asp Tyr Tyr Cys Leu Gln
            100                 105                 110

Tyr Val Ser Ser Pro Pro Thr Phe Gly Ala Gly Thr Lys Leu Glu Leu
        115                 120                 125
```

Lys Arg Ala Asp Ala Ala Pro Thr Val Phe Ile Phe Pro Pro Ser Asp
    130                 135                 140

Glu Gln Leu Lys Ser Gly Thr Ala Ser
145                 150

<210> SEQ ID NO 43
<211> LENGTH: 766
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 43
ccatggccca ggtgcagctg caggagtcgg gcccaggact ggtgaagcct tcacagaccc      60
tgtccctcac ctgcactgtc tctggtggct ccatcagcag tggtgattac tactggagtt     120
ggatccgcca gcccccaggg aagggtctgg agtggattgg gtacatctat tacagtggga     180
gcacctacta caacccgtcc ctcaagagtc gagttaccat atcagtagac acgtccaaga     240
accagttctc cctgaagctg agctctgtga ctgccgcaga cacggccgtg tattactgtg     300
ccagatctga gtggtcccta gcttttgata tctggggcca agggacaatg gtcaccgtct     360
cttcaaagct ttcagggagt gcatccgccc caaaacttga agaaggtgaa ttttcagaag     420
cacgcgtaca gcctgtgctg actcagccac cctcagcgtc tgggaccccc gggcagaggg     480
tcaccatccc ttgttctgga agcagctcca acatcggagg taatgatgta tactggtacc     540
agcaagtccc aggaatggcc cccaaactcc tcatctatcg gaatcatcag cggccctcag     600
gggtccctga ccgattctct ggctccaagt ctggcacctc cgcctccctg gccatcagtg     660 gctccggtc cgaggatgag gctgattatt attgtgcagc gtgggatgac agcctgggtg      720
gggtggtgtt cggcggaggg accaaggtca ccgtcctagc ggccgc               766

<210> SEQ ID NO 44
<211> LENGTH: 247
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Asp Tyr Tyr Trp Ser Trp Ile Arg Gln Pro Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Ser Glu Trp Ser Leu Ala Phe Asp Ile Trp Gly Gln Gly
            100                 105                 110

Thr Met Val Thr Val Ser Ser Lys Leu Ser Gly Ser Ala Ser Ala Pro
        115                 120                 125

-continued

```
Lys Leu Glu Glu Gly Glu Phe Ser Glu Ala Arg Val Gln Pro Val Leu
    130                 135                 140
Thr Ser Ala Ser Gly Thr Pro Gly Gln Arg Val Thr Ile Pro Cys Ser
145             150                 155                 160
Gly Ser Ser Ser Asn Ile Gly Gly Asn Asp Val Tyr Trp Tyr Gln Gln
                165                 170                 175
Val Pro Gly Met Ala Pro Lys Leu Leu Ile Tyr Arg Asn His Gln Arg
            180                 185                 190
Pro Ser Gly Val Pro Asp Arg Phe Ser Gly Ser Lys Ser Gly Thr Ser
        195                 200                 205
Ala Ser Leu Ala Ile Ser Gly Leu Arg Ser Glu Asp Glu Ala Asp Tyr
    210                 215                 220
Tyr Cys Ala Ala Trp Asp Asp Ser Leu Gly Gly Val Val Phe Gly Gly
225             230                 235                 240
Gly Thr Lys Val Thr Val Leu
                245
```